US011046775B2

(12) United States Patent
Alvarez Rodriguez et al.

(10) Patent No.: US 11,046,775 B2
(45) Date of Patent: Jun. 29, 2021

(54) CD70 BINDING MOLECULES AND METHODS OF USE THEREOF

(71) Applicant: KITE PHARMA, INC., Santa Monica, CA (US)

(72) Inventors: Ruben Alvarez Rodriguez, Los Angeles, CA (US); Armen Mardiros, Tujunga, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 435 days.

(21) Appl. No.: 15/896,619

(22) Filed: Feb. 14, 2018

(65) Prior Publication Data
US 2018/0230224 A1 Aug. 16, 2018

Related U.S. Application Data

(60) Provisional application No. 62/458,879, filed on Feb. 14, 2017.

(51) Int. Cl.
C07K 16/28 (2006.01)
C07K 14/705 (2006.01)
C07K 14/725 (2006.01)
C12N 5/0783 (2010.01)
A61P 35/00 (2006.01)

(52) U.S. Cl.
CPC .......... C07K 16/2875 (2013.01); A61P 35/00 (2018.01); C07K 14/7051 (2013.01); C07K 14/70521 (2013.01); C07K 14/70578 (2013.01); C12N 5/0636 (2013.01); C07K 2317/53 (2013.01); C07K 2317/54 (2013.01); C07K 2317/55 (2013.01); C07K 2317/56 (2013.01); C07K 2317/565 (2013.01); C07K 2317/569 (2013.01); C07K 2317/622 (2013.01); C07K 2317/92 (2013.01); C07K 2319/03 (2013.01); C07K 2319/33 (2013.01)

(58) Field of Classification Search
None
See application file for complete search history.

(56) References Cited

U.S. PATENT DOCUMENTS

| | | | |
|---|---|---|---|
| 5,223,409 | A | 6/1993 | Ladner |
| 7,709,226 | B2 | 5/2010 | Foote |
| 8,987,422 | B2 | 3/2015 | Delaney et al. |
| 9,574,008 | B2 | 2/2017 | Delaney et al. |
| 2014/0308259 | A1* | 10/2014 | Scholler ........... G01N 33/57492 424/93.21 |
| 2017/0129961 | A1* | 5/2017 | Raum ..................... A61P 35/00 |

FOREIGN PATENT DOCUMENTS

WO 2016/016859 A1 2/2016

OTHER PUBLICATIONS

Mariuzza et al. (Annu. Rev. Biophys. Biophys. Chem., 16: 139-159, 1987).*
Winkler et al (J. Imm., 265:4505-4514, 2000).*
Giusti et al (PNAS, 9: 2926-2930, 1987).*
Rudikoff et al (PNAS, 79:1979-1983, 1982).*
Choi et al, MB 7:3327-334, 2011.*
Wang et al (CIR, 2(2):154-166, 2014).*
Wang, Qiong J et al: "Preclinical Evaluation of Chimeric Antigen Receptors Targeting CD70-Expressing Cancers"; Clinical Cancer Research: An Official Journal of the American Association for Cancer Research May 1, 2017, vol. 23, No. 9, Nov. 1, 2016 (Nov. 1, 2016), pp. 2267-22769; XP055465432; ISSN: 1078-0432.
Shaffer, D R et al: "T cells redirected against CD70 for the immunotherapy of CD70-positive malignancies", Blood, American Society of Hematology, US, vol. 117, No. 16, Apr. 21, 2011 (Apr. 21, 2011), pp. 4304-4314, XP002738263, ISSN: 0006-4971, DOI: 10.1182/BLOOD-2010-04-278218.
Park, Yuk Pheel et al; "CD70 as a target for chimeric antigen receptor T cells in head and neck squamous cell carcinoma.", Oral Oncology Mar. 2018, vol. 78, Mar. 2018 (Mar. 2018). pp. 145-150, ISSN: 1879-0593.
Jin, Linchun et al, CD70, A novel target of CART-cell therapy for gliomas, Neuro-Oncology, vol. 20, No. 1., Jan. 10, 2018 (Jan. 10, 2018), pp. 55-65, XP055464384, US, ISSN: 1522-8517, DOI: 10.1093/neuonc/nox116.
European Patent Office; International Search Report issued in the PCT application No. PCT/US2018/018152 dated Apr. 18, 2018.
Golub, et al., "Immunology—A Synthesis (2nd Edition)", Sinauer Assoc., Sunderland, Mass. (1991), table of contents only, 13 pages.
Stocks, "Intrabodies: production and promise" Drug Discovery Today, 2004, 9(22):960-66.
Bird et al., "Single-chain antigen-binding proteins", 1988, Science 242:423-26.
Huston et al., Protein engineering of antibody binding sites: recovery of specific activity in an anti-digoxin single-chain Fv analogue produced in Escherichia coli PNAS, Aug. 1, 1988, 85 (16) 5879-5883.
Holliger et al., "Diabodies: Small Bivalen and Bispecific Antibody Fagments" Proc Natl Acad Sci U.S.A., 1993, 90:6444-48 Biophysics.
Poljak et al., "Production and structure of diabodies" Structure, 1994, vol. 2, No. 12: 1121-23.
Perisic et al., "Crystal structure of a diabody, a bivalent antibody fragment" Structure, 1994, 2(12): 1217-26.

(Continued)

Primary Examiner — Brad Duffy
(74) Attorney, Agent, or Firm — Barnes & Thornburg LLP

(57) ABSTRACT

The disclosure provides anti-CD70 antibodies, antigen binding fragments thereof, chimeric antigen receptors (CARs) and engineered T cell receptors (TCRs) comprising an antigen binding molecule that specifically binds to CD70, polynucleotides encoding the same, and in vitro cells comprising the same. The polynucleotides, polypeptides, and in vitro cells described herein can be used in an engineered TCR and/or CAR T cell therapy for the treatment of a patient suffering from a cancer. In one embodiment, the polynucleotides, polypeptides, and in vitro cells described herein can be used for the treatment of multiple myeloma.

50 Claims, 45 Drawing Sheets
Specification includes a Sequence Listing.

(56) References Cited

OTHER PUBLICATIONS

Korndorfer et al., "Crystallographic Analysis of an "Anticalin" With Tailored Specificity for Fluorescein Reveals High Structural Plasticity of the Lipocalin Loop Region" Proteins: Structure, Function, and Bioinformatics, 2003, 53 (1):121-129 Wiley-Liss, Inc.
Roque et al., "Antibodies and Genetically Engineered Related Molecules: Production and Purification", Biotechnol. Prog. 20:639-654 (2004).
Kabat et al. "Sequences of Proteins of Immunological Interest", 1991, 5th Ed., NIH Publication 91-3242, Bethesda MD title page, publication page, and table of contents only, 10 pages.
Chothia et al., "Canonical structures for the hypervariable regions of immunoglobulins", J Mol Biol, 1987, 196: 901-917.
Al-Lazikani et al., "Standard conformations for the canonical structures of immunoglobulins" J Mol Biol, 1997, 273: 927-948.
Chothia et al., "Structural repertoire of the human VH segments" J Mol Biol, 1992, 227: 799-817.
Tramontano et al., "Framework residue 71 is a major determinant of the position and conformation of the second hypervariable region in the VH domains of immunoglobulins" J Mol Biol, 1990, 215(1): 175-82.
Bricogne, "Direct phase determination by entropy maximization and likelihood ranking: status report and perspectives", Acta Crystallogr D Biol Crystallogr, 1993, 49(Pt 1): 37-60.
Bricogne, "[23] Bayesian statistical viewpoint on structure determination: Basic concepts and examples", Meth Enzymol, 1997, 276A: 361-423.
Roversi et al., "Modeling prior distributions of atoms for macromolecular refinement and completion", Acta Crystallogr D Biol Crystallogr, 2000, 56 (Pt 10): 1316-1323.
Champe et al., "Monoclonal Antibodies That Block the Activity of Leukocyte Function-associated Antigen 1 Recognize Three Discrete Epitopes in the Inserted Domain of CD11a", J Biol Chem, 1995, 270(3): 1388-94.
Cunningham et al., "High-resolution epitope mapping of hGH-receptor interactions by alanine-scanning mutagenesis", Science 244(4908): 1081-85 (1989).
Goodwin et al.,"Molecular and biological characterization of a ligand for CD27 defines a new family of cytokines with homology to tumor necrosis factor", Cell, , 1993 73(3):447-56.
Bowman et al., "The cloning of CD70 and its identification as the ligand for CD27", Journal of immunology (Baltimore, MD. : 1950), 1994 152(4):1756-61.
Hartl et al., "Genetics: Principles and Analysis", 1997, Jones and Bartlett Publishers.
Dayhoff et al. A model of evolutionary change in proteins, in Dayhoff, M.O. Edition, Atlas of Protein Sequence and Structure, 1978, Natl. Biomed. Res. Found., Washington DC, 5(3), 345- 352.

Henilkoff et al. "Amino acid substitution matrices from protein blocks", Proc Natl Acad Sci U S A., 89(22): 10915-10919, Nov. 15, 1992.
Bruggenmann et al. "Production of human antibody repertoires in transgenic mice", 1Curr. Opin. Biotechnol. 1997, 8:455-58.
Burton et al., "Human Antibodies from Combinatorial libraries", Advances in immunology, 1994, vol. 57, 191-280.
Winter, et al., "Making Antibodies by Phage Display Technology", Annual Review of Immunology, Publication Annual Review of Immunology, 1994, 12(1):433-455.
Huse, et al., "Generation of a Large Combinatorial Library of the Immunoglobulin Repertoire in Phage Lambda", Science, 1989, 246(4935):1275-1281.
Sastry et al. "Cloning of the immunological repertoire in *Escherichia coli* for generation of monoclonal catalytic antibodies: construction of a heavy chain variable region-specific cDNA library". Proceedings of the National Academy of Sciences of the United States of America. 1989, 86(15):5728-5732.
Kang et al., "Linkage of recognition and replication functions by assembling combinatorial antibody Fab libraries along phage surfaces", Proc Nati Aced Sci U S A., May 15, 1991, 88(10):4363-6.
Hoogenboom et al., "By-passing immunisation", Journal of Molecular Biology, 1992, 227(2):381-388.
Berzofsky, et al. "Antigen-Antibody interaction and Monoclonal Antibodies", Fundamental immunology, editor, William E. Paul.—7th ed., (2013), Ch 7, Lippincott Williams & Wilkins.
Schlebusch et al., "Production of a Single-Chain Fragment of the Murine Anti-Idiotypic Antibody ACA125 as Phage-Displayed and Soluble Antibody by Recombinant Phage Antibody Technique", 1997, Hybridoma 16:47-52.
Baines and Thorpe, "Purification ofImmunoglobulin G (IgG)", (1992) in Methods in Molecular Biology, 10:79-104 (The Humana Press).
Littman et al., "The isolation and sequence of the gene encoding T8: a molecule defining functional classes of T lymphocytes", Cell, 1985, 40(2):237-46.
Wyckoff et al., eds., Methods in Enzymology vol. 114-Diffraction Methods for Biological Macromolecules, Academic Press, Orlando, FL; title page, publication page, and table of contents only, 5 pages (1985).
Wyckoff et al., eds., Methods in Enzymology vol. 115. Diffraction Methods for Biological Macromolecules, Academic Press, Orlando, FL; title page, publication page, and table of contents only, 4 pages (1985).
Alting-Mees et al., "Monoclonal Antibody Expression Libraries: A Rapid Alternative to Hybridomas", (1990) Strategies in Molecular Biology 3:1-9.
Decision of Rejection, issued in TW Application No. 107105546, dated Dec. 3, 2020.

* cited by examiner

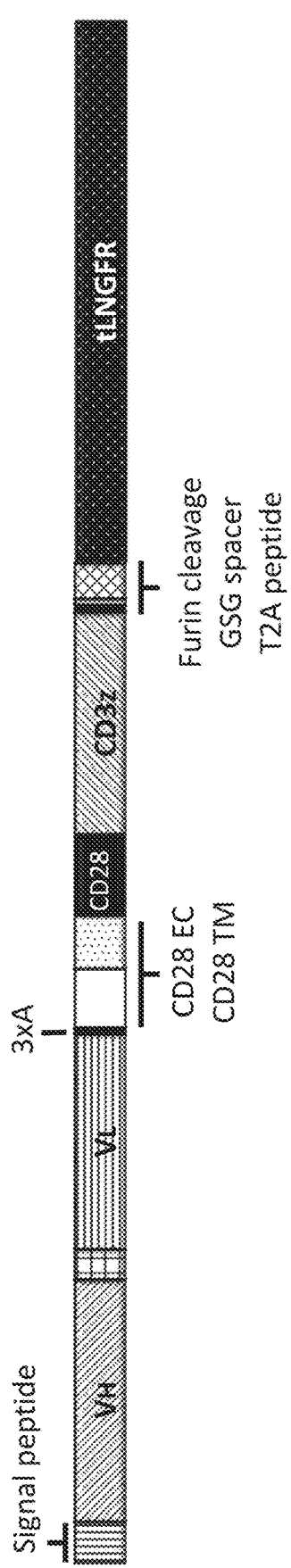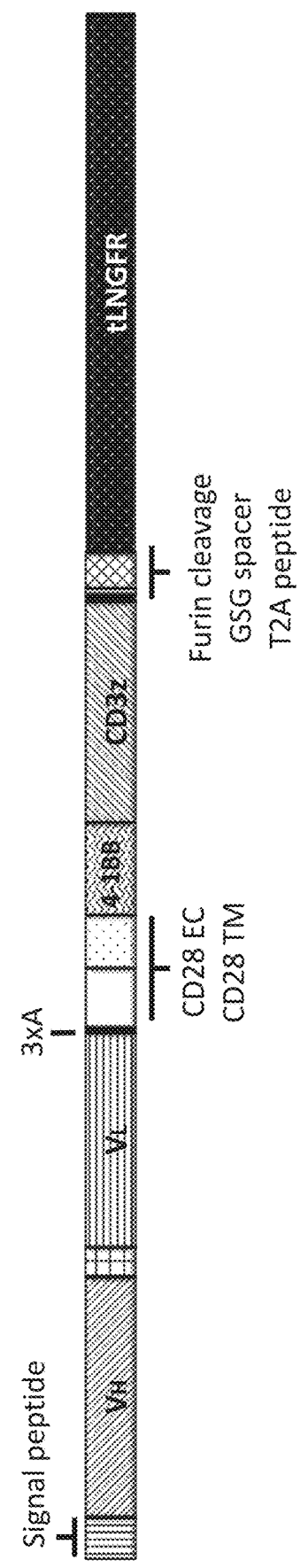
Figure 1A
Figure 1B

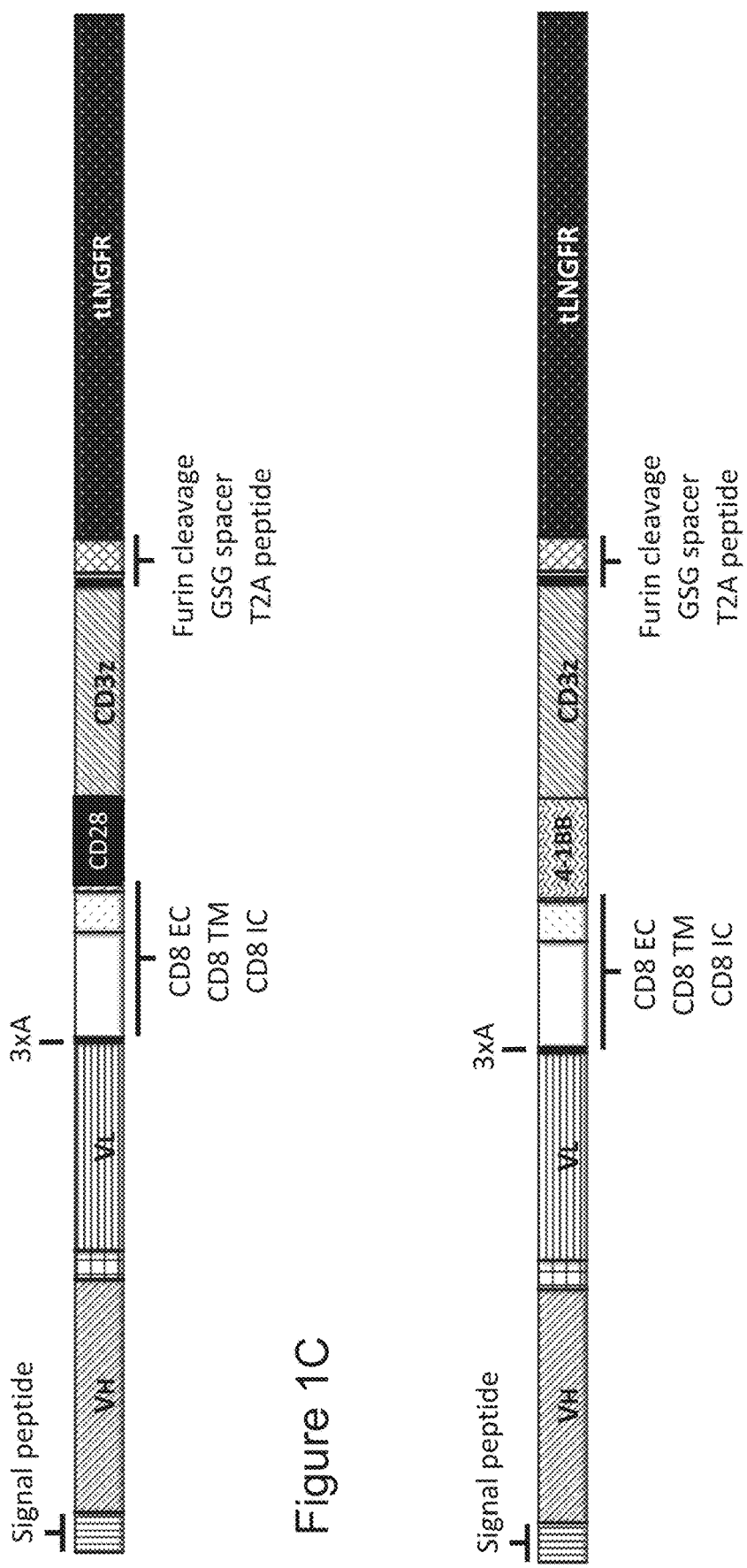

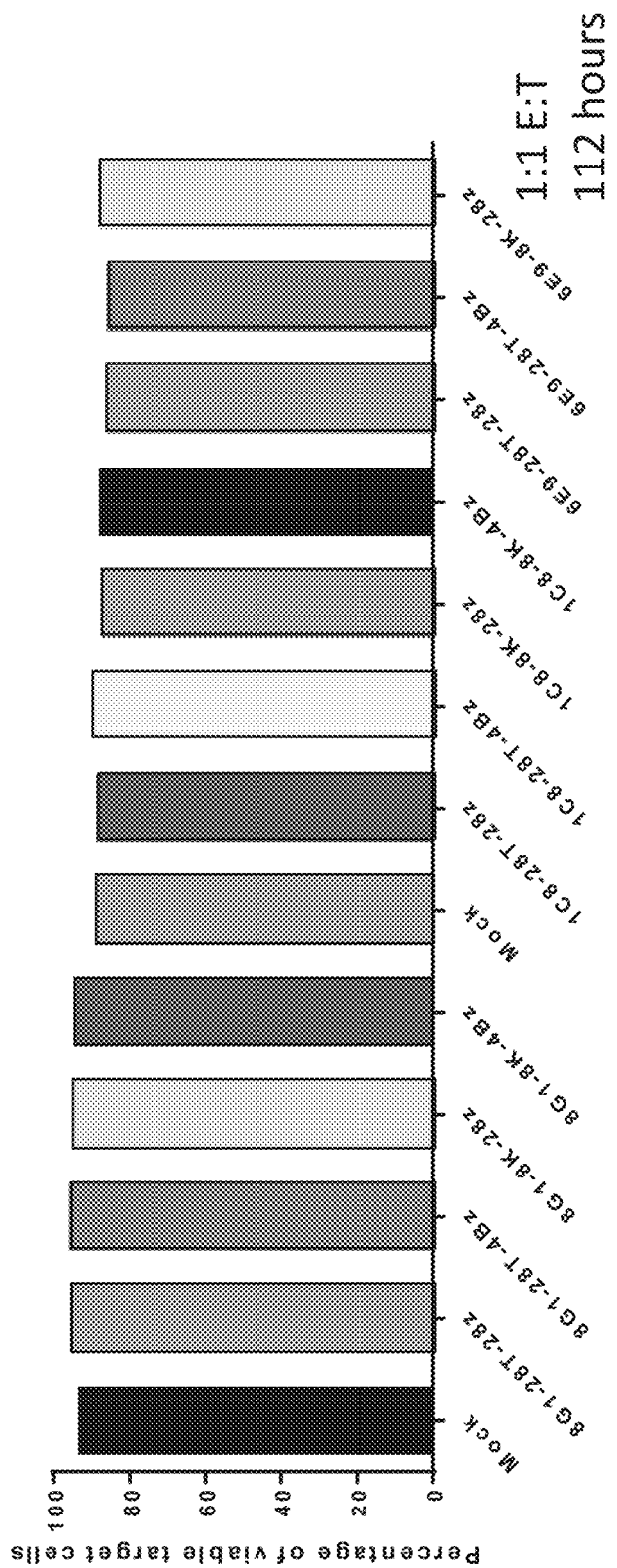

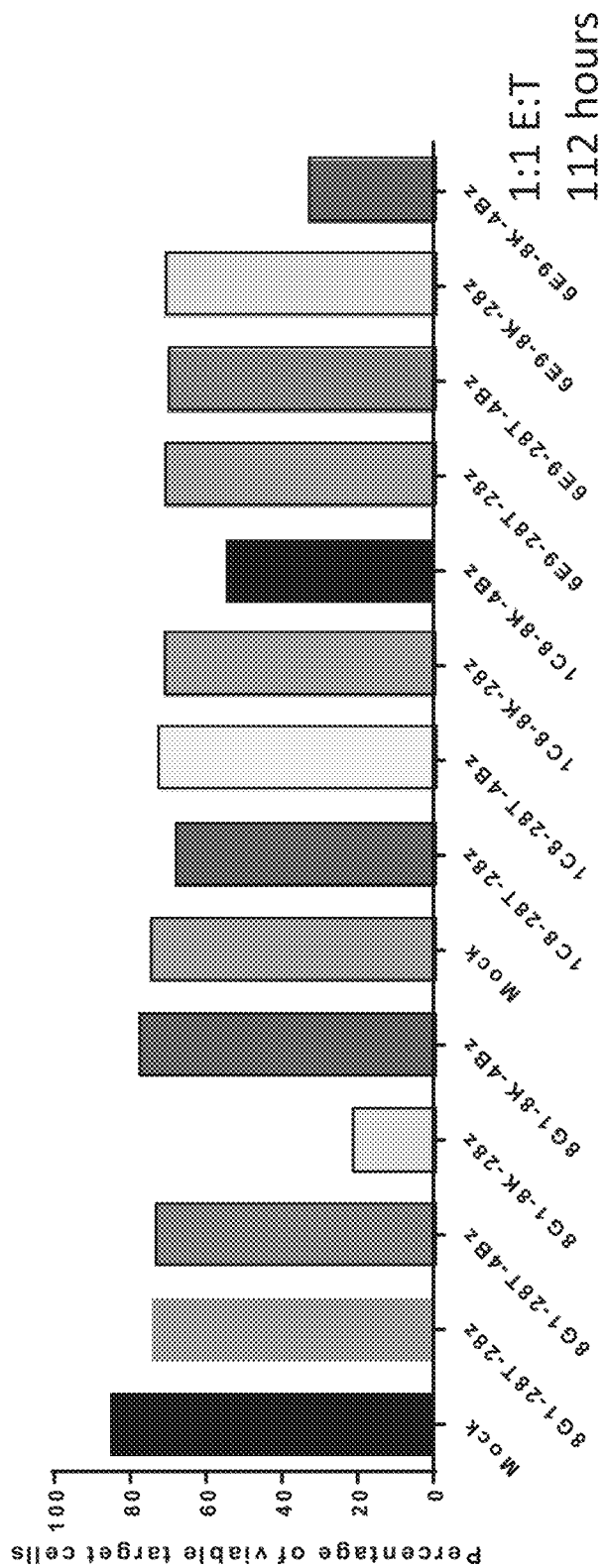

| Sequence | CDR1 | Seq ID | CDR2 | Seq ID | CDR3 | Seq ID |
|---|---|---|---|---|---|---|
| 8G1_VL | RASQSLRRIYLA | 53 | DVFDRAT | 54 | QQYSDSPFT | 55 |
| 1C8_VL | RASQFIGRYFN | 56 | AESSLQS | 57 | QQSYSTPFT | 58 |
| 6E9_VL | SGSSSNIGTNTVN | 59 | INNQRPS | 60 | ATWDDSLNGPVV | 61 |
| 8G1_VH | SYGMH | 62 | VTWYDGSNKYYGDSVKG | 63 | DLLRGVKGYAMDV | 64 |
| 1C8_VH | SGGYYWS | 65 | YIFYSGSTDYNPSLKS | 66 | SGYSYALFDH | 67 |
| 6E9_VH | SYYLH | 68 | IVDPSGGSTSYDQKFQG | 69 | DYGDYVFDY | 70 |

Table 1. CDR Table (Kabat)

| Sequence | CDR1 | Seq ID | CDR2 | Seq ID | CDR3 | Seq ID |
|---|---|---|---|---|---|---|
| 8G1_VL | RASQSLRRIYLA | 53 | DVFDRAT | 54 | QQYSDSPFT | 55 |
| 1C8_VL | RASQFIGRYFN | 56 | AESSLQS | 57 | QQSYSTPFT | 58 |
| 6E9_VL | SGSSSNIGTNTVN | 59 | INNQRPS | 60 | ATWDDSLNGPVV | 61 |
| 8G1_VH | GFTFSSY | 71 | WYDGSN | 72 | DLLRGVKGYAMDV | 64 |
| 1C8_VH | GDSIISGGY | 73 | FYSGS | 74 | SGYSYALFDH | 67 |
| 6E9_VH | GYTFTSY | 75 | DPSGGS | 76 | DYGDYVFDY | 70 |

Table 2. CDR Table (Chothia)

| Sequence | CDR1 | Seq ID | CDR2 | Seq ID | CDR3 | Seq ID |
|---|---|---|---|---|---|---|
| 8G1_VL | RASQSLRRIYLA | 53 | DVFDRAT | 54 | QQYSDSPFT | 55 |
| 1C8_VL | RASQFIGRYFN | 56 | AESSLQS | 57 | QQSYSTPFT | 58 |
| 6E9_VL | SGSSSNIGTNTVN | 59 | INNQRPS | 60 | ATWDDSLNGPVV | 61 |
| 8G1_VH | GFTFSSYGMH | 77 | VTWYDGSNKYYGDSVKG | 63 | DLLRGVKGYAMDV | 64 |
| 1C8_VH | GDSIISGGYYWS | 78 | YIFYSGSTDYNPSLKS | 66 | SGYSYALFDH | 67 |
| 6E9_VH | GYTFTSYYLH | 79 | IVDPSGGSTSYDQKFQG | 69 | DYGDYVFDY | 70 |

Table 3. CDR Table (IMGT)

Figure 6

| SEQ ID NO | Description | Sequence |
|---|---|---|
| 2 | 8G1 VH | CAAGAGCAGCTGGTTGAGTCTGGGGGAGGCGGTCGTCCAACCCGGCCGGAGTCTGAGGTTGTCCTG CGCTGCAAGCGGATTTACATTTCATCTTACGGCATGCACTGGGTTAGGCAGGCTCCTGGAAAAGG GCTGGAGTGGGTCGCGGTGACTGGGTACGACGGCTCCAATAAGTATTATGGGGATTCCGTGAAAG GTCGATTCACAATTAGCAGGGATAACTCCAAAAACACTGTATCTCCAAATGAACTCCTTGAGGGC CGAGGACACGGCCGTCTATTATTGTGCAAGAGACCTCCTCCGGGGCGTAAAGGGATATGCtATGGA CGTGTGGGGTCAGGGACCACAGTTACTGTCAGTTCA |
| 3 | 8G1 VH | QEQLVESGGGVVQPGRSLRLSCAASGFTFSSYGMHWVRQAPGKGLEWVAVTWYDGSNKYYGDSVKG RFTISRDNSKNTLYLQMNSLRAEDTAVYYCARDLLRGVKGYAMDVWGQGTTVTVSS |
| 62 | 8G1 VH CDR1 (Kabat) | SYGMH |
| 63 | 8G1 VH CDR2 (Kabat) | VTWYDGSNKYYGDSVKG |
| 64 | 8G1 VH CDR3 (Kabat) | DLLRGVKGYAMDV |
| 71 | 8G1 VH CDR1 (Chothia) | GFTFSSY |
| 72 | 8G1 VH CDR2 (Chothia) | WYDGSN |
| 64 | 8G1 VH CDR3 (Chothia) | DLLRGVKGYAMDV |
| 77 | 8G1 VH CDR1 (IGMT) | GFTFSSYGMH |
| 63 | 8G1 VH CDR2 (IGMT) | VTWYDGSNKYYGDSVKG |
| 64 | 8G1 VH CDR3 (IGMT) | DLLRGVKGYAMDV |

Figure 7A

| SEQ ID NO | Description | Sequence |
|---|---|---|
| 4 | 8G1 VL | GAAATCGTTCTCACTCAGTCTCCGGGCACACTGTCCCTCAGCCCCGGAGAGAGCGAGCCACTTTGAGCTGCCGGGCCAGCCAGTCACTTAGAGACGCATTATTTGGCTGGTATCAGCAGAAACCAGGCCAGGCGCCCAGGCTGCTGATATACGATGTTCGATAGGGCACCGGGTATCCCCGATAGGTTCTGGCGGGGGGTCCGGGACTGACTTCACCCTCACTATATCAGACTGAGCCCGAAGACTTCGCAGTTTATTATTGCCAGCAGTACTCCGACTCCCCATTCACCTTCGGCCCTGGTACCAAAGTGGATATTAAACGG |
| 5 | 8G1 VL | EIVLTQSPGTLSLSPGERATLSCRASQSLRRIYLAWYQQKPGQAPRLLIYDVFDRATGIPDRFSGGSGTDFTLTISRLEPEDFAVYYCQQYSDSPFTFGPGTKVDIKR |
| 53 | 8G1 VL CDR1 (Kabat) | RASQSLRRIYLA |
| 54 | 8G1 VL CDR2 (Kabat) | DVFDRAT |
| 55 | 8G1 VL CDR3 (Kabat) | QQYSDSPFT |
| 53 | 8G1 VL CDR1 (Chothia) | RASQSLRRIYLA |
| 54 | 8G1 VL CDR2 (Chothia) | DVFDRAT |
| 55 | 8G1 VL CDR3 (Chothia) | QQYSDSPFT |
| 53 | 8G1 VL CDR1 (IGMT) | RASQSLRRIYLA |
| 54 | 8G1 VL CDR2 (IGMT) | DVFDRAT |
| 55 | 8G1 VL CDR3 (IGMT) | QQYSDSPFT |

Figure 7B

| SEQ ID NO | Description | Sequence |
|---|---|---|
| 6 | 1C8 VH | CAGGTGCAGCTCCAAGAATCTGGACCGGGTCTCGTCAAGCCATCACAGACACTGTCCCTGACCTGC ACCGTCTCCGGCGACTCTATCATTTCAGGCGGCTACTATTGGTCCTGGATTAGACAACATCCGGGAA AGGGTCTTGAATGGATCGGCTATATTTCTACAGGGGAGTACGGATTACAATCCTAGTCTCAAGAG CCGCGTTACCATTTCAGTGGATACTTCAAAAAACCAGTTTAGCCTGAAGCTGTCTTCTGTAACAGCTG CTGACACAGCCGTGTACTACTATTGCGCCAGGAGCGGCTACAGTTATGCCCCTGTTTGACCACTGGGGC AAGGCACTCTTGTGACGGTGTCAAGT |
| 7 | 1C8 VH | QVQLQESGPGLVKPSQTLSLTCTVSGDSIISGGYYWSWIRQHPGKGLEWIGYIFYSGSTDYNPSLKSRVTI SVDTSKNQFSLKLSSVTAADTAVYYCARSGYSYALFDHWGQGTLVTVSS |
| 65 | 1C8 VH CDR1 (Kabat) | SGGYYWS |
| 66 | 1C8 VH CDR2 (Kabat) | YIFYSGSTDYNPSLKS |
| 67 | 1C8 VH CDR3 (Kabat) | SGYSYALFDH |
| 73 | 1C8 VH CDR1 (Chothia) | GDSIISGGY |
| 74 | 1C8 VH CDR2 (Chothia) | FYSGS |
| 67 | 1C8 VH CDR3 (Chothia) | SGYSYALFDH |
| 78 | 1C8 VH CDR1 (IGMT) | GDSIISGGYYWS |
| 66 | 1C8 VH CDR2 (IGMT) | YIFYSGSTDYNPSLKS |
| 67 | 1C8 VH CDR3 (IGMT) | SGYSYALFDH |

Figure 7C

| SEQ ID NO | Description | Sequence |
|---|---|---|
| 8 | 1C8 VL | GACATTCAAATGACGCAGTCCCCAAGTTCTCTGTCCGCTAGCGTCGGGCGACCGAGTGACCATCAGCT GCCGAGCATCCAGTTTATCGGTAGATATTCAATTGGTACCAGCAACAACCGGGCAAAGCGCCCA AGGTCCTGATCTACGCTGAGAGCAGTCTGCAATCCGGCGTACTAGCGGGTTCTCCGAAGTGGCA GCGGAACCGAGTTCACCCTGACAATTAGCTCCTTGCAGCCCGAGGATTTCGCTCGCTATTACTGTCA ACAGAGTTATTCAACCCCTTTACATTCGGACAGGGAACTAAAGTTGAAATTAAGAGG |
| 9 | 1C8 VL | DIQMTQSPSSLSASVGDRVTISCRASQFIGRYFNWYQQKPGKAPKVLIYAESSLQSGVPSRFSGSGSGTE FTLTISSLQPEDFARYYCQQSYSTPFTFGQGTKVEIKR |
| 56 | 1C8 VL CDR1 (Kabat) | RASQFIGRYFN |
| 57 | 1C8 VL CDR2 (Kabat) | AESSLQS |
| 58 | 1C8 VL CDR3 (Kabat) | QQSYSTPFT |
| 56 | 1C8 VL CDR1 (Chothia) | RASQFIGRYFN |
| 57 | 1C8 VL CDR2 (Chothia) | AESSLQS |
| 58 | 1C8 VL CDR3 (Chothia) | QQSYSTPFT |
| 56 | 1C8 VL CDR1 (IGMT) | RASQFIGRYFN |
| 57 | 1C8 VL CDR2 (IGMT) | AESSLQS |
| 58 | 1C8 VL CDR3 (IGMT) | QQSYSTPFT |

Figure 7D

| SEQ ID NO | Description | Sequence |
|---|---|---|
| 10 | 6E9 VH | CAGGTACACCTGGTGCAGAGCGGGGGCGGAGGTCAAGAAACCGGGCGCATCCGTACGCGTGAGCTGCAAGGCCTCCGGATACACTTTTACTTCTTACTATCTGCATTGGGTCAGGCACCGGGTCAGGGACTGGAGTGGATGGCATTGTGGACCCAAGCGAGGGAGTACGTCATATGGAAGTTTCAAGGTAGGTTTACCATGACAGGGACGTCAACGAGTCTACGTCTACATGGAGCTCAGTAGTCTGCGGAGCGAAGACACCGCAGTGCTACTACTGCGCACGCGATTATGGAGACTATGTCTTTGACTATTGGGGGCAGGGGACGCTCGTGACCGTTTCAAGC |
| 11 | 6E9 VH | QVHLVQSGAEVKKPGASVRVSCKASGYTFTSYYLHWVRQAPGQGLEWMGIVDPSGGSTSYDQKFQGRFTMTRDTSTSTVVMELSSLRSEDTAVYYCARDYGDYVFDYWGQGTLVTVSS |
| 68 | 6E9 VH CDR1 (Kabat) | SYYLH |
| 69 | 6E9 VH CDR2 (Kabat) | IVDPSGGSTSYDQKFQG |
| 70 | 6E9 VH CDR3 (Kabat) | DYGDYVFDY |
| 75 | 6E9 VH CDR1 (Chothia) | GYTFTSY |
| 76 | 6E9 VH CDR2 (Chothia) | DPSGGS |
| 70 | 6E9 VH CDR3 (Chothia) | DYGDYVFDY |
| 79 | 6E9 VH CDR1 (IGMT) | GYTFTSYYLH |
| 69 | 6E9 VH CDR2 (IGMT) | IVDPSGGSTSYDQKFQG |
| 70 | 6E9 VH CDR3 (IGMT) | DYGDYVFDY |

Figure 7E

| SEQ ID NO | Description | Sequence |
|---|---|---|
| 12 | 6E9 VL | CAAAGGTACTGACACAGCCCCCGAGTGCATCCGGACCCCGGCCAAAGGGTTACAATCAGCTGC TCTGGCAGCTCCAGTAACATAGGTACCAACACGGTGAACTGGTACCAGCAGCTTGCCTGGCACAGCG CCTCAGCTGCTCATCTATATCAACAATCAGCGGCCCTCAAGTGGCGTGCCCGATAGATTCTCAGGTCAA AGAGCGGAACCAGGCTAGCTTGGCAATCAGTGGCCTTCAATCCGAAGACGAAGCCGATTACTATT GTGCGACCTGGGACGATAGCCTGAACGGCCCGTCGTGGGGGACGAAACTGACAGTGTTG GGC |
| 13 | 6E9 VL | QSVLTQPPSASGTPGQRVTISCSGSSSNIGTNTVNWYQQLPGTAPQLLIYINNQRPSGVPDRFSGSKSGT SASLAISGLQSEDEADYYCATWDDSLNGPVVGGGTKLTVLG |
| 59 | 6E9 VL CDR1 (Kabat) | SGSSSNIGTNTVN |
| 60 | 6E9 VL CDR2 (Kabat) | INNQRPS |
| 61 | 6E9 VL CDR3 (Kabat) | ATWDDSLNGPVV |
| 59 | 6E9 VL CDR1 (Chothia) | SGSSSNIGTNTVN |
| 60 | 6E9 VL CDR2 (Chothia) | INNQRPS |
| 61 | 6E9 VL CDR3 (Chothia) | ATWDDSLNGPVV |
| 59 | 6E9 VL CDR1 (IGMT) | SGSSSNIGTNTVN |
| 60 | 6E9 VL CDR2 (IGMT) | INNQRPS |
| 61 | 6E9 VL CDR3 (IGMT) | ATWDDSLNGPVV |

Figure 7F

8G1.1_C28T_28z Coding Sequence

ATGGCACTCCCCGTAACTGCTCTGCTGCTGCCGTTGGCATTGCTCCTGCACGCCGCACGCCCGCAAGAGCAGCTGG
TTGAGTCTGGGGGCGGCGTCGTCCAACCCGGCCGGAGTCTGAGGTTGTCCTGCGCTGCAAGCGGATTTACATTTT
CATCTTACGGCATGCACTGGGTTAGGCAGGCTCCTGGAAAAGGGCTGGAGTGGGTCGCGGTGACTTGGTACGAC
GGCTCCAATAAGTATTATGGGGATTCCGTGAAAGGTCGATTCACAATTAGCAGGGATAACTCCAAAAACACACTG
TATCTCCAAATGAACTCCTTGAGGGCCGAGGACACGGCCGTCTATTATTGTGCAAGAGACCTCCTCCGGGGCGTA
AAGGGATATGCtATGGACGTGTGGGGTCAGGGGACCACAGTTACTGTCAGTTCAGGTGGCGGTGGCAGTGGCGG
CGGGGGAAGTGGAGGCGGGGGCTCTGAAATCGTTCTCACTCAGTCTCCGGGCACACTGTCCCTCAGCCCCGGAG
AGCGAGCCACTTTGAGCTGCCGGGCCAGCCAGTCACTTAGACGCATTTATTTGGCCTGGTATCAGCAGAAACCAG
GCCAGGCGCCCAGGCTGCTGATATACGATGTGTTCGATAGGGCCACGGGTATCCCCGATAGGTTCTCTGGCGGGG
GGTCCGGGACTGACTTCACCCTCACTATATCACGACTCGAGCCCGAAGACTTCGCAGTTTATTATTGCCAGCAGTA
CTCCGACTCCCCATTCACCTTCGGCCCTGGTACCAAAGTGGATATTAAACGGGCCGCTGCCCTTGATAATGAAAAG
TCAAACGGAACAATCATTCACGTGAAGGGCAAGCACCTCTGTCCGTCACCCTTGTTCCCTGGTCCATCCAAGCCATT
CTGGGTGTTGGTCGTAGTGGGTGGAGTCCTCGCTTGTTACTCTGCTCGTCACCGTGGCTTTTATAATCTTCTGGG
TTAGATCCAAAAGAAGCCGCCTGCTCCATAGCGATTACATGAATATGACTCCACGCCGCCCTGGCCCCACAAGGAA
ACACTACCAGCCTTACGCACCACCTAGAGATTTCGCTGCCTATCGGAGCAGGGTGAAGTTTTCCAGATCTGCAGAT
GCACCAGCGTATCAGCAGGGCCAGAACCAACTGTATAACGAGCTCAACCTGGGACGCAGGGAAGAGTATGACGT
TTTGGACAAGCGCAGAGGACGGGACCCTGAGATGGGTGGCAAACCAAGACGAAAAAACCCCCAGGAGGGTCTCT
ATAATGAGCTGCAGAAGGATAAGATGGCTGAAGCCTATTCTGAAATAGGCATGAAAGGAGAGCGGAGAAGGGG
AAAAGGGCACGACGGTTTGTACCAGGGACTCAGCACTGCTACGAAGGATACTTATGACGCTCTCCACATGCAAGC
CCTGCCACCTAGG (Seq. ID No. 29)

8G1.1_C28T_28z Amino Acid Sequence

MALPVTALLLPLALLLHAARPQEQLVESGGGVVQPGRSLRLSCAASGFTFSSYGMHWVRQAPGKGLEWVAVTWYDG
SNKYYGDSVKGRFTISRDNSKNTLYLQMNSLRAEDTAVYYCARDLLRGVKGYAMDVWGQGTTVTVSSGGGGSGGGG
SGGGGSEIVLTQSPGTLSLSPGERATLSCRASQSLRRIYLAWYQQKPGQAPRLLIYDVFDRATGIPDRFSGGGSGTDFTLT
ISRLEPEDFAVYYCQQYSDSPFTFGPGTKVDIKRAAALDNEKSNGTIIHVKGKHLCPSPLFPGPSKPFWVLVVVGGVLACY
SLLVTVAFIIFWVRSKRSRLLHSDYMNMTPRRPGPTRKHYQPYAPPRDFAAYRSRVKFSRSADAPAYQQGQNQLYNEL
NLGRREEYDVLDKRRGRDPEMGGKPRRKNPQEGLYNELQKDKMAEAYSEIGMKGERRRGKGHDGLYQGLSTATKDT
YDALHMQALPPR (Seq. ID No. 30)

Figure 8A

8G1.1_C28T_4Bz Coding Sequence

TGGCACTCCCCGTAACTGCTCTGCTGCTGCCGTTGGCATTGCTCCTGCACGCCGCACGCCCGCAAGAGCAGCTGGT
TGAGTCTGGGGGCGGCGTCGTCCAACCCGGCCGGAGTCTGAGGTTGTCCTGCGCTGCAAGCGGATTTACATTTTC
ATCTTACGGCATGCACTGGGTTAGGCAGGCTCCTGGAAAAGGGCTGGAGTGGGTCGCGGTGACTTGGTACGACG
GCTCCAATAAGTATTATGGGGATTCCGTGAAAGGTCGATTCACAATTAGCAGGGATAACTCCAAAAACACACTGT
ATCTCCAAATGAACTCCTTGAGGGCCGAGGACACGGCCGTCTATTATTGTGCAAGAGACCTCCTCCGGGGCGTAA
AGGGATATGCtATGGACGTGTGGGGTCAGGGGACCACAGTTACTGTCAGTTCAGGTGGCGGTGGCAGTGGCGGC
GGGGGAAGTGGAGGCGGGGGCTCTGAAATCGTTCTCACTCAGTCTCCGGGCACACTGTCCCTCAGCCCCGGAGA
GCGAGCCACTTTGAGCTGCCGGGCCAGCCAGTCACTTAGACGCATTTATTTGGCCTGGTATCAGCAGAAACCAGG
CCAGGCGCCCAGGCTGCTGATATACGATGTGTTCGATAGGGCCACGGGTATCCCCGATAGGTTCTCTGGCGGGGG
GTCCGGGACTGACTTCACCCTCACTATATCACGACTCGAGCCCGAAGACTTCGCAGTTTATTATTGCCAGCAGTACT
CCGACTCCCCATTCACCTTCGGCCCTGGTACCAAAGTGGATATTAAACGGGCCGCTGCCCTTGATAATGAAAGTC
AAACGGAACAATCATTCACGTGAAGGGCAAGCACCTCTGTCCGTCACCCTTGTTCCCTGGTCCATCCAAGCCATTCT
GGGTGTTGGTCGTAGTGGGTGGAGTCCTCGCTTGTTACTCTCTGCTCGTCACCGTGGCTTTTATAATCTTCTGGGTT
CGCTTTTCCGTCGTTAAGCGGGGGAGAAAAAAGCTGCTGTACATTTTCAAACAGCCGTTTATGAGGCCGGTCCAA
ACGACTCAGGAAGAAGACGGCTGCTCCTGCCGCTTTCCTGAGGAGGAGGAGGGCGGGTGCGAACTGAGGGTGA
AGTTTTCCAGATCTGCAGATGCACCAGCGTATCAGCAGGGCCAGAACCAACTGTATAACGAGCTCAACCTGGGAC
GCAGGGAAGAGTATGACGTTTTGGACAAGCGCAGAGGACGGGACCCTGAGATGGGTGGCAAACCAAGACGAAA
AAACCCCCAGGAGGGTCTCTATAATGAGCTGCAGAAGGATAAGATGGCTGAAGCCTATTCTGAAATAGGCATGAA
AGGAGAGCGGAGAAGGGGAAAAGGGCACGACGGTTTGTACCAGGGACTCAGCACTGCTACGAAGGATACTTAT
GACGCTCTCCACATGCAAGCCCTGCCACCTAGG (Seq. ID No. 31)

8G1.1_C28T_4Bz Amino Acid Sequence

MALPVTALLLPLALLLHAARPQEQLVESGGGVVQPGRSLRLSCAASGFTFSSYGMHWVRQAPGKGLEWVAVTWYDG
SNKYYGDSVKGRFTISRDNSKNTLYLQMNSLRAEDTAVYYCARDLLRGVKGYAMDVWGQGTTVTVSSGGGGSGGGG
SGGGGSEIVLTQSPGTLSLSPGERATLSCRASQSLRRIYLAWYQQKPGQAPRLLIYDVFDRATGIPDRFSGGGSGTDFTLT
ISRLEPEDFAVYYCQQYSDSPFTFGPGTKVDIKRAAALDNEKSNGTIIHVKGKHLCPSPLFPGPSKPFWVLVVVGGVLACY
SLLVTVAFIIFWVRFSVVKRGRKKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEIGMKGERRRGKGHDGLYQGLST
ATKDTYDALHMQALPPR (Seq ID No. 32)

Figure 8B

8G1.1_C8K_28z Coding Sequence

ATGGCACTCCCCGTAACTGCTCTGCTGCTGCCGTTGGCATTGCTCCTGCACGCCGCACGCCCGCAAGAGCAGCTGG
TTGAGTCTGGGGGCGGCGTCGTCCAACCCGGCCGGAGTCTGAGGTTGTCCTGCGCTGCAAGCGGATTTACATTTT
CATCTTACGGCATGCACTGGGTTAGGCAGGCTCCTGGAAAAGGGCTGGAGTGGGTCGCGGTGACTTGGTACGAC
GGCTCCAATAAGTATTATGGGGATTCCGTGAAAGGTCGATTCACAATTAGCAGGGATAACTCCAAAAACACACTG
TATCTCCAAATGAACTCCTTGAGGGCCGAGGACACGGCCGTCTATTATTGTGCAAGAGACCTCCTCCGGGGCGTA
AAGGGATATGCtATGGACGTGTGGGGTCAGGGGACCACAGTTACTGTCAGTTCAGGTGGCGGTGGCAGTGGCGG
CGGGGGAAGTGGAGGCGGGGGCTCTGAAATCGTTCTCACTCAGTCTCCGGGCACACTGTCCCTCAGCCCCGGAG
AGCGAGCCACTTTGAGCTGCCGGGCCAGCCAGTCACTTAGACGCATTTATTTGGCCTGGTATCAGCAGAAACCAG
GCCAGGCGCCCAGGCTGCTGATATACGATGTGTTCGATAGGGCCACGGGTATCCCCGATAGGTTCTCTGGCGGGG
GGTCCGGGACTGACTTCACCCTCACTATATCACGACTCGAGCCCGAAGACTTCGCAGTTTATTATTGCCAGCAGTA
CTCCGACTCCCCATTCACCTTCGGCCCTGGTACCAAAGTGGATATTAAACGGGCCGCTGCCTTCGTGCCTGTTTTC
TGCCCGCGAAACCCACAACTACCCCGCCCCTCGGCCCCAACTCCTGCACCAACTATCGCTTCCCAACCCCTGTCT
CTGAGACCTGAGGCATGCCGCCCCGCGGCAGGCGGCGCCGTGCACACTAGAGGCCTGGACTTCGCCTGCGATATT
TATATCTGGGCCCCCCTTGCCGGGACATGCGGGGTACTGCTGCTGTCTCTGGTGATTACCCTCTACTGCAACCACA
GAAACAGATCCAAAAGAAGCCGCCTGCTCCATAGCGATTACATGAATATGACTCCACGCCGCCCTGGCCCCACAA
GGAAACACTACCAGCCTTACGCACCACCTAGAGATTTCGCTGCCTATCGGAGCAGGGTGAAGTTTTCCAGATCTGC
AGATGCACCAGCGTATCAGCAGGGCCAGAACCAACTGTATAACGAGCTCAACCTGGGACGCAGGGAAGAGTATG
ACGTTTTGGACAAGCGCAGAGGACGGGACCCTGAGATGGGTGGCAAACCAAGACGAAAAAACCCCCAGGAGGG
TCTCTATAATGAGCTGCAGAAGGATAAGATGGCTGAAGCCTATTCTGAAATAGGCATGAAAGGAGAGCGGAGAA
GGGGAAAAGGGCACGACGGTTTGTACCAGGGACTCAGCACTGCTACGAAGGATACTTATGACGCTCTCCACATGC
AAGCCCTGCCACCTAGG (Seq. ID No. 33)

8G1.1_C8K_28z Amino Acid Sequence

MALPVTALLLPLALLLHAARPQEQLVESGGGVVQPGRSLRLSCAASGFTFSSYGMHWVRQAPGKGLEWVAVTWYDG
SNKYYGDSVKGRFTISRDNSKNTLYLQMNSLRAEDTAVYYCARDLLRGVKGYAMDVWGQGTTVTVSSGGGGSGGGG
SGGGGSEIVLTQSPGTLSLSPGERATLSCRASQSLRRIYLAWYQQKPGQAPRLLIYDVFDRATGIPDRFSGGGSGTDFTLT
ISRLEPEDFAVYYCQQYSDSPFTFGPGTKVDIKRAAAFVPVFLPAKPTTTPAPRPPTPAPTIASQPLSLRPEACRPAAGGA
VHTRGLDFACDIYIWAPLAGTCGVLLLSLVITLYCNHRNRSKRSRLLHSDYMNMTPRRPGPTRKHYQPYAPPRDFAAYR
SRVKFSRSADAPAYQQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR (Seq. ID No. 34)

Figure 8C

8G1.1_C8K_4Bz Coding Sequence

GTTCTCACTCAGTCTCCGGGCACACTGTCCCTCAGCCCCGGAGAGCGAGCCACTTTGAGCTGCCGGGCCAGCCAGT
CACTTAGACGCATTTATTTGGCCTGGTATCAGCAGAAACCAGGCCAGGCGCCCAGGCTGCTGATATACGATGTGTT
CGATAGGGCCACGGGTATCCCCGATAGGTTCTCTGGCGGGGGGTCCGGGACTGACTTCACCCTCACTATATCACG
ACTCGAGCCCGAAGACTTCGCAGTTTATTATTGCCAGCAGTACTCCGACTCCCCATTCACCTTCGGCCCTGGTACCA
AAGTGGATATTAAACGGGCCGCTGCCTTCGTGCCTGTTTTTCTGCCCGCGAAACCCACAACTACCCCCGCCCCTCG
GCCCCCAACTCCTGCACCAACTATCGCTTCCCAACCCCTGTCTCTGAGACCTGAGGCATGCCGCCCCGCGGCAGGC
GGCGCCGTGCACACTAGAGGCCTGGACTTCGCCTGCGATATTTATATCTGGGCCCCCCTTGCCGGGACATGCGGG
GTACTGCTGCTGTCTCTGGTGATTACCCTCTACTGCAACCACAGAAACCGCTTTTCCGTCGTTAAGCGGGGGAGAA
AAAAGCTGCTGTACATTTTCAAACAGCCGTTTATGAGGCCGGTCCAAACGACTCAGGAAGAAGACGGCTGCTCCT
GCCGCTTTCCTGAGGAGGAGGAGGGCGGGTGCGAACTGAGGGTGAAGTTTTCCAGATCTGCAGATGCACCAGCG
TATCAGCAGGGCCAGAACCAACTGTATAACGAGCTCAACCTGGGACGCAGGGAAGAGTATGACGTTTTGGACAA
GCGCAGAGGACGGGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAAGGGGAAAAGGGC
ACGACGGTTTGTACCAGGGACTCAGCACTGCTACGAAGGATACTTATGACGCTCTCCACATGCAAGCCCTGCCACC
TAGG (Seq ID No. 35)

8G1.1_C8K_4Bz Amino Acid Sequence

MALPVTALLLPLALLLHAARPQEQLVESGGGVVQPGRSLRLSCAASGFTFSSYGMHWVRQAPGKGLEWVAVTWYDG
SNKYYGDSVKGRFTISRDNSKNTLYLQMNSLRAEDTAVYYCARDLLRGVKGYAMDVWGQGTTVTVSSGGGGSGGGG
SGGGGSEIVLTQSPGTLSLSPGERATLSCRASQSLRRIYLAWYQQKPGQAPRLLIYDVFDRATGIPDRFSGGGSGTDFTLT
ISRLEPEDFAVYYCQQYSDSPFTFGPGTKVDIKRAAAFVPVFLPAKPTTTPAPRPPTPAPTIASQPLSLRPEACRPAAGGA
VHTRGLDFACDIYIWAPLAGTCGVLLLSLVITLYCNHRNRFSVVKRGRKKLLYIFKQPFMRPVQTTQEEDGCSCRFPEEEE
GGCELRVKFSRSADAPAYQQGQNQLYNELNLGRREEYDVLDKRRGRDPEMGGKPRRKNPQEGLYNELQKDKMAEAY
SEIGMKGERRRGKGHDGLYQGLSTATKDTYDALHMQALPPR (Seq. ID No. 36)

Figure 8D

1C8.1.001_C28T_28z Coding Sequence

ATGGCACTCCCCGTAACTGCTCTGCTGCTGCCGTTGGCATTGCTCCTGCACGCCGCACGCCCGCAGGTGCAGCTCC
AAGAATCTGGACCGGGTCTCGTCAAGCCATCACAGACACTGTCCCTGACCTGCACCGTCTCCGGCGACTCTATCAT
TTCAGGCGGCTACTATTGGTCCTGGATTAGACAACATCCGGGAAAGGGTCTTGAATGGATCGGCTATATTTTCTAC
AGCGGGAGTACGGATTACAATCCTAGTCTCAAGAGCCGCGTTACCATTTCAGTGGATACTTCAAAAAACCAGTTTA
GCCTGAAGCTGTCTTCTGTAACAGCTGCTGACACAGCCGTGTACTATTGCGCCAGGAGCGGCTACAGCTATGCCCT
GTTTGACCACTGGGGCAAGGCACTCTTGTGACGGTGTCAAGTGGAGGGGAGGATCAGGCGGCGGGGGATCC
GGCGGCGGGGGTAGTGACATTCAAATGACGCAGTCCCCAAGTTCTCTGTCCGCTAGCGTCGGCGACCGAGTGACC
ATCAGCTGCCGAGCATCCCAGTTTATCGGTAGATATTTCAATTGGTACCAGCAACAACCGGGCAAAGCGCCCAAG
GTCCTGATCTACGCTGAGAGCAGTCTGCAATCCGGCGTACCTAGCAGGTTCTCCGGAAGTGGCAGCGGAACCGAG
TTCACCCTGACAATTAGCTCCTTGCAGCCCGAGGATTTCGCTCGCTATTACTGTCAACAGAGTTATTCAACCCCTTTT
ACATTCGGACAGGGAACTAAAGTTGAAATTAAGAGGGCCGCTGCCCTTGATAATGAAAAGTCAAACGGAACAATC
ATTCACGTGAAGGGCAAGCACCTCTGTCCGTCACCCTTGTTCCCTGGTCCATCCAAGCCATTCTGGGTGTTGGTCGT
AGTGGGTGGAGTCCTCGCTTGTTACTCTCTGCTCGTCACCGTGGCTTTTATAATCTTCTGGGTTAGATCCAAAAGAA
GCCGCCTGCTCCATAGCGATTACATGAATATGACTCCACGCCGCCCTGGCCCCACAAGGAAACACTACCAGCCTTA
CGCACCACCTAGAGATTTCGCTGCCTATCGGAGCAGGGTGAAGTTTTCCAGATCTGCAGATGCACCAGCGTATCA
GCAGGGCCAGAACCAACTGTATAACGAGCTCAACCTGGGACGCAGGGAAGAGTATGACGTTTTGGACAAGCGCA
GAGGACGGGACCCTGAGATGGGTGGCAAACCAAGACGAAAAAACCCCAGGAGGGTCTCTATAATGAGCTGCAG
AAGGATAAGATGGCTGAAGCCTATTCTGAAATAGGCATGAAAGGAGAGCGGAGAAGGGGAAAAGGGCACGACG
GTTTGTACCAGGGACTCAGCACTGCTACGAAGGATACTTATGACGCTCTCCACATGCAAGCCCTGCCACCTAGG
(Seq. ID No. 37)

1C8.1.001_C28T_28z Amino Acid Sequence

MALPVTALLLPLALLLHAARPQVQLQESGPGLVKPSQTLSLTCTVSGDSIISGGYYWSWIRQHPGKGLEWIGYIFYSGST
DYNPSLKSRVTISVDTSKNQFSLKLSSVTAADTAVYYCARSGYSYALFDHWGQGTLVTVSSGGGGSGGGGSGGGGSDI
QMTQSPSSLSASVGDRVTISCRASQFIGRYFNWYQQQPGKAPKVLIYAESSLQSGVPSRFSGSGSGTEFTLTISSLQPEDF
ARYYCQQSYSTPFTFGQGTKVEIKRAAALDNEKSNGTIIHVKGKHLCPSPLFPGPSKPFWVLVVVGGVLACYSLLVTVAFI
IFWVRSKRSRLLHSDYMNMTPRRPGPTRKHYQPYAPPRDFAAYRSVKFSRSADAPAYQQGQNQLYNELNLGRREEY
DVLDKRRGRDPEMGGKPRRKNPQEGLYNELQKDKMAEAYSEIGMKGERRRGKGHDGLYQGLSTATKDTYDALHMQ
ALPPR (Seq. ID No. 38)

Figure 8E

1C8.1.001_C28T_4Bz Coding Sequence

ATGGCACTCCCCGTAACTGCTCTGCTGCTGCCGTTGGCATTGCTCCTGCACGCCGCACGCCCGCAGGTGCAGCTCC
AAGAATCTGGACCGGGTCTCGTCAAGCCATCACAGACACTGTCCCTGACCTGCACCGTCTCCGGCGACTCTATCAT
TTCAGGCGGCTACTATTGGTCCTGGATTAGACAACATCCGGGAAAGGGTCTTGAATGGATCGGCTATATTTTCTAC
AGCGGGAGTACGGATTACAATCCTAGTCTCAAGAGCCGCGTTACCATTTCAGTGGATACTTCAAAAAACCAGTTTA
GCCTGAAGCTGTCTTCTGTAACAGCTGCTGACACAGCCGTGTACTATTGCGCCAGGAGCGGCTACAGCTATGCCCT
GTTTGACCACTGGGGCAAGGCACTCTTGTGACGGTGTCAAGTGGAGGGGGAGGATCAGGCGGCGGGGGATCC
GGCGGCGGGGGTAGTGACATTCAAATGACGCAGTCCCCAAGTTCTCTGTCCGCTAGCGTCGGCGACCGAGTGACC
ATCAGCTGCCGAGCATCCCAGTTTATCGGTAGATATTTCAATTGGTACCAGCAACAACCGGGCAAAGCGCCCAAG
GTCCTGATCTACGCTGAGAGCAGTCTGCAATCCGGCGTACCTAGCAGGTTCTCCGGAAGTGGCAGCGGAACCGAG
TTCACCCTGACAATTAGCTCCTTGCAGCCCGAGGATTTCGCTCGCTATTACTGTCAACAGAGTTATTCAACCCCTTTT
ACATTCGGACAGGGAACTAAAGTTGAAATTAAGAGGGCCGCTGCCCTTGATAATGAAAAGTCAAACGGAACAATC
ATTCACGTGAAGGGCAAGCACCTCTGTCCGTCACCCTTGTTCCCTGGTCCATCCAAGCCATTCTGGGTGTTGGTCGT
AGTGGGTGGAGTCCTCGCTTGTTACTCTCTGCTCGTCACCGTGGCTTTTATAATCTTCTGGGTTCGCTTTTCCGTCGT
TAAGCGGGGAGAAAAAAGCTGCTGTACATTTTCAAACAGCCGTTTATGAGGCCGGTCCAAACGACTCAGGAAG
AAGACGGCTGCTCCTGCCGCTTTCCTGAGGAGGAGGAGGGCGGGTGCGAACTGAGGGTGAAGTTTTCCAGATCT
GCAGATGCACCAGCGTATCAGCAGGGCCAGAACCAACTGTATAACGAGCTCAACCTGGGACGCAGGGAAGAGTA
TGACGTTTTGGACAAGCGCAGAGGACGGGACCCTGAGATGGGTGGCAAACCAAGACGAAAAAACCCCCAGGAG
GGTCTCTATAATGAGCTGCAGAAGGATAAGATGGCTGAAGCCTATTCTGAAATAGGCATGAAAGGAGAGCGGAG
AAGGGGAAAAGGGCACGACGGTTTGTACCAGGGACTCAGCACTGCTACGAAGGATACTTATGACGCTCTCCACAT
GCAAGCCCTGCCACCTAGG (Seq. ID 39)

1C8.1.001_C28T_4Bz Amino Acid Sequence

MALPVTALLLPLALLLHAARPQVQLQESGPGLVKPSQTLSLTCTVSGDSIISGGYYWSWIRQHPGKGLEWIGYIFYSGST
DYNPSLKSRVTISVDTSKNQFSLKLSSVTAADTAVYYCARSGYSYALFDHWGQGTLVTVSGGGGSGGGGSGGGGSDI
QMTQSPSSLSASVGDRVTISCRASQFIGRYFNWYQQQPGKAPKVLIYAESSLQSGVPSRFSGSGSGTEFTLTISSLQPEDF
ARYYCQQSYSTPFTFGQGTKVEIKRAAALDNEKSNGTIIHVKGKHLCPSPLFPGPSKPFWVLVVVGGVLACYSLLVTVAFI
IFWVRFSVVKRGRKKLLYIFKQPFMRPVQTTQEEDGCSCRFPEEEEGGCELRVKFSRSADAPAYQQGQNQLYNELNLG
RREEYDVLDKRRGRDPEMGGKPRRKNPQEGLYNELQKDKMAEAYSEIGMKGERRRGKGHDGLYQGLSTATKDTYDA
LHMQALPPR (Seq. ID 40)

Figure 8F

1C8.1.001_C8K_28z Coding Sequence

ATGGCACTCCCCGTAACTGCTCTGCTGCTGCCGTTGGCATTGCTCCTGCACGCCGCACGCCCGCAGGTGCAGCTCC
AAGAATCTGGACCGGGTCTCGTCAAGCCATCACAGACACTGTCCCTGACCTGCACCGTCTCCGGCGACTCTATCAT
TTCAGGCGGCTACTATTGGTCCTGGATTAGACAACATCCGGGAAAGGGTCTTGAATGGATCGGCTATATTTTCTAC
AGCGGGAGTACGGATTACAATCCTAGTCTCAAGAGCCGCGTTACCATTTCAGTGGATACTTCAAAAAACCAGTTTA
GCCTGAAGCTGTCTTCTGTAACAGCTGCTGACACAGCCGTGTACTATTGCGCCAGGAGCGGCTACAGCTATGCCCT
GTTTGACCACTGGGGGCAAGGCACTCTTGTGACGGTGTCAAGTGGAGGGGGAGGATCAGGCGGCGGGGGATCC
GGCGGCGGGGGTAGTGACATTCAAATGACGCAGTCCCCAAGTTCTCTGTCCGCTAGCGTCGGCGACCGAGTGACC
ATCAGCTGCCGAGCATCCCAGTTTATCGGTAGATATTTCAATTGGTACCAGCAACAACCGGGCAAAGCGCCCAAG
GTCCTGATCTACGCTGAGAGCAGTCTGCAATCCGGCGTACCTAGCAGGTTCTCCGGAAGTGGCAGCGGAACCGAG
TTCACCCTGACAATTAGCTCCTTGCAGCCCGAGGATTTCGCTCGCTATTACTGTCAACAGAGTTATTCAACCCCTTTT
ACATTCGGACAGGGAACTAAAGTTGAAATTAAGAGGGCCGCTGCCTTCGTGCCTGTTTTTCTGCCCGCGAAACCCA
CAACTACCCCCGCCCCTCGGCCCCCAACTCCTGCACCAACTATCGCTTCCCAACCCCTGTCTCTGAGACCTGAGGCA
TGCCGCCCCGCGGCAGGCGGCGCCGTGCACACTAGAGGCCTGGACTTCGCCTGCGATATTTATATCTGGGCCCCC
CTTGCCGGGACATGCGGGGTACTGCTGCTGTCTCTGGTGATTACCCTCTACTGCAACCACAGAAACAGATCCAAAA
GAAGCCGCCTGCTCCATAGCGATTACATGAATATGACTCCACGCCGCCCTGGCCCCACAAGGAAACACTACCAGCC
TTACGCACCACCTAGAGATTTCGCTGCCTATCGGAGCAGGGTGAAGTTTTCCAGATCTGCAGATGCACCAGCGTAT
CAGCAGGGCCAGAACCAACTGTATAACGAGCTCAACCTGGGACGCAGGGAAGAGTATGACGTTTTGGACAAGCG
CAGAGGACGGGACCCTGAGATGGGTGGCAAACCAAGACGAAAAAACCCCAGGAGGGTCTCTATAATGAGCTGC
AGAAGGATAAGATGGCTGAAGCCTATTCTGAAATAGGCATGAAAGGAGAGCGGAGAAGGGGAAAAGGGCACGA
CGGTTTGTACCAGGGACTCAGCACTGCTACGAAGGATACTTATGACGCTCTCCACATGCAAGCCCTGCCACCTAGG (Seq. ID 41)

1C8.1.001_C8K_28z Amino Acid Sequence

MALPVTALLLPLALLLHAARPQVQLQESGPGLVKPSQTLSLTCTVSGDSIISGGYYWSWIRQHPGKGLEWIGYIFYSGST
DYNPSLKSRVTISVDTSKNQFSLKLSSVTAADTAVYYCARSGYSYALFDHWGQGTLVTVSSGGGGSGGGGSGGGGSDI
QMTQSPSSLSASVGDRVTISCRASQFIGRYFNWYQQQPGKAPKVLIYAESSLQSGVPSRFSGSGSGTEFTLTISSLQPEDF
ARYYCQQSYSTPFTFGQGTKVEIKRAAAFVPVFLPAKPTTTPAPRPPTPAPTIASQPLSLRPEACRPAAGGAVHTRGLDF
ACDIYIWAPLAGTCGVLLLSLVITLYCNHRNRSKRSRLLHSDYMNMTPRRPGPTRKHYQPYAPPRDFAAYRSRVKFSRSA
DAPAYQQGQNQLYNELNLGRREEYDVLDKRRGRDPEMGGKPRRKNPQEGLYNELQKDKMAEAYSEIGMKGERRRG
KGHDGLYQGLSTATKDTYDALHMQALPPR (Seq. ID 42)

Figure 8G

1C8.1.001_C8K_4Bz Coding Sequence

ATGGCACTCCCCGTAACTGCTCTGCTGCTGCCGTTGGCATTGCTCCTGCACGCCGCACGCCCGCAGGTGCAGCTCC
AAGAATCTGGACCGGGTCTCGTCAAGCCATCACAGACACTGTCCCTGACCTGCACCGTCTCCGGCGACTCTATCAT
TTCAGGCGGCTACTATTGGTCCTGGATTAGACAACATCCGGGAAAGGGTCTTGAATGGATCGGCTATATTTTCTAC
AGCGGGAGTACGGATTACAATCCTAGTCTCAAGAGCCGCGTTACCATTTCAGTGGATACTTCAAAAAACCAGTTTA
GCCTGAAGCTGTCTTCTGTAACAGCTGCTGACACAGCCGTGTACTATTGCGCCAGGAGCGGCTACAGCTATGCCCT
GTTTGACCACTGGGGGCAAGGCACTCTTGTGACGGTGTCAAGTGGAGGGGGAGGATCAGGCGGCGGGGGATCC
GGCGGCGGGGGTAGTGACATTCAAATGACGCAGTCCCCAAGTTCTCTGTCCGCTAGCGTCGGCGACCGAGTGACC
ATCAGCTGCCGAGCATCCCAGTTTATCGGTAGATATTCAATTGGTACCAGCAACAACCGGGCAAAGCGCCCAAG
GTCCTGATCTACGCTGAGAGCAGTCTGCAATCCGGCGTACCTAGCAGGTTCTCCGGAAGTGGCAGCGGAACCGAG
TTCACCCTGACAATTAGCTCCTTGCAGCCCGAGGATTTCGCTCGCTATTACTGTCAACAGAGTTATTCAACCCCTTTT
ACATTCGGACAGGGAACTAAAGTTGAAATTAAGAGGGCCGCTGCCTTCGTGCCTGTTTTTCTGCCCGCGAAACCCA
CAACTACCCCCGCCCCTCGGCCCCCAACTCCTGCACCAACTATCGCTTCCCAACCCCTGTCTCTGAGACCTGAGGCA
TGCCGCCCCGCGGCAGGCGGCGCCGTGCACACTAGAGGCCTGGACTTCGCCTGCGATATTTATATCTGGGCCCCC
CTTGCCGGGACATGCGGGGTACTGCTGCTGTCTCTGGTGATTACCCTCTACTGCAACCACAGAAACCGCTTTTCCG
TCGTTAAGCGGGGAGAAAAAAGCTGCTGTACATTTTCAAACAGCCGTTTATGAGGCCGGTCCAAACGACTCAGG
AAGAAGACGGCTGCTCCTGCCGCTTTCCTGAGGAGGAGGAGGGCGGGTGCGAACTGAGGGTGAAGTTTTCCAGA
TCTGCAGATGCACCAGCGTATCAGCAGGGCCAGAACCAACTGTATAACGAGCTCAACCTGGGACGCAGGGAAGA
GTATGACGTTTTGGACAAGCGCAGAGGACGGGACCCTGAGATGGGTGGCAAACCAAGACGAAAAAACCCCCAGG
AGGGTCTCTATAATGAGCTGCAGAAGGATAAGATGGCTGAAGCCTATTCTGAAATAGGCATGAAAGGAGAGCGG
AGAAGGGGAAAAGGGCACGACGGTTTGTACCAGGGACTCAGCACTGCTACGAAGGATACTTATGACGCTCTCCA
CATGCAAGCCCTGCCACCTAGG (Seq. ID NO. 43)

1C8.1.001_C8K_4Bz Amino Acid Sequence

MALPVTALLLPLALLLHAARPQVQLQESGPGLVKPSQTLSLTCTVSGDSIISGGYYWSWIRQHPGKGLEWIGYIFYSGST
DYNPSLKSRVTISVDTSKNQFSLKLSSVTAADTAVYYCARSGYSYALFDHWGQGTLVTVSSGGGGSGGGGSGGGGSDI
QMTQSPSSLSASVGDRVTISCRASQFIGRYFNWYQQQPGKAPKVLIYAESSLQSGVPSRFSGSGSGTEFTLTISSLQPEDF
ARYYCQQSYSTPFTFGQGTKVEIKRAAAFVPVFLPAKPTTTPAPRPPTPAPTIASQPLSLRPEACRPAAGGAVHTRGLDF
ACDIYIWAPLAGTCGVLLLSLVITLYCNHRNRFSVVKRGRKKLLYIFKQPFMRPVQTTQEEDGCSCRFPEEEEGGCELRVK
FSRSADAPAYQQGQNQLYNELNLGRREEYDVLDKRRGRDPEMGGKPRRKNPQEGLYNELQKDKMAEAYSEIGMKGE
RRRGKGHDGLYQGLSTATKDTYDALHMQALPPR (Seq. ID NO. 44)

Figure 8H

6E9.1_C28T_28z Coding Sequence

ATGGCACTCCCCGTAACTGCTCTGCTGCTGCCGTTGGCATTGCTCCTGCACGCCGCACGCCCGCAGGTACACCTGG
TGCAGAGCGGGGCGGAGGTCAAGAAACCGGGCGCATCCGTACGCGTGAGCTGCAAGGCCTCCGGATACACTTTT
ACTTCTTACTATCTGCATTGGGTCAGGCAGGCACCGGGTCAGGGACTGGAGTGGATGGGCATTGTGGACCCAAGC
GGAGGGAGTACGTCATATGATCAGAAGTTTCAAGGTAGGTTTACCATGACACGGGACACGTCAACGAGTACCGTC
TACATGGAGCTCAGTAGTCTGCGGAGCGAAGACACCGCAGTCTACTACTGCGCACGCGATTATGGAGACTATGTC
TTTGACTATGGGGGCAGGGGACGCTCGTGACCGTTTCAAGCGGGGGGGCGGATCCGGTGGGGAGGTTCCG
GCGGTGGGGGTTCACAAAGCGTACTGACACAGCCCCGAGTGCATCCGGGACCCCCGGCCAAAGGGTTACAATC
AGCTGCTCTGGCAGCTCCAGTAACATAGGTACCAACACGGTGAACTGGTACCAGCAGTTGCCTGGCACAGCGCCT
CAGCTGCTCATCTATATCAACAATCAGCGGCCAAGTGGCGTGCCCGATAGATTCTCAGGCTCAAAGAGCGGAACC
AGCGCTAGCTTGGCAATCAGTGGCCTTCAATCCGAAGACGAAGCCGATTACTATTGTGCGACCTGGGACGATAGC
CTGAACGGCCCCGTCGTGGGCGGCGGGACGAAACTGACAGTGTTGGGCGCCGCTGCCCTTGATAATGAAAAGTC
AAACGGAACAATCATTCACGTGAAGGGCAAGCACCTCTGTCCGTCACCCTTGTTCCCTGGTCCATCCAAGCCATTCT
GGGTGTTGGTCGTAGTGGGTGGAGTCCTCGCTTGTTACTCTCTGCTCGTCACCGTGGCTTTTATAATCTTCTGGGTT
AGATCCAAAAGAAGCCGCCTGCTCCATAGCGATTACATGAATATGACTCCACGCCGCCCTGGCCCCACAAGGAAA
CACTACCAGCCTTACGCACCACCTAGAGATTTCGCTGCCTATCGGAGCAGGGTGAAGTTTTCCAGATCTGCAGATG
CACCAGCGTATCAGCAGGGCCAGAACCAACTGTATAACGAGCTCAACCTGGGACGCAGGGAAGAGTATGACGTT
TTGGACAAGCGCAGAGGACGGGACCCTGAGATGGGTGGCAAACCAAGACGAAAAAACCCCCAGGAGGGTCTCT
ATAATGAGCTGCAGAAGGATAAGATGGCTGAAGCCTATTCTGAAATAGGCATGAAAGGAGAGCGGAGAAGGGG
AAAAGGGCACGACGGTTTGTACCAGGGACTCAGCACTGCTACGAAGGATACTTATGACGCTCTCCACATGCAAGC
CCTGCCACCTAGG (Seq. ID NO. 45)

6E9.1_C28T_28z Amino Acid Sequence

MALPVTALLLPLALLLHAARPQVHLVQSGAEVKKPGASVRVSCKASGYTFTSYYLHWVRQAPGQGLEWMGIVDPSGG
STSYDQKFQGRFTMTRDTSTSTVYMELSSLRSEDTAVYYCARDYGDYVFDYWGQGTLVTVSSGGGGSGGGGSGGGG
SQSVLTQPPSASGTPGQRVTISCSGSSSNIGTNTVNWYQQLPGTAPQLLIYINNQRPSGVPDRFSGSKSGTSASLAISGL
QSEDEADYYCATWDDSLNGPVVGGGTKLTVLGAAALDNEKSNGTIIHVKGKHLCPSPLFPGPSKPFWVLVVVGGVLAC
YSLLVTVAFIIFWVRSKRSRLLHSDYMNMTPRRPGPTRKHYQPYAPPRDFAAYRSRVKFSRSADAPAYQQGQNQLYNE
LNLGRREEYDVLDKRRGRDPEMGGKPRRKNPQEGLYNELQKDKMAEAYSEIGMKGERRRGKGHDGLYQGLSTATKD
TYDALHMQALPPR (Seq. ID NO. 46)

Figure 8I

6E9.1_C28T_4Bz Coding Sequence

ATGGCACTCCCCGTAACTGCTCTGCTGCTGCCGTTGGCATTGCTCCTGCACGCCGCACGCCCGCAGGTACACCTGG
TGCAGAGCGGGGCGGAGGTCAAGAAACCGGGCGCATCCGTACGCGTGAGCTGCAAGGCCTCCGGATACACTTTT
ACTTCTTACTATCTGCATTGGGTCAGGCAGGCACCGGGTCAGGGACTGGAGTGGATGGGCATTGTGGACCCAAGC
GGAGGGAGTACGTCATATGATCAGAAGTTTCAAGGTAGGTTTACCATGACACGGGACACGTCAACGAGTACCGTC
TACATGGAGCTCAGTAGTCTGCGGAGCGAAGACACCGCAGTCTACTACTGCGCACGCGATTATGGAGACTATGTC
TTTGACTATTGGGGGCAGGGGACGCTCGTGACCGTTTCAAGCGGGGGGGGCGGATCCGGTGGGGAGGTTCCG
GCGGTGGGGGTTCACAAAGCGTACTGACACAGCCCCGAGTGCATCCGGGACCCCCGGCCAAAGGGTTACAATC
AGCTGCTCTGGCAGCTCCAGTAACATAGGTACCAACACGGTGAACTGGTACCAGCAGTTGCCTGGCACAGCGCCT
CAGCTGCTCATCTATATCAACAATCAGCGGCCAAGTGGCGTGCCCGATAGATTCTCAGGCTCAAAGAGCGGAACC
AGCGCTAGCTTGGCAATCAGTGGCCTTCAATCCGAAGACGAAGCCGATTACTATTGTGCGACCTGGGACGATAGC
CTGAACGGCCCCGTCGTGGGCGGCGGGACGAAACTGACAGTGTTGGGCGCCGCTGCCCTTGATAATGAAAAGTC
AAACGGAACAATCATTCACGTGAAGGGCAAGCACCTCTGTCCGTCACCCTTGTTCCCTGGTCCATCCAAGCCATTCT
GGGTGTTGGTCGTAGTGGGTGGAGTCCTCGCTTGTTACTCTCTGCTCGTCACCGTGGCTTTTATAATCTTCTGGGTT
CGCTTTTCCGTCGTTAAGCGGGGAGAAAAAAGCTGCTGTACATTTTCAAACAGCCGTTTATGAGGCCGGTCCAA
ACGACTCAGGAAGAAGACGGCTGCTCCTGCCGCTTTCCTGAGGAGGAGGAGGGCGGGTGCGAACTGAGGGTGA
AGTTTTCCAGATCTGCAGATGCACCAGCGTATCAGCAGGGCCAGAACCAACTGTATAACGAGCTCAACCTGGGAC
GCAGGGAAGAGTATGACGTTTTGGACAAGCGCAGAGGACGGGACCCTGAGATGGGTGGCAAACCAAGACGAAA
AAACCCCCAGGAGGGTCTCTATAATGAGCTGCAGAAGGATAAGATGGCTGAAGCCTATTCTGAAATAGGCATGAA
AGGAGAGCGGAGAAGGGGAAAAGGGCACGACGGTTTGTACCAGGGACTCAGCACTGCTACGAAGGATACTTAT
GACGCTCTCCACATGCAAGCCCTGCCACCTAGG (Seq. ID NO. 47)

6E9.1_C28T_4Bz Amino Acid Sequence

MALPVTALLLPLALLLHAARPQVHLVQSGAEVKKPGASVRVSCKASGYTFTSYYLHWVRQAPGQGLEWMGIVDPSGG
STSYDQKFQGRFTMTRDTSTSTVYMELSSLRSEDTAVYYCARDYGDYVFDYWGQGTLVTVSSGGGGSGGGGSGGGG
SQSVLTQPPSASGTPGQRVTISCSGSSSNIGTNTVNWYQQLPGTAPQLLIYINNQRPSGVPDRFSGSKSGTSASLAISGL
QSEDEADYYCATWDDSLNGPVVGGGTKLTVLGAAALDNEKSNGTIIHVKGKHLCPSPLFPGPSKPFWVLVVVGGVLAC
YSLLVTVAFIIFWVRFSVVKRGRKKLLYIFKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMAEAYSEIGMKGERRRGKGHDGLYQGLS
TATKDTYDALHMQALPPR (Seq. ID NO. 48)

Figure 8J

6E9.1_C8K_28z Coding Sequence

ATGGCACTCCCCGTAACTGCTCTGCTGCTGCCGTTGGCATTGCTCCTGCACGCCGCACGCCCGCAGGTACACCTGG
TGCAGAGCGGGGCGGAGGTCAAGAAACCGGGCGCATCCGTACGCGTGAGCTGCAAGGCCTCCGGATACACTTTT
ACTTCTTACTATCTGCATTGGGTCAGGCAGGCACCGGGTCAGGGACTGGAGTGGATGGGCATTGTGGACCCAAGC
GGAGGGAGTACGTCATATGATCAGAAGTTTCAAGGTAGGTTTACCATGACACGGGACACGTCAACGAGTACCGTC
TACATGGAGCTCAGTAGTCTGCGGAGCGAAGACACCGCAGTCTACTACTGCGCACGCGATTATGGAGACTATGTC
TTTGACTATTGGGGGCAGGGGACGCTCGTGACCGTTTCAAGCGGGGGGGGCGGATCCGGTGGGGAGGTTCCG
GCGGTGGGGGTTCACAAAGCGTACTGACACAGCCCCCGAGTGCATCCGGGACCCCCGGCCAAAGGGTTACAATC
AGCTGCTCTGGCAGCTCCAGTAACATAGGTACCAACACGGTGAACTGGTACCAGCAGTTGCCTGGCACAGCGCCT
CAGCTGCTCATCTATATCAACAATCAGCGGCCAAGTGGCGTGCCCGATAGATTCTCAGGCTCAAAGAGCGGAACC
AGCGCTAGCTTGGCAATCAGTGGCCTTCAATCCGAAGACGAAGCCGATTACTATTGTGCGACCTGGGACGATAGC
CTGAACGGCCCCGTCGTGGGCGGCGGGACGAAACTGACAGTGTTGGGCGCCGCTGCCCTTGATAATGAAAAGTC
AAACGGAACAATCATTCACGTGAAGGGCAAGCACCTCTGTCCGTCACCCTTGTTCCCTGGTCCATCAAGCCATTCT
GGGTGTTGGTCGTAGTGGGTGGAGTCCTCGCTTGTTACTCTCTGCTCGTCACCGTGGCTTTTATAATCTTCTGGGTT
CGCTTTTCCGTCGTTAAGCGGGGGAGAAAAAAGCTGCTGTACATTTTCAAACAGCCGTTTATGAGGCCGGTCCAA
ACGACTCAGGAAGAAGACGGCTGCTCCTGCCGCTTTCCTGAGGAGGAGGAGGGCGGGTGCGAACTGAGGGTGA
AGTTTTCCAGATCTGCAGATGCACCAGCGTATCAGCAGGGCCAGAACCAACTGTATAACGAGCTCAACCTGGGAC
GCAGGGAAGAGTATGACGTTTTGGACAAGCGCAGAGGACGGGACCCTGAGATGGGTGGCAAACCAAGACGAAA
AAACCCCCAGGAGGGTCTCTATAATGAGCTGCAGAAGGATAAGATGGCTGAAGCCTATTCTGAAATAGGCATGAA
AGGAGAGCGGAGAAGGGGAAAAGGGCACGACGGTTTGTACCAGGGACTCAGCACTGCTACGAAGGATACTTAT
GACGCTCTCCACATGCAAGCCCTGCCACCTAGG (Seq ID NO. 49)

6E9.1_C8K_28z Amino Acid Sequence

MALPVTALLLPLALLLHAARPQVHLVQSGAEVKKPGASVRVSCKASGYTFTSYYLHWVRQAPGQGLEWMGIVDPSGG
STSYDQKFQGRFTMTRDTSTSTVYMELSSLRSEDTAVYYCARDYGDYVFDYWGQGTLVTVSSGGGGSGGGGSGGGG
SQSVLTQPPSASGTPGQRVTISCSGSSSNIGTNTVNWYQQLPGTAPQLLIYINNQRPSGVPDRFSGSKSGTSASLAISGL
QSEDEADYYCATWDDSLNGPVVGGGTKLTVLGAAAFVPVFLPAKPTTTPAPRPPTPAPTIASQPLSLRPEACRPAAGGA
VHTRGLDFACDIYIWAPLAGTCGVLLLSLVITLYCNHRNRSKRSRLLHSDYMNMTPRRPGPTRKHYQPYAPPRDFAAYR
SRVKFSRSADAPAYQQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR (Seq. ID NO. 50)

Figure 8K

6E9.1_C8K_4Bz Coding Sequence

ATGGCACTCCCCGTAACTGCTCTGCTGCTGCCGTTGGCATTGCTCCTGCACGCCGCACGCCCGCAGGTACACCTGG
TGCAGAGCGGGGCGGAGGTCAAGAAACCGGGCGCATCCGTACGCGTGAGCTGCAAGGCCTCCGGATACACTTTT
ACTTCTTACTATCTGCATTGGGTCAGGCAGGCACCGGGTCAGGGACTGGAGTGGATGGGCATTGTGGACCCAAGC
GGAGGGAGTACGTCATATGATCAGAAGTTTCAAGGTAGGTTTACCATGACACGGGACACGTCAACGAGTACCGTC
TACATGGAGCTCAGTAGTCTGCGGAGCGAAGACACCGCAGTCTACTACTGCGCACGCGATTATGGAGACTATGTC
TTTGACTATGGGGGCAGGGGACGCTCGTGACCGTTTCAAGCGGGGGGGGCGGATCCGGTGGGGAGGTTCCG
GCGGTGGGGGTTCACAAAGCGTACTGACACAGCCCCCGAGTGCATCCGGGACCCCCGGCCAAAGGGTTACAATC
AGCTGCTCTGGCAGCTCCAGTAACATAGGTACCAACACGGTGAACTGGTACCAGCAGTTGCCTGGCACAGCGCCT
CAGCTGCTCATCTATATCAACAATCAGCGGCCAAGTGGCGTGCCCGATAGATTCTCAGGCTCAAAGAGCGGAACC
AGCGCTAGCTTGGCAATCAGTGGCCTTCAATCCGAAGACGAAGCCGATTACTATTGTGCGACCTGGGACGATAGC
CTGAACGGCCCCGTCGTGGGCGGCGGGACGAAACTGACAGTGTTGGGCGCCGCTGCCTTCGTGCCTGTTTTTCTG
CCCGCGAAACCCACAACTACCCCCGCCCCTCGGCCCCCAACTCCTGCACCAACTATCGCTTCCCAACCCCTGTCTCT
GAGACCTGAGGCATGCCGCCCCGCGGCAGGCGGCGCCGTGCACACTAGAGGCCTGGACTTCGCCTGCGATATTTA
TATCTGGGCCCCCCTTGCCGGGACATGCGGGTACTGCTGCTGTCTCTGGTGATTACCCTCTACTGCAACCACAGA
AACCGCTTTTCCGTCGTTAAGCGGGGGAGAAAAAAGCTGCTGTACATTTTCAAACAGCCGTTTATGAGGCCGGTCC
AAACGACTCAGGAAGAAGACGGCTGCTCCTGCCGCTTTCCTGAGGAGGAGGAGGGCGGGTGCGAACTGAGGGT
GAAGTTTTCCAGATCTGCAGATGCACCAGCGTATCAGCAGGGCCAGAACCAACTGTATAACGAGCTCAACCTGGG
ACGCAGGGAAGAGTATGACGTTTTGGACAAGCGCAGAGGACGGGACCCTGAGATGGGTGGCAAACCAAGACGA
AAAAACCCCCAGGAGGGTCTCTATAATGAGCTGCAGAAGGATAAGATGGCTGAAGCCTATTCTGAAATAGGCATG
AAAGGAGAGCGGAGAAGGGGAAAAGGGCACGACGGTTTGTACCAGGGACTCAGCACTGCTACGAAGGATACTT
ATGACGCTCTCCACATGCAAGCCCTGCCACCTAGG (Seq. ID NO. 51)

6E9.1_C8K_4Bz Amino Acid Sequence

MALPVTALLLPLALLLHAARPQVHLVQSGAEVKKPGASVRVSCKASGYTFTSYYLHWVRQAPGQGLEWMGIVDPSGG
STSYDQKFQGRFTMTRDTSTSTVYMELSSLRSEDTAVYYCARDYGDYVFDYWGQGTLVTVSSGGGGSGGGGSGGGG
SQSVLTQPPSASGTPGQRVTISCSGSSSNIGTNTVNWYQQLPGTAPQLLIYINNQRPSGVPDRFSGSKSGTSASLAISGL
QSEDEADYYCATWDDSLNGPVVGGGTKLTVLGAAAFVPVFLPAKPTTTPAPRPPTPAPTIASQPLSLRPEACRPAAGGA
VHTRGLDFACDIYIWAPLAGTCGVLLLSLVITLYCNHRNRFSVVKRGRKKLLYIFKQPFMRPVQTTQEEDGCSCRFPEEEE
GGCELRVKFSRSADAPAYQQGQNQLYNELNLGRREEYDVLDKRRGRDPEMGGKPRRKNPQEGLYNELQKDKMAEAY
SEIGMKGERRRGKHDGLYQGLSTATKDTYDALHMQALPPR (Seq. ID NO. 52)

Figure 8L

CD70 BINDING MOLECULES AND METHODS OF USE THEREOF

CROSS REFERENCE TO RELATED APPLICATIONS

This application claims priority to U.S. Provisional Patent Application Ser. No. 62/458,879 filed Feb. 14, 2017, the entirety of which is hereby incorporated by reference.

SEQUENCE LISTING

The instant application contains a Sequence Listing which has been submitted electronically in ASCII format and is hereby incorporated by reference in its entirety. Said ASCII copy, created on Feb. 8, 2018, is named K-1034_02_SL.txt and is 183,361 kilobytes in size.

TECHNICAL FIELD

This instant disclosure relates to chimeric antigen receptors (CARs) and engineered T cell receptors (TCRs) comprising an antigen binding molecule which binds to CD70, polynucleotides encoding the same, and methods of treating a cancer in a patient using the same.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

Current therapies for hematologic malignancies have shown varying levels of effectiveness. Therefore, a need exists to identify novel and improved therapies for treating CD70-related diseases and disorders.

SUMMARY

In one aspect, an isolated polynucleotide encoding a chimeric antigen receptor (CAR) or T cell receptor (TCR) comprising an antigen binding molecule that specifically binds to CD70 is provided. In one embodiment the antigen binding molecule comprises: (a) a heavy chain variable region (VH) complementarity determining region (CDR) 1 comprising, consisting of, or consisting essentially of an amino acid sequence selected from the group consisting of GFTFSSY (SEQ ID NO: 71), GDSIISGGY (SEQ ID NO: 73) and GYTFTSY (SEQ ID NO: 75); (b) a heavy chain variable region (VH) complementarity determining region (CDR) 2 comprising, consisting of, or consisting essentially of an amino acid sequence selected from the group consisting of WYDGSN (SEQ ID NO: 72), FYSGS (SEQ ID NO: 74) and DPSGGS (SEQ ID NO: 76); (c) a heavy chain variable region (VH) complementarity determining region (CDR) 3 comprising, consisting of, or consisting essentially of an amino acid sequence selected from the group consisting of DLLRGVKGYAMDV (SEQ ID NO: 64), SGYSYALFDH (SEQ ID NO: 67) and DYGDYVFDY (SEQ ID NO: 76); (d) a light chain variable region (VL) complementarity determining region (CDR) 1 comprising, consisting of, or consisting essentially of an amino acid sequence selected from the group consisting of RASQSLRRIYLA (SEQ ID NO: 53), RASQFIGRYFN (SEQ ID NO: 56), and SGSSSNIGTNTVN (SEQ ID NO: 59); (e) a light chain variable region (VL) complementarity determining region (CDR) 2 comprising, consisting of, or consisting essentially of an amino acid sequence selected from the group consisting of DVFDRAT (SEQ ID NO: 54), AESSLQS (SEQ ID NO: 57), and INNQRPS (SEQ ID NOL 60); (f) a light chain variable region (VL) complementarity determining region (CDR) 3 comprising, consisting of, or consisting essentially of an amino acid sequence selected from the group consisting of QQYSDSPFT (SEQ ID NO: 55), QQSYSTPFT (SEQ ID NO: 58), and ATWDDSLNGPVV (SEQ ID NO: 61). In one embodiment the VH CDR3 comprises an amino acid sequence selected from the group consisting of SEQ ID NO: 64, 67 and 70.

In another aspect, an isolated polynucleotide encoding a chimeric antigen receptor (CAR) or T cell receptor (TCR) comprising an antigen binding molecule that specifically binds to CD70 is disclosed. In one embodiment the antigen binding molecule comprises a VH CDR3 comprising an amino acid sequence selected from the group consisting of SEQ ID NO: 64, 67 and 70. In one embodiments the VH CDR1 comprises an amino acid sequence selected from the group consisting of SEQ ID NO: 71, 73 and 75.

In another embodiment the VH CDR2 comprises an amino acid sequence selected from the group consisting of SEQ ID NO: 72, 74 and 76.

In another embodiment the VL CDR1 comprises an amino acid sequence selected from the group consisting of SEQ ID NO: 53, 56 and 59. In another embodiment the VL CDR2 comprises an amino acid sequence selected from the group consisting of SEQ ID NO: 54, 57 and 60. In another embodiment the VL CDR3 comprises an amino acid sequence selected from the group consisting of SEQ ID NO: 55, 58 and 61.

In another embodiment the VH CDR1, VH CDR2, and VH CDR3 each comprise the amino acid sequence of the VH CDR1, VH CDR2, and VH CDR3 of a variable light chain shown in FIG. 7A, 7C or 7E.

In another embodiment the VL CDR1, VL CDR2, and VL CDR3 each comprise the amino acid sequence of the VL CDR1, VL CDR2, and VL CDR3 of an antibody in FIG. 7B, 7D or 7F. In another embodiment the antigen binding molecule comprises a heavy chain variable region sequence comprising an amino acid sequence selected from the group consisting of SEQ ID NOs: 3, 7 and 11.

In another embodiment the antigen binding molecule comprises a light chain variable region sequence comprising an amino acid sequence selected from the group consisting of SEQ ID NOs: 5, 9 and 13.

In another embodiment the antigen binding molecule comprises one of: (a) a VH CDR1 region comprising the amino acid sequence of SEQ ID NO: 71; a VH CDR2 region comprising the amino acid sequence of SEQ ID NO: 72; a VH CDR3 region comprising the amino acid sequence of SEQ ID NO: 64; a VL CDR1 region comprising the amino acid sequence of SEQ ID NO: 53; a VL CDR2 region comprising the amino acid sequence of SEQ ID NO: 54; and a VL CDR3 region comprising the amino acid sequence of SEQ ID NO: 55; (b) a VH CDR1 region comprising the amino acid sequence of SEQ ID NO: 73; a VH CDR2 region comprising the amino acid sequence of SEQ ID NO: 74; a VH CDR3 region comprising the amino acid sequence of SEQ ID NO: 67; a VL CDR1 region comprising the amino acid sequence of SEQ ID NO: 56; a VL CDR2 region comprising the amino acid sequence of SEQ ID NO: 57; and a VL CDR3 region comprising the amino acid sequence of SEQ ID NO: 58; or (c) a VH CDR1 region comprising the amino acid sequence of SEQ ID NO: 75; a VH CDR2 region comprising the amino acid sequence of SEQ ID NO: 76; a VH CDR3 region comprising the amino acid sequence of SEQ ID NO: 70; a VL CDR1 region comprising the amino acid sequence of SEQ ID NO: 59; a VL CDR2 region comprising the amino acid sequence of SEQ ID NO: 60; and a VL CDR3 region comprising the amino acid sequence of SEQ ID NO: 61. In another embodiment the antigen binding molecule comprises one of: (a) a VH comprising the amino acid sequence of SEQ ID NO: 3; and a VL comprising the amino acid sequence of SEQ ID NO: 5; (b) a VH comprising the amino acid sequence of SEQ ID NO: 7; and a VL comprising the amino acid sequence of SEQ ID NO: 9; or (c) a VH comprising the amino acid sequence of SEQ ID NO: 11; and a VL comprising the amino acid sequence of SEQ ID NO: 13.

In another embodiment the nucleotide sequence is at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 2 and 4.

In another embodiment the nucleotide sequence is at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 6 and 8.

In another embodiment the nucleotide sequence is at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 10 and 12.

In another embodiment the antigen binding molecule is single chained.

In various embodiments the antigen binding molecule is selected from the group consisting of scFv, Fab, Fab', Fv, F(ab')$_2$, dAb, and any combination thereof, and in a specific embodiment the antigen binding molecule comprises an scFv.

In another embodiment the VH and the VL are joined by a linker. In a specific embodiment the VH is located at the N terminus of the linker and the VL is located at the C terminus of the linker, and in another embodiment the VL is located at the N terminus of the linker and the VH is located at the N terminus of the linker.

In another embodiment the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids, and in another embodiment the linker comprises an amino acid sequence at least 75%, at least 85%, at least 85%, at least 90%, at least 95%, at least 96%, at least 97%, at least 98%, at least 99%, or 100% identical to the amino acid sequence of one of SEQ ID NOs: 80 and 81.

In another embodiment the antigen binding molecule binds to CD70 with a $K_D$ of less than about $1 \times 10^{-6}$ M, less than about $1 \times 10^{-7}$ M, less than about $1 \times 10^{-8}$ M, or less than about $1 \times 10^{-9}$ M.

In another embodiment the CAR or TCR further comprises a constant region, and in another embodiment the CAR or TCR further comprises a transmembrane domain and in still further embodiments. the transmembrane domain is a transmembrane domain of CD28, 4-1BB/CD137, CD8 alpha, CD4, CD19, CD3 epsilon, CD45, CD5, CD9, CD16, CD22, CD33, CD37, CD64, CD80, CD86, CD134, CD137, CD154, an alpha chain of a T cell receptor, a beta chain of a T cell receptor, a zeta chain of a T cell receptor, or any combination thereof. In a specific embodiment the transmembrane domain is a CD28T transmembrane domain. In another embodiment the CD28T transmembrane domain comprises an amino acid sequence at least about 80%, at least about 85%, at least about 90%, at least about 95%, at least about 96%, at least about 97%, at least about 98%, at least about 99%, or about 100% identical to SEQ ID NO: 15 or 19.

In another embodiment the CD28T transmembrane domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 16 or 18.

In another embodiment the transmembrane domain is a CD8 alpha transmembrane domain. In another embodiment the CD8 alpha transmembrane domain comprises an amino acid sequence at least about 80%, at least about 85%, at least about 90%, at least about 95%, at least about 96%, at least about 97%, at least about 98%, at least about 99%, or about 100% identical to SEQ ID NO: 17, 21 or 94.

In another embodiment the CD8 alpha transmembrane domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 16 or 20.

In another embodiment the CAR or TCR further comprises a hinge region between the transmembrane domain and the antigen binding molecule. In another embodiment the hinge region comprises all or a fragment of IgG1, IgG2, IgG3, IgG4, IgA, IgD, IgE, IgM, CD28, or CD8 alpha. In another embodiment the hinge region is of CD28T. In another embodiment wherein the hinge region comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NOs: 15, and 83. In another embodiment the hinge region is encoded by a nucleotide sequence at least about 80%, at least about 85%, at least about 90%, at least about 95%, at least about 96%, at least about 97%, at least about 98%, at least about 99%, or about 100% identical to a sequence selected from the group consisting of SEQ ID NOs: 14 and 82.

In another embodiment the hinge region is of CD8 alpha. In another embodiment the hinge region comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 17 and 85, and in another embodiment the hinge region is encoded by a nucleotide sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 16 and 84.

In another embodiment the CAR or TCR further comprises a costimulatory region. In another embodiment the costimulatory region is a signaling region of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and or fragments or combinations thereof.

In another embodiment the costimulatory region is a CD28 costimulatory region. In another embodiment the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 23, and in another embodiment the costimulatory region is encoded by a nucleotide sequence at least about 80%, at least about 85%, at least about 90%, at least about 95%, at least about 96%, at least about 97%, at least about 98%, at least about 99%, or about 100% identical to SEQ ID NO: 22.

In another embodiment the costimulatory region is a CD137 (4-1BB) costimulatory region. In another embodiment the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 25 and in another embodiment the costimulatory region is encoded by a nucleotide sequence at least about 80%, at least about 85%, at least about 90%, at least about 95%, at least about 96%, at least about 97%, at least about 98%, at least about 99%, or about 100% identical to SEQ ID NO: 24.

In another embodiment the CAR or TCR further comprises an activation domain. And in another embodiment the activation domain is a CD3 zeta domain. In another embodiment the activation domain comprises an amino acid sequence at least about 80%, at least about 85%, at least about 90%, at least about 95%, at least about 96%, at least about 97%, at least about 98%, at least about 99%, or about 100% identical to SEQ ID NO: 27 or 92, and in another embodiment the activation domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 26.

In another embodiment the CAR or TCR further comprises a leader peptide. In another embodiment the leader peptide comprises an amino acid sequence at least about 80%, at least about 85%, at least about 90%, at least about 95%, at least about 96%, at least about 97%, at least about 98%, at least about 99%, or about 100% identical to SEQ ID NO: 28, and in another embodiment the leader peptide is encoded by a nucleotide sequence at least about 80%, at least about 85%, at least about 90%, at least about 95%, at least about 96%, at least about 97%, at least about 98%, at least about 99%, or about 100% identical to SEQ ID NO: 95.

In another aspect a polynucleotide encoding a CAR or TCR is provided. In a specific embodiment the polynucleotide is selected from the group consisting of SEQ ID NOs: 29, 31, 33, 35, 37, 39, 41, 43, 45, 47, 49 and 51. In another aspect, a vector comprising any of the polynucleotides disclosed herein. In another embodiment the vector is a retroviral vector, a DNA vector, a plasmid, a RNA vector, an adenoviral vector, an adenovirus associated vector, a lentiviral vector, or any combination thereof.

In another aspect a CAR or TCR encoded by a polynucleotide disclosed herein or a vector disclosed herein. In another aspect a cell comprising a polynucleotide disclosed herein, a vector disclosed herein, a CAR or TCR disclosed herein, or any combination thereof provided. In another embodiment the cell comprises an immune cell, and in another embodiment the cell is a T cell. In another embodiment the T cell is a tumor-infiltrating lymphocyte (TIL), autologous T cell, engineered autologous T cell (eACT), an allogeneic T cell, or any combination thereof, and in another embodiment the cell is an in vitro cell.

In another aspect a composition comprising a polynucleotide disclosed herein, a vector disclosed herein, a CAR or TCR disclosed herein, or a cell disclosed herein. In another embodiment a composition is formulated to be delivered to a subject.

In another aspect a method of making a cell expressing a CAR or TCR comprising transducing a cell with a polynucleotide disclosed herein under suitable conditions. In another embodiment the method further comprises isolating the cell.

In another aspect a method of inducing an immunity against a tumor is provided, and in an embodiment comprises administering to a subject an effective amount of a cell comprising a polynucleotide disclosed herein, a vector disclosed herein, or a CAR or TCR disclosed herein.

In another aspect a method of treating a cancer in a subject in need thereof is provided, and in an embodiment comprises administering to the subject a polynucleotide disclosed herein, a vector disclosed herein, a CAR or TCR disclosed herein, a cell disclosed herein, or a composition of disclosed herein. In an embodiment the cancer is a hematologic cancer. In another embodiment the cancer is of the white blood cells. In a further embodiment the cancer is of the plasma cells. In another embodiment the cancer is leukemia, lymphoma, or myeloma. In a specific embodiment the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof. In a specific embodiment the cancer is multiple myeloma. Also disclosed is a CAR or TCR, wherein the CAR or TCR comprises an amino acid sequence selected form the group consisting of SEQ ID NOs: 30, 32, 34, 36, 38, 40, 42, 44, 46, 48, 50 and 52. In various embodiments the CAR or TCR comprises a leader sequence of SEQ ID NOs: 30, 32, 34, 36, 38, 40, 42, 44, 46, 48, 50 and 52 is absent.

BRIEF DESCRIPTION OF THE FIGURES

FIGS. 1A-1H are cartoons depicting examples of the CAR constructs provided herein; the representative components and a preferred arrangement thereof, are shown.

FIGS. 4A and 4B show the IFNγ (pg/ml; y-axis) production in lentivirus transduced CAR T cells from donor 1 (FIG. 4A) and donor 2 (FIG. 4B), FIGS. 4C and 4D show the TNFα (pg/ml; y-axis) production in lentivirus transduced CAR T cells from donor 1 (FIG. 4C) and donor 2 (FIG. 4D), and FIGS. 4E and 4F show the IL-2 production (pg/ml; y-axis) in lentivirus transduced CAR T cells obtained from a first donor (FIG. 4E) and a second donor (FIG. 4F).

FIGS. 5A-5D show the cytolytic activity (as a percentage of viable target cells remaining; y-axis) over time of lentivirus transduced T cell obtained from healthy donor 1 (FIGS. 5A and 5C) or healthy donor 2 (FIGS. 5B and 5D) expressing the indicated CARs cocultured for 112 hours with KG-1a (CD70–) (FIGS. 5A and 5B), Raji (CD70+) (FIG. 5C), or Namalwa (CD70+) (FIG. 5D) target cells.

FIG. 6 is a table showing the complementarity determining regions (CDRs) of the antigen binding molecule disclosed herein, as numbered using the Kabat, Chothia and IGMT systems.

FIGS. 7A-7F are a series of tables showing the variable heavy (VH) and variable light (VL) sequences for each of the CARs or TCRs provided herein; the CDRs are also presented and are showing as numbered using the Kabat, Chothia and IGMT systems.

FIGS. 8A-8L depict nucleic acid sequences encoding the various CARs disclosed herein; corresponding amino acid sequences are also provided.

FIGS. 11A and 11B show the IFNγ (pg/ml; y-axis) production in lentivirus transduced CAR T cells from donor 3 at an E:T ratio of 4:1 and 1:1, respectively; FIGS. 11C and 11D show the IFNγ (pg/ml; y-axis) production in lentivirus transduced CAR T cells from donor 4 at an E:T ratio of 4:1 and 1:1, respectively.

FIGS. 12A and 12B show the IL2 (pg/ml; y-axis) production in lentivirus transduced CART cells from donor 3 at an E:T ratio of 4:1 and 1:1, respectively; FIGS. 12C and 12D show the IL2 (pg/ml; y-axis) production in lentivirus transduced CAR T cells from donor 4 at an E:T ratio of 4:1 and 1:1, respectively.

FIGS. 13A and 13B show the IL2 (pg/ml; y-axis) production in lentivirus transduced CART cells from donor 3 at an E:T ratio of 4:1 and 1:1, respectively; FIGS. 13C and 13D show the TNFα (pg/ml; y-axis) production in lentivirus transduced CAR T cells from donor 4 at an E:T ratio of 4:1 and 1:1, respectively.

DETAILED DESCRIPTION

Figure 1E:
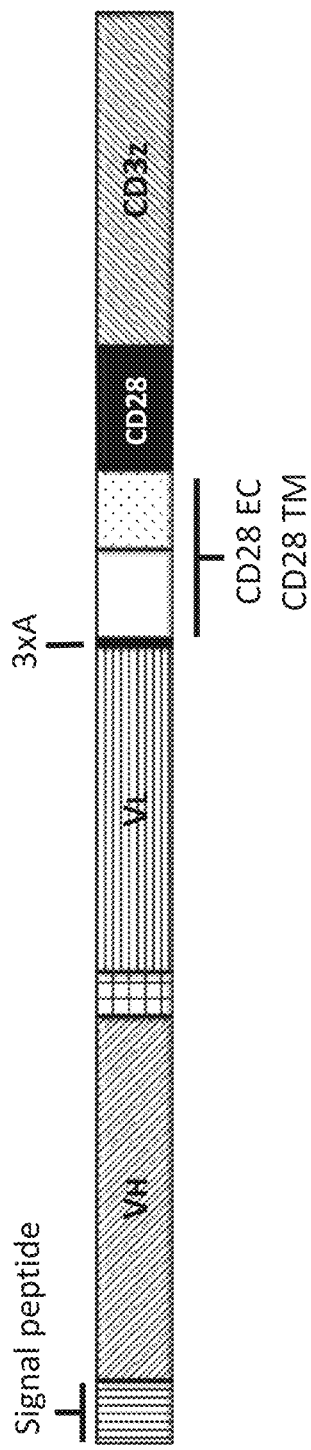
Figure 1F:
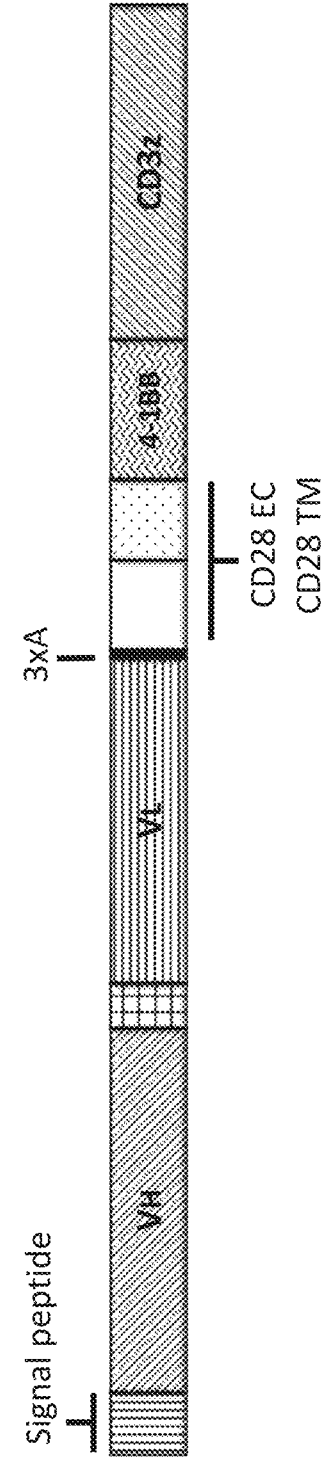
Figure 1G:
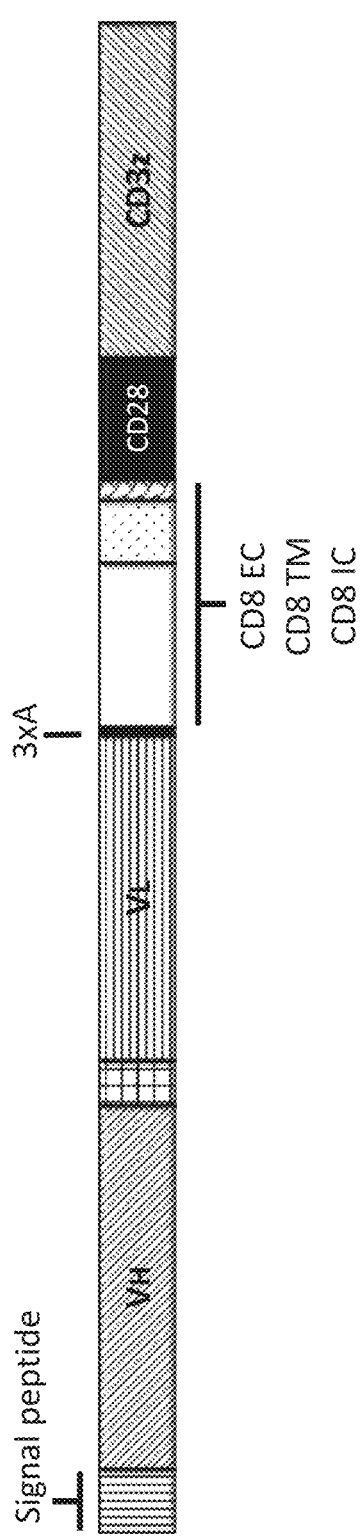
Figure 1H:
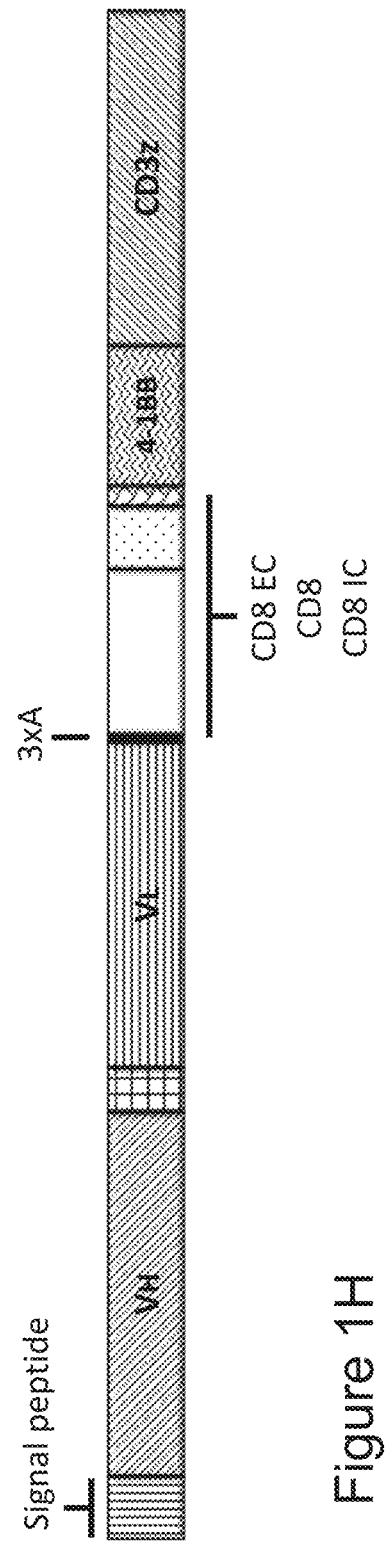

The instant disclosure relates to antibodies, antigen binding molecules thereof, chimeric antigen receptors (CARs), and engineered T cell receptors (TCRs), which bind CD70, polynucleotides encoding the same, and in vitro cells comprising the same. The polynucleotides, polypeptides, and in vitro cells described herein can be used in an engineered CAR T cell therapy, e.g., an autologous cell therapy (eACT™), for the treatment of a patient suffering from a cancer. In particular, the polynucleotides, polypeptides, and in vitro cells described herein can be used for the treatment of multiple myeloma.

Definitions

In order that the instant disclosure can be more readily understood, some terms are first defined. As used in this application, except as otherwise expressly provided herein, each of the following terms shall have the meaning set forth below. Additional definitions are set forth throughout the application. The headings provided herein are not limitations of the various aspects of the disclosure, which aspects can be understood by reference to the specification as a whole.

It is understood that wherever aspects are described herein with the language "comprising," otherwise analogous aspects described in terms of "consisting of" and/or "consisting essentially of" are also provided.

The use of the alternative (e.g., "or") should be understood to mean either one, both, or any combination thereof of the alternatives. As used herein, the indefinite articles "a" or "an" should be understood to refer to "one or more" of any recited or enumerated component.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, *The Concise Dictionary of Biomedicine and Molecular Biology*, 2$^{nd}$ ed., (2001), CRC Press; *The Dictionary of Cell & Molecular Biology*, 5$^{th}$ ed., (2013), Academic Press; and *The Oxford Dictionary Of Biochemistry And Molecular Biology*, Cammack et al. eds., 2$^{nd}$ ed, (2006), Oxford University Press, provide those of skill in the art with a general dictionary for many of the terms used in this disclosure.

As used herein, the twenty conventional (e.g., naturally occurring) amino acids and their abbreviations follow conventional usage. See, e.g., *Immunology—A Synthesis* (2nd Edition), Golub and Green, eds., Sinauer Assoc., Sunderland, Mass. (1991), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the instant disclosure. Examples of unconventional amino acids include: 4-hydroxyproline, gamma-carboxyglutamate, epsilon-N,N,N-trimethyllysine, e-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. Alternatively, "about" or "comprising essentially of" can mean a range of up to 10% (i.e., ±10%). For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen binding molecule thereof. Each H chain comprises a heavy chain variable region (abbreviated herein as VH) and a heavy chain constant region. The heavy chain constant region comprises three constant domains, CHL CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs can mediate the binding of the immunoglobulin to host tissues or factors, including various cells of the immune system (e.g., effector cells) and the first component (C1q) of the classical complement system.

Antibodies can include, for example, both naturally occurring and non-naturally occurring (recombinantly-produced) antibodies, human and non-human antibodies, monospecific antibodies, multispecific antibodies (including bispecific antibodies), immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies (see, e.g., Stocks, (2004) *Drug Discovery Today* 9(22):960-66), antibody fusions (which term encompasses antibody-drug conjugates) and which are sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments thereof. In some embodiments, antibodies described herein refer to polyclonal antibody populations.

An immunoglobulin is a tetrameric molecule, normally composed of two identical pairs of polypeptide chains, each pair having one "light" (about 25 kDa) and one "heavy" chain (about 50-70 kDa). The amino-terminal portion of each chain includes a variable region of about 100 to 130 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, or IgE, respectively. Within light and heavy chains, the variable and constant regions are joined by a "J" region of about 12 or more amino acids, with the heavy chain also including a "D" region of about 10 more amino acids. See generally, Berzofsky & Berkower, Ch. 7 in *Fundamental Immunology* (Paul, W., ed., Lippincott Williams & Wilkins (2012); which chapter and volume is incorporated by reference in its entirety for all purposes). The variable regions of each light/heavy chain pair form the antibody binding site such that an intact immunoglobulin has two primary binding sites.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen binding molecule of any of the aforementioned immunoglobulins, and includes a monovalent and a divalent fragment or portion, and a single chain antibody (i.e., a scFv).

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci.* U.S.A. 85:5879-83 (1988).

As used herein, the term "diabody" or dAB means bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., (1993) *Proc Natl Acad Sci* U.S.A. 90:6444-48, Poljak et al., (1994) *Structure* 2: 1121-23, and Perisic et al., (1994) *Structure* 2(12): 1217-26). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

As used herein, the term "Fab fragment" means is a monovalent fragment having the VL, VH, CL and CH domains; a "F(ab')2 fragment" is a bivalent fragment having two Fab fragments linked by a disulfide bridge at the hinge region; a "Fv fragment" has the VH and VL domains of a single arm of an antibody; and a "dAb fragment" has a VH domain, a VL domain, or an antigen-binding fragment of a VH or VL domain.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')$_2$, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD70. In further embodiments, the antigen binding molecule is an antibody of fragment thereof, including one or more of the complementarity determining regions (CDRs) thereof. In further embodiments, the antigen binding molecule is a single chain variable fragment (scFv). In some embodiments, the antigen binding molecule comprises or consists of avimers.

An antigen binding molecule can comprise, for example, an alternative protein scaffold or artificial scaffold with grafted complementarity determining regions (CDRs) or CDR derivatives. Such scaffolds include, but are not limited to, antibody-derived scaffolds comprising mutations introduced to, for example, stabilize the three-dimensional structure of the antigen binding molecule as well as wholly synthetic scaffolds comprising, for example, a biocompatible polymer. See, e.g., Korndorfer et al., 2003, *Proteins: Structure, Function, and Bioinformatics*, 53(1):121-129 (2003); Roque et al., *Biotechnol. Prog.* 20:639-654 (2004). In addition, peptide antibody mimetics ("PAMs") can be used, as well as scaffolds based on antibody mimetics utilizing various components (e.g., fibronectin) as a scaffold. An antigen binding molecule can have, for example, the structure of a naturally occurring immunoglobulin.

An antigen binding molecule can form a component of a CAR or TCR, and can serve to direct the CAR or TCR to recognize a target of interest (e.g., CD70). As used herein, in the context of a disclosed CAR or TCR, an antigen binding molecule means any component of a CAR or TCR that directs the CAR or TCR to a desired target and associates with that target. In specific embodiments, an antigen binding molecule component of a CAR or TCR comprises a scFv comprising a heavy and light chain variable region joined by a linker. The heavy and light variable regions can be derived from the same antibody or two different antibodies. Antigen binding molecules used in a CAR or TCR can be derived from an antibody known or suspect to bind to a target of interest. In specific embodiments, an antigen binding molecule used in a CAR or TCR include the pairs of sequences comprising the amino acid sequences of SEQ ID NOs: 3 and 5, SEQ ID NOs: 7 and 9, and SEQ ID NOs: 11 and 13, which are also presented in FIGS. 7A-7F.

As used herein, the terms "variable region" or "variable domain" are used interchangeably and mean a portion of an antibody, generally a portion of a light or heavy chain, typically about the amino-terminal end of the antibody and comprising about 100-130 amino acids in the heavy chain and about 90 to 115 amino acids in the light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In some embodiments, the variable region is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VL", "VL chain" and "VL domain" are used interchangeably and mean the light chain variable region of an antigen binding molecule, antibody or an antigen binding fragment thereof.

The terms "VH", "VH chain" and "VH domain" are used interchangeably and mean the heavy chain variable region of an antigen binding molecule, antibody or an antigen binding fragment thereof.

As used herein, the term "complementarity determining region" or "CDR" means an amino acid sequence that contributes to antigen binding specificity and affinity. Framework regions can aid in maintaining the proper confirmation of the CDRs to promote binding between the antigen binding molecule and an antigen. A number of definitions of CDRs are commonly in use: Kabat numbering, Chothia numbering, contact numbering, AbM numbering or IMGT numbering. The AbM definition is a compromise between the two used by Oxford Molecular's AbM antibody modelling software. The contact definition is based on an analysis of the available complex crystal structures. Table 1 summarizes the definitions of these systems of nomenclature.

TABLE 1

| CDR Numbering | | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32..34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen binding molecule thereof. In some aspects, the CDRs of an antibody can be determined according to the Kabat numbering system (see, e.g., Kabat et al. in Sequences of *Proteins of Immunological Interest*, 5th Ed., NIH Publication 91-3242, Bethesda Md. 1991). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

In a specific embodiment, the CDRs of the antibodies described herein can be described according to the Kabat numbering scheme, as shown in FIG. 6 (although they can readily be construed in other numbering systems using Table 1 above). FIG. 6 also provides the CDRs using the Chothia and IMGT numbering schemes.

In some aspects, the CDRs of an antibody can be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). See Table 1.

In a specific embodiment, the CDRs of the antibodies described herein have been determined according to the Chothia numbering scheme, as shown in FIG. 6.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by standard techniques known to one of ordinary skill in the art, such as BIAcore® or KinExA or surface plasmon resonance.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, one or more amino acid residues within a CDR(s) or within a framework region(s) of an antibody or antigen-binding fragment thereof can be replaced with an amino acid residue with a similar side chain.

Conservative amino acid substitutions, which are encompassed by the instant disclosure, can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:

hydrophobic: norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro; and
aromatic: Trp, Tyr, Phe.

Non-conservative substitutions can involve the exchange of a member of one of these classes for a member from another class. Such substituted residues can be introduced, for example, into regions of a human antibody that are homologous with non-human antibodies, or into the non-homologous regions of the molecule. Exemplary conservative amino acid substitutions are set forth in Table 2 below.

TABLE 2

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |

TABLE 2-continued

Amino Acid Substitutions

| Original Residues | Exemplary Substitutions | Preferred Substitutions |
|---|---|---|
| Val | Ile, Met, Leu, Phe, Ala, Norleucine | Leu |

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege et al., (1994) *Acta Crystallogr D Biol Crystallogr* 50(Pt 4): 339-350; McPherson, (1990) *Eur J Biochem* 189: 1-23; Chayen, (1997) *Structure* 5: 1269-1274; McPherson, (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., *Meth Enzymol* (1985) Vols 114 & 115, eds Wyckoff et al.), and BUSTER (Bricogne, (1993) *Acta Crystallogr D Biol Crystallogr* 49(Pt 1): 37-60; Bricogne, (1997) *Meth Enzymol* 276A: 361-423, ed. Carter; Roversi et al., (2000) *Acta Crystallogr D Biol Crystallogr* 56(Pt 10): 1316-1323). Mutagenesis mapping studies can be accomplished using any method known to one of skill in the art. See, e.g., Champe et al., (1995) *J Biol Chem* 270: 1388-94 and Cunningham & Wells, (1989) *Science* 244: 1081-85 for a description of mutagenesis techniques, including alanine and arginine scanning mutagenesis techniques.

As used herein, the term "cross competes" means the situation in which the interaction between an antigen (e.g., CD70) and a first antigen binding molecule or binding fragment thereof blocks, limits, inhibits, or otherwise reduces the ability of a reference antigen binding molecule or binding fragment thereof (such as the antigen binding molecules, CARs and TCRs provided herein) to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In some embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., (1983) *Method Enzymol* 9:242-53); solid phase direct biotin-avidin EIA (Kirkland et al., (1986) *J Immunol* 137:3614-19); solid phase direct labeled assay, solid phase direct labeled sandwich assay (Harlow and Lane, 1988, *Antibodies, A Laboratory Manual*, Cold Spring Harbor Press); solid phase direct label RIA using $I^{125}$ label (Morel et al., (1988) *Molec Immunol* 25:7-15); solid phase direct biotin-avidin EIA (Cheung et al., (1990) *Virology* 176:546-52); and direct labeled RIA (Moldenhauer et al., (1990) *Scand J Immunol* 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, molecules that specifically bind to an antigen (e.g., CD70), as well as molecules comprising this sequence and cells presenting such molecules) bind with a dissociation constant ($K_d$) of about $1 \times 10^{-7}$ M. In some embodiments, the antigen binding molecule specifically binds an antigen (e.g., CD70) with "high affinity" when the $K_d$ is about $1 \times 10^{-9}$ M to about $5 \times 10^{-9}$ M. In some embodiments, the antigen binding molecule specifically binds an antigen (e.g., CD70) with "very high affinity" when the $K_d$ is $1 \times 10^{-10}$ M to about $5 \times 10^{-10}$ M.

In another specific embodiment, molecules that specifically bind to an antigen do not cross react with other proteins under similar binding conditions. In another specific embodiment, molecules that specifically bind to an antigen do not cross react with other non-CD70 proteins. In a specific embodiment, provided herein is an antibody or fragment thereof that binds to CD70 with higher affinity than to another unrelated antigen. In some embodiments, provided herein is an antibody or fragment thereof that binds to CD70 (e.g., human CD70) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CD70 antibody or antigen-binding fragment thereof described herein to an unrelated, non-CD70 protein is less than 10%, 15%, or 20% of the binding of the antibody to CD70 protein as measured by, e.g., a radioimmunoassay.

In a specific embodiment, provided herein is an antibody or fragment thereof that binds to human CD70 with higher affinity than to another species of CD70. In some embodiments, provided herein is an antibody or fragment thereof that binds to human CD70 with a 5%, 10%, 15%, 20%, 25%, 30%, 35%, 40%, 45%, 50%, 55%, 60%, 65%, 70% or higher affinity than to another species of CD70 as measured by, e.g., a radioimmunoassay, surface plasmon resonance, or kinetic exclusion assay. In a specific embodiment, an antibody or fragment thereof described herein, which binds to human CD70, will bind to another species of CD70 protein with less than 10%, 15%, or 20% of the binding of the antibody or fragment thereof to the human CD70 protein as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response can involve either antibody production, or the activation of specific immunologically-competent cells, or both. Those of skill in the art will readily understand that any macromolecule, including virtually all proteins or peptides, can serve as an antigen. Generally, an antigen can be endogenously expressed, i.e. expressed by genomic DNA, or it can be recombinantly expressed, or it can be chemically synthesized. An antigen can be specific to a some tissue, such as a cancer cell, or it can be broadly expressed. In addition, fragments of larger molecules can act as antigens. In one embodiment, antigens are tumor antigens. In some embodiments, the antigen is CD70, which can optionally be conjugated to an adjuvant such as keyhole limpet hemocyanin (KLH).

The term "neutralizing" refers to an antigen binding molecule, scFv, antibody, or a fragment thereof, which binds to a ligand (e.g., CD70) and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "CD70" means a molecule that belongs to the tumor necrosis factor (TNF) ligand family, and is also known as CD27LG and TNFSF7. CD70 is a ligand for CD27 (TNFRSF27). It is a surface antigen on activated, but not on resting, T and B lymphocytes. It induces proliferation of costimulated T cells, enhances the generation of cytolytic T cells, and contributes to T cell activation. CD70 also plays a role in regulating B-cell activation, cytotoxic function of natural killer cells, and immunoglobulin synthesis. See, e.g., Goodwin et al., (1993) Cell 73(3):447-56 and Bowman et al., (1994) J. Immunol. 152(4):1756-61. The term CD70 can include, but is not limited to, native CD70, an isoform of CD70, or an inter-species CD70 homolog of CD70. CD70 (also known as CD27LG, CD27L and TNFSF7) is expressed on the surface of T and B cell lymphoma cells. The amino acid sequence of human CD70 (hCD70) is provided in NCBI Accession NP_001243.1 (GI:4507605) (SEQ ID NO: 1), and has the amino acid sequence:

```
                                         (SEQ ID NO: 1)
MPEEGSGCSVRRRPYGCVLRAALVPLVAGLVICLVVCIQRFAQAQQ

QLPLESLGWDVAELQLNHTGPQQDPRLYWQGGPALGRSFLHGPELD

KGQLRIHRDGIYMVHIQVTLAICSSTTASRHHPTTLAVGICSPASR

SISLLRLSFHQGCTIASQRLTPLARGDTLCTNLTGTLLPSRNTDET

FFGVQWVRP.
```

Residues 1-17 of SEQ ID NO: 1 correspond to the cytoplasmic region of hCD70, residues 18-38 correspond to the transmembrane region of hCD70, and residues 39-193 correspond to the extracellular region of hCD70. At least one other isoform of hCD70 is known and is identified by the UniProt identifier P32970-2.

As used herein, CD70 includes human CD70 and non-human CD70 homologs, as well as variants, fragments, or post-translationally modified forms thereof, including, but not limited to, N- and O-linked glycosylated forms of CD70. CD70 proteins can further include fragments comprising all or a portion of SEQ ID NO: 1 (e.g., amino acids 39-193 of SEQ ID NO: 1, corresponding to an extracellular component of hCD70, amino acids 18-193, corresponding to a trans-membrane and extracellular component of hCD70).

As used herein, the term "autologous" mean any material derived from the same individual to which it is later to be re-introduced. For example, the engineered autologous cell therapy (eACT™) methods described herein involve collection of lymphocytes from a patient, which are then engineered to express a construct, e.g., a CAR construct, and then administered back to the same patient.

As used herein the term "allogeneic" means any material derived from one individual which is then introduced to another individual of the same species, e.g., allogeneic T cell transplantation.

As used herein, the terms "transduction" and "transduced" means the process whereby foreign DNA is introduced into a cell via viral vector (see Hartl and Jones (1997) Genetics: Principles and Analysis, 4$^{th}$ ed, Jones & Bartlett). In some embodiments, the vector is a retroviral vector, a DNA vector, a RNA vector, an adenoviral vector, a baculoviral vector, an Epstein Barr viral vector, a papoviral vector, a vaccinia viral vector, a herpes simplex viral vector, an adenovirus associated vector, a lentiviral vector, or any combination thereof.

As used herein, the term "cancer" refers to a broad group of various diseases characterized by the uncontrolled growth of abnormal cells. Unregulated cell division and growth in the body results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the instant disclosure include, but are not limited to, cancers of the immune system including lymphoma, leukemia, myeloma, and other leukocyte malignancies. In some embodiments, the methods of the instant disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some embodiments, the cancer is multiple myeloma. The particular cancer can be responsive to chemo- or radiation therapy, or the cancer can be refractory. The term "refractory cancer" means a cancer that is not amendable to surgical intervention and the cancer is either initially unresponsive to chemo- or radiation therapy or the cancer becomes unresponsive over time.

As used herein, the term "anti-tumor effect" means a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

As used herein, the term "cytokine" means a non-antibody protein that is released by one cell in response to contact with a specific antigen, wherein the cytokine interacts with a second cell to mediate a response in the second cell. A cytokine can be endogenously expressed by a cell or administered to a subject. Cytokines can be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin 7 (IL-7) and interleukin 15 (IL-15), promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

As used herein, the term "chemokine" means a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, the terms "therapeutically effective amount," "effective dose," "effective amount," and "therapeutically effective dosage" of a therapeutic agent, e.g., engineered CAR T cells or cells expressing a TCR comprising a desired alpha chain, beta chain or both alpha and beta chains, are used interchangeably and mean any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, the term "lymphocyte" means a white blood cell found in a vertebrate's immune system. Lymphocytes include natural killer (NK) cells, T cells and B cells. NK cells are a type of cytotoxic (cell toxic) lymphocyte that represent a major component of the inherent immune system. NK cells reject tumors and cells infected by viruses through the process of apoptosis or programmed cell death. They were termed "natural killers" because they do not require activation in order to kill cells.

T cells play a major role in cell-mediated-immunity (no antibody involvement). Types of T cells include:
1) helper T cells (e.g., CD4+ cells);
2) cytotoxic T cells (also known as TC, cytotoxic T lymphocyte, CTL, T-killer cell, cytolytic T cell, CD8+ T-cells or killer T cell);
3) memory T-cells, including:
   (i) stem memory $T_{SCM}$ cells which, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells);
   (ii) central memory $T_{CM}$ cells, which express L-selectin and the CCR7, they secrete IL-2, but not IFNγ or IL-4; and
   (iii) effector memory $T_{EM}$ cells, however, do not express L-selectin or CCR7 but produce effector cytokines like IFNγ and IL-4);
4) regulatory T-cells (Tregs, suppressor T cells, or CD4+ CD25+ regulatory T cells);
5) natural killer T cells (NKTs);
6) γδ (Gamma Delta) T cells; and
7) mucosal associated invariant T cells (MAITs).

B cells play a principal role in humoral immunity (with antibody involvement). B cells make antibodies and antigens, perform the role of antigen-presenting cells (APCs) and turn into memory B cells after activation by antigen interaction.

As used herein, the terms "genetic engineering" or "engineering" are used interchangeably and mean a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

As used herein, the term "immune response" means the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

As used herein, the term "immunotherapy" means the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. Those of skill in the art will recognize that the conditioning methods disclosed herein would enhance the effectiveness of any transplanted T cell therapy. Examples of T cell therapies are described in U.S. Patent Publication No. 2014/0154228, U.S. Pat. Nos. 5,728,388 and 6,406,699, and International Publication No. WO 2008/081035.

The T cells of an immunotherapy can come from any source. For example, T cells can be differentiated in vitro from a stem cell population, or T cells can be obtained from a subject. T cells can also be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, T cells can be derived from one or more available T cell lines. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," abbreviated as "eACT™," also known as adoptive cell transfer, is a process by which a patient's own T cells are collected and subsequently genetically engineered to recognize and target one or more antigens expressed on the cell surface of one or more specific tumor cells or malignancies. T cells can be engineered to express, for example, a chimeric antigen receptor (CAR) or a T cell receptor (TCR). CAR positive (CAR+) T cells are engineered to express a CAR. CARs can comprise, e.g., an extracellular single chain variable fragment (scFv) with specificity for a particular tumor antigen, which is directly or indirectly linked to an intracellular signaling part comprising at least one costimulatory domain, which is directly or indirectly linked to at least one activating domain; the components can be arranged in any order. The costimulatory domain can be derived from, e.g., CD28 or CD28T, and the activating domain can be derived from, e.g., any form of CD3-zeta. In some embodiments, the CAR is designed to have two, three, four, or more costimulatory domains. A CAR scFv can be designed to target, for example, CD19, which is a transmembrane protein expressed by cells in the B cell lineage, including all normal B cells, and B cell malignances such as NHL, CLL, and non-T cell ALL. In some embodiments, a CAR is engineered such that the costimulatory domain is expressed as a separate polypeptide chain. Examples of CAR T cell therapies and constructs are described in U.S. Patent Publication Nos. 2013/0287748, 2014/0227237, 2014/0099309, and 2014/0050708, which are incorporated by reference in their entirety for any purpose.

As used herein, the term "in vitro cell" refers to any cell which is cultured ex vivo. An in vitro cell can include a human cell such as a T cell or dendritic cell, or it can include CHO, sP2/0, rabbit and other non-human cells. In some embodiments, an in vitro cell can include a T cell.

As used herein, the term "patient" means any human who is being treated for an abnormal physiological condition, such as cancer or has been formally diagnosed with a disorder, those without formally recognized disorders, those receiving medical attention, those at risk of developing the disorders, etc. The terms "subject" and "patient" are used interchangeably herein and include both human and non-human animal subjects. As used herein, the terms "patient" and "subject" are used interchangeably. In some embodiments the terms "subject" or "patient" mean any human who is afflicted with a cancer (e.g., a lymphoma or a leukemia).

As used herein, the terms "peptide," "polypeptide," and "protein" are used interchangeably, and mean a compound comprising two or more amino acid residues covalently linked by peptide bonds. A protein or peptide must contain at least two amino acids, but no limitation is placed on the maximum number of amino acids that can comprise a protein's or peptide's sequence. Polypeptides include any peptide or protein comprising two or more amino acids joined to each other by peptide bonds. As used herein, the terms encompass both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The term "polypeptides" include natural peptides, recombinant peptides, synthetic peptides, or a combination thereof.

In some aspects, the polypeptides have deletions from, additions to, and/or substitutions of one or more amino acid of antigen-binding protein, and in some embodiments preferably no more than 1, 2, 3, 4, 5, 6, 7, 8, 9, or 10 amino acid substitutions therein. Useful polypeptide fragments may include immunologically functional fragments of antigen binding molecules, including not limited to one or more CDR regions, variable domains of a heavy and/or light chain, a portion of other portions of an antibody chain, and the like. Moieties that can be substituted for one or more amino acids of an antigen binding molecule include, e.g., D or L forms of amino acids, an amino acid different from the amino acid normally found in the same position of an antigen binding molecule, deletions, non-naturally occurring amino acids, and chemical analogs of amino acids. Additionally, polypeptide fragments of activating and/or costimulatory molecules and the like are within the scope of the instant disclosure.

As used herein, the terms "activation" and "stimulation" and "stimulatory signal" mean a primary response induced by binding of an activating molecule with its cognate ligand, wherein the binding mediates a signal transduction event. Examples of activating molecules are provided herein. In one example, an "activating molecule" or "stimulating molecule" means a molecule on a T cell, e.g., the TCR/CD3 complex, which specifically binds with a cognate stimulatory ligand present on an antigen present cell. This type of signaling is sometimes referred to as "Signal 1" in the context of T cell activation.

As used herein, a "stimulatory ligand" means a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

As used herein, the term "costimulatory signal," means a signal which, in combination with a primary signal such as TCR/CD3 ligation, leads to a T cell response, such as, but not limited to, proliferation and/or upregulation or down regulation of key molecules. In an example, a costimulatory signal is induced upon the association of CD28 on a T cell with its cognate ligand B7 on an antigen presenting cell. This type of signaling is sometimes referred to as "Signal 2" in the context of T cell activation.

As used herein, the terms "costimulatory molecule" and "costimulatory ligand" means a cognate binding partner on a T cell that specifically binds with a costimulatory ligand, thereby mediating a costimulatory response by the T cell, such as, but not limited to, proliferation. Costimulatory molecules include, but are not limited to, CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, PD-1, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and or fragments or combinations thereof.

The terms "reducing" and "decreasing" are used interchangeably herein and indicate any change that is less than the original. "Reducing" and "decreasing" are relative terms, requiring a comparison between pre- and post-measurements. The terms "reducing" and "decreasing" include complete depletions.

As used herein, the terms "treatment" of a subject and "treating" a subject means any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission, as that term is defined in the context of a given therapeutic regimen. In another embodiment, "treatment" or "treating" includes a complete remission, as that term is defined in the context of a given therapeutic regimen.

As used herein, the term "percent identity" means the percent of identical residues between the amino acids or nucleotides in the compared molecules. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, ed.), (1988) New York: Oxford University Press; *Biocomputing Informatics and Genome Projects*, (Smith, ed.), 1993, New York: Academic Press; *Computer Analysis of Sequence Data, Part I*, (Griffin and Griffin, eds.), 1994, New Jersey: Humana Press; von Heinje, (1987) *Sequence Analysis in Molecular Biology*, New York: Academic Press; *Sequence Analysis Primer*, (Gribskov and Devereux, eds.), 1991, New York: M. Stockton Press; and Carillo et al., (1988) *J Applied Math.* 48:1073.

In calculating percent identity, the sequences being compared are aligned in a way that gives the largest match between the sequences. The computer program used to determine percent identity can be, e.g., MOE (Chemical Computing Group) or DNASTAR (University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In some embodiments, a standard comparison matrix (see, e.g., Dayhoff et al., (1978) *Atlas of Protein Sequence and Structure* 5:345-352 for the PAM 250 comparison matrix; Henikoff et al., (1992) *Proc. Natl. Acad. Sci.* U.S.A. 89: 10915-10919 for the BLOSUM 62 comparison matrix) is also used by the algorithm.

Some alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if desired to result in an alignment that spans at least 50 contiguous amino acids of the target polypeptide.

Various aspects of the disclosure are described in further detail in the following subsections.

II. Antigen Binding Molecules and Polynucleotides Encoding the Same

The instant disclosure is directed to antigen binding molecules, including antibodies, that specifically bind CD70, molecules comprising this sequence (such as the CARs and TCRs disclosed herein) and cells presenting such molecules, and/or antigen binding molecules which cross compete with one or more antigen binding molecules described herein (i.e., one or more of those described in FIGS. 7A-7H and/or disclosed in the appended Sequence Listing). Polynucleotides encoding the antigen binding molecules are also provided, and form an aspect of the instant disclosure. The antigen binding molecules can form an antigen binding component of one or more of the CARs and TCRs disclosed herein.

An antibody or antigen binding molecule encoded of the instant disclosure can be single chained or double chained. In some embodiments, the antibody or antigen binding molecule is single chained. In some embodiments, the antigen binding molecule is selected from the group consisting of an scFv, a Fab, a Fab', a Fv, a F(ab')$_2$, a dAb, and any combination thereof. In some embodiments, the antibody or antigen binding molecule comprises an scFv. In some embodiments, an antigen binding molecule comprises a single chain, wherein the heavy chain variable region and the light chain variable region are connected by a linker to form an scFv (e.g., an antigen binding molecule of instant disclosure). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 10 amino acids). Examples of suitable linkers for joining a VH to a VL to form an scFv (e.g., an antigen binding molecule of instant disclosure) include (Gly-Gly-Gly-Gly-Ser)$_3$ (SEQ ID NO: 80) and GSTSGSGKPGSGEGSTKG (SEQ ID NO: 81).

In some embodiments, the antigen binding molecules of the instant disclosure specifically bind to CD70, molecules comprising this sequence and cells presenting such molecules. In some embodiments, an antigen binding molecule of the instant disclosure specifically binds CD70, with a $K_D$ of less than $1\times10^{-6}$ M, less than $1\times10^{-7}$ M, less than $1\times10^{-8}$ M, or less than $1\times10^{-9}$ M. In some embodiments, an antigen binding molecule specifically binds to CD70, with a $K_D$ of less than $1\times10^{-7}$ M. In another embodiment, an antigen binding molecule specifically binds SEQ ID NO: 1, as well as molecules comprising this sequence and cells presenting such molecules, with a $K_D$ of less than $1\times10^{-8}$ M. In some embodiments, an antigen binding molecule binds CD70, with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. $K_D$ can be calculated using standard methodologies, as described herein.

In specific embodiments, an antigen binding molecule of the instant disclosure is an antibody, or scFv formed therefrom, identified herein as Clone 8G1 or Clone 1C8 or 6E9. Each of the disclosed antigen binding molecules comprises one each of the following heavy and light chain amino acid, coding, variable, and CDR sequences, as provided and labeled:

```
Clone 8G1 VH DNA Coding Sequence
                                      (SEQ ID NO: 2)
CAAGAGCAGCTGGTTGAGTCTGGGGGCGGCGTCGTCCAACCCGGC

CGGAGTCTGAGGTTGTCCTGCGCTGCAAGCGGATTTACATTTTCA

TCTTACGGCATGCACTGGGTTAGGCAGGCTCCTGGAAAAGGGCTG

GAGTGGGTCGCGGTGACTTGGTACGACGGCTCCAATAAGTATTAT

GGGGATTCCGTGAAAGGTCGATTCACAATTAGCAGGGATAACTCC

AAAAACACACTGTATCTCCAAATGAACTCCTTGAGGGCCGAGGAC

ACGGCCGTCTATTATTGTGCAAGAGACCTCCTCCGGGGCGTAAAG

GGATATGCtATGGACGTGTGGGGTCAGGGGACCACAGTTACTGTC

AGTTCA

Clone 8G1 VH AA (CDRs underlined)
                                      (SEQ ID NO: 3)
QEQLVESGGGVVQPGRSLRLSCAASGFTFSSYGMHWVRQAPGKGL

EWVAVTWYDGSNKYYGDSVKGRFTISRDNSKNTLYLQMNSLRAED

TAVYYCARDLLRGVKGYAMDVWGQGTTVTVSS

Clone 8G1 VH CDR1 AA
                                      (SEQ ID NO: 71)
GFTFSSY Clone 8G1 VH CDR2 AA
                                      (SEQ ID NO: 72)
WYDGSN Clone 8G1 VH CDR3 AA
                                      (SEQ ID NO: 64)
DLLRGVKGYAMDV Clone 8G1 VL DNA Coding Sequence
                                      (SEQ ID NO: 4)
GAAATCGTTCTCACTCAGTCTCCGGGCACACTGTCCCTCAGCCCC

GGAGAGCGAGCCACTTTGAGCTGCCGGGCCAGCCAGTCACTTAGA

CGCATTTATTTGGCCTGGTATCAGCAGAAACCAGGCCAGGCGCCC

AGGCTGCTGATATACGATGTGTTCGATAGGGCCACGGGTATCCCC

GATAGGTTCTCTGGCGGGGGGTCCGGGACTGACTTCACCCTCACT

ATATCACGACTCGAGCCCGAAGACTTCGCAGTTTATTATTGCCAG

CAGTACTCCGACTCCCCATTCACCTTCGGCCCTGGTACCAAAGTG

GATATTAAACGG

Clone 8G1 VL AA (CDRs underlined)
                                      (SEQ ID NO: 5)
EIVLTQSPGTLSLSPGERATLSCRASQSLRRIYLAWYQQKPGQAP

RLLIYDVFDRATGIPDRFSGGGSGTDFTLTISRLEPEDFAVYYCQ

QYSDSPFTFGPGTKVDIKR

Clone 8G1 VL CDR1 AA
                                      (SEQ ID NO: 53)
RASQSLRRIYLA Clone 8G1 VL CDR2 AA
                                      (SEQ ID NO: 54)
DVFDRAT Clone 8G1 VL CDR3 AA
                                      (SEQ ID NO: 55)
QQYSDSPFT
```

Clone 1C8 VH DNA Coding Sequence
(SEQ ID NO: 6)
CAGGTGCAGCTCCAAGAATCTGGACCGGGTCTCGTCAAGCCATCA

CAGACACTGTCCCTGACCTGCACCGTCTCCGGCGACTCTATCATT

TCAGGCGGCTACTATTGGTCCTGGATTAGACAACATCCGGGAAAG

GGTCTTGAATGGATCGGCTATATTTTCTACAGCGGGAGTACGGAT

TACAATCCTAGTCTCAAGAGCCGCGTTACCATTTCAGTGGATACT

TCAAAAAACCAGTTTAGCCTGAAGCTGTCTTCTGTAACAGCTGCT

GACACAGCCGTGTACTATTGCGCCAGGAGCGGCTACAGCTATGCC

CTGTTTGACCACTGGGGGCAAGGCACTCTTGTGACGGTGTCAAGT

Clone 1C8 VH AA (CDRs underlined)
(SEQ ID NO: 7)
QVQLQESGPGLVKPSQTLSLTCTVS<u>GDSIISGGY</u>YWSWIRQHPGK GLEWIGYI<u>FYSGS</u>TDYNPSLKSRVTISVDTSKNQFSLKLSSVTAA DTAVYYCAR<u>SGYSYALFDH</u>WGQGTLVTVSS Clone 1C8 VH CDR1 AA
(SEQ ID NO: 73)
GDSIISGGY Clone 1C8 VH CDR2 AA
(SEQ ID NO: 74)
FYSGS Clone 1C8 VH CDR3 AA
(SEQ ID NO: 67)
SGYSYALFDH Clone 1C8 VL DNA Coding Sequence
(SEQ ID NO: 8)
GACATTCAAATGACGCAGTCCCCAAGTTCTCTGTCCGCTAGCGTC

GGCGACCGAGTGACCATCAGCTGCCGAGCATCCCAGTTTATCGGT

AGATATTTCAATTGGTACCAGCAACAACCGGGCAAAGCGCCCAAG

GTCCTGATCTACGCTGAGAGCAGTCTGCAATCCGGCGTACCTAGC

AGGTTCTCCGGAAGTGGCAGCGGAACCGAGTTCACCCTGACAATT

AGCTCCTTGCAGCCCGAGGATTTCGCTCGCTATTACTGTCAACAG

AGTTATTCAACCCCTTTTACATTCGGACAGGGAACTAAAGTTGAA

ATTAAGAGG

Clone 1C8 VL AA (CDRs underlined)
(SEQ ID NO: 9)
DIQMTQSPSSLSASVGDRVTISC<u>RASQFIGRYFN</u>WYQQQPGKAPK VLIY<u>AESSLQS</u>GVPSRFSGSGSGTEFTLTISSLQPEDFARYYC<u>QQ</u>

<u>SYSTPFT</u>FGQGTKVEIKR

Clone 1C8 VL CDR1 AA
(SEQ ID NO: 56)
RASQFIGRYFN

Clone 1C8 VL CDR2 AA
(SEQ ID NO: 57)
AESSLQS

Clone 1C8 VL CDR3 AA
(SEQ ID NO: 58)
QQSYSTPFT

Clone 6E9 VH DNA Coding Sequence
(SEQ ID NO: 10)
CAGGTACACCTGGTGCAGAGCGGGCGGAGGTCAAGAAACCGGGC

GCATCCGTACGCGTGAGCTGCAAGGCCTCCGGATACACTTTTACT

TCTTACTATCTGCATTGGGTCAGGCAGGCACCGGGTCAGGGACTG

GAGTGGATGGGCATTGTGGACCCAAGCGGAGGGAGTACGTCATAT

GATCAGAAGTTTCAAGGTAGGTTTACCATGACACGGGACACGTCA

ACGAGTACCGTCTACATGGAGCTCAGTAGTCTGCGGAGCGAAGAC

ACCGCAGTCTACTACTGCGCACGCGATTATGGAGACTATGTCTTT

GACTATTGGGGCAGGGGACGCTCGTGACCGTTTCAAGC

Clone 6E9 VH AA (CDRs underlined)
(SEQ ID NO: 11)
QVHLVQSGAEVKKPGASVRVSCKAS<u>GYTFTSY</u>YLHWVRQAPGQGL EWMGIV<u>DPSGGS</u>TSYDQKFQGRFTMTRDTSTSTVYMELSSLRSED TAVYYCAR<u>DYGDYVFDY</u>WGQGTLVTVSS Clone 6E9 VH CDR1 AA
(SEQ ID NO: 75)
GYTFTSY Clone 6E9 VH CDR2 AA
(SEQ ID NO: 76)
DPSGGS Clone 6E9 VH CDR3 AA
(SEQ ID NO: 70)
DYGDYVFDY Clone 6E9 VL DNA Coding Sequence
(SEQ ID NO: 12)
CAAAGCGTACTGACACAGCCCCCGAGTGCATCCGGGACCCCCGGC

CAAAGGGTTACAATCAGCTGCTCTGGCAGCTCCAGTAACATAGGT

ACCAACACGGTGAACTGGTACCAGCAGTTGCCTGGCACAGCGCCT

CAGCTGCTCATCTATATCAACAATCAGCGGCCAAGTGGCGTGCCC

GATAGATTCTCAGGCTCAAAGAGCGGAACCAGCGCTAGCTTGGCA

ATCAGTGGCCTTCAATCCGAAGACGAAGCCGATTACTATTGTGCG

ACCTGGGACGATAGCCTGAACGGCCCCGTCGTGGGCGGCGGGACG

AAACTGACAGTGTTGGGC

Clone 6E9 VL AA (CDRs underlined)
(SEQ ID NO: 13)
QSVLTQPPSASGTPGQRVTISC<u>SGSSSNIGTNTVN</u>WYQQLPGTAP QLLIY<u>INNQRPS</u>GVPDRFSGSKSGTSASLAISGLQSEDEADYYC<u>A</u>

<u>TWDDSLNGPVV</u>GGGTKLTVLG

Clone 6E9 VL CDR1 AA
(SEQ ID NO: 59)
SGSSSNIGTNTVN

Clone 6E9 VL CDR2 AA
(SEQ ID NO: 60)
INNQRPS

Clone 6E9 VL CDR3 AA
(SEQ ID NO: 61)
ATWDDSLNGPVV

In one embodiment, the antigen binding molecules of the instant disclosure are antibodies and antigen binding fragments thereof (e.g., scFvs). In one embodiment, the antibodies and antigen binding molecules of the instant disclosure comprise at least one CDR set forth in FIG. 6. In another aspect, the instant disclosure provides hybridomas capable of producing the antibodies and antigen binding molecules disclosed herein, and also methods of producing antibodies from hybridomas, as described herein and as known in the art.

An antigen binding molecule of the instant disclosure can also be a humanized monoclonal antibody, from which an scFv can be generated, which can then form a component of a CAR or TCR provided herein. In one embodiment, a humanized monoclonal antibody comprises the variable domain of a murine or rabbit antibody (or all or part of the antigen binding site thereof) and a constant domain derived from a human antibody. Alternatively, a humanized antibody fragment can comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) *Nature* 332:323, Liu et al., (1987) *Proc. Nat. Acad. Sci.* USA 84:3439, Larrick et al., (1989) *Bio/Technology* 7:934, and Winter et al., (1993) *TIPS* 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J* 9:133-39; Tamura et al., (2000) *J. Immunol.* 164:1432-41; Zhang et al., (2005) *Mol. Immunol.* 42(12):1445-1451; Hwang et al., *Methods.* (2005) 36(1):35-42; Dall'Acqua et al., (2005) *Methods* 36(1):43-60; and Clark, (2000) *Immunology Today* 21(8):397-402.

An antigen binding molecule of the instant disclosure can also be a fully human monoclonal antibody, from which an scFv can be generated, which can then form a component of a CAR or TCR provided herein. Fully human monoclonal antibodies can be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) *Curr. Opin. Biotechnol.* 8:455-58).

Examples of techniques for production and use of transgenic animals for the production of human or partially human antibodies are described in U.S. Pat. Nos. 5,814,318, 5,569,825, and 5,545,806; Davis et al., *Antibody Engineering: Methods and Protocols*, (Lo, ed) Humana Press, NJ, 191-200 (2003); Kellermann et al., (2002) *Curr Opin Biotechnol.* 13:593-97; Russel et al., (2000) *Infect Immun.* 68:1820-26; Gallo et al., (2000) *Eur J. Immun.* 30:534-40; Davis et al., (1999) *Cancer Metastasis Rev.* 18:421-25; Green, (1999) *J Immunol Methods* 231:11-23; Jakobovits, (1998) *Advanced Drug Delivery Reviews* 31:33-42; Green et al., (1998) *J Exp Med.* 188:483-95; Jakobovits, (1998) *Exp. Opin. Invest. Drugs.* 7:607-14; Tsuda et al., (1997) *Genomics*, 42:413-21; Mendez et al., (1997) *Nat. Genet.* 15:146-56; Jakobovits, (1994) *Curr Biol.* 4:761-63; Arbones et al., (1994) *Immunity* 1:247-60; Green et al., (1994) *Nat. Genet.* 7:13-21; Jakobovits et al., (1993) *Nature* 362:255-58; Jakobovits et al., (1993) *Proc Natl Acad Sci USA* 90:2551-55; Chen et al., (1993) *Intl Immunol* 5:647-656; Choi et al., (1993) *Nature Genetics* 4:117-23; Fishwild et al., (1996) *Nature Biotechnology* 14:845-51; Lonberg et al., (1994) *Nature* 368: 856-59; Lonberg, (1994) *Handbook of Experimental Pharmacology* 113: 49-101; Neuberger, (1996) *Nature Biotech* 14:826; Taylor et al., (1992) *Nucleic Acids Research* 20:6287-95; Taylor et al., (1994) *Intl Immunol* 6:579-91; Tomizuka et al., (1997) *Nature Genetics* 16:133-43; Tomizuka et al., (2000) *Proc Nat Acad Sci* USA 97:722-27; Tuaillon et al., (1993) *Proc Nat Acad Sci* USA 90:3720-24; Tuaillon et al., (1994) *J Immunol* 152:2912-20; Lonberg et al., (1994) *Nature* 368:856; Taylor et al., (1994) *Intl Immunol* 6:579; U.S. Pat. No. 5,877,397; Bruggemann et al., (1997) *Curr. Opin. Biotechnol.* 8:455-58; Jakobovits et al., (1995) *Ann. N.Y. Acad. Sci.* 764:525-35.

An additional method for obtaining antigen binding molecules of the instant disclosure is by the use of phage display, which is well-established for this purpose. See, e.g., Winter et al., (1994) *Ann. Rev. Immunol.* 12:433-55; Burton et al., (1994) *Adv. Immunol* 57:191-280. Human or murine immunoglobulin variable region gene combinatorial libraries can be created in phage vectors that can be screened to select Ig fragments (Fab, Fv, sFv, or multimers thereof) that bind the scFv FMC63, as well as molecules comprising this sequence and cells presenting such molecules. See, e.g., U.S. Pat. No. 5,223,409; Huse et al., (1989) *Science* 246:1275-81; Sastry et al., (1989) *Proc. Natl. Acad. Sci.* USA 86:5728-32; Alting-Mees et al., (1990) *Strategies in Molecular Biology* 3:1-9; Kang et al., (1991) *Proc. Natl. Acad. Sci.* USA 88:4363-66; Hoogenboom et al., (1992) *J. Mol. Biol.* 227: 381-388; Schlebusch et al., (1997) *Hybridoma* 16:47-52 and references cited therein. For example, a library containing a plurality of polynucleotide sequences encoding Ig variable region fragments can be inserted into the genome of a filamentous bacteriophage, such as M13 or lambda phage (λImmunoZap™(H) and λImmunoZap™(L) vectors (Stratagene, La Jolla, Calif.) can also be used in this approach) or a variant thereof, in frame with the sequence encoding a phage coat protein.

Briefly, mRNA is isolated from a B-cell population, and used to create heavy and light chain immunoglobulin cDNA expression libraries in the λImmunoZap™(H) and λImmunoZap™(L) vectors. These vectors can be screened individually or co-expressed to form Fab fragments or antibodies. Positive plaques can subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers can be synthesized by one of ordinary skill in the art, or can be purchased from commercial sources, which also sell primers for mouse and human variable regions including, among others, primers for $V_H$, $V_L$, $C_H$ and $C_L$ regions). These primers can be used to amplify heavy or light chain variable regions, which can then be inserted into vectors. These vectors can then be introduced into *E. coli*, yeast, or mammalian-based systems for expression. Large amounts of a single-chain protein containing a fusion of the $V_H$ and $V_L$ domains can be produced using these methods.

Once cells producing the antigen binding molecules provided herein have been obtained using any of the above-described immunization and other techniques, the specific antibody genes can be cloned by isolating and amplifying DNA or mRNA therefrom according to standard procedures as described herein. The antibodies produced therefrom can be sequenced and the CDRs identified and the DNA coding for the CDRs can be manipulated as described so as to generate other antibodies according to the instant disclosure.

It will be understood by those of skill in the art that some proteins, such as antibodies, can undergo a variety of post-translational modifications. The type and extent of these modifications often depends on the host cell line used to express the protein as well as the culture conditions. Such modifications can include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in, e.g., Harris, (1995) *J Chromatog* 705:129-34).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, e.g., Baines and Thorpe, (1992) in *Methods in Molecular Biology,* 10:79-104 (The Humana Press). Monoclonal antibodies can be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, and an anti-idiotype antibody.

The instant disclosure provides antigen binding molecules (e.g., scFv's) that specifically bind to CD70, molecules comprising this sequence and cells presenting such molecules. Antigen binding molecules that cross compete with the antigen binding molecules disclosed herein form another aspect of the instant disclosure.

In some embodiments, an antigen binding molecule cross competes with a reference antibody comprising an amino acid sequence selected from the group consisting of SEQ ID NOs: 3, 5, 7, 9, 11 or 13. In some embodiments, the antigen binding molecule cross competes with a reference antibody, wherein the reference antibody comprises a VH CDR1 comprising an amino acid sequence of SEQ ID NOs: 62, 65, 68, 71, 73, 75, 77, 78 and 79.

In some embodiments, an antigen binding molecule cross competes with a reference antibody comprising an amino acid sequence selected from the group consisting of SEQ ID NOs: 3, 5, 7, 9, 11 or 13, wherein the reference antibody comprises a VH CDR2 comprising an amino acid sequence of SEQ ID NOs: 63, 66, 69, 72, 74, 76, 63, 66 and 69.

In some embodiments, an antigen binding molecule cross competes with a reference antibody comprising an amino acid sequence selected from the group consisting of SEQ ID NOs: 3, 5, 7, 9, 11 or 13, wherein the reference antibody comprises a VH CDR3 comprising an amino acid sequence of SEQ ID NOs: 64, 67, and 70.

In some embodiments, an antigen binding molecule cross competes with a reference antibody comprising an amino acid sequence selected from the group consisting of SEQ ID NOs: 3, 5, 7, 9, 11 or 13, wherein the reference antibody comprises a VL CDR1 comprising an amino acid sequence of SEQ ID NOs: 53, 56 and 59.

In some embodiments, an antigen binding molecule cross competes with a reference antibody comprising an amino acid sequence selected from the group consisting of SEQ ID NOs: 3, 5, 7, 9, 11 or 13, wherein the reference antibody comprises a VL CDR2 comprising an amino acid sequence of SEQ ID NOs: 54, 57 and 60.

In some embodiments, an antigen binding molecule cross competes with a reference antibody comprising an amino acid sequence selected from the group consisting of SEQ ID NOs: 3, 5, 7, 9, 11 or 13, wherein the reference antibody comprises a VL CDR3 comprising an amino acid sequence of SEQ ID NOs: 55, 58 and 61.

In some embodiments, an antibody or antigen binding molecule that specifically binds CD70, molecules comprising this sequence and cells presenting such molecules, binds the same or an overlapping epitope as a reference antibody disclosed herein (e.g., those comprising sequences presented herein, which can comprise a CDR presented in FIG. 6).

In some embodiments, the antibody or antigen binding molecule binds the same or an overlapping epitope as a reference antibody.

II.A. Clone 8G1

In some embodiments, an antigen binding molecule, such as an scFv, or antibody that specifically binds to CD70, molecules comprising this sequence and cells presenting such molecules, comprises a VH CDR1 comprising, consisting of, or consisting essentially of the amino acid sequence GFTFSSY (SEQ ID NO: 71).

In some embodiments, an antigen binding molecule, such as an scFv, or antibody that specifically binds to CD70, molecules comprising this sequence and cells presenting such molecules, comprises a VH CDR2 comprising, consisting of, or consisting essentially of the amino acid sequence WYDGSN (SEQ ID NO:72).

In some embodiments, an antigen binding molecule, such as an scFv, or antibody that specifically binds to CD70, molecules comprising this sequence and cells presenting such molecules, comprises a VH CDR3 comprising, consisting of, or consisting essentially of the amino acid sequence DLLRGVKGYAMDV (SEQ ID NO: 64).

In some embodiments, an antigen binding molecule, such as an scFv, or antibody that specifically binds to CD70, molecules comprising this sequence and cells presenting such molecules, comprises a heavy chain VH comprising: (a) a VH CDR1 comprising, consisting of, or consisting essentially of the amino acid sequence GFTFSSY (SEQ ID NO: 71); and/or (b) a VH CDR2 comprising, consisting of, or consisting essentially of the amino acid sequence WYDGSN (SEQ ID NO: 72); and/or (c) a VH CDR3 comprising, consisting of, or consisting essentially of the amino acid sequence DLLRGVKGYAMDV (SEQ ID NO: 64).

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise an amino acid sequence of a VH CDR1, VH CDR2, and VH CDR3 presented in FIG. 6.

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 of an antigen binding molecule presented in FIGS. 6 and 7A (SEQ ID NOs: 71, 72 and 64, respectively).

In some embodiments, the antibody or antigen binding molecule, such as an scFv, that specifically binds to CD70, molecules comprising this sequence and cells presenting such molecules, comprises a heavy chain variable region sequence comprising an amino acid sequence of FIG. 7A. In some embodiments, the antibody or antigen binding molecule comprises a heavy chain variable region sequence comprising SEQ ID NO: 3.

In some embodiments, the antibody or antigen binding molecule, such as an scFv, that specifically binds to CD70, molecules comprising this sequence and cells presenting such molecules, comprises one or more of any of the VH CDRs listed above or described in FIG. 6. In some embodiments, the antibody or antigen binding molecule comprises the VH framework regions (FRs) described herein. In specific embodiments, the antibody or antigen binding molecule comprises a VH FR as set forth in, or derivable from, the sequences presented in FIG. 7A (e.g., one, two, three, or four of the FRs in one sequence of FIG. 7A).

In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7A). In one embodiment, the antibody or antigen binding molecule comprises a heavy chain variable region comprising the amino acid sequence QEQLVES-GGGVVQPGRSLRLSCAASGFTFSSYG-MEIWVRQAPGKGLEWVAVTWYD GSNKYYGDSVKGRFTISRDNSKNTLYLQMNSLRAE-DTAVYYCARDLLRGVKGYA MDVWGQGTTVTVSS (SEQ ID NO: 3), encoded by the nucleic acid

```
                                            (SEQ ID NO: 2)
CAAGAGCAGCTGGTTGAGTCTGGGGGCGGCGTCGTCCAACCCGGCCGGA

GTCTGAGGTTGTCCTGCGCTGCAAGCGGATTTACATTTTCATCTTACGG

CATGCACTGGGTTAGGCAGGCTCCTGGAAAAGGGCTGGAGTGGGTCGCG

GTGACTTGGTACGACGGCTCCAATAAGTATTATGGGGATTCCGTGAAAG

GTCGATTCACAATTAGCAGGGATAACTCCAAAAACACACTGTATCTCCA

AATGAACTCCTTGAGGGCCGAGGACACGGCCGTCTATTATTGTGCAAGA

GACCTCCTCCGGGGCGTAAAGGGATATGCtATGGACGTGTGGGGTCAGG

GGACCACAGTTACTGTCAGTTCA.
```

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 3.

In some embodiments, an antigen binding molecule, such as an scFv, or antibody that specifically binds to CD70, molecules comprising this sequence and cells presenting such molecules, comprises a VL CDR1 comprising, consisting of, or consisting essentially of the amino acid sequence RASQSLRRIYLA (SEQ ID NO: 53).

In some embodiments, an antigen binding molecule, such as an scFv, or antibody that specifically binds to CD70, molecules comprising this sequence and cells presenting such molecules, comprises a VL CDR2 comprising, consisting of, or consisting essentially of the amino acid sequence DVFDRAT (SEQ ID NO: 54).

In some embodiments, an antigen binding molecule, such as an scFv, or antibody that specifically binds to CD70, molecules comprising this sequence and cells presenting such molecules, comprises a VL CDR3 comprising, consisting of, or consisting essentially of the amino acid sequence QQYSDSPFT (SEQ ID NO: 55).

In some embodiments, an antigen binding molecule, such as an scFv, or antibody that specifically binds to CD70, molecules comprising this sequence and cells presenting such molecules, comprises a heavy chain VL comprising: (a) a VL CDR1 comprising, consisting of, or consisting essentially of the amino acid sequence RASQSLRRIYLA (SEQ ID NO: 53); and/or (b) a VL CDR2 comprising, consisting of, or consisting essentially of the amino acid sequence DVFDRAT (SEQ ID NO: 54); and/or (c) a VL CDR3 comprising, consisting of, or consisting essentially of the amino acid sequence QQYSDSPFT (SEQ ID NO: 55).

In some embodiments, the antibody or antigen binding molecule, such as an scFv, that specifically binds to CD70, molecules comprising this sequence and cells presenting such molecules, wherein the antibody or antigen binding molecule comprises a VL CDR1, a VL CDR2, and VL CDR3, wherein the VL CDR1, VL CDR2, and VL CDR3 comprise the amino acid sequence of a VL CDR1, VL CDR2, and VL CDR3 presented in FIG. 6.

In some embodiments, the antibody or antigen binding molecule, such as an scFv, that specifically binds to CD70, molecules comprising this sequence and cells presenting such molecules, comprises a light chain variable region sequence comprising an amino acid sequence of FIG. 7B. In some embodiments, the antibody or antigen binding molecule comprises a light chain variable region sequence comprises SEQ ID NO: 5.

In some embodiments, the antibody or antigen binding molecule, such as an scFv, that specifically binds to CD70, molecules comprising this sequence and cells presenting such molecules, wherein the antibody or antigen binding molecule comprises the VL framework regions (FRs) described herein. In specific embodiments, the antibody or antigen binding molecule comprises the VL FRs of an amino acid sequence as set forth in, or derivable from, the sequences presented in FIG. 7B (e.g., one, two, three, or four of the FRs in one sequence of FIG. 7B).

In some embodiments, the antibody or antigen binding molecule, such as an scFv, that specifically binds to CD70, molecules comprising this sequence and cells presenting such molecules, comprises a light chain sequence disclosed herein (e.g., in FIG. 7B). In one embodiment, the antibody or antigen binding molecule comprises a light chain variable region comprising the amino acid sequence of EIVLTQSPGTLSLSPGERATLSCRASQSLRRIY-LAWYQQKPGQAPRLLIYDVFDRAT GIPDRFSGGGSGTDFTLTISRLEPEDFAVYYCQQYSD-SPFTFGPGTKVDIKR (SEQ ID NO: 5), encoded by the nucleic acid

```
                                            (SEQ ID NO: 4)
GAAATCGTTCTCACTCAGTCTCCGGGCACACTGTCCCTCAGCCCCGGAG

AGCGAGCCACTTTGAGCTGCCGGGCCAGCCAGTCACTTAGACGCATTTA

TTTGGCCTGGTATCAGCAGAAACCAGGCCAGGCGCCCAGGCTGCTGATA

TACGATGTGTTCGATAGGGCCACGGGTATCCCCGATAGGTTCTCTGGCG

GGGGGTCCGGGACTGACTTCACCCTCACTATATCACGACTCGAGCCCGA
```

-continued

```
AGACTTCGCAGTTTATTATTGCCAGCAGTACTCCGACTCCCCATTCACC

TTCGGCCCTGGTACCAAAGTGGATATTAAACGG.
```

In various embodiments, the light chain variable region is 80%, 85%, 90%, 91%, 92%, 93%, 94%, 95%, 96%, 97%, 98% or 99% identical to the light chain variable region sequence of SEQ ID NO: 4.

In some embodiments, the antibody or antigen binding molecule, such as an scFv, that specifically binds to CD70, molecules comprising this sequence and cells presenting such molecules, comprises any one, two, and/or three VH CDR sequences disclosed herein. In some embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In some embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule, such as an scFv, that specifically binds to CD70, molecules comprising this sequence and cells presenting such molecules, comprises: (a) a VH CDR1 region comprising the amino acid sequence of SEQ ID NO: 71; (b) a VH CDR2 region comprising the amino acid sequence of SEQ ID NO: 72; (c) a VH CDR3 region comprising the amino acid sequence of SEQ ID NO: 64; (d) a VL CDR1 region comprising the amino acid sequence of SEQ ID NO: 53; (e) a VL CDR2 region comprising the amino acid sequence of SEQ ID NO: 54; and (f) a VL CDR3 region comprising the amino acid sequence of SEQ ID NO: 55.

In one embodiment, the antibody or antigen binding molecule, such as an scFv, that specifically binds to CD70, molecules comprising this sequence and cells presenting such molecules, comprises: (a) a VH CDR1 region; (b) a VH CDR2 region; (c) a VH CDR3 region; (d) a VL CDR1 region comprising; (e) a VL CDR2 region; and (f) a VL CDR3 region, wherein the VH and VL CDRs are shown in FIGS. 7A and 7B, respectively, and in FIG. 6.

In some embodiments, the antibody or antigen binding molecule, such as an scFv, that specifically binds to CD70, molecules comprising this sequence and cells presenting such molecules, comprises a heavy chain variable region sequence disclosed herein (e.g., in FIG. 7A) and a light chain variable region sequence disclosed herein (e.g., in FIG. 7B).

In one embodiment, the antibody or antigen binding molecule, such as an scFv, comprises: (a) a heavy chain variable region comprising the amino acid sequence of SEQ ID NO: 3; and (b) a light chain variable region comprising the amino acid sequence of SEQ ID NO: 5. Nucleotide sequences encoding the heavy chain variable region and the light chain variable regions are provided herein and in FIGS. 7A and 7B, respectively In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7A) and a light chain sequence disclosed herein (e.g., in FIG. 7B).

In one embodiment, the antibody or antigen binding molecule, such as an scFv, comprises: (a) a heavy chain variable region comprising the amino acid sequence of QEQLVESGGGVVQPGRSLRLS-
CAASGFTFSSYGMHWVRQAPGKGLEWVAVTWYD
GSNKYYGDSVKGRFTISRDNSKNTLYLQMNSLRAE-
DTAVYYCARDLLRGVKGYA MDVWGQGTTVTVSS
(SEQ ID NO: 3); and (b) a light chain variable region comprising the amino acid sequence of

```
                                                  (SEQ ID NO: 5)
EIVLTQSPGTLSLSPGERATLSCRASQSLRRIYLAWYQQKPGQAPRLLIY

DVFDRATGIPDRFSGGGSGTDFTLTISRLEPEDFAVYYCQQYSDSPFTFG

PGTKVDIKR.
```

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 3; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 5.

II.B. Clone 1C8

In some embodiments, an antigen binding molecule, such as an scFv, or antibody that specifically binds to CD70, molecules comprising this sequence and cells presenting such molecules, comprises a VH CDR1 comprising, consisting of, or consisting essentially of the amino acid sequence GDSIISGGY (SEQ ID NO: 73).

In some embodiments, an antigen binding molecule, such as an scFv, or antibody that specifically binds to CD70, molecules comprising this sequence and cells presenting such molecules, comprises a VH CDR2 comprising, consisting of, or consisting essentially of the amino acid sequence FYSGS (SEQ ID NO:74).

In some embodiments, an antigen binding molecule, such as an scFv, or antibody that specifically binds to CD70, molecules comprising this sequence and cells presenting such molecules, comprises a VH CDR3 comprising, consisting of, or consisting essentially of the amino acid sequence SGYSYALFDH (SEQ ID NO: 67).

In some embodiments, an antigen binding molecule, such as an scFv, or antibody that specifically binds to CD70, molecules comprising this sequence and cells presenting such molecules, comprises a heavy chain VH comprising: (a) a VH CDR1 comprising, consisting of, or consisting essentially of the amino acid sequence GDSIISGGY (SEQ ID NO: 73); and/or (b) a VH CDR2 comprising, consisting of, or consisting essentially of the amino acid sequence FYSGS (SEQ ID NO: 74); and/or (c) a VH CDR3 comprising, consisting of, or consisting essentially of the amino acid sequence SGYSYALFDH (SEQ ID NO: 67).

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise an amino acid sequence of a VH CDR1, VH CDR2, and VH CDR3 presented in FIGS. 6 and 7C.

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 of an antigen binding molecule presented in FIG. 7C (SEQ ID NOs: 73, 74 and 67, respectively).

In some embodiments, the antibody or antigen binding molecule, such as an scFv, that specifically binds to CD70, molecules comprising this sequence and cells presenting such molecules, comprises a heavy chain variable region sequence comprising an amino acid sequence of FIG. 7C. In some embodiments, the antibody or antigen binding molecule comprises a heavy chain variable region sequence comprising SEQ ID NO: 7.

In some embodiments, the antibody or antigen binding molecule, such as an scFv, that specifically binds to CD70, molecules comprising this sequence and cells presenting such molecules, comprises one or more of any of the VH CDRs listed above or described in FIG. 6. In some embodiments, the antibody or antigen binding molecule comprises the VH framework regions (FRs) described herein. In specific embodiments, the antibody or antigen binding molecule comprises a VH FR as set forth in, or derivable from, the sequences presented in FIG. 7C (e.g., one, two, three, or four of the FRs in one sequence of FIG. 7C).

In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7C). In one embodiment, the antibody or antigen binding molecule comprises a heavy chain variable region comprising the amino acid sequence QVQLQESGPGLVKPSQTLSLTCTVSGDSIISG-GYYWSWIRQHPGKGLEWIGYIFYSG STDYNPSLKSRVTISVDTSKNQFSLKLSSVTAAD-TAVYYCARSGYSYALFDHWGQG TLVTVSS (SEQ ID NO: 7), encoded by the nucleic acid

```
                                            (SEQ ID NO: 6)
CAGGTGCAGCTCCAAGAATCTGGACCGGGTCTCGTCAAGCCATCACAGAC

ACTGTCCCTGACCTGCACCGTCTCCGGCGACTCTATCATTTCAGGCGGCT

ACTATTGGTCCTGGATTAGACAACATCCGGGAAAGGGTCTTGAATGGATC

GGCTATATTTTCTACAGCGGGAGTACGGATTACAATCCTAGTCTCAAGAG

CCGCGTTACCATTTCAGTGGATACTTCAAAAAACCAGTTTAGCCTGAAGC

TGTCTTCTGTAACAGCTGCTGACACAGCCGTGTACTATTGCGCCAGGAGC

GGCTACAGCTATGCCCTGTTTGACCACTGGGGGCAAGGCACTCTTGTGAC

GGTGTCAAGT.
```

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:7C.

In some embodiments, an antigen binding molecule, such as an scFv, or antibody that specifically binds to CD70, molecules comprising this sequence and cells presenting such molecules, comprises a VL CDR1 comprising, consisting of, or consisting essentially of the amino acid sequence RASQFIGRYFN (SEQ ID NO: 56).

In some embodiments, an antigen binding molecule, such as an scFv, or antibody that specifically binds to CD70, molecules comprising this sequence and cells presenting such molecules, comprises a VL CDR2 comprising, consisting of, or consisting essentially of the amino acid sequence AESSLQS (SEQ ID NO: 57).

In some embodiments, an antigen binding molecule, such as an scFv, or antibody that specifically binds to CD70, molecules comprising this sequence and cells presenting such molecules, comprises a VL CDR3 comprising, consisting of, or consisting essentially of the amino acid sequence QQSYSTPFT (SEQ ID NO: 58).

In some embodiments, an antigen binding molecule, such as an scFv, or antibody that specifically binds to CD70, molecules comprising this sequence and cells presenting such molecules, comprises a heavy chain VL comprising: (a) a VL CDR1 comprising, consisting of, or consisting essentially of the amino acid sequence RASQFIGRYFN (SEQ ID NO: 56); and/or (b) a VL CDR2 comprising, consisting of, or consisting essentially of the amino acid sequence AESSLQS (SEQ ID NO: 57); and/or (c) a VL CDR3 comprising, consisting of, or consisting essentially of the amino acid sequence QQSYSTPFT (SEQ ID NO: 58).

In some embodiments, the antibody or antigen binding molecule, such as an scFv, that specifically binds to CD70, molecules comprising this sequence and cells presenting such molecules, wherein the antibody or antigen binding molecule comprises a VL CDR1, a VL CDR2, and VL CDR3, wherein the VL CDR1, VL CDR2, and VL CDR3 comprise the amino acid sequence of a VL CDR1, VL CDR2, and VL CDR3 presented in FIGS. 6 and 7D.

In some embodiments, the antibody or antigen binding molecule, such as an scFv, that specifically binds to CD70, molecules comprising this sequence and cells presenting such molecules, comprises a light chain variable region sequence comprising an amino acid sequence of FIG. 7D. In some embodiments, the antibody or antigen binding molecule comprises a light chain variable region sequence comprises SEQ ID NO: 9.

In some embodiments, the antibody or antigen binding molecule, such as an scFv, that specifically binds to CD70, molecules comprising this sequence and cells presenting such molecules, wherein the antibody or antigen binding molecule comprises the VL framework regions (FRs) described herein. In specific embodiments, the antibody or antigen binding molecule comprises the VL FRs of an amino acid sequence as set forth in, or derivable from, the sequences presented in FIG. 7D (e.g., one, two, three, or four of the FRs in one sequence of FIG. 7D).

In some embodiments, the antibody or antigen binding molecule, such as an scFv, that specifically binds to CD70, molecules comprising this sequence and cells presenting such molecules, comprises a light chain sequence disclosed herein (e.g., in FIG. 7D). In one embodiment, the antibody or antigen binding molecule comprises a light chain variable region comprising the amino acid sequence of DIQMTQSPSSLSASVGDRVTISCRASQFI-GRYFNWYQQQPGKAPKVLIYAESSLQSG VPSRFSGSGSGTEFTLTISSLQPEDFARYYCQQSYS-TPFTFGQGTKVEIKR (SEQ ID NO: 9), encoded by the nucleic acid

```
                                            (SEQ ID NO: 8)
GACATTCAAATGACGCAGTCCCCAAGTTCTCTGTCCGCTAGCGTCGGCGA

CCGAGTGACCATCAGCTGCCGAGCATCCCAGTTTATCGGTAGATATTTCA

ATTGGTACCAGCAACAACCGGGCAAAGCGCCCAAGGTCCTGATCTACGCT

GAGAGCAGTCTGCAATCCGGCGTACCTAGCAGGTTCTCCGGAAGTGGCAG

CGGAACCGAGTTCACCCTGACAATTAGCTCCTTGCAGCCCGAGGATTTCG
```

-continued

```
CTCGCTATTACTGTCAACAGAGTTATTCAACCCCTTTTACATTCGGACAG

GGAACTAAAGTTGAAATTAAGAGG.
```

In various embodiments, the light chain variable region is 80%, 85%, 90%, 91%, 92%, 93%, 94%, 95%, 96%, 97%, 98% or 99% identical to the light chain variable region sequence of SEQ ID NO: 9.

In some embodiments, the antibody or antigen binding molecule, such as an scFv, that specifically binds to CD70, molecules comprising this sequence and cells presenting such molecules, comprises any one, two, and/or three VH CDR sequences disclosed herein. In some embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In some embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule, such as an scFv, that specifically binds to CD70, molecules comprising this sequence and cells presenting such molecules, comprises: (a) a VH CDR1 region comprising the amino acid sequence of SEQ ID NO: 73; (b) a VH CDR2 region comprising the amino acid sequence of SEQ ID NO: 74; (c) a VH CDR3 region comprising the amino acid sequence of SEQ ID NO: 67; (d) a VL CDR1 region comprising the amino acid sequence of SEQ ID NO: 56; (e) a VL CDR2 region comprising the amino acid sequence of SEQ ID NO: 57; and (f) a VL CDR3 region comprising the amino acid sequence of SEQ ID NO: 58.

In one embodiment, the antibody or antigen binding molecule, such as an scFv, that specifically binds to CD70, molecules comprising this sequence and cells presenting such molecules, comprises: (a) a VH CDR1 region; (b) a VH CDR2 region; (c) a VH CDR3 region; (d) a VL CDR1 region comprising; (e) a VL CDR2 region; and (f) a VL CDR3 region, wherein the VH and VL CDRs are shown in FIGS. 7C and 7D, respectively, and in FIG. 6.

In some embodiments, the antibody or antigen binding molecule, such as an scFv, that specifically binds to CD70, molecules comprising this sequence and cells presenting such molecules, comprises a heavy chain variable region sequence disclosed herein (e.g., in FIG. 7C) and a light chain variable region sequence disclosed herein (e.g., in FIG. 7D).

In one embodiment, the antibody or antigen binding molecule, such as an scFv, comprises: (a) a heavy chain variable region comprising the amino acid sequence of SEQ ID NO: 7; and (b) a light chain variable region comprising the amino acid sequence of SEQ ID NO: 9. Nucleotide sequences encoding the heavy chain variable region and the light chain variable regions are provided herein and in FIGS. 7C and 7D, respectively.

In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7C) and a light chain sequence disclosed herein (e.g., in FIG. 7D).

In one embodiment, the antibody or antigen binding molecule, such as an scFv, comprises: (a) a heavy chain variable region comprising the amino acid sequence of QVQLQESGPGLVKPSQTLSLTCTVSGDSIISG-GYYWSWIRQHPGKGLEWIGYIFYSG STDYNPSLKSRVTISVDTSKNQFSLKLSSVTAAD-TAVYYCARSGYSYALFDHWGQG TLVTVSS (SEQ ID NO: 7); and (b) a light chain variable region comprising the amino acid sequence of

```
                                              (SEQ ID NO: 9)
DIQMTQSPSSLSASVGDRVTISCRASQFIGRYFNWYQQQPGKAPKVLIYA

ESSLQSGVPSRFSGSGSGTEFTLTISSLQPEDFARYYCQQSYSTPFTFGQ

GTKVEIKR.
```

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 7; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 9.

II.C. Clone 6E9

In some embodiments, an antigen binding molecule, such as an scFv, or antibody that specifically binds to CD70, molecules comprising this sequence and cells presenting such molecules, comprises a VH CDR1 comprising, consisting of, or consisting essentially of the amino acid sequence GYTFTSY (SEQ ID NO: 75).

In some embodiments, an antigen binding molecule, such as an scFv, or antibody that specifically binds to CD70, molecules comprising this sequence and cells presenting such molecules, comprises a VH CDR2 comprising, consisting of, or consisting essentially of the amino acid sequence DPSGGS (SEQ ID NO: 76).

In some embodiments, an antigen binding molecule, such as an scFv, or antibody that specifically binds to CD70, molecules comprising this sequence and cells presenting such molecules, comprises a VH CDR3 comprising, consisting of, or consisting essentially of the amino acid sequence DYGDYVFDY (SEQ ID NO: 70).

In some embodiments, an antigen binding molecule, such as an scFv, or antibody that specifically binds to CD70, molecules comprising this sequence and cells presenting such molecules, comprises a heavy chain VH comprising: (a) a VH CDR1 comprising, consisting of, or consisting essentially of the amino acid sequence GYTFTSY (SEQ ID NO: 75); and/or (b) a VH CDR2 comprising, consisting of, or consisting essentially of the amino acid sequence DPSGGS (SEQ ID NO: 76); and/or (c) a VH CDR3 comprising, consisting of, or consisting essentially of the amino acid sequence DYGDYVFDY (SEQ ID NO: 70).

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise an amino acid sequence of a VH CDR1, VH CDR2, and VH CDR3 presented in FIGS. 6 and 7E.

In some embodiments, the antibody or antigen binding molecule, such as an scFv, that specifically binds to CD70, molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 of an antigen binding molecule presented in FIG. 7E (SEQ ID NOs: 75, 76 and 70, respectively).

In some embodiments, the antibody or antigen binding molecule, such as an scFv, that specifically binds to CD70, molecules comprising this sequence and cells presenting such molecules, comprises a heavy chain variable region sequence comprising an amino acid sequence of FIG. 7E. In some embodiments, the antibody or antigen binding molecule comprises a heavy chain variable region sequence comprising SEQ ID NO: 11.

In some embodiments, the antibody or antigen binding molecule, such as an scFv, that specifically binds to CD70, molecules comprising this sequence and cells presenting such molecules, comprises one or more of any of the VH CDRs listed above or described in FIG. 6. In some embodiments, the antibody or antigen binding molecule comprises the VH framework regions (FRs) described herein. In specific embodiments, the antibody or antigen binding molecule comprises a VH FR as set forth in, or derivable from, the sequences presented in FIG. 7E (e.g., one, two, three, or four of the FRs in one sequence of FIG. 7E).

In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7E). In one embodiment, the antibody or antigen binding molecule comprises a heavy chain variable region comprising the amino acid sequence QVHLVQSGAEVKKPGASVRVSCKASGYTFT-SYYLHWVRQAPGQGLEWMGIVDPS GGST-SYDQKFQGRFTMTRDTSTSTVYMELSSLRSED-TAVYYCARDYGDYVFDYW GQGTLVTVSS (SEQ ID NO: 11), encoded by the nucleic acid

```
                                         (SEQ ID NO: 10)
CAGGTACACCTGGTGCAGAGCGGGGCGGAGGTCAAGAAACCGGGCGCATC

CGTACGCGTGAGCTGCAAGGCCTCCGGATACACTTTTACTTCTTACTATC

TGCATTGGGTCAGGCAGGCACCGGGTCAGGGACTGGAGTGGATGGGCATT

GTGGACCCAAGCGGAGGGAGTACGTCATATGATCAGAAGTTTCAAGGTAG

GTTTACCATGACACGGGACACGTCAACGAGTACCGTCTACATGGAGCTCA

GTAGTCTGCGGAGCGAAGACACCGCAGTCTACTACTGCGCACGCGATTAT

GGAGACTATGTCTTTGACTATTGGGGCAGGGGACGCTCGTGACCGTTTC

AAGC.
```

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 7E.

In some embodiments, an antigen binding molecule, such as an scFv, or antibody that specifically binds to CD70, molecules comprising this sequence and cells presenting such molecules, comprises a VL CDR1 comprising, consisting of, or consisting essentially of the amino acid sequence SGSSSNIGTNTVN (SEQ ID NO: 59).

In some embodiments, an antigen binding molecule, such as an scFv, or antibody that specifically binds to CD70, molecules comprising this sequence and cells presenting such molecules, comprises a VL CDR2 comprising, consisting of, or consisting essentially of the amino acid sequence INNQRPS (SEQ ID NO: 60).

In some embodiments, an antigen binding molecule, such as an scFv, or antibody that specifically binds to CD70, molecules comprising this sequence and cells presenting such molecules, comprises a VL CDR3 comprising, consisting of, or consisting essentially of the amino acid sequence ATWDDSLNGPVV (SEQ ID NO: 61).

In some embodiments, an antigen binding molecule, such as an scFv, or antibody that specifically binds to CD70, molecules comprising this sequence and cells presenting such molecules, comprises a heavy chain VL comprising: (a) a VL CDR1 comprising, consisting of, or consisting essentially of the amino acid sequence SGSSSNIGTNTVN (SEQ ID NO: 59); and/or (b) a VL CDR2 comprising, consisting of, or consisting essentially of the amino acid sequence INNQRPS (SEQ ID NO: 60); and/or (c) a VL CDR3 comprising, consisting of, or consisting essentially of the amino acid sequence ATWDDSLNGPVV (SEQ ID NO: 61).

In some embodiments, the antibody or antigen binding molecule, such as an scFv, that specifically binds to CD70, molecules comprising this sequence and cells presenting such molecules, wherein the antibody or antigen binding molecule comprises a VL CDR1, a VL CDR2, and VL CDR3, wherein the VL CDR1, VL CDR2, and VL CDR3 comprise the amino acid sequence of a VL CDR1, VL CDR2, and VL CDR3 presented in FIGS. 6 and 7F.

In some embodiments, the antibody or antigen binding molecule, such as an scFv, that specifically binds to CD70, molecules comprising this sequence and cells presenting such molecules, comprises a light chain variable region sequence comprising an amino acid sequence of FIG. 7F. In some embodiments, the antibody or antigen binding molecule comprises a light chain variable region sequence comprises SEQ ID NO: 13.

In some embodiments, the antibody or antigen binding molecule, such as an scFv, that specifically binds to CD70, molecules comprising this sequence and cells presenting such molecules, wherein the antibody or antigen binding molecule comprises the VL framework regions (FRs) described herein. In specific embodiments, the antibody or antigen binding molecule comprises the VL FRs of an amino acid sequence as set forth in, or derivable from, the sequences presented in FIG. 7F (e.g., one, two, three, or four of the FRs in one sequence of FIG. 7F).

In some embodiments, the antibody or antigen binding molecule, such as an scFv, that specifically binds to CD70, molecules comprising this sequence and cells presenting such molecules, comprises a light chain sequence disclosed herein (e.g., in FIG. 7F). In one embodiment, the antibody or antigen binding molecule comprises a light chain variable region comprising the amino acid sequence of QSVLTQPP-SASGTPGQRVTISCSGSSSNIGTNTVNWYQQLPGTAP-QLLIYINNQRPSG VPDRFSGSKSGTSASLAIS-GLQSEDEADYYCATWDDSLNGPVVGGGTKLTVLG (SEQ ID NO: 13), encoded by the nucleic acid

```
                                         (SEQ ID NO: 12)
CAAAGCGTACTGACACAGCCCCCGAGTGCATCCGGGACCCCCGGCCAAAG

GGTTACAATCAGCTGCTCTGGCAGCTCCAGTAACATAGGTACCAACACGG

TGAACTGGTACCAGCAGTTGCCTGGCACAGCGCCTCAGCTGCTCATCTAT

ATCAACAATCAGCGGCCAAGTGGCGTGCCCGATAGATTCTCAGGCTCAAA

GAGCGGAACCAGCGCTAGCTTGGCAATCAGTGGCCTTCAATCCGAAGACG

AAGCCGATTACTATTGTGCGACCTGGGACGATAGCCTGAACGGCCCCGTC

GTGGGCGGCGGGACGAAACTGACAGTGTTGGGC.
```

In various embodiments, the light chain variable region is 80%, 85%, 90%, 91%, 92%, 93%, 94%, 95%, 96%, 97%, 98% or 99% identical to the light chain variable region sequence of SEQ ID NO:13.

In some embodiments, the antibody or antigen binding molecule, such as an scFv, that specifically binds to CD70, molecules comprising this sequence and cells presenting such molecules, comprises any one, two, and/or three VH CDR sequences disclosed herein. In some embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In some embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule, such as an scFv, that specifically binds to CD70, molecules comprising this sequence and cells presenting such molecules, comprises: (a) a VH CDR1 region comprising the amino acid sequence of SEQ ID NO: 75; (b) a VH CDR2 region comprising the amino acid sequence of SEQ ID NO: 76; (c) a VH CDR3 region comprising the amino acid sequence of SEQ ID NO: 70; (d) a VL CDR1 region comprising the amino acid sequence of SEQ ID NO: 59; (e) a VL CDR2 region comprising the amino acid sequence of SEQ ID NO: 60; and (f) a VL CDR3 region comprising the amino acid sequence of SEQ ID NO: 61.

In one embodiment, the antibody or antigen binding molecule, such as an scFv, that specifically binds to CD70, molecules comprising this sequence and cells presenting such molecules, comprises: (a) a VH CDR1 region; (b) a VH CDR2 region; (c) a VH CDR3 region; (d) a VL CDR1 region comprising; (e) a VL CDR2 region; and (f) a VL CDR3 region, wherein the VH and VL CDRs are shown in FIGS. 7E and 7F, respectively, and in FIG. 6.

In some embodiments, the antibody or antigen binding molecule, such as an scFv, that specifically binds to CD70, molecules comprising this sequence and cells presenting such molecules, comprises a heavy chain variable region sequence disclosed herein (e.g., in FIG. 7E) and a light chain variable region sequence disclosed herein (e.g., in FIG. 7F).

In one embodiment, the antibody or antigen binding molecule, such as an scFv, comprises: (a) a heavy chain variable region comprising the amino acid sequence of SEQ ID NO: 11; and (b) a light chain variable region comprising the amino acid sequence of SEQ ID NO: 13. Nucleotide sequences encoding the heavy chain variable region and the light chain variable regions are provided herein and in FIGS. 7E and 7F, respectively In some embodiments, the antibody or antigen binding molecule, such as an scFv, that specifically binds to CD70, molecules comprising this sequence and cells presenting such molecules, comprises a heavy chain sequence disclosed herein (e.g., in FIG. 7E) and a light chain sequence disclosed herein (e.g., in FIG. 7F).

In one embodiment, the antibody or antigen binding molecule, such as an scFv, comprises: (a) a heavy chain variable region comprising the amino acid sequence of QVHLVQSGAEVKKPGASVRVSCKASGYTFT-SYYLHWVRQAPGQGLEWMGIVDPS GGST-SYDQKFQGRFTMTRDTSTSTVYMELSSLRSED-TAVYYCARDYGDYVFDYW GQGTLVTVSS (SEQ ID NO: 11); and (b) a light chain variable region comprising the amino acid sequence of

```
                                            (SEQ ID NO: 13)
QSVLTQPPSASGTPGQRVTISCSGSSSNIGTNTVNWYQQLPGTAPQLLIY

INNQRPSGVPDRFSGSKSGTSASLAISGLQSEDEADYYCATWDDSLNGPV

VGGGTKLTVLG.
```

In one embodiment, the antibody or antigen binding molecule, such as an scFv, comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 11; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 13.

III. Polynucleotides Encoding Antigen Binding Molecules, Chimeric Antigen Receptors and T Cell Receptors Comprising Such Antigen Binding Molecules The instant disclosure is also directed to polynucleotides encoding antibodies and antigen binding molecules, such as an scFv, that specifically bind to CD70, molecules comprising this sequence and cells presenting such molecules.

In some embodiments, a polynucleotide of the instant disclosure encodes an antigen binding molecule, such as an scFv, wherein the antigen binding molecule comprises a heavy chain variable region amino acid sequence that is at least about 75%, at least about 85%, at least about 85%, at least about 90%, at least about 95%, at least about 96%, at least about 97%, at least about 98%, at least about 99%, or 100% identical to a heavy chain variable region amino acid sequence selected from the group consisting of SEQ ID NOs: 3, 7, and 11.

In some embodiments, a polynucleotide of the instant disclosure encodes antigen binding molecule, such as an scFv, wherein the antigen binding molecule comprises a light chain variable amino acid sequence that is at least about 75%, at least about 85%, at least about 85%, at least about 90%, at least about 95%, at least about 96%, at least about 97%, at least about 98%, at least about 99%, or 100% identical to a light chain variable region amino acid sequence selected from the group consisting of SEQ ID NOs: 5, 9 and 13.

In some embodiments, the polynucleotide comprises a heavy chain coding sequence selected from the group consisting of SEQ ID NOs: 2, 6 and 10.

In another embodiment, the polynucleotide comprises a light chain coding sequence selected from the group consisting of SEQ ID NOs: 4, 8 and 12.

In another embodiment, the polynucleotide comprises a heavy chain coding sequence comprising SEQ ID NO: 2 and a light chain coding sequence comprising SEQ ID NO: 4.

In another embodiment, the polynucleotide comprises a heavy chain coding sequence comprising SEQ ID NO: 6 and a light chain coding sequence comprising SEQ ID NO: 8.

In another embodiment, the polynucleotide comprises a heavy chain coding sequence comprising SEQ ID NO: 10 and a light chain coding sequence comprising SEQ ID NO: 12.

As will be appreciated by those of skill in the art, variations of the disclosed polynucleotide sequences are possible due to the degeneracy of the genetic code. Such variants of the disclosed polynucleotide sequences thus form an aspect of the instant disclosure.

IV. Chimeric Antigen Receptors and T Cell Receptors

The instant disclosure is also directed to chimeric antigen receptors (CARs) or T cell receptors (TCRs) comprising an antigen binding molecule, such as an scFv, that specifically binds to CD70 described herein, and engineered T cells comprising an antigen binding molecule that specifically binds to CD70 described herein. In some embodiments, an anti-CD70 CAR or TCR of the instant disclosure comprises an antigen binding molecule that specifically binds to CD70. In some embodiments, the anti-CD70 CAR or TCR further comprises a costimulatory domain, and/or an extracellular domain (i.e., a "hinge" or "spacer" region), and/or a transmembrane domain, and/or an intracellular (signaling) domain, and/or a CD3 zeta activating domain. In some embodiments, the anti-CD70 CAR or TCR comprises an scFv antigen binding molecule that specifically binds CD70 (e.g., hCD70) disclosed herein, a costimulatory domain, an extracellular domain, a transmembrane domain, and a CD3 zeta activating domain.

In some embodiments, a TCR of the instant disclosure comprises an antigen binding molecule that specifically binds to CD70, and wherein the TCR further comprises a fourth complementarity determining region (CDR4). In some embodiments, the TCR comprises an antigen binding molecule that specifically binds to CD70, and a constant region. In some embodiments, the constant region is selected from a constant region of IgG1, IgG2, IgG3, IgG4, IgA, IgD, IgE, and IgM. CAR and TCR design is discussed further below.

It will further be appreciated that where desired, the various domains and regions described herein can be expressed in a separate chain from the antigen binding molecule (e.g., scFv) and activating domains, in so-called "trans" configuration. Thus, in one embodiment an activating domain can be expressed on one chain, while the antigen binding molecule, and/or an extracellular domain, and/or a transmembrane domain and/or a costimulatory domain (depending on the desired construction of the CAR or TCR) can be expressed on a separate chain.

As described more fully herein, it will be further appreciated that the N to C-terminal, or extracellular to intracellular, order of the components of a CAR of the instant disclosure can be varied as desired. The antigen binding molecule (the scFv) will be extracellular in order to associated with the target antigen, and can include a leader or signal peptide at the N terminal end the scFv that is most distal to the cell membrane. A preferred orientation and ordering for a CAR of the instant disclosure is: optional leader sequence (e.g., the leader sequence of CD8a)—anti-CD70 scFv—optional mini-linker, such as GSG or AAA-hinge—optional mini-linker, such as GSG or AAA—transmembrane region (e.g., CD8a transmembrane region)—optional mini-linker, such as GSG or AAA—costimulatory region (e.g., CD28T or a subsequence of 4-1BB)—optional mini-linker, such as GSG or AAA—activation domain (e.g., a CD3 zeta domain, such as one of those provided herein).

Another preferred orientation and ordering for a CAR of the instant disclosure comprises two costimulatory domains and is: optional leader sequence (e.g., the leader sequence of CD8a)—anti-CD70 scFv—optional mini-linker, such as GSG or AAA-hinge—optional mini-linker, such as GSG or AAA—transmembrane region (e.g., CD8a transmembrane region)—optional mini-linker, such as GSG or AAA—costimulatory region (e.g., CD28T or a subsequence of 4-1BB)—costimulatory region (e.g., CD28T or a subsequence of 4-1BB)—optional mini-linker, such as GSG or AAA—activation domain (e.g., a CD3 zeta domain, such as one of those provided herein).

A more detailed description of the components of a CAR are provided below.

IV.A. Extracellular or "Hinge" Domain

In one embodiment, a CAR or TCR of the instant disclosure comprises an "extracellular" or "hinge" or "spacer" domain or region, which terms are used interchangeably herein. In another embodiment, an extracellular domain is from or derived from (e.g., comprises all or a fragment of) CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. An "extracellular" or "hinge" or "spacer" domain or region can be derived either from a natural or from a synthetic source.

In some embodiments, an "extracellular" or "hinge" or "spacer" domain or region is positioned between an antigen binding molecule (e.g., an scFv) and a transmembrane domain. In this orientation the hinge domain provides distance between the antigen binding molecule and the surface of a cell membrane on which the CAR or TCR is expressed. In some embodiments, an "extracellular" or "hinge" or "spacer" domain or region is from or derived from an immunoglobulin. In some embodiments, an "extracellular" or "hinge" or "spacer" domain or region is selected from the hinge regions of IgG1, IgG2, IgG3, IgG4, IgA, IgD, IgE, and IgM, or a fragment thereof. In other embodiments, an "extracellular" or "hinge" or "spacer" domain or region comprises, is from, or is derived from the hinge region of CD8 alpha. In some embodiments, an "extracellular" or "hinge" or "spacer" domain or region comprises, is from, or is derived from the hinge region of CD28T. In some embodiments, an "extracellular" or "hinge" or "spacer" domain or region comprises a fragment of the hinge region of CD8 alpha or a fragment of the hinge region of CD28T, wherein the fragment is anything less than the whole hinge region. In some embodiments, the fragment of the CD8 alpha hinge region or the fragment of the CD28 hinge region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge region, or of the CD28T hinge region.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence LDNEKSNGTIIHVKGKHLCPSPLFPGPSKPF-WVLVVVGGVLACYSLLVTVAFIIFWV (SEQ ID NO: 15) or a fragment thereof. In some embodiments, an "extracellular" or "hinge" or "spacer" domain or region comprises the amino acid sequence of SEQ ID NO: 15 or a fragment thereof.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence LDNEKSNGTIIHVKGKHLCPSPLFPGPSKP (SEQ ID NO: 15) or a fragment thereof. In some embodiments, an "extracellular" or "hinge" or "spacer" domain or region comprises the amino acid sequence of SEQ ID NO: 83, or a fragment thereof.

In some embodiments, an "extracellular" or "hinge" or "spacer" domain or region is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence CTTGATAATGAAAAGTCAAACGGAACAATCATT-CACGTGAAGGGCAAGCACCT CTGTCCGT-CACCCTTGTTCCCTGGTCCATCCAAGCCAT-TCTGGGTGTTGGTCGTA GTGGGTGGAGTCCTCGCTTGTTACTCTCTGCTCGT-CACCGTGGCTTTTATAATCT TCTGGGTT (SEQ ID NO: 14) or a fragment thereof. In some embodiments, an "extracellular" or "hinge" or "spacer" domain or region is encoded by a nucleotide sequence that comprises the nucleotide sequence of SEQ ID NO: 14 or a fragment thereof.

In some embodiments, an "extracellular" or "hinge" or "spacer" domain or region is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence CTTGATAATGAAAAGTCAAACGGAACAATCATT-CACGTGAAGGGCAAGCACCT CTGTCCGT-CACCCTTGTTCCCTGGTCCATCCAAGCCA (SEQ ID NO: 82) or a fragment thereof. In some embodiments, an "extracellular" or "hinge" or "spacer" domain or region is encoded by a nucleotide sequence that comprises the nucleotide sequence of SEQ ID NO: 82 or a fragment thereof.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence FVPVFLPAKPTTTPAPRPPTPAPTIA-SQPLSLRPEACRPAAGGAVHTRGLDFACDIYI WAPLAGTCGVLLLSLVITLYCNHRN (SEQ ID NO: 17) or a fragment thereof. In some embodiments, an "extracellular" or "hinge" or "spacer" domain or region comprises the amino acid sequence of SEQ ID NO: 17 or a fragment thereof.

In some embodiments, an "extracellular" or "hinge" or "spacer" domain or region is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence TTCGTGCCTGTTTTTCTGCCCGCGAAACCCACAAC-TACCCCCGCCCCTCGGCCCC CAACTCCTGCAC-CAACTATCGCTTCCCAACCCCTGTCTCTGAGACCT-GAGGCAT GCCGCCCCGCGGCAGGCGGCGCC-GTGCACACTAGAGGCCTGGACTTCGCCTGC GATAT-TTATATCTGGGCCCCCCTTGCCGGGA-CATGCGGGGTACTGCTGCTGTCT CTGGTGAT-TACCCTCTACTGCAACCACAGAAAC (SEQ ID NO: 16) or a fragment thereof. In some embodiments, an "extracellular" or "hinge" or "spacer" domain or region is encoded by a nucleotide sequence that comprises the nucleotide sequence of SEQ ID NO: 16 or a fragment thereof.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence FVPVFLPAKPTTTPAPRPPTPAPTIA-SQPLSLRPEACRPAAGGAVHTRGLDFACD (SEQ ID NO: 85) or a fragment thereof. In some embodiments, an "extracellular" or "hinge" or "spacer" domain or region comprises the amino acid sequence of SEQ ID NO: 85 or a fragment thereof.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence TTTPAPRPPTPAPTIASQPLSLRPEACR-PAAGGAVHTRGLDFACDIY (SEQ ID NO: 93) or a fragment thereof. In some embodiments, an "extracellular" or "hinge" or "spacer" domain or region comprises the amino acid sequence of SEQ ID NO: 85 or a fragment thereof.

In some embodiments, an "extracellular" or "hinge" or "spacer" domain or region is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence TTCGTGCCTGTTTTTCTGCCCGCGAAACCCACAAC-TACCCCCGCCCCTCGGCCCC CAACTCCTGCAC-CAACTATCGCTTCCCAACCCCTGTCTCTGAGACCT-GAGGCAT GCCGCCCCGCGGCAGGCGGCG-CCGTGCACACTAGAGGCCTGGACTTCGCCTGC GAT (SEQ ID NO: 84) or a fragment thereof. In some embodiments, an "extracellular" or "hinge" or "spacer" domain or region is encoded by a nucleotide sequence that comprises the nucleotide sequence of SEQ ID NO: 84 or a fragment thereof.

In some embodiments, the CD28T domain is derived from a human CD28T hinge region, and can comprise SEQ ID NO: 15. In other embodiments, the CD28T domain is derived from a rodent, murine, or primate (e.g., non-human primate) CD28T hinge region. In some embodiments, the CD28T domain is derived from a chimeric CD28T hinge region.

In some embodiments, the CD28T domain is derived from a human CD28T hinge region, and can comprise SEQ ID NO: 83. In other embodiments, the CD28T domain is derived from a rodent, murine, or primate (e.g., non-human primate) CD28T hinge region. In some embodiments, the CD28T domain is derived from a chimeric CD28T hinge region.

In some embodiments, the CD8 domain is derived from a human CD8 hinge region, and can comprise SEQ ID NO: 17. In other embodiments, the CD8 domain is derived from a rodent, murine, or primate (e.g., non-human primate) CD8 hinge region. In some embodiments, the CD8 domain is derived from a chimeric CD8 hinge region.

In some embodiments, the CD8 domain is derived from a human CD8 hinge region, and can comprise SEQ ID NO: 85. In other embodiments, the CD8 domain is derived from a rodent, murine, or primate (e.g., non-human primate) CD8 hinge region. In some embodiments, the CD8 domain is derived from a chimeric CD8 hinge region.

In some embodiments, an extracellular domain comprises some or all of a member of the immunoglobulin family such as IgG1, IgG2, IgG3, IgG4, IgA, IgD, IgE, IgM, or fragment thereof.

Optionally, a short peptide or polypeptide linker, preferably between 2 and 10 amino acids in length can form the linkage between the hinge domain and the antigen binding domain, or between the hinge domain and a transmembrane domain of a CAR. Optionally, a short oligo- or polypeptide linker, preferably between 2 and 10 amino acids in length can form the linkage. A glycine-serine doublet (GS), glycine-serine-glycine triplet (GSG), or alanine-alanine-alanine triplet (AAA) provides a particularly suitable linker.

IV.B. Transmembrane Domain

A CAR or TCR of the instant disclosure can further comprise a transmembrane domain. A transmembrane domain can be designed to be fused to the hinge domain. It can similarly be fused to an intracellular domain, such as a costimulatory domain. In one embodiment, a transmembrane domain that naturally is associated with one of the domains in a CAR can be used. For example, a transmembrane domain can comprise the natural transmembrane region of a costimulatory domain (e.g., the TM region of a CD28T or 4-1BB employed as a costimulatory domain) or the natural transmembrane domain of a hinge region (e.g., the TM region of a CD8 alpha or CD28T employed as a hinge domain).

In some instances, the transmembrane domain can be selected or modified by amino acid substitution to avoid binding of such domains to the transmembrane domains of the same or different surface membrane proteins to minimize interactions with other members of the receptor complex. A transmembrane domain can be derived either from a natural or from a synthetic source. When the transmembrane domain is derived from a naturally-occurring source, the domain can be derived from any membrane-bound or transmembrane protein. In some embodiments, a transmembrane domain is derived from CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and combinations thereof.

In some embodiments, a transmembrane domain can comprise a sequence that spans a cell membrane, but extends into the cytoplasm of a cell and/or into the extracellular space. For example, a transmembrane can comprise a membrane-spanning sequence which itself can further comprise 1, 2, 3, 4, 5, 6, 7, 8, 9, 10 or more amino acids that extend into the cytoplasm of a cell, and/or the extracellular space. Thus, a transmembrane domain comprises a membrane-spanning region, yet can further comprise an amino acid(s) that extend beyond the internal or external surface of the membrane itself; such sequences can still be considered to be a "transmembrane domain."

In one embodiment, a transmembrane domain of a CAR of the instant disclosure comprises the CD28T transmembrane domain. In one embodiment, the CD28T transmembrane domain comprises the transmembrane portion of the protein encoded by the nucleic acid sequence:

```
                                      (SEQ ID NO: 14)
CTTGATAATGAAAAGTCAAACGGAACAATCATTCACGTGAAGGGCAAGCA

CCTCTGTCCGTCACCCTTGTTCCCTGGTCCATCCAAGCCATTCTGGGTGT

TGGTCGTAGTGGGTGGAGTCCTCGCTTGTTACTCTCTGCTCGTCACCGTG

GCTTTTATAATCTTCTGGGTT.
```

For example, a transmembrane domain can be encoded by a nucleic acid sequence comprising the nucleic acid sequence

```
                                      (SEQ ID NO: 18)
TTCTGGGTGTTGGTCGTAGTGGGTGGAGTCCTCGCTTGTTACTCTCTGCT

CGTCACCGTGGCTTTTATAATCTTCTGGGTT.
```

In another embodiment, the CD28T transmembrane domain comprises the transmembrane amino acid sequence contained within the amino acid sequence:

```
                                      (SEQ ID NO: 15)
LDNEKSNGTIIHVKGKHLCPSPLFPGPSKPFWVLVVVGGVLACYSLLVTV

AFIIFWV.
```

For example, a transmembrane domain can comprise the amino acid sequence FWVLVVVGGVLACYSLL-VTVAFIIFWV (SEQ ID NO: 19).

In one embodiment, a transmembrane domain of a CAR of the instant disclosure comprises the CD8 transmembrane domain. In one embodiment, the CD8 transmembrane domain comprises the transmembrane portion of the protein encoded by the nucleic acid sequence:

(SEQ ID NO: 16)
TTCGTGCCTGTTTTTCTGCCCGCGAAACCCACAACTACCCCGCCCCTCG

GCCCCCAACTCCTGCACCAACTATCGCTTCCCAACCCCTGTCTCTGAGAC

CTGAGGCATGCCGCCCCGCGGCAGGCGGCGCCGTGCACACTAGAGGCCTG

GACTTCGCCTGCGATATTTATATCTGGGCCCCCCTTGCCGGGACATGCGG

GGTACTGCTGCTGTCTCTGGTGATTACCCTCTACTGCAACCACAGAAAC.

For example, a transmembrane domain can be encoded by a nucleic acid sequence comprising the nucleic acid sequence (SEQ ID NO: 20)
ATTTATATCTGGGCCCCCCTTGCCGGGACATGCGGGGTACTGCTGCTGTC

TCTGGTGATTACC.

In another embodiment, the CD8 transmembrane domain comprises the transmembrane amino acid sequence contained within the amino acid sequence:

(SEQ ID NO: 17)
FVPVFLPAKPTTTPAPRPPTPAPTIASQPLSLRPEACRPAAGGAVHTRGL

DFACDIYIWAPLAGTCGVLLLSLVITLYCNHRN.

For example, a transmembrane domain can comprise the amino acid sequence IYIWAPLAGTCGVLLLSLVIT (SEQ ID NO: 21).

In some embodiments, a transmembrane domain is a CD28T transmembrane domain. In some embodiments, the transmembrane domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence (SEQ ID NO: 19)
FWVLVVVGGVLACYSLLVTVAFIIFWV.

In some embodiments, the transmembrane domain comprises the amino acid sequence of SEQ ID NO: 19.

In some embodiments, the CD28T transmembrane domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence (SEQ ID NO: 18)
TTCTGGGTGTTGGTCGTAGTGGGTGGAGTCCTCGCTTGTTACTCTCTGCT

CGTCACCGTGGCTTTTATAATCTTCTGGGTT.

In some embodiments, the transmembrane domain is encoded by a nucleic acid sequence comprising the nucleic acid sequence of SEQ ID NO: 18.

In another embodiment, a transmembrane domain is a CD8 transmembrane domain. In some embodiments, the transmembrane domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence IYIWAPLAGTCGVLLLSLVIT (SEQ ID NO: 21).

In some embodiments, the transmembrane domain comprises the amino acid sequence of SEQ ID NO: 21.

In another embodiment, a transmembrane domain is a CD8 transmembrane domain. In some embodiments, the transmembrane domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence (SEQ ID NO: 94)
IWAPLAGTCGVLLLSLVITLYC.

In some embodiments, the transmembrane domain comprises the amino acid sequence of SEQ ID NO: 94.

In some embodiments, the CD8 transmembrane domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence (SEQ ID NO: 20)
ATTTATATCTGGGCCCCCCTTGCCGGGACATGCGGGGTACTGCTGCTGTC

TCTGGTGATTACC.

In some embodiments, the transmembrane domain is encoded by a nucleotide sequence that comprises the nucleotide sequence of SEQ ID NO: 20.

As noted herein, the various domains of a CAR of the instant disclosure can optionally comprise amino acids in addition to those sequences provided herein. For example, a transmembrane domain can comprise amino acids that extend the domain into the cytoplasm and/or extracellular space, which can be naturally occurring in the molecule from which the transmembrane domain was derived. Accordingly, in some embodiments, a CD8 transmembrane domain further comprises the contiguous amino acid sequence LYCNHRN (SEQ ID NO: 87), encoded by the nucleic acid sequence CTCTACTGCAACCACAGAAAC (SEQ ID NO: 86), and which extend the transmembrane domain into the cytoplasm or intracellular space.

Optionally, a short peptide or polypeptide linker, preferably between 2 and 10 amino acids in length can form the linkage between the transmembrane domain and a proximal cytoplasmic signaling domain of the CAR, such as a costimulatory or activation domain, or to an antigen binding molecule (e.g., an anti-CD70 scFv). Optionally, a short oligo- or polypeptide linker, preferably between 2 and 10 amino acids in length can form the linkage. A glycine-serine doublet (GS), glycine-serine-glycine triplet (GSG), or alanine-alanine-alanine triplet (AAA) provides a particularly suitable linker.

IV.C. Costimulatory Domain

In some embodiments, the instant disclosure comprises a CAR, wherein the CAR comprises an antigen binding molecule that specifically binds to CD70 (one or more antigen binding molecules provided herein, in the Figures and in the attached Sequence Listing), and wherein the CAR further comprises a costimulatory domain. In some embodiments, a costimulatory domain is positioned between an antigen binding molecule (e.g., an scFv), and an activating domain. In some embodiments, a costimulatory domain can, but need not, comprise an extracellular domain, and/or a transmembrane domain, in addition to an intracellular signaling domain. In some embodiments, a costimulatory domain can comprise a transmembrane domain and an intracellular signaling domain. In some embodiments, a costimulatory domain can comprise an extracellular domain and a transmembrane domain. In some embodiments a costimulatory domain can comprise an intracellular signaling domain. A CAR, TCR or engineered T cell of the instant disclosure can comprise one, two or three costimulatory domains, which can be configured in series or flanking one or more other components of the CAR.

A costimulatory domain of the CARs, TCRs and engineered T cells disclosed herein can provide signaling to an activating domain, which then activates at least one of the normal effector functions of the immune cell. Effector function of a T cell, for example, can be cytolytic activity or helper activity including the secretion of cytokines.

In some embodiments, suitable costimulatory domains include (i.e., comprise), but are not limited to CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof.

An example of a nucleotide sequence encoding a costimulatory domain is set forth in SEQ ID NO. 22:

AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC

In one embodiment, the polynucleotide encoding costimulatory signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of (SEQ ID NO: 22)
AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC.

An example of a costimulatory signaling domain is (SEQ ID NO. 23)
RSKRSRLLHSDYMNMTPRRPGPTRKHYQPYAPPRDFAAYRS.

In some embodiments, the intracellular signaling domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of RSKRSRLLHSDYMNMTPRRPGPTRKHYQPYAPPRDFAAYRS (SEQ ID NO: 23).

Another example of a nucleotide sequence encoding an intracellular signaling domain is (SEQ ID NO: 24)
CGCTTTTCCGTCGTTAAGCGGGGAGAAAAAAGCTGCTGTACATTTTCAA

ACAGCCGTTTATGAGGCCGGTCCAAACGACTCAGGAAGAAGACGGCTGCT

CCTGCCGCTTTCCTGAGGAGGAGGAGGGCGGGTGCGAACTG.

In one embodiment, the polynucleotide encoding a costimulatory signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of (SEQ ID NO: 24)
CGCTTTTCCGTCGTTAAGCGGGGAGAAAAAAGCTGCTGTACATTTTCAA

ACAGCCGTTTATGAGGCCGGTCCAAACGACTCAGGAAGAAGACGGCTGCT

CCTGCCGCTTTCCTGAGGAGGAGGAGGGCGGGTGCGAACTG.

Another example of an intracellular signaling domain is set forth in SEQ ID NO. 25: RFSVVKRGRKKLLYIFKQPFMRPVQTTQEEDGCSCRFPEEEEGGCEL.

In some embodiments, an intracellular signaling domain comprises an amino acid sequence at least about 80%, at least about 85%, at least about 90%, at least about 95%, at least about 96%, at least about 97%, at least about 98%, at least about 99%, or about 100% identical to the amino acid sequence of (SEQ ID NO: 25)
RFSVVKRGRKKLLYIFKQPFMRPVQTTQEEDGCSCRFPEEEEGGCEL.

A costimulatory signaling sequence of a CAR of the instant disclosure can be directly linked to another costimulatory domain, to an activating domain, to a transmembrane domain, or other component of the CAR in a random or specified order. Optionally, a short oligo- or polypeptide linker, preferably between 2 and 10 amino acids in length can form the linkage. A glycine-serine doublet (GS), glycine-serine-glycine triplet (GSG), or alanine-alanine-alanine triplet (AAA) provides a particularly suitable linker.

It is further noted that multiple costimulatory domains can be incorporated into a CAR or TCR of the instant disclosure. For example, a CD28T costimulatory domain and a 4-1BB costimulatory domain can both be incorporated into a CAR or TCR of the instant disclosure and, by virtue of the antigen binding component of the CAR or TCR, still be directed against CD70 and cells expressing CD70 on their surfaces.

IV.D Activating Domain

In some embodiments, intracellular domains for use in the engineered T cell of the disclosure include cytoplasmic sequences of the T cell receptor (TCR) and co-receptors that act in concert to initiate signal transduction following antigen/receptor engagement, as well as any derivative or variant of these sequences and any synthetic sequence that has the same functional capability. CD3 is an element of the T cell receptor on native T cells, and has been shown to be an important intracellular activating element in CARs. In one embodiment, the activating domain is CD3, e.g., CD3 zeta, the nucleotide sequence of which is set forth in SEQ ID NO: 26:

AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG.

In some embodiments, the polynucleotide encoding an activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of (SEQ ID NO: 26)
AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG.

The corresponding amino acid of intracellular CD3 zeta is (SEQ ID NO: 27)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In some embodiments, the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of:

(SEQ ID NO: 27)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In some embodiments, the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of:

(SEQ ID NO: 92)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

IV.E. Leader Peptide

In some embodiments, a polynucleotide of the instant disclosure encodes a CAR or a TCR, wherein the CAR or the TCR comprises an antigen binding molecule that specifically binds to CD70, and wherein the CAR or the TCR further comprises a leader peptide (also referred to herein as a "signal peptide" or "signal sequence"). The inclusion of a signal sequence in a CAR or TCR of the instant disclosure is optional. If a leader sequence is included in a CAR or TCR of the instant disclosure, it can be expressed on the N terminus of the CAR or TCR. Thus, a leader sequence can be associated with the VH or VL component of an antigen binding molecule of a CAR or TCR of the instant disclosure, depending on which domain is at the N terminus of the CAR or TCR.

If it is desired to include a leader sequence, such a leader sequence can be synthesized or it can be derived from a naturally occurring molecule. For example, the naturally occurring 21 residue leader sequence of CD8 (see, e.g., Littman et al., (1985) *Cell* 40:237-46) can be employed as a leader sequence in the disclosed CAR and TCR constructs.

Thus, in some embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLLPLALLLHAARP (SEQ ID NO: 28).

In some embodiments, the signal peptide comprises the amino acid sequence of SEQ ID NO: 28. In some embodiments, the leader peptide is encoded by a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to (SEQ ID NO: 95)
ATGGCACTCCCCGTAACTGCTCTGCTGCTGCCGTTGGCATTGCTCCTGCA

CGCCGCACGC.

In some embodiments, the polynucleotide of the instant disclosure encodes a CAR, wherein the CAR comprises a leader peptide (P), an antigen binding molecule such as an scFv that associates with human CD70 (B), a hinge domain (H), a transmembrane domain (T), one or more costimulatory regions (C), and an activation domain (A), wherein the CAR is configured according to the following: P-B-H-T-C-A. In some embodiments the components of the CAR are optionally joined though a linker sequence, such as AAA or GSG. In some embodiments, the antigen binding molecule comprises a VH and a VL, wherein the CAR is configured according to the following: P-VH-VL-H-T-C-A or P-VL-VH-H-T-C-A. In some embodiments, the VH and the VL are connected by a linker (L) such as SEQ ID NO: 80 or 81, wherein the CAR is configured according to the following, from N-terminus to C-terminus: P-VH-L-VL-H-T-C-A or P-VH-L-VL-H-T-C-A.

In some embodiments, a polynucleotide of the instant disclosure encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence shown in FIGS. 8A-8L and in Table 2. In some embodiments, a polynucleotide of the instant disclosure encodes a CAR, wherein the CAR comprises an amino acid sequence shown in FIGS. 8A-8L and in Table 2.

TABLE 2

Example CAR Sequences

| Anti-CD70 CAR | | SEQ ID NO: | | SEQ ID NO: |
|---|---|---|---|---|
| 8G1.1_C28T_28z | ATGGCACTCCCCGTAACTGCTCTGCTGCTGCC GTTGGCATTGCTCCTGCACGCCGCACGCCCGC AAGAGCAGCTGGTTGAGTCTGGGGGCGGCGTC GTCCAACCCGGCCGGAGTCTGAGGTTGTCCTG CGCTGCAAGCGGATTTACATTTTCATCTTACG GCATGCACTGGGTTAGGCAGGCTCCTGGAAAA GGGCTGGAGTGGGTCGCGGTGACTTGGTACGA CGGCTCCAATAAGTATTATGGGATTCCGTGA AAGGTCGATTCACAATTAGCAGGGATAACTCC AAAAACACACTGTATCTCCAAATGAACTCCTT GAGGGCCGAGGACACGGCCGTCTATTATTGTG CAAGAGACCTCCTCCGGGGCGTAAAGGGATAT GCtATGGACGTGTGGGGTCAGGGGACCACAGT TACTGTCAGTTCAGGTGGCGGTGGCAGTGGCG GCGGGGGAAGTGGAGGCGGGGGCTCTGAAATC GTTCTCACTCAGTCTCCGGGCACACTGTCCCT CAGCCCCGGAGAGCGAGCCACTTTGAGCTGCC GGGCCAGCCAGTCACTTAGACGCATTTATTTG GCCTGGTATCAGCAGAAACCAGGCCAGGCGCC CAGGCTGCTGATATACGATGTGTTCGATAGGG CCACGGGTATCCCCGATAGGTTCTCTGGCGGG GGGTCCGGGACTGACTTCACCCTCACTATATC ACGACTCGAGCCCGAAGACTTCGCAGTTTATT ATTGCCAGCAGTACTCCGACTCCCCATTCACC TTCGGCCCTGGTACCAAAGTGGATATTAAACG GGCCGCTGCCCTTGATAATGAAAAGTCAAACG GAACAATCATTCACGTGAAGGGCAAGCACCTC TGTCCGTCACCCTTGTTCCCTGGTCCATCCAA GCCATTCTGGGTGTTGGTCGTAGTGGGTGGAG TCCTCGCTTGTTACTCTCTGCTCGTCACCGTG GCTTTTATAATCTTCTGGGTTAGATCCAAAAG AAGCCGCCTGCTCCATAGCGATTACATGAATA TGACTCCACGCCGCCCTGGCCCCACAAGGAAA CACTACCAGCCTTACGCACCACCTAGAGATTT CGCTGCCTATCGGAGCAGGGTGAAGTTTTCCA GATCTGCAGATGCACCAGCGTATCAGCAGGGC CAGAACCAACTGTATAACGAGCTCAACCTGGG ACGCAGGGAAGAGTATGACGTTTTGGACAAGC GCAGAGGACGGGACCCTGAGATGGGTGGCAAA CCAAGACGAAAAAACCCCCAGGAGGGTCTCTA TAATGAGCTGCAGAAGGATAAGATGGCTGAAG CCTATTCTGAAATAGGCATGAAAGGAGAGCGG AGAAGGGGAAAAGGGCACGACGGTTTGTACCA GGGACTCAGCACTGCTACGAAGGATACTTATG ACGCTCTCCACATGCAAGCCCTGCCACCTAGG | 29 | MALPVTALLLPLALLLHAARP QEQLVESGGGVVQPGRSLRLS CAASGFTFSSYGMHWVRQAPG KGLEWVAVTWYDGSNKYYGDS VKGRFTISRDNSKNTLYLQMN SLRAEDTAVYYCARDLLRGVK GYAMDVWGQGTTVTVSSGGGG SGGGGSGGGGSEIVLTQSPGT LSLSPGERATLSCRASQSLRR IYLAWYQQKPGQAPRLLIYDV FDRATGIPDRFSGGGSGTDFT LTISRLEPEDFAVYYCQQYSD SPFTFGPGTKVDIKRAAALDN EKSNGTIIHVKGKHLCPSPLF PGPSKPFWVLVVVGGVLACYS LLVTVAFIIFWVRSKRSRLLH SDYMNMTPRRPGPTRKHYQPY APPRDFAAYRSRVKFSRSADA PAYQQGQNQLYNELNLGRREE YDVLDKRRGRDPEMGGKPRRK NPQEGLYNELQKDKMAEAYSE IGMKGERRRGKGHDGLYQGLS TATKDTYDALHMQALPPR | 30 |
| 8G1.1_C28T_4Bz | ATGGCACTCCCCGTAACTGCTCTGCTGCTGCC GTTGGCATTGCTCCTGCACGCCGCACGCCCGC AAGAGCAGCTGGTTGAGTCTGGGGGCGGCGTC GTCCAACCCGGCCGGAGTCTGAGGTTGTCCTG CGCTGCAAGCGGATTTACATTTTCATCTTACG GCATGCACTGGGTTAGGCAGGCTCCTGGAAAA GGGCTGGAGTGGGTCGCGGTGACTTGGTACGA CGGCTCCAATAAGTATTATGGGATTCCGTGA AAGGTCGATTCACAATTAGCAGGGATAACTCC AAAAACACACTGTATCTCCAAATGAACTCCTT | 31 | MALPVTALLLPLALLLHAARP QEQLVESGGGVVQPGRSLRLS CAASGFTFSSYGMHWVRQAPG KGLEWVAVTWYDGSNKYYGDS VKGRFTISRDNSKNTLYLQMN SLRAEDTAVYYCARDLLRGVK GYAMDVWGQGTTVTVSSGGGG SGGGGSGGGGSEIVLTQSPGT LSLSPGERATLSCRASQSLRR IYLAWYQQKPGQAPRLLIYDV | 32 |

TABLE 2-continued

Example CAR Sequences

| Anti-CD70 CAR | | SEQ ID NO: | | SEQ ID NO: |
|---|---|---|---|---|
| | GAGGGCCGAGGACACGGCCGTCTATTATTGTG CAAGAGACCTCCTCCGGGGCGTAAAGGGATAT GCtATGGACGTGTGGGGTCAGGGGACCACAGT TACTGTCAGTTCAGGTGGCGGTGGCAGTGGCG GCGGGGGAAGTGGAGGCGGGGGCTCTGAAATC GTTCTCACTCAGTCTCCGGGCACACTGTCCCT CAGCCCCGGAGAGCGAGCCACTTTGAGCTGCC GGGCCAGCCAGTCACTTAGACGCATTTATTTG GCCTGGTATCAGCAGAAACCAGGCCAGGCGCC CAGGCTGCTGATATACGATGTGTTCGATAGGG CCACGGGTATCCCCGATAGGTTCTCTGGCGGG GGGTCCGGGACTGACTTCACCCTCACTATATC ACGACTCGAGCCCGAAGACTTCGCAGTTTATT ATTGCCAGCAGTACTCCGACTCCCCATTCACC TTCGGCCCTGGTACCAAAGTGGATATTAAACG GGCCGCTGCCCTTGATAATGAAAGTCAAACG GAACAATCATTCACGTGAAGGGCAAGCACCTC TGTCCGTCACCCTTGTTCCCTGGTCCATCCAA GCCATTCTGGGTGTTGGTCGTAGTGGGTGGAG TCCTCGCTTGTTACTCTCTGCTCGTCACCGTG GCTTTTATAATCTTCTGGGTTCGCTTTTCCGT CGTTAAGCGGGGGAGAAAAAAGCTGCTGTACA TTTTCAAACAGCCGTTTATGAGGCCGGTCCAA ACGACTCAGGAAGAAGACGGCTGCTCCTGCCG CTTTCCTGAGGAGGAGGAGGGCGGGTGCGAAC TGAGGGTGAAGTTTTCCAGATCTGCAGATGCA CCAGCGTATCAGCAGGGCCAGAACCAACTGTA TAACGAGCTCAACCTGGGACGCAGGGAAGAGT ATGACGTTTTGGACAAGCGCAGAGGACGGGAC CCTGAGATGGGTGGCAAACCAAGACGAAAAAA CCCCCAGGAGGGTCTCTATAATGAGCTGCAGA AGGATAAGATGGCTGAAGCCTATTCTGAAATA GGCATGAAAGGAGAGCGGAGAAGGGGAAAAGG GCACGACGGTTTGTACCAGGGACTCAGCACTG CTACGAAGGATACTTATGACGCTCTCCACATG CAAGCCCTGCCACCTAGG | | | FDRATGIPDRFSGGGSGTDFT LTISRLEPEDFAVYYCQQYSD SPFTFGPGTKVDIKRAAALDN EKSNGTIIHVKGKHLCPSPLF PGPSKPFWVLVVVGGVLACYS LLVTVAFIIFWVRFSVVKRGR KKLLYIFKQPFMRPVQTTQEE DGCSCRFPEEEEGGCELRVKF SRSADAPAYQQGQNQLYNELN LGRREEYDVLDKRRGRDPEMG GKPRRKNPQEGLYNELQKDKM AEAYSEIGMKGERRRGKHDG LYQGLSTATKDTYDALHMQAL PPR | |
| 8G1.1_C8K_28z | ATGGCACTCCCCGTAACTGCTCTGCTGCTGCC GTTGGCATTGCTCCTGCACGCCGCACGCCCGC AAGAGCAGCTGGTTGAGTCTGGGGGCGGGGTG GTCCAACCCGGCCGGAGTCTGAGGTTGTCCTG CGCTGCAAGCGGATTTACATTTTCATCTTACG GCATGCACTGGGTTAGGCAGGCTCCTGGAAAA GGGCTGGAGTGGGTCGCGGTGACTTGGTACGA CGGCTCCAATAAGTATTATGGGGATTCCGTGA AAGGTCGATTCACAATTAGCAGGGATAACTCC AAAAACACACTGTATCTCCAAATGAACTCCTT GAGGGCCGAGGACACGGCCGTCTATTATTGTG CAAGAGACCTCCTCCGGGGCGTAAAGGGATAT GCtATGGACGTGTGGGGTCAGGGGACCACAGT TACTGTCAGTTCAGGTGGCGGTGGCAGTGGCG GCGGGGGAAGTGGAGGCGGGGGCTCTGAAATC GTTCTCACTCAGTCTCCGGGCACACTGTCCCT CAGCCCCGGAGAGCGAGCCACTTTGAGCTGCC GGGCCAGCCAGTCACTTAGACGCATTTATTTG GCCTGGTATCAGCAGAAACCAGGCCAGGCGCC CAGGCTGCTGATATACGATGTGTTCGATAGGG CCACGGGTATCCCCGATAGGTTCTCTGGCGGG GGGTCCGGGACTGACTTCACCCTCACTATATC ACGACTCGAGCCCGAAGACTTCGCAGTTTATT ATTGCCAGCAGTACTCCGACTCCCCATTCACC TTCGGCCCTGGTACCAAAGTGGATATTAAACG GGCCGCTGCCTTCGTGCCTGTTTTTCTGCCCG CGAAACCCACAACTACCCCGCCCCTCGGCCC CCAACTCCTGCACCAACTATCGCTTCCCAACC CCTGTCTCTGAGACCTGAGGCATGCCGCCCCG CGGCAGGCGGCGCCGTGCACACTAGAGGCCTG GACTTCGCCTGCGATATTTATATCTGGGCCCC CCTTGCCGGACATGCGGGTACTGCTGCTGT CTCTGGTGATTACCCTCTACTGCAACCACAGA AACAGATCCAAAAGAAGCCGCCTGCTCCATAG CGATTACATGAATATGACTCCACGCCGCCCTG GCCCCACAAGGAAACACTACCAGCCTTACGCA CCACCTAGAGATTTCGCTGCCTATCGGAGCAG | 33 | MALPVTALLLPLALLLHAARP QEQLVESGGGVVQPGRSLRLS CAASGFTFSSYGMHWVRQAPG KGLEWVAVTWYDGSNKYYGDS VKGRFTISRDNSKNTLYLQMN SLRAEDTAVYYCARDLLRGVK GYAMDVWGQGTTVTVSSGGGG SGGGGSGGGGSEIVLTQSPGT LSLSPGERATLSCRASQSLRR IYLAWYQQKPGQAPRLLIYDV FDRATGIPDRFSGGGSGTDFT LTISRLEPEDFAVYYCQQYSD SPFTFGPGTKVDIKRAAAFVP VFLPAKPTTTPAPRPPTPAPT IASQPLSLRPEACRPAAGGAV HTRGLDFACDIYIWAPLAGTC GVLLLSLVITLYCNHRNRSKR SRLLHSDYMNMTPRRPGPTRK HYQPYAPPRDFAAYRSRVKFS RSADAPAYQQGQNQLYNELNL GRREEYDVLDKRRGRDPEMGG KPRRKNPQEGLYNELQKDKMA EAYSEIGMKGERRRGKHDGL YQGLSTATKDTYDALHMQALP PR | 34 |

TABLE 2-continued

Example CAR Sequences

| Anti-CD70 CAR | | SEQ ID NO: | | SEQ ID NO: |
|---|---|---|---|---|
| | GGTGAAGTTTTCCAGATCTGCAGATGCACCAG<br>CGTATCAGCAGGGCCAGAACCAACTGTATAAC<br>GAGCTCAACCTGGGACGCAGGGAAGAGTATGA<br>CGTTTTGGACAAGCGCAGAGGACGGGACCCTG<br>AGATGGGTGGCAAACCAAGACGAAAAAACCCC<br>CAGGAGGGTCTCTATAATGAGCTGCAGAAGGA<br>TAAGATGGCTGAAGCCTATTCTGAAATAGGCA<br>TGAAAGGAGAGCGGAGAAGGGGAAAAGGGCAC<br>GACGGTTTGTACCAGGGACTCAGCACTGCTAC<br>GAAGGATACTTATGACGCTCTCCACATGCAAG<br>CCCTGCCACCtAGG | | | |
| 8G1.1_<br>C8K_4Bz | ATGGCACTCCCCGTAACTGCTCTGCTGCTGCC<br>GTTGGCATTGCTCCTGCACGCCGCACGCCCGC<br>AAGAGCAGCTGGTTGAGTCTGGGGGCGGAGTC<br>GTCCAACCCGGCCGGAGTCTGAGGTTGTCCTG<br>CGCTGCAAGCGGATTTACATTTTCATCTTACG<br>GCATGCACTGGGTTAGGCAGGCTCCTGGAAAA<br>GGGCTGGAGTGGGTCGCGGTGACTTGGTACGA<br>CGGCTCCAATAAGTATTATGGGGATTCCGTGA<br>AAGGTCGATTCACAATTAGCAGGGATAACTCC<br>AAAAACACACTGTATCTCCAAATGAACTCCTT<br>GAGGGCCGAGGACACGGCCGTCTATTATTGTG<br>CAAGAGACCTCCTCCGGGGCGTAAAGGGATAT<br>GCtATGGACGTGTGGGGTCAGGGGACCACAGT<br>TACTGTCAGTTCAGGTGGCGGTGGCAGTGGCG<br>GCGGGGGAGTGGAGGCGGGGGCTCTGAAATC<br>GTTCTCACTCAGTCTCCGGGCACACTGTCCCT<br>CAGCCCCGGAGAGCGAGCCACTTTGAGCTGCC<br>GGGCCAGCCAGTCACTTAGACGCATTTATTTG<br>GCCTGGTATCAGCAGAAACCAGGCCAGGCGCC<br>CAGGCTGCTGATATACGATGTGTTCGATAGGG<br>CCACGGGTATCCCCGATAGGTTCTCTGGCGGG<br>GGGTCCGGGACTGACTTCACCCTCACTATATC<br>ACGACTCGAGCCCGAAGACTTCGCAGTTTATT<br>ATTGCCAGCAGTACTCCGACTCCCCATTCACC<br>TTCGGCCCTGGTACCAAAGTGGATATTAAACG<br>GGCCGCTGCCTTCGTGCCTGTTTTTCTGCCCG<br>CGAAACCCACAACTACCCCGCCCCTCGGCCC<br>CCAACTCCTGCACCAACTATCGCTTCCCAACC<br>CCTGTCTCTGAGACCTGAGGCATGCCGCCCCG<br>CGGCAGGCGGCGCCGTGCACACTAGAGGCCTG<br>GACTTCGCCTGCGATATTTATATCTGGGCCCC<br>CCTTGCCGGGACATGCGGGTACTGCTGCTGT<br>CTCTGGTGATTACCCTCTACTGCAACCACAGA<br>AACCGCTTTTCCGTCGTTAAGCGGGGGAGAAA<br>AAAGCTGCTGTACATTTTCAAACAGCCGTTTA<br>TGAGGCCGGTCCAAACGACTCAGGAAGAAGAC<br>GGCTGCTCCTGCCGCTTTCCTGAGGAGGAGGA<br>GGGCGGGTGCGAACTGAGGGTGAAGTTTTCCA<br>GATCTGCAGATGCACCAGCGTATCAGCAGGGC<br>CAGAACCAACTGTATAACGAGCTCAACCTGGG<br>ACGCAGGGAAGAGTATGACGTTTTGGACAAGC<br>GCAGAGGACGGGACCCTGAGATGGGTGGCAAA<br>CCAAGACGAAAAAACCCCCAGGAGGGTCTCTA<br>TAATGAGCTGCAGAAGGATAAGATGGCTGAAG<br>CCTATTCTGAAATAGGCATGAAAGGAGAGCGG<br>AGAAGGGGAAAAGGGCACGACGGTTTGTACCA<br>GGGACTCAGCACTGCTACGAAGGATACTTATG<br>ACGCTCTCCACATGCAAGCCCTGCCACCTAGG | 35 | MALPVTALLLPLALLLHAARP<br>QEQLVESGGGVVQPGRSLRLS<br>CAASGFTFSSYGMHWVRQAPG<br>KGLEWVAVTWYDGSNKYYGDS<br>VKGRFTISRDNSKNTLYLQMN<br>SLRAEDTAVYYCARDLLRGVK<br>GYAMDVWGQGTTVTVSSGGGG<br>SGGGGSGGGGSEIVLTQSPGT<br>LSLSPGERATLSCRASQSLRR<br>IYLAWYQQKPGQAPRLLIYDV<br>FDRATGIPDRFSGGGSGTDFT<br>LTISRLEPEDFAVYYCQQYSD<br>SPFTFGPGTKVDIKRAAAFVP<br>VFLPAKPTTTPAPRPPTPAPT<br>IASQPLSLRPEACRPAAGGAV<br>HTRGLDFACDIYIWAPLAGTC<br>GVLLLSLVITLYCNHRNRFSV<br>VKRGRKKLLYIFKQPFMRPVQ<br>TTQEEDGCSCRFPEEEEGGCE<br>LRVKFSRSADAPAYQQGQNQL<br>YNELNLGRREEYDVLDKRRGR<br>DPEMGGKPRRKNPQEGLYNEL<br>QKDKMAEAYSEIGMKGERRRG<br>KGHDGLYQGLSTATKDTYDAL<br>HMQALPPR | 36 |
| 1C8.1.001_<br>C28T_28z | ATGGCACTCCCCGTAACTGCTCTGCTGCTGCC<br>GTTGGCATTGCTCCTGCACGCCGCACGCCCGC<br>AGGTGCAGCTCCAAGAATCTGGACCGGGTCTC<br>GTCAAGCCATCACAGACACTGTCCCTGACCTG<br>CACCGTCTCCGGCGACTCTATCATTTCAGGCG<br>GCTACTATTGGTCCTGGATTAGACAACATCCG<br>GGAAAGGGTCTTGAATGGATCGGCTATATTTT<br>CTACAGCGGGAGTACGGATTACAATCCTAGTC<br>TCAAGAGCCGCGTTACCATTTCAGTGGATACT<br>TCAAAAACCAGTTTAGCCTGAAGCTGTCTTC<br>TGTAACAGCTGCTGACACAGCCGTGTACTATT<br>GCGCCAGGAGCGGCTACAGCTATGCCCTGTTT<br>GACCACTGGGGGCAAGGCACTCTTGTGACGGT | 37 | MALPVTALLLPLALLLHAARP<br>QVQLQESGPGLVKPSQTLSLT<br>CTVSGDSIISGGYYWSWIRQH<br>PGKGLEWIGYIFYSGSTDYNP<br>SLKSRVTISVDTSKNQFSLKL<br>SSVTAADTAVYYCARSGYSYA<br>LFDHWGQGTLVTVSSGGGGSG<br>GGGSGGGGSDIQMTQSPSSLS<br>ASVGDRVTISCRASQFIGRYF<br>NWYQQQPGKAPKVLIYAESSL<br>QSGVPSRFSGSGSGTEFTLTI<br>SSLQPEDFARYYCQQYSTPF<br>TFGQGTKVEIKRAAALDNEKS | 38 |

TABLE 2-continued

Example CAR Sequences

| Anti-CD70 CAR | | SEQ ID NO: | | SEQ ID NO: |
|---|---|---|---|---|
| | GTCAAGTGGAGGGGAGGATCAGGCGGCGGGG GATCCGGCGGCGGGGGTAGTGACATTCAAATG ACGCAGTCCCCAAGTTCTCTGTCCGCTAGCGT CGGCGACCGAGTGACCATCAGCTGCCGAGCAT CCCAGTTTATCGGTAGATATTTCAATTGGTAC CAGCAACAACCGGGCAAAGCGCCCAAGGTCCT GATCTACGCTGAGAGCAGTCTGCAATCCGGCG TACCTAGCAGGTTCTCCGGAAGTGGCAGCGGA ACCGAGTTCACCCTGACAATTAGCTCCTTGCA GCCCGAGGATTTCGCTCGCTATTACTGTCAAC AGAGTTATTCAACCCCTTTTACATTCGGACAG GGAACTAAAGTTGAAATTAAGAGGGCCGCTGC CCTTGATAATGAAAAGTCAAACGGAACAATCA TTCACGTGAAGGGCAAGCACCTCTGTCCGTCA CCCTTGTTCCCTGGTCCATCCAAGCCATTCTG GGTGTTGGTCGTAGTGGGTGGAGTCCTCGCTT GTTACTCTCTGCTCGTCACCGTGGCTTTTATA ATCTTCTGGGTTAGATCCAAAAGAAGCCGCCT GCTCCATAGCGATTACATGAATATGACTCCAC GCCGCCCTGGCCCCACAAGGAAACACTACCAG CCTTACGCACCACCTAGAGATTTCGCTGCCTA TCGGAGCAGGGTGAAGTTTTCCAGATCTGCAG ATGCACCAGCGTATCAGCAGGGCCAGAACCAA CTGTATAACGAGCTCAACCTGGGACGCAGGGA AGAGTATGACGTTTTGGACAAGCGCAGAGGAC GGGACCCTGAGATGGGTGGCAAACCAAGACGA AAAAACCCCCAGGAGGGTCTCTATAATGAGCT GCAGAAGGATAAGATGGCTGAAGCCTATTCTG AAATAGGCATGAAGGAGAGCGGAGAAGGGGA AAAGGGCACGACGGTTTGTACCAGGGACTCAG CACTGCTACGAAGGATACTTATGACGCTCTCC ACATGCAAGCCCTGCCACCTAGG | | NGTIIHVKGKHLCPSPLFPGP SKPFWVLVVVGGVLACYSLLV TVAFIIFWVRSKRSRLLHSDY MNMTPRRPGPTRKHYQPYAPP RDFAAYRSRVKFSRSADAPAY QQGQNQLYNELNLGRREEYDV LDKRRGRDPEMGGKPRRKNPQ EGLYNELQKDKMAEAYSEIGM KGERRRGKGHDGLYQGLSTAT KDTYDALHMQALPPR | |
| 1C8.1.001_ C28T_4Bz | ATGGCACTCCCCGTAACTGCTCTGCTGCTGCC GTTGGCATTGCTCCTGCACGCCGCACGCCCGC AGGTGCAGCTCCAAGAATCTGGACCGGGTCTC GTCAAGCCATCACAGACACTGTCCCTGACCTG CACCGTCTCCGGCGACTCTATCATTTCAGGCG GCTACTATTGGTCCTGGATTAGACAACATCCG GGAAAGGGTCTTGAATGGATCGGCTATATTTT CTACAGCGGGAGTACGGATTACAATCCTAGTC TCAAGAGCCGCGTTACCATTTCAGTGGATACT TCAAAAAACCAGTTTAGCCTGAAGCTGTCTTC TGTAACAGCTGCTGACACAGCCGTGTACTATT GCGCCAGGAGCGGCTACAGCTATGCCCTGTTT GACCACTGGGGGCAAGGCACTCTTGTGACGGT GTCAAGTGGAGGGGAGGATCAGGCGGCGGGG GATCCGGCGGCGGGGGTAGTGACATTCAAATG ACGCAGTCCCCAAGTTCTCTGTCCGCTAGCGT CGGCGACCGAGTGACCATCAGCTGCCGAGCAT CCCAGTTTATCGGTAGATATTTCAATTGGTAC CAGCAACAACCGGGCAAAGCGCCCAAGGTCCT GATCTACGCTGAGAGCAGTCTGCAATCCGGCG TACCTAGCAGGTTCTCCGGAAGTGGCAGCGGA ACCGAGTTCACCCTGACAATTAGCTCCTTGCA GCCCGAGGATTTCGCTCGCTATTACTGTCAAC AGAGTTATTCAACCCCTTTTACATTCGGACAG GGAACTAAAGTTGAAATTAAGAGGGCCGCTGC CCTTGATAATGAAAAGTCAAACGGAACAATCA TTCACGTGAAGGGCAAGCACCTCTGTCCGTCA CCCTTGTTCCCTGGTCCATCCAAGCCATTCTG GGTGTTGGTCGTAGTGGGTGGAGTCCTCGCTT GTTACTCTCTGCTCGTCACCGTGGCTTTTATA ATCTTCTGGGTTCGTTTTCCGTCGTTAAGCG GGGGAGAAAAAAGCTGCTGTACATTTTCAAAC AGCCGTTTATGAGGCCGGTCCAAACGACTCAG GAAGAAGACGGCTGCTCCTGCCGCTTTCCTGA GGAGGAGGAGGGCGGGTGCGAACTGAGGGTGA AGTTTTCCAGATCTGCAGATGCACCAGCGTAT CAGCAGGGCCAGAACCAACTGTATAACGAGCT CAACCTGGGACGCAGGGAAGAGTATGACGTTT TGGACAAGCGCAGAGGACGGGACCCTGAGATG GGTGGCAAACCAAGACGAAAAAACCCCCAGGA GGGTCTCTATAATGAGCTGCAGAAGGATAAGA | 39 | MALPVTALLLPLALLLHAARP QVQLQESGPGLVKPSQTLSLT CTVSGDSITSGGYYWSIRQH PGKGLEWIGYIFYSGSTDYNP SLKSRVTISVDTSKNQFSLKL SSVTAADTAVYYCARSGYSYA LFDHWGQGTLVTVSSGGGGSG GGGSGGGGSDIQMTQSPSSLS ASVGDRVTISCRASQFIGRYF NWYQQQPGKAPKVLIYAESSL QSGVPSRFSGSGSGTEFTLTI SSLQPEDFARYYCQQSYSTPF TFGQGTKVEIKRAAALDNEKS NGTIIHVKGKHLCPSPLFPGP SKPFWVLVVVGGVLACYSLLV TVAFIIFWVRFSVVKRGRKKL LYIFKQPFMRPVQTTQEEDGC SCRFPEEEEGGCELRVKFSRS ADAPAYQQGQNQLYNELNLGR REEYDVLDKRRGRDPEMGGKP RRKNPQEGLYNELQKDKMAEA YSEIGMKGERRRGKGHDGLYQ GLSTATKDTYDALHMQALPPR | 40 |

TABLE 2-continued

Example CAR Sequences

| Anti-CD70 CAR | | SEQ ID NO: | | SEQ ID NO: |
|---|---|---|---|---|
| | TGGCTGAAGCCTATTCTGAAATAGGCATGAAA<br>GGAGAGCGGAGAAGGGGAAAAGGGCACGACGG<br>TTTGTACCAGGGACTCAGCACTGCTACGAAGG<br>ATACTTATGACGCTCTCCACATGCAAGCCCTG<br>CCACCTAGG | | | |
| 1C8.1.001_<br>C8K_28z | ATGGCACTCCCCGTAACTGCTCTGCTGCTGCC<br>GTTGGCATTGCTCCTGCACGCCGCACGCCCGC<br>AGGTGCAGCTCCAAGAATCTGGACCGGGTCTC<br>GTCAAGCCATCACAGACACTGTCCCTGACCTG<br>CACCGTCTCCGGCGACTCTATCATTTCAGGCG<br>GCTACTATTGGTCCTGGATTAGACAACATCCG<br>GGAAAGGGTCTTGAATGGATCGGCTATATTTT<br>CTACAGCGGGAGTACGGATTACAATCCTAGTC<br>TCAAGAGCCGCGTTACCATTTCAGTGGATACT<br>TCAAAAAACCAGTTTAGCCTGAAGCTGTCTTC<br>TGTAACAGCTGCTGACACAGCCGTGTACTATT<br>GCGCCAGGAGCGGCTACAGCTATGCCCTGTTT<br>GACCACTGGGGGCAAGGCACTCTTGTGACGGT<br>GTCAAGTGGAGGGGGAGGATCAGGCGGCGGGG<br>GATCCGGCGGCGGGGTAGTGACATTCAAATG<br>ACGCAGTCCCCAAGTTCTCTGTCCGCTAGCGT<br>CGGCGACCGAGTGACCATCAGCTGCCGAGCAT<br>CCCAGTTTATCGGTAGATATTTCAATTGGTAC<br>CAGCAACAACCGGGCAAAGCGCCCAAGGTCCT<br>GATCTACGCTGAGAGCAGTCTGCAATCCGGCG<br>TACCTAGCAGGTTCTCCGGAAGTGGCAGCGGA<br>ACCGAGTTCACCCTGACAATTAGCTCCTTGCA<br>GCCCGAGGATTTCGCTCGCTATTACTGTCAAC<br>AGAGTTATTCAACCCCTTTTACATTCGGACAG<br>GGAACTAAAGTTGAAATTAAGAGGGCCGCTGC<br>CTTCGTGCCTGTTTTTCTGCCCGCGAAACCCA<br>CAACTACCCCCGCCCCTCGGCCCCCAACTCCT<br>GCACCAACTATCGCTTCCCAACCCCTGTCTCT<br>GAGACCTGAGGCATGCCGCCCCGCGGCAGGCG<br>GCGCCGTGCACACTAGAGGCCTGGACTTCGCC<br>TGCGATATTTATATCTGGGCCCCCCTTGCCGG<br>GACATGCGGGGTACTGCTGCTGTCTCTGGTGA<br>TTACCCTCTACTGCAACCACAGAAACAGATCC<br>AAAAGAAGCCGCCTGCTCCATAGCGATTACAT<br>GAATATGACTCCACGCCGCCCTGGCCCCACAA<br>GGAAACACTACCAGCCTTACGCACCACCTAGA<br>GATTTCGCTGCCTATCGGAGCAGGGTGAAGTT<br>TTCCAGATCTGCAGATGCACCAGCGTATCAGC<br>AGGGCCAGAACCAACTGTATAACGAGCTCAAC<br>CTGGGACGCAGGGAAGAGTATGACGTTTTGGA<br>CAAGCGCAGAGGACGGGACCCTGAGATGGGTG<br>GCAAAACCAAGACGAAAAAACCCCCAGGAGGGT<br>CTCTATAATGAGCTGCAGAAGGATAAGATGGC<br>TGAAGCCTATTCTGAAATAGGCATGAAAGGAG<br>AGCGGAGAAGGGGAAAAGGGCACGACGTTTTG<br>TACCAGGGACTCAGCACTGCTACGAAGGATAC<br>TTATGACGCTCTCCACATGCAAGCCCTGCCAC<br>CTAGG | 41 | MALPVTALLLPLALLLHAARP<br>QVQLQESGPGLVKPSQTLSLT<br>CTVSGDSITSGGYYWSWIRQH<br>PGKGLEWIGYIFYSGSTDYNP<br>SLKSRVTISVDTSKNQFSLKL<br>SSVTAADTAVYYCARSGYSYA<br>LFDHWGQGTLVTVSSGGGGSG<br>GGGSGGGGSDIQMTQSPSSLS<br>ASVGDRVTISCRASQFIGRYF<br>NWYQQQPGKAPKVLIYAESSL<br>QSGVPSRFSGSGSGTEFTLTI<br>SSLQPEDFARYYCQQSYSTPF<br>TFGQGTKVEIKRAAAFVPVFL<br>PAKPTTTPAPRPPTPAPTIAS<br>QPLSLRPEACRPAAGGAVHTR<br>GLDFACDIYIWAPLAGTCGVL<br>LLSLVITLYCNHRNRSKRSRL<br>LHSDYMNMTPRRPGPTRKHYQ<br>PYAPPRDFAAYRSRVKFSRSA<br>DAPAYQQGQNQLYNELNLGRR<br>EEYDVLDKRRGRDPEMGGKPR<br>RKNPQEGLYNELQKDKMAEAY<br>SEIGMKGERRRGKGHDGLYQG<br>LSTATKDTYDALHMQALPPR | 42 |
| 1C8.1.001_<br>C8K_4Bz | ATGGCACTCCCCGTAACTGCTCTGCTGCTGCC<br>GTTGGCATTGCTCCTGCACGCCGCACGCCCGC<br>AGGTGCAGCTCCAAGAATCTGGACCGGGTCTC<br>GTCAAGCCATCACAGACACTGTCCCTGACCTG<br>CACCGTCTCCGGCGACTCTATCATTTCAGGCG<br>GCTACTATTGGTCCTGGATTAGACAACATCCG<br>GGAAAGGGTCTTGAATGGATCGGCTATATTTT<br>CTACAGCGGGAGTACGGATTACAATCCTAGTC<br>TCAAGAGCCGCGTTACCATTTCAGTGGATACT<br>TCAAAAAACCAGTTTAGCCTGAAGCTGTCTTC<br>TGTAACAGCTGCTGACACAGCCGTGTACTATT<br>GCGCCAGGAGCGGCTACAGCTATGCCCTGTTT<br>GACCACTGGGGGCAAGGCACTCTTGTGACGGT<br>GTCAAGTGGAGGGGGAGGATCAGGCGGCGGGG<br>GATCCGGCGGCGGGGTAGTGACATTCAAATG<br>ACGCAGTCCCCAAGTTCTCTGTCCGCTAGCGT<br>CGGCGACCGAGTGACCATCAGCTGCCGAGCAT<br>CCCAGTTTATCGGTAGATATTTCAATTGGTAC<br>CAGCAACAACCGGGCAAAGCGCCCAAGGTCCT | 43 | MALPVTALLLPLALLLHAARP<br>QVQLQESGPGLVKPSQTLSLT<br>CTVSGDSIISGGYYWSWIRQH<br>PGKGLEWIGYIFYSGSTDYNP<br>SLKSRVTISVDTSKNQFSLKL<br>SSVTAADTAVYYCARSGYSYA<br>LFDHWGQGTLVTVSSGGGGSG<br>GGGSGGGGSDIQMTQSPSSLS<br>ASVGDRVTISCRASQFIGRYF<br>NWYQQQPGKAPKVLIYAESSL<br>QSGVPSRFSGSGSGTEFTLTI<br>SSLQPEDFARYYCQQSYSTPF<br>TFGQGTKVEIKRAAAFVPVFL<br>PAKPTTTPAPRPPTPAPTIAS<br>QPLSLRPEACRPAAGGAVHTR<br>GLDFACDIYIWAPLAGTCGVL<br>LLSLVITLYCNHRNRFSVVKR<br>GRKKLLYIFKQPFMRPVQTTQ<br>EEDGCSCRFPEEEEGGCELRV | 44 |

TABLE 2-continued

Example CAR Sequences

| Anti-CD70 CAR | | SEQ ID NO: | | SEQ ID NO: |
|---|---|---|---|---|
| | GATCTACGCTGAGAGCAGTCTGCAATCCGGCG<br>TACCTAGCAGGTTCTCCGGAAGTGGCAGCGGA<br>ACCGAGTTCACCCTGACAATTAGCTCCTTGCA<br>GCCCGAGGATTTCGCTCGCTATTACTGTCAAC<br>AGAGTTATTCAACCCCTTTTACATTCGGACAG<br>GGAACTAAAGTTGAAATTAAGAGGGCCGCTGC<br>CTTCGTGCCTGTTTTTCTGCCCGCGAAACCCA<br>CAACTACCCCCGCCCCTCGGCCCCCAACTCCT<br>GCACCAACTATCGCTTCCCAACCCCTGTCTCT<br>GAGACCTGAGGCATGCCGCCCCGCGGCAGGCG<br>GCGCCGTGCACACTAGAGGCCTGGACTTCGCC<br>TGCGATATTTATATCTGGGCCCCCCTTGCCGG<br>GACATGCGGGTACTGCTGCTGTCTCTGGTGA<br>TTACCCTCTACTGCAACCACAGAAACCGCTTT<br>TCCGTCGTTAAGCGGGGAGAAAAAAGCTGCT<br>GTACATTTTCAAACAGCCGTTTATGAGGCCGG<br>TCCAAACGACTCAGGAAGAAGACGGCTGCTCC<br>TGCCGCTTTCCTGAGGAGGAGGAGGGCGGGTG<br>CGAACTGAGGGTGAAGTTTTCCAGATCTGCAG<br>ATGCACCAGCGTATCAGCAGGGCCAGAACCAA<br>CTGTATAACGAGCTCAACCTGGGACGCAGGGA<br>AGAGTATGACGTTTTGGACAAGCGCAGAGGAC<br>GGGACCCTGAGATGGGTGGCAAACCAAGACGA<br>AAAAACCCCCAGGAGGGTCTCTATAATGAGCT<br>GCAGAAGGATAAGATGGCTGAAGCCTATTCTG<br>AAATAGGCATGAAAGGAGAGCGGAGAAGGGA<br>AAAGGGCACGACGGTTTGTACCAGGGACTCAG<br>CACTGCTACGAAGGATACTTATGACGCTCTCC<br>ACATGCAAGCCCTGCCACCtAGG | | KFSRSADAPAYQQGQNQLYNE<br>LNLGRREEYDVLDKRRGRDPE<br>MGGKPRRKNPQEGLYNELQKD<br>KMAEAYSEIGMKGERRRGKGH<br>DGLYQGLSTATKDTYDALHMQ<br>ALPPR | |
| 6E9.1_<br>C28T_28z | ATGGCACTCCCCGTAACTGCTCTGCTGCTGCC<br>GTTGGCATTGCTCCTGCACGCCGCACGCCCGC<br>AGGTACACCTGGTGCAGAGCGGGGCGGAGGTC<br>AAGAAACCGGGCGCATCCGTACGCGTGAGCTG<br>CAAGGCCTCCGGATACACTTTTACTTCTTACT<br>ATCTGCATTGGGTCAGGCAGGCACCGGGTCAG<br>GGACTGGAGTGGATGGGCATTGTGGACCCAAG<br>CGGAGGGAGTACGTCATATGATCAGAAGTTTC<br>AAGGTAGGTTTACCATGACACGGGACACGTCA<br>ACGAGTACCGTCTACATGGAGCTCAGTAGTCT<br>GCGGAGCGAAGACACCGCAGTCTACTACTGCG<br>CACGCGATTATGGAGACTATGTCTTTGACTAT<br>TGGGGGCAGGGGACGCTCGTGACCGTTTCAAG<br>CGGGGGGGGCGGATCCGGTGGGGAGGTTCCG<br>GCGGTGGGGGTTCACAAAGCGTACTGACACAG<br>CCCCCGAGTGCATCCGGGACCCCCGGCCAAAG<br>GGTTACAATCAGCTGCTCTGGCAGCTCCAGTA<br>ACATAGGTACCAACACGGTGAACTGGTACCAG<br>CAGTTGCCTGGCACAGCGCCTCAGCTGCTCAT<br>CTATATCAACAATCAGCGGCCAAGTGGCGTGC<br>CCGATAGATTCTCAGGCTCAAAGAGCGGAACC<br>AGCGCTAGCTTGGCAATCAGTGGCCTTCAATC<br>CGAAGACGAAGCGATTACTATTGTGCGACCT<br>GGGACGATAGCCTGAACGGCCCCGTCGTGGGC<br>GGCGGGACGAAACTGACAGTGTTGGGCGCCGC<br>TGCCCTTGATAATGAAAAGTCAAACGGAACAA<br>TCATTCACGTGAAGGGCAAGCACCTCTGTCCG<br>TCACCCTTGTTCCCTGGTCCATCCAAGCCATT<br>CTGGGTGTTGGTCGTAGTGGGTGGAGTCCTCG<br>CTTGTTACTCTCTGCTCGTCACCGTGGCTTTT<br>ATAATCTTCTGGGTTAGATCAAAAGAAGCCG<br>CCTGCTCCATAGCGATTACATGAATATGACTC<br>CACGCCGCCCTGGCCCCACAAGGAAACACTAC<br>CAGCCTTACGCACCACCTAGAGATTTCGCTGC<br>CTATCGGAGCAGGGTGAAGTTTTCCAGATCTG<br>CAGATGCACCAGCGTATCAGCAGGGCCAGAAC<br>CAACTGTATAACGAGCTCAACCTGGGACGCAG<br>GGAAGAGTATGACGTTTTGGACAAGCGCAGAG<br>GACGGGACCCTGAGATGGGTGGCAAACCAAGA<br>CGAAAAAACCCCCAGGAGGGTCTCTATAATGA<br>GCTGCAGAAGGATAAGATGGCTGAAGCCTATT<br>CTGAAATAGGCATGAAAGGAGAGCGGAGAAGG | 45 | MALPVTALLLPLALLLHAARP<br>QVHLVQSGAEVKKPGASVRVS<br>CKASGYTFTSYYLHWVRQAPG<br>QGLEWMGIVDPSGGSTSYDQK<br>FQGRFTMTRDTSTSTVYMELS<br>SLRSEDTAVYYCARDYGDYVF<br>DYWGQGTLVTVSSGGGGSGGG<br>GSGGGGSQSVLTQPPSASGTP<br>GQRVTISCSGSSSNIGTNTVN<br>WYQQLPGTAPQLLIYINNQRP<br>SGVPDRFSGSKSGTSASLAIS<br>GLQSEDEADYYCATWDDSLNG<br>PVVGGGTKLTVLGAAALDNEK<br>SNGTIIHVKGKHLCPSPLFPG<br>PSKPFWVLVVVGGVLACYSLL<br>VTVAFIIFWVRSKRSRLLHSD<br>YMNMTPRRPGPTRKHYQPYAP<br>PRDFAAYRSRVKFSRSADAPA<br>YQQGQNQLYNELNLGRREEYD<br>VLDKRRGRDPEMGGKPRRKNP<br>QEGLYNELQKDKMAEAYSEIG<br>MKGERRRGKGHDGLYQGLSTA<br>TKDTYDALHMQALPPR | 46 |

TABLE 2-continued

Example CAR Sequences

| Anti-CD70 CAR | | SEQ ID NO: | | SEQ ID NO: |
|---|---|---|---|---|
| | GGAAAAGGGCACGACGGTTTGTACCAGGGACT CAGCACTGCTACGAAGGATACTTATGACGCTC TCCACATGCAAGCCCTGCCACCTAGG | | | |
| 6E9.1_ C28T_4Bz | ATGGCACTCCCCGTAACTGCTCTGCTGCTGCC GTTGGCATTGCTCCTGCACGCCGCACGCCCGC AGGTACACCTGGTGCAGAGCGGGGCGGAGGTC AAGAAACCGGGCGCATCCGTACGCGTGAGCTG CAAGGCCTCCGGATACACTTTTACTTCTTACT ATCTGCATTGGGTCAGGCAGGCACCGGGTCAG GGACTGGAGTGGATGGGCATTGTGGACCCAAG CGGAGGGAGTACGTCATATGATCAGAAGTTTC AAGGTAGGTTTACCATGACACGGGACACGTCA ACGAGTACCGTCTACATGGAGCTCAGTAGTCT GCGGAGCGAAGACACCGCAGTCTACTACTGCG CACGCGATTATGGAGACTATGTCTTTGACTAT TGGGGGCAGGGGACGCTCGTGACCGTTTCAAG CGGGGGGGCGGATCCGGTGGGGAGGTTCCG GCGGTGGGGTTCACAAAGCGTACTGACACAG CCCCCGAGTGCATCCGGACCCCCGGCCAAAG GGTTACAATCAGCTGCTCTGGCAGCTCCAGTA ACATAGGTACCAACACGGTGAACTGGTACCAG CAGTTGCCTGGCACAGCGCCTCAGCTGCTCAT CTATATCAACAATCAGCGGCCAAGTGGCGTGC CCGATAGATTCTCAGGCTCAAAGAGCGGAACC AGCGCTAGCTTGGCAATCAGTGGCCTTCAATC CGAAGACGAAGCCGATTACTATTGTGCGACCT GGGACGATAGCCTGAACGGCCCCGTCGTGGGC GGCGGGACGAAACTGACAGTGTTGGCGCCGC TGCCCTTGATAATGAAAAGTCAAACGGAACAA TCATTCACGTGAAGGGCAAGCACCTCTGTCCG TCACCCTTGTTCCCTGGTCCATCCAAGCCATT CTGGGTGTTGGTCGTAGTGGGTGGAGTCCTCG CTTGTTACTCTCTGCTCGTCACCGTGGCTTTT ATAATCTTCTGGGTTCGCTTTTCCGTCGTTAA GCGGGGAGAAAAAAGCTGCTGTACATTTTCA AACAGCCGTTTATGAGGCCGGTCCAAACGACT CAGGAAGAAGACGGCTGCTCCTGCCGCTTTCC TGAGGAGGAGGAGGGCGGGTGCGAACTGAGGG TGAAGTTTTCCAGATCTGCAGATGCACCAGCG TATCAGCAGGGCCAGAACCAACTGTATAACGA GCTCAACCTGGGACGCAGGGAAGAGTATGACG TTTTGGACAAGCGCAGAGGACGGGACCCTGAG ATGGGTGGCAAACCAAGACGAAAAAACCCCCA GGAGGGTCTCTATAATGAGCTGCAGAAGGATA AGATGGCTGAAGCCTATTCTGAAATAGGCATG AAAGGAGAGCGGAGAAGGGGAAAAGGGCACGA CGGTTTGTACCAGGGACTCAGCACTGCTACGA AGGATACTTATGACGCTCTCCACATGCAAGCC CTGCCACCTAGG | 47 | MALPVTALLLPLALLLHAARP QVHLVQSGAEVKKPGASVRVS CKASGYTFTSYYLHWVRQAPG QGLEWMGIVDPSGGSTSYDQK FQGRFTMTRDTSTSTVYMELS SLRSEDTAVYYCARDYGDYVF DYWGQGTLVTVSSGGGGSGGG GSGGGGSQSVLTQPPSASGTP GQRVTISCSGSSSNIGTNTVN WYQQLPGTAPQLLIYINNQRP SGVPDRFSGSKSGTSASLAIS GLQSEDEADYYCATWDDSLNG PVVGGGTKLTVLGAAALDNEK SNGTIIHVKGKHLCPSPLFPG PSKPFWVLVVVGGVLACYSLL VTVAFIIFWVRFSVVKRGRKK LLYIFKQPFMRPVQTTQEEDG CSCRFPEEEEGGCELRVKFSR SADAPAYQQGQNQLYNELNLG RREEYDVLDKRRGRDPEMGGK PRRKNPQEGLYNELQKDKMAE AYSEIGMKGERRRGKGHDGLY QGLSTATKDTYDALHMQALPP R | 48 |
| 6E9.1_ C8K_28z | ATGGCACTCCCCGTAACTGCTCTGCTGCTGCC GTTGGCATTGCTCCTGCACGCCGCACGCCCGC AGGTACACCTGGTGCAGAGCGGGGCGGAGGTC AAGAAACCGGGCGCATCCGTACGCGTGAGCTG CAAGGCCTCCGGATACACTTTTACTTCTTACT ATCTGCATTGGGTCAGGCAGGCACCGGGTCAG GGACTGGAGTGGATGGGCATTGTGGACCCAAG CGGAGGGAGTACGTCATATGATCAGAAGTTTC AAGGTAGGTTTACCATGACACGGGACACGTCA ACGAGTACCGTCTACATGGAGCTCAGTAGTCT GCGGAGCGAAGACACCGCAGTCTACTACTGCG CACGCGATTATGGAGACTATGTCTTTGACTAT TGGGGGCAGGGGACGCTCGTGACCGTTTCAAG CGGGGGGGCGGATCCGGTGGGGAGGTTCCG GCGGTGGGGTTCACAAAGCGTACTGACACAG CCCCCGAGTGCATCCGGACCCCCGGCCAAAG GGTTACAATCAGCTGCTCTGGCAGCTCCAGTA ACATAGGTACCAACACGGTGAACTGGTACCAG CAGTTGCCTGGCACAGCGCCTCAGCTGCTCAT CTATATCAACAATCAGCGGCCAAGTGGCGTGC CCGATAGATTCTCAGGCTCAAAGAGCGGAACC | 49 | MALPVTALLLPLALLLHAARP QVHLVQSGAEVKKPGASVRVS CKASGYTFTSYYLHWVRQAPG QGLEWMGIVDPSGGSTSYDQK FQGRFTMTRDTSTSTVYMELS SLRSEDTAVYYCARDYGDYVF DYWGQGTLVTVSSGGGGSGGG GSGGGGSQSVLTQPPSASGTP GQRVTISCSGSSSNIGTNTVN WYQQLPGTAPQLLIYINNQRP SGVPDRFSGSKSGTSASLAIS GLQSEDEADYYCATWDDSLNG PVVGGGTKLTVLGAAAFVPVF LPAKPTTTPAPRPPTPAPTIA SQPLSLRPEACRPAAGGAVHT RGLDFACDIYIWAPLAGTCGV LLLSLVITLYCNHRNRSKRSR LLHSDYMNMTPRRPGPTRKHY QPYAPPRDFAAYRSVKFSRS ADAPAYQQGQNQLYNELNLGR REEYDVLDKRRGRDPEMGGKP | 50 |

TABLE 2-continued

Example CAR Sequences

| Anti-CD70 CAR | | SEQ ID NO: | | SEQ ID NO: |
|---|---|---|---|---|
| | AGCGCTAGCTTGGCAATCAGTGGCCTTCAATC CGAAGACGAAGCCGATTACTATTGTGCGACCT GGGACGATAGCCTGAACGGCCCCGTCGTGGGC GGCGGGACGAAACTGACAGTGTTGGGCGCCGC TGCCTTCGTGCCTGTTTTTCTGCCCGCGAAAC CCACAACTACCCCCGCCCCTCGGCCCCAACT CCTGCACCAACTATCGCTTCCCAACCCCTGTC TCTGAGACCTGAGGCATGCCGCCCCGCGGCAG GCGGCGCCGTGCACACTAGAGGCCTGGACTTC GCCTGCGATATTTATATCTGGGCCCCCCTTGC CGGGACATGCGGGTACTGCTGCTGTCTCTGG TGATTACCCTCTACTGCAACCACAGAAACAGA TCCAAAAGAAGCCGCCTGCTCCATAGCGATTA CATGAATATGACTCCACGCCGCCCTGGCCCCA CAAGGAAACACTACCAGCCTTACGCACCACCT AGAGATTTCGCTGCCTATCGGAGCAGGGTGAA GTTTTCCAGATCTGCAGATGCACCAGCGTATC AGCAGGGCCAGAACCAACTGTATAACGAGCTC AACCTGGGACGCAGGGAAGAGTATGACGTTTT GGACAAGCGCAGAGGACGGGACCCTGAGATGG GTGGCAAACCAAGACGAAAAAACCCCCAGGAG GGTCTCTATAATGAGCTGCAGAAGGATAAGAT GGCTGAAGCCTATTCTGAAATAGGCATGAAAG GAGAGCGGAGAAGGGGAAAAGGGCACGACGGT TTGTACCAGGGACTCAGCACTGCTACGAAGGA TACTTATGACGCTCTCCACATGCAAGCCCTGC CACCtAGG | | RRKNPQEGLYNELQKDKMAEA YSEIGMKGERRRGKGHDGLYQ GLSTATKDTYDALHMQALPPR | |
| 6E9.1_C8K_4Bz | ATGGCACTCCCCGTAACTGCTCTGCTGCTGCC GTTGGCATTGCTCCTGCACGCCGCACGCCCGC AGGTACACCTGGTGCAGAGCGGGGCGGAGGTC AAGAAACCGGGCGCATCCGTACGCGTGAGCTG CAAGGCCTCCGGATACACTTTTACTTCTTACT ATCTGCATTGGGTCAGGCAGGCACCGGGTCAG GGACTGGAGTGGATGGGCATTGTGGACCCAAG CGGAGGGAGTACGTCATATGATCAGAAGTTTC AAGGTAGGTTTACCATGACACGGGACACGTCA ACGAGTACCGTCTACATGGAGCTCAGTAGTCT GCGGAGCGAAGACACCGCAGTCTACTACTGCG CACGCGATTATGGAGACTATGTCTTTGACTAT TGGGGGCAGGGGACGCTCGTGACCGTTTCAAG CGGGGGGGGCGGATCCGGTGGGGAGGTTCCG GCGGTGGGGGTTCACAAAGCGTACTGACACAG CCCCCGAGTGCATCCGGACCCCCGGCCAAAG GGTTACAATCAGCTGCTCTGGCAGCTCCAGTA ACATAGGTACCAACACGGTGAACTGGTACCAG CAGTTGCCTGGCACAGCGCCTCAGCTGCTCAT CTATATCAACAATCAGCGGCCAAGTGGCGTGC CCGATAGATTCTCAGGCTCAAAGAGCGGAACC AGCGCTAGCTTGGCAATCAGTGGCCTTCAATC CGAAGACGAAGCCGATTACTATTGTGCGACCT GGGACGATAGCCTGAACGGCCCCGTCGTGGGC GGCGGGACGAAACTGACAGTGTTGGGCGCCGC TGCCTTCGTGCCTGTTTTTCTGCCCGCGAAAC CCACAACTACCCCCGCCCCTCGGCCCCAACT CCTGCACCAACTATCGCTTCCCAACCCCTGTC TCTGAGACCTGAGGCATGCCGCCCCGCGGCAG GCGGCGCCGTGCACACTAGAGGCCTGGACTTC GCCTGCGATATTTATATCTGGGCCCCCCTTGC CGGGACATGCGGGTACTGCTGCTGTCTCTGG TGATTACCCTCTACTGCAACCACAGAAACCGC TTTTCCGTCGTTAAGCGGGGGAGAAAAAAGCT GCTGTACATTTTCAAACAGCCGTTTATGAGGC CGGTCCAAACGACTCAGGAAGAAGACGGCTGC TCCTGCCGCTTTCCTGAGGAGGAGGGCGG GTGCGAACTGAGGGTGAAGTTTTCCAGATCTG CAGATGCACCAGCGTATCAGCAGGGCCAGAAC CAACTGTATAACGAGCTCAACCTGGGACGCAG GGAAGAGTATGACGTTTTGGACAAGCGCAGAG GACGGGACCCTGAGATGGGTGGCAAACCAAGA CGAAAAAACCCCCAGGAGGGTCTCTATAATGA GCTGCAGAAGGATAAGATGGCTGAAGCCTATT CTGAAATAGGCATGAAAGGAGAGCGGAGAAGG GGAAAAGGGCACGACGGTTTGTACCAGGGACT | 51 | MALPVTALLLPLALLLHAARP QVHLVQSGAEVKKPGASVRVS CKASGYTFTSYYLHWVRQAPG QGLEWMGIVDPSGGSTSYDQK FQGRFTMTRDTSTSTVYMELS SLRSEDTAVYYCARDYGDYVF DYWGQGTLVTVSSGGGGSGGG GSGGGGSQSVLTQPPSASGTP GQRVTISCSGSSSNIGTNTVN WYQQLPGTAPQLLIYINNQRP SGVPDRFSGSKSGTSASLAIS GLQSEDEADYYCATWDDSLNG PVVGGGTKLTVLGAAAFVPVF LPAKPTTTPAPRPPTPAPTIA SQPLSLRPEACRPAAGGAVHT RGLDFACDIYIWAPLAGTCGV LLLSLVITLYCNHRNRFSVVK RGRKKLLYIFKQPFMRPVQTT QEEDGCSCRFPEEEEGGCELR VKFSRSADAPAYQQGQNQLYN ELNLGRREEYDVLDKRRGRDP EMGGKPRRKNPQEGLYNELQK DKMAEAYSEIGMKGERRRGKG HDGLYQGLSTATKDTYDALHM QALPPR | 52 |

TABLE 2-continued

Example CAR Sequences

| Anti-CD70 CAR | SEQ ID NO: | | SEQ ID NO: |
|---|---|---|---|
| | CAGCACTGCTACGAAGGATACTTATGACGCTC TCCACATGCAAGCCCTGCCACCTAGG | | |

In some embodiments, a polynucleotide of the instant disclosure encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 30, 32, 34, 36, 38, 40, 42, 44, 46, 48, 50 and 52. In some embodiments, the CAR comprises an amino acid sequence selected from the group consisting of SEQ ID NOs: 30, 32, 34, 36, 38, 40, 42, 44, 46, 48, 50 and 52. In one embodiment, the CAR comprises the amino acid sequence of SEQ ID NO: 30. In another embodiment, the CAR comprises the amino acid sequence of SEQ ID NO: 32. In another embodiment, the CAR comprises the amino acid sequence of SEQ ID NO: 34. In another embodiment, the CAR comprises the amino acid sequence of SEQ ID NO: 36. In another embodiment, the CAR comprises the amino acid sequence of SEQ ID NO: 38. In another embodiment, the CAR comprises the amino acid sequence of SEQ ID NO: 40. In another embodiment, the CAR comprises the amino acid sequence of SEQ ID NO: 42. In another embodiment, the CAR comprises the amino acid sequence of SEQ ID NO: 44. In another embodiment, the CAR comprises the amino acid sequence of SEQ ID NO: 46. In another embodiment, the CAR comprises the amino acid sequence of SEQ ID NO: 48. In another embodiment, the CAR comprises the amino acid sequence of SEQ ID NO: 50. In another embodiment, the CAR comprises the amino acid sequence of SEQ ID NO: 52.

In some embodiments, a polynucleotide of the instant disclosure encoding a CAR comprises an nucleotide sequence at least about 50%, at least about 60%, at least about 65%, at least about 70%, at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 29, 31, 33, 35, 37, 39, 41, 43, 45, 47, 49 and 51. In some embodiments, the polynucleotide comprises a nucleotide sequence selected from the group consisting of SEQ ID NOs: 29. In one embodiment, the polynucleotide comprises the nucleotide sequence of SEQ ID NO: 31. In another embodiment, the polynucleotide comprises the nucleotide sequence of SEQ ID NO: 33. In another embodiment, the polynucleotide comprises the nucleotide sequence of SEQ ID NO: 35. In another embodiment, the polynucleotide comprises the nucleotide sequence of SEQ ID NO: 37. In another embodiment, the polynucleotide comprises the nucleotide sequence of SEQ ID NO: 39. In another embodiment, the polynucleotide comprises the nucleotide sequence of SEQ ID NO: 41. In another embodiment, the polynucleotide comprises the nucleotide sequence of SEQ ID NO: 43. In another embodiment, the polynucleotide comprises the nucleotide sequence of SEQ ID NO: 45. In another embodiment, the polynucleotide comprises the nucleotide sequence of SEQ ID NO: 47. In another embodiment, the polynucleotide comprises the nucleotide sequence of SEQ ID NO: 49. In another embodiment, the polynucleotide comprises the nucleotide sequence of SEQ ID NO: 51.

IV. Vectors, Cells, and Pharmaceutical Compositions

In some aspects, provided herein are vectors comprising a polynucleotide of the instant disclosure. In some embodiments, the instant disclosure is directed to a vector or a set of vectors comprising a polynucleotide encoding a CAR or a TCR, as described herein. In other embodiments, the instant disclosure is directed to a vector or a set of vectors comprising a polynucleotide encoding an antibody or an antigen binding molecule thereof that specifically binds to CD70, as disclosed herein.

Any vector known in the art can be suitable for the instant disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. In some embodiments of the instant disclosure one, two or more vectors can be employed. For example, in one embodiment, one or more components of a CAR or TCR can be disposed on one vector, while one or more different components of a CAR or TCR can be disposed on a different vector.

In other aspects, provided herein are cells comprising a polynucleotide or a vector of the instant disclosure. In some embodiments, the instant disclosure is directed to host cells, such as in vitro cells, comprising a polynucleotide encoding a CAR or a TCR, as described herein. In some embodiments, the instant disclosure is directed to host cells, e.g., in vitro cells, comprising a polynucleotide encoding an antibody or an antigen binding molecule thereof that specifically binds to CD70, as disclosed herein.

In other embodiments, the instant disclosure is directed to in vitro cells comprising a polypeptide encoded by a polynucleotide encoding a CAR or a TCR, as disclosed herein. In other embodiments, the instant disclosure is directed to cells, in vitro cells, comprising a polypeptide encoded by a polynucleotide encoding an antigen binding molecule that specifically binds to CD70, as disclosed herein.

Any cell can be used as a host cell for the polynucleotides, the vectors, or the polypeptides of the instant disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobacteriaceae such as *Escherichia*, e.g., *E. coli*; *Enterobacter*; *Erwinia*; *Klebsiella*; *Proteus*; *Salmonella*, e.g., *Salmonella typhimurium*; *Serratia*, e.g., *Serratia marcescans*, and *Shigella*; Bacilli such as *B. subtilis* and *B. licheniformis*; *Pseudomonas* such as *P. aeruginosa*; and *Streptomyces*. In some embodiments, the host cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In some embodiments, the T cell is a tumor-infiltrating lymphocyte (TIL), autologous T cell, engineered autologous T cell (eACT™), an allogeneic T cell, a heterologous T cell, or any combination thereof.

A cell of the instant disclosure can be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the COBE™ 2991 cell processor, the Baxter CYTOMATE™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Publication No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as $CD28^+$, $CD4^+$, $CD8^+$, $CD45RA^+$, and $CD45RO^+$ T cells can be further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD14, CD20, CD11b, CD16, HLA-DR, and CD8. In some embodiments, flow cytometry and cell sorting are used to isolate cell populations of interest for use in the instant disclosure. Using these standard techniques, the engineered T cells administered to a patient when performing the methods provided herein can comprise any desired proportion of cells. For example, it may be desirable to provide only engineered $CD8^+$ cells to a patient, only engineered $CD4^+$ cells to a patient, or a desired ratio of $CD4^+$ to $CD8^+$ cells, such as equal numbers of $CD4^+$ and $CD8^+$ cells.

In some embodiments, PBMCs are used directly for genetic modification with the immune cells (such as CARs or TCRs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CD3, CD28, CD44, CD45RO, CD45RA and CD127 and are negative for granzyme B. In some embodiments, central memory T cells are $CD3^+$, $CD28^+$, $CD44^{hi}$, $CD45RO^{hi}$, $CD45RA^{low}$ and $CD127^{hi}$ $CD8^+$ T cells. In some embodiments, effector T cells are negative for CD62L, CCR7, CD28, and CD127 and positive for granzyme B and perforin. In some embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In other embodiments, the donor subject is a human patient not afflicted with a cancer or a tumor. In another embodiment, the T cells are derived from pluripotent stem cells maintained under conditions favorable to the differentiation of the stem cells to T cells.

Other aspects of the instant disclosure are directed to compositions comprising a polynucleotide provided herein, a vector provided herein, a polypeptide provided herein, or an in vitro cell provided herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR, wherein the CAR or the TCR comprises an antigen binding molecule that specifically binds to CD70. In another embodiment, the composition comprises a CAR or a TCR encoded by a polynucleotide provided herein, wherein the CAR or the TCR comprises an antigen binding molecule that specifically binds to CD70. In another embodiment, the composition comprises a T cell comprising a polynucleotide encoding a CAR or a TCR, wherein the CAR or the TCR comprises an antigen binding molecule that specifically binds to CD70. In another embodiment, the composition comprises an antibody or an antigen binding molecule thereof encoded by a polynucleotide provided herein. In another embodiment, the composition comprises an in vitro cell comprising a polynucleotide encoding an antibody or an antigen binding molecule thereof encoded by a polynucleotide provided herein. In another embodiment, the composition comprises a CAR or a TCR provided herein, wherein the CAR or the TCR comprises a component comprising an antigen binding molecule that specifically binds to CD70.

In some embodiments, the composition includes more than one different CAR or the TCR comprising a component comprising an antigen binding molecule that specifically binds to CD70. In some embodiments, the composition included more than one CAR or the TCR comprising a component comprising an antigen binding molecule that specifically binds to CD70, wherein the antigen binding molecules to CD70 bind more than one epitope. In some embodiments, the CARs or the TCRs comprising a component comprising an antigen binding molecule that specifically binds to CD70 will not compete with one another for binding to CD70. In some embodiments, any of the CARs or the TCRs comprising a component comprising an antigen binding molecule that specifically binds to CD70 provided herein are combined together in a pharmaceutical composition.

In other embodiments, the composition is selected for parenteral delivery. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a desired CAR or the TCR comprising a component comprising an antigen binding molecule that specifically binds to CD70, with or without additional therapeutic agents, in a pharmaceutically acceptable vehicle. In some embodiments the vehicle for parenteral injection is sterile distilled water in which a CAR or the TCR comprising a component comprising an antigen binding molecule that specifically binds to CD70, with or without at least one additional therapeutic agent, is formulated as a sterile, isotonic solution, properly preserved. In some embodiments, the preparation involves the formulation of the desired CAR or the TCR comprising a component comprising an antigen binding molecule that specifically binds to CD70 with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

V. Methods of Using the Disclosed Antigen Binding Molecules, CARs and TCR

Another aspect of the instant disclosure is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, wherein the CAR or the TCR comprises an antigen binding molecule that specifically binds to CD70, as disclosed herein. In some embodiments, the method comprises transducing a cell with a vector comprising a polynucleotide encoding a CAR or a TCR, wherein the CAR or the TCR comprises an antigen binding molecule that specifically binds to CD70. In other embodiments, the method comprises transducing a cell with a polynucleotide encoding a CAR or TCR comprising an antigen binding molecule that specifically binds to CD70, as disclosed herein. In some embodiments, the method comprises transducing a cell with a vector comprising the polynucleotide encoding the CAR or the TCR comprises an antigen binding molecule that specifically binds to CD70, as described herein. In some embodiments, the method further comprises isolating the cell.

Another aspect of the instant disclosure is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR, wherein the CAR or TCR comprises an antigen binding molecule that specifically binds to CD70, as disclosed herein. In another embodiment, the method comprises administering to a subject an effective amount of a cell comprising a vector comprising a polynucleotide encoding a CAR or a TCR, wherein the CAR or the TCR comprises an antigen binding molecule that specifically binds to CD70, as disclosed herein. In another embodiment, the method comprises administering to a subject an effective amount of a cell comprising a CAR or a TCR encoded by a polynucleotide disclosed herein, wherein the CAR or the TCR comprises an antigen binding molecule that specifically binds to CD70.

In other embodiments, the method comprises administering to a subject an effective amount of a cell comprising a polynucleotide encoding a CAR or TCR comprises an antigen binding molecule that specifically binds to CD70, as disclosed herein. In another embodiment, the method comprises administering to a subject an effective amount of a cell comprising a vector comprising a polynucleotide encoding a CAR or TCR comprising an antigen binding molecule that specifically binds to CD70, as disclosed herein. In another embodiment, the method comprises administering to a subject an effective amount of a cell comprising an antibody or antigen binding molecule thereof encoded by a polynucleotide disclosed herein (e.g., a CAR or TCR), wherein the antibody or antigen binding molecule thereof specifically binds to CD70.

Another aspect of the instant disclosure is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR, such as those provided herein. In some embodiments, the target cell is a tumor cell.

Another aspect of the instant disclosure is directed to a method for treating or preventing a malignancy, said method comprising administering to a subject in need thereof an effective amount of at least one isolated antigen binding molecule described herein or at least one immune cell, wherein the immune cell comprises at least one CAR, TCR, and/or isolated antigen binding molecule as described herein.

Another aspect of the instant disclosure is directed to a method of treating a hyperproliferative disorder or an inflammatory disease in a subject in need thereof comprising administering to the subject a polynucleotide disclosed herein, a vector disclosed herein, a CAR or a TCR disclosed herein, a cell disclosed herein, or a composition disclosed herein. In some embodiments, the inflammatory disease is selected from the group consisting of rheumatoid arthritis, psoriasis, allergies, asthma, autoimmune diseases such as Crohn's, IBD, fibromyalgia, mastocytosis, Celiac disease, and any combination thereof.

Another aspect of the instant disclosure is directed to a method of treating a cancer in a subject in need thereof comprising administering to the subject a polynucleotide disclosed herein, a vector disclosed herein, a CAR or a TCR disclosed herein, a cell disclosed herein, or a composition disclosed herein. In one embodiment, the method comprises administering a polynucleotide encoding a CAR or a TCR, wherein the CAR or the TCR comprises an antigen binding molecule that specifically binds to CD70, as disclosed herein. In another embodiment, the method comprises administering a vector comprising a polynucleotide encoding a CAR or a TCR, wherein the CAR or the TCR comprises an antigen binding molecule that specifically binds to CD70, as disclosed herein. In another embodiment, the method comprises administering a CAR or a TCR encoded by a polynucleotide disclosed herein, wherein the CAR or the TCR comprises an antigen binding molecule that specifically binds to CD70. In another embodiment, the method comprises administering a cell comprising the polynucleotide, or a vector comprising the polynucleotide, encoding a CAR or a TCR, wherein the CAR or the TCR comprises an antigen binding molecule that specifically binds to CD70, as disclosed herein. In other embodiments, the method comprises administering a polynucleotide encoding a CAR or a TCR, wherein the CAR or the TCR comprises an antigen binding molecule that specifically binds to CD70, as disclosed herein. In another embodiment, the method comprises administering a vector comprising a polynucleotide encoding a CAR or a TCR, wherein the CAR or the TCR comprises an antigen binding molecule that specifically binds to CD70, as disclosed herein. In another embodiment, the method comprises administering an antibody, CAR or TCR, wherein the CAR or the TCR comprises an antigen binding molecule that specifically binds to CD70, and is encoded by a polynucleotide disclosed herein. In another embodiment, the method comprises administering a cell comprising the polynucleotide, or a vector comprising the polynucleotide, encoding an antibody, CAR or TCR, wherein the CAR or the TCR comprises an antigen binding molecule that specifically binds to CD70, as disclosed herein.

In some embodiments, an antibody, CAR or TCR, wherein the CAR or the TCR comprises an antigen binding molecule that specifically binds to CD70, is administered alone. In such immune cells, the antibody, CAR or TCR, wherein the CAR or the TCR comprises an antigen binding molecule that specifically binds to CD70, can be under the control of the same promoter region, or a separate promoter. In some embodiments, the genes encoding protein agents and/or an antibody, CAR or TCR, wherein the CAR or the TCR comprises an antigen binding molecule that specifically binds to CD70, can be in separate vectors.

In some embodiments, the methods of treating a cancer in a subject in need thereof comprise a T cell therapy. In one embodiment, the T cell therapy of the instant disclosure is engineered Autologous Cell Therapy (eACT™). According to this embodiment, the method can include collecting blood cells from the patient. The isolated blood cells (e.g., T cells) can then be engineered to express an anti-CD70 CAR of the instant disclosure ("anti-CD70 CAR T cells"). In a particular embodiment, the anti-CD70 CAR T cells are administered to the patient. In some embodiments, the anti-CD70 CAR T cells treat a tumor or a cancer in the patient. In one embodiment the anti-CD70 CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient (e.g., allogeneic T cell therapy).

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$ cells, at least about $10^{10}$ cells, or at least about $10^{11}$ cells. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the anti-CD70 CAR T cells is about $1\times10^5$ cells/kg, $2\times10^5$ cells/kg, $3\times10^5$ cells/kg, $4\times10^5$ cells/kg, $5\times10^5$ cells/kg, $1\times10^6$ cells/kg, $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

Another aspect of the instant disclosure is directed to methods of diagnosis, detection, or validation. In some embodiments, the antigen binding molecule is used as a diagnostic or validation tool. In some embodiments, the antigen binding molecules disclosed herein are used to assay the amount of CD70 present in a sample and/or subject. In some embodiments, the diagnostic antigen binding molecule is not neutralizing. In some embodiments, the antigen binding molecules disclosed herein are used or provided in an assay kit and/or method for the detection of CD70 in mammalian tissues or cells in order to screen/diagnose for a disease or disorder associated with changes in levels of CD70. In some embodiments, the kit comprises an antigen binding molecule that binds CD70, along with means for indicating the binding of the antigen binding molecule with CD70, if present, and optionally CD70 protein levels. Various means for indicating the presence of an antigen binding molecule can be used. For example, fluorophores, other molecular probes, or enzymes can be linked to the antigen binding molecule and the presence of the antigen binding molecule can be observed in a variety of ways. Examples of fluorophores include fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes), FITC, Rhodamine, and Texas Red (Pierce), Cy5, Cy5.5, Cy7 (Amersham Life Science). As will be appreciated by one of skill in the art, the degree of antigen binding molecule binding can be used to determine how much CD70 is in a sample.

V.A. Cancer Treatment

The methods of the disclosure can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that can be treated using the CARs, YCR and antibodies provided herein include tumors that are not vascularized, not yet substantially vascularized, or vascularized. The cancer can also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, myeloid diseases including but not limited to acute myeloid leukemia (AML), chronic myeloid leukemia (CML), acute lymphoblastic leukemia (ALL) (including non T cell ALL), chronic lymphocytic leukemia (CLL), T-cell lymphoma, one or more of B cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, hairy cell leukemia, small cell- or a large cell-follicular lymphoma, malignant lymphoproliferative conditions, MALT lymphoma, mantle cell lymphoma, marginal zone lymphoma, myelodysplasia and myelodysplastic syndrome (MDS), hemophagocytic syndrome (Macrophage Activating Syndrome (MAS), and hemophagocytic lymphohistocytosis (HLH)), chronic or acute granulomatous disease, large cell granuloma, leukocyte adhesion deficiency, plasmablastic lymphoma, plasmacytoid dendritic cell neoplasm, Waldenstrom macroglobulinemia, plasma cell proliferative disorders (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (Crow-Fukase syndrome, Takatsuki disease, PEP syndrome), or combinations thereof. In one embodiment, the cancer is a myeloma. In some embodiments, the cancer is multiple myeloma. In another particular embodiment the cancer is T or B cell lymphoma.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. patent application Ser. Nos. 15/167,977 and 15/295,931 and published US Patent Application PCT/US2016/034885 which are hereby incorporated by reference in their entirety herein. These describe, e.g., methods of conditioning a patient in need of a T cell therapy comprising administering to the patient specified beneficial doses of cyclophosphamide (between about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) alone or in combination with specified doses of fludarabine (between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day).

In some embodiments, the dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In some embodiments, the dose regimen involves treating a patient comprising administering daily to the patient about 600 mg/m$^2$/day of cyclophosphamide and about 30 mg/m$^2$/day of fludarabine for three days prior to administration of a therapeutically effective amount of engineered T cells to the patient.

In some embodiments, the dose regimen involves treating a patient comprising administering daily to the patient about 500 mg/m$^2$/day of cyclophosphamide for two days and about 30 mg/m$^2$/day of fludarabine for four days prior to administration of a therapeutically effective amount of engineered T cells to the patient.

In some embodiments, the dose regimen involves treating a patient comprising administering daily to the patient about 600 mg/m$^2$/day of cyclophosphamide for three days and about 30 mg/m$^2$/day of fludarabine for three days prior to administration of a therapeutically effective amount of engineered T cells to the patient.

In some embodiments, the dose regimen involves treating a patient comprising administering daily to the patient about 550 mg/m$^2$/day of cyclophosphamide for three days and about 30 mg/m$^2$/day of fludarabine for three days prior to administration of a therapeutically effective amount of engineered T cells to the patient.

In some embodiments, the dose regimen involves treating a patient comprising administering daily to the patient about 500 mg/m$^2$/day of cyclophosphamide for three days and about 30 mg/m$^2$/day of fludarabine for three days prior to administration of a therapeutically effective amount of engineered T cells to the patient.

In some embodiments, the dose regimen involves treating a patient comprising administering daily to the patient about 450 mg/m$^2$/day of cyclophosphamide for three days and about 30 mg/m$^2$/day of fludarabine for three days prior to administration of a therapeutically effective amount of engineered T cells to the patient.

In some embodiments, the dose regimen involves treating a patient comprising administering daily to the patient about 400 mg/m$^2$/day of cyclophosphamide for three days and about 30 mg/m$^2$/day of fludarabine for three days prior to administration of a therapeutically effective amount of engineered T cells to the patient.

In some embodiments, the dose regimen involves treating a patient comprising administering daily to the patient about 440 mg/m$^2$/day of cyclophosphamide for two days and about 100 mg/m²/day of etoposide for two days prior to administration of a therapeutically effective amount of engineered T cells to the patient.

In some embodiments, the dose regimen involves treating a patient comprising administering daily to the patient about 2-4 g/m²/day of cyclophosphamide for three days and about 200 mg/m²/day of etoposide for three days prior to administration of a therapeutically effective amount of engineered T cells to the patient.

In some embodiments, the dose regimen involves treating a patient comprising administering daily to the patient about 300 mg/m²/day of cyclophosphamide for three days and about 30 mg/m²/day of fludarabine for three days prior to administration of a therapeutically effective amount of engineered T cells to the patient.

In some embodiments, the dose regimen involves treating a patient comprising administering daily to the patient about 30-60 mg/kg (about 1100 mg/m²-2200 mg/m²) of cyclophosphamide for three-five days and about 25 mg/m² of fludarabine for three-five days prior to administration of a therapeutically effective amount of engineered T cells to the patient.

In some embodiments, the dose regimen involves treating a patient comprising administering daily to the patient about 1 g/m²) of cyclophosphamide prior to administration of a therapeutically effective amount of engineered T cells to the patient.

In some embodiments, the dose regimen involves treating a patient comprising administering daily to the patient about 1.2 g/m²) of cyclophosphamide for four days prior to administration of a therapeutically effective amount of engineered T cells to the patient.

In some embodiments, the regimen involves treating a patient comprising administering daily to the patient about 2 g/m²) of cyclophosphamide prior to administration of a therapeutically effective amount of engineered T cells to the patient.

In some embodiments, the dose regimen involves treating a patient comprising administering daily to the patient about 25 mg/m² of fludarabine for three days prior to administration of a therapeutically effective amount of engineered T cells to the patient.

In some embodiments, the dose regimen involves treating a patient comprising administering daily to the patient about 90 mg/m² of bendamustine for two days prior to administration of a therapeutically effective amount of engineered T cells to the patient.

In some embodiments, the dose regimen involves treating a patient comprising administering daily to the patient about 500 mg/m²/day of cyclophosphamide for two days and about 30 mg/m²/day of fludarabine for four days prior to administration of a therapeutically effective amount of engineered T cells to the patient.

In some embodiments, the dose regimen involves treating a patient comprising administering to the patient about 1000 mg/m² of methotrexate on day 1, about 1000 mg/m² every 12 hours on days 2 and 3 prior to administration of a therapeutically effective amount of engineered T cells to the patient.

Another preferred dose regimen involves treating a patient comprising administering to the patient about 300 mg/m² of cyclophosphamide every 12 hours on days one, two and three, 2 mg of vincristine on day three and 50 mg/m² of adriamycin on day three prior to administration of a therapeutically effective amount of engineered T cells to the patient.

Another preferred dose regimen involves treating a patient comprising administering daily to the patient about 200 mg/m²/day of cyclophosphamide for three days and about 20 mg/m²/day of fludarabine for three days prior to administration of a therapeutically effective amount of engineered T cells to the patient.

In some embodiments, the antigen binding molecule, transduced (or otherwise engineered) cells (such as CARs or TCRs), and the chemotherapeutic agent are administered each in an amount effective to treat the disease or condition in the subject.

In some embodiments, compositions comprising CAR- and/or TCR-expressing immune effector cells disclosed herein can be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as TARGRETIN™ (bexarotene), PANRETIN™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein can be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON™); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (CYTOXAN®), Doxorubicin (hydroxydoxorubicin), Vincristine (ONCOVIN®), and Prednisone; EPOCH (etoposide, prednisone, vincristine (ONCOVIN®) and doxorubicin hydrochloride (hydroxydaunorubicin hydrochloride)); and carboplatin and gemcitabine.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents can be used in conjunction with the compositions described herein. For example, potentially useful additional therapeutic agents include PD-1 inhibitors such as nivolumab (OPDIVO®), pembrolizumab (KEYTRUDA®), pidilizumab (CureTech), and atezolizumab (TECENTRIQ®).

Additional therapeutic agents suitable for use in combination with the disclosure include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab (REMOVAB®), ibritumomab (ZEVALIN®), tositumomab, brentuximab (ADCETRIS®), alemtuzumab (LEMTRADA®), gemtuzumab, erlotinib (TARCEVA®), gefitinib (IRESSA®), vandetanib (CAPRELSA®), afatinib (GIOTRIF®), lapatinib (TYKERB®), neratinib, axitinib (INLYTA®), masitinib (MASIVET®), pazopanib (VOTRIENT®), sunitinib (SUTENT®), sorafenib (NEXAVAR®), lestaurtinib, cediranib, lenvatinib)(LENVIMA®), nintedanib (OFEV®), regorafenib (STIVARGA®), semaxanib, tivozanib, entrectinib, cabozantinib (CABOMETYX®), dasatinib (SPRYCEL®), nilotinib (TASIGNA®), ponatinib (ICLUSIG®), radotinib (SUPECT®), bosutinib (BOSULIF®), ruxolitinib (JAKAVI®), pacritinib, cobimetinib (COTELLIC®), selumetinib, trametinib (MEKINIST®), binimetinib, alectinib (ALECENSA®), ceritinib (ZYKADIA®), crizotinib (XALKORI®), aflibercept (EYELEA®), adipotide, denileukin diftitox (ONTAK®), mTOR inhibitors such as everolimus (AFINITOR®) and temsirolimus (TORISEL®), hedgehog inhibitors such as sonidegib (ODOZMO®) and vismodegib (ERIVEDGE®), CDK inhibitors such as CDK inhibitor (palbociclib; IBRANCE®).

In some embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of propoxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the instant disclosure. To the extent that any of the definitions or terms provided in the references incorporated by reference differ from the terms and discussion provided herein, the present terms and definitions control.

The instant disclosure is further illustrated by the following examples which should not be construed as further limiting. The contents of all references cited throughout this application are expressly incorporated herein by reference.

EXAMPLES

Example 1

CD70 expression was measured in various cell lines. CD70 was found to be expressed, with a fragments/kilobase of exon/million reads mapped (FPKM) greater than 35, in 99% of the multiple myeloma tumor cell lines tested.

Figure 2:
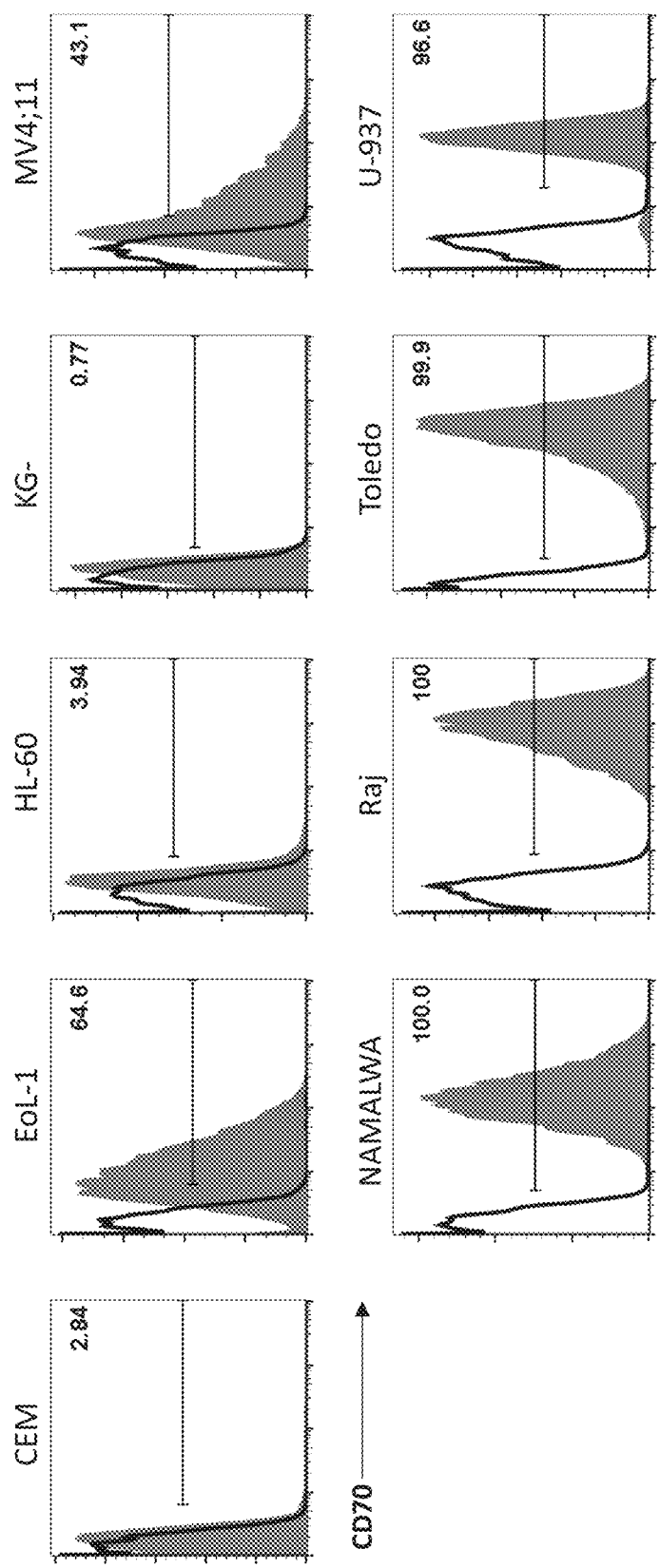
FIG. 2 is a series of plots demonstrating CD70 expression in various target cell lines, which correspond to a range of blood cancers; top row from left panel to right panel, the human lymphoblast cell line CEM (also referred to as CCRF-CEM), the human eosinophil cell line EoL-1, the human myeloid cell line HL-60, the human myeloid cell line KG-1a, and the human myeloid cell line MV4-11; bottom row, from left panel to right panel, the human B cell line Namalwa, B lymphocyte cell line Raji, human B lymphocyte cell line Toledo, and human myeloid cell line U-937.

To further characterize the expression of CD70, CEM (ATCC), EoL-1 (Sigma), HL-60 (ATCC), KG-1a (ATCC), MV4; 11 (ATCC), NAMALWA (ATCC), Raji (ATCC), Toledo (ATCC), and U-937 (ATCC) cells were stained with an anti-CD70 antibody conjugated to PE (BD Pharmingen) in stain buffer (BD Pharmingen) for 30 minutes at 4° C. Cells were then washed and resuspended in stain buffer with propidium iodide (BD Pharmingen) prior to data acquisition. Samples were then acquired by flow cytometry and data analyzed (FIG. 2). CD70 expression was observed in the cell lines EoL-1, MV4; 11, NAMALWA, Raji, Toledo, and U-937 (FIG. 2), but not in the cell lines CEM, HL-60, and KG-1a (FIG. 2).

Example 2

A third generation lentiviral transfer vector containing the CD70 CAR constructs shown schematically in FIGS. 1A-1H, having the sequences shown in FIGS. 8A-8L, and in the appended Sequence Listing (SEQ ID NOs: 29-52) were used along with the ViraPower Lentiviral Packaging Mix (Life Technologies) to generate the lentiviral supernatants. Briefly, a transfection mix was generated by mixing 15 µg of DNA and 22.5 µl of polyethileneimine (Polysciences, 1 mg/ml) in 600 µl of OptiMEM media. The transfection mix was incubated for 5 minutes at room temperature. Simultaneously, 293T cells (ATCC) were trypsinized and counted. A total of $10\times10^6$ total 293T cells were then plated in a T75 flask with the transfection mix. Following culture for three days, supernatants were collected and filtered through a 0.45 µm filter and stored at −80° C.

Peripheral blood mononuclear cells (PBMCs) were isolated from two different healthy donor leukopaks (Hemacare) using Ficoll®-Paque density centrifugation according to the manufacturer's instructions. PBMCs were stimulated using OKT3 (Muromonab-CD3, 50 ng/ml, Miltenyi Biotec) in R10 media supplemented with IL-2 (300 IU/ml, Proleukin®, Prometheus® Therapeutics and Diagnostics). Forty-eight hours post-stimulation, cells were transduced using lentivirus containing the different CD70 CAR constructs at a multiplicity of infection (MOI) of 10. Cells were maintained at $0.5\times10^6$-$2.0\times10^6$ cells/ml prior to use in activity assays.

Figure 3A:
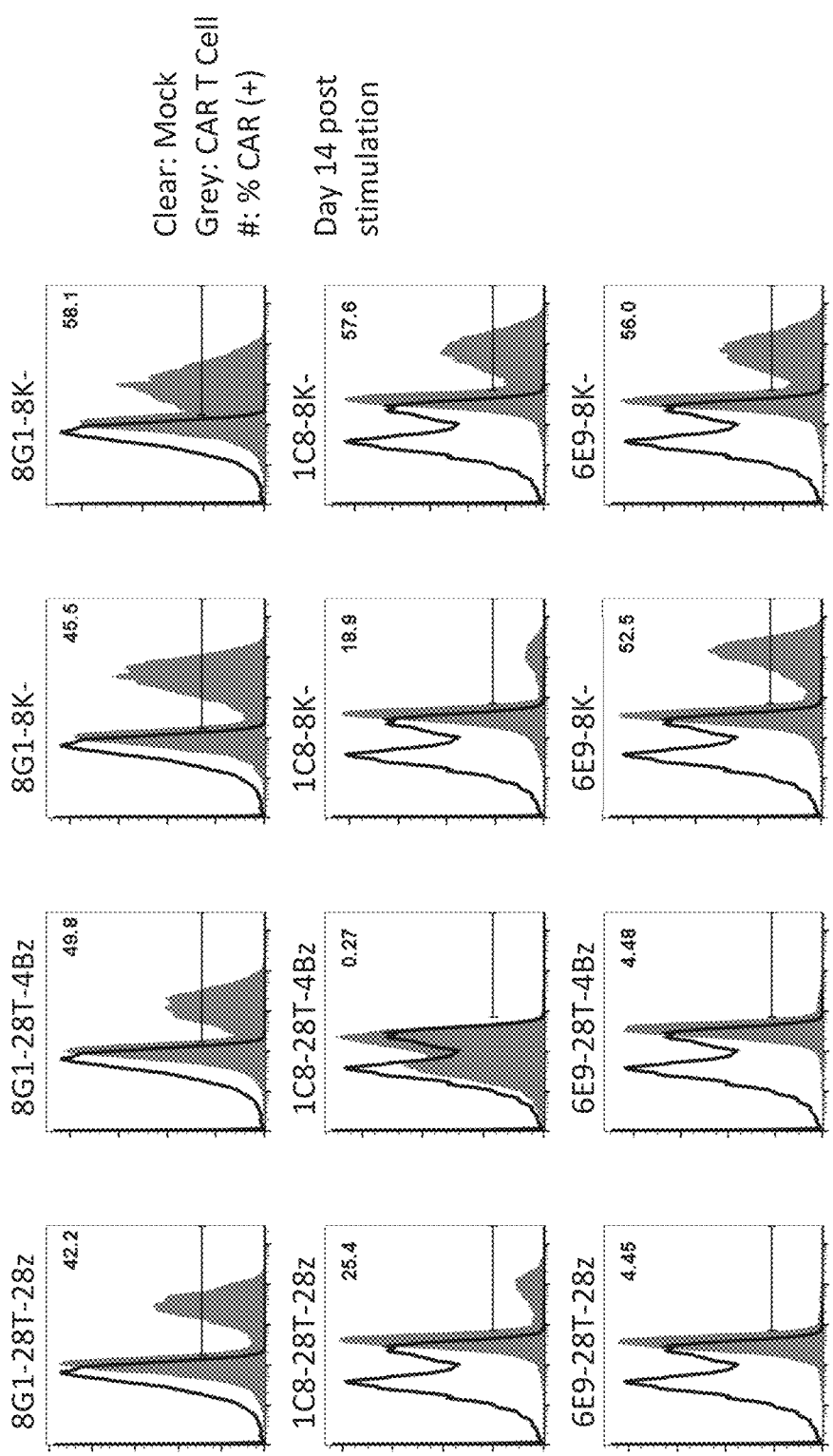
FIGS. 3A and 3B are a series of plots demonstrating expression of various CARs directed against CD70 in lentivirus transduced T cells isolated from a first healthy human T cell donor (FIG. 3A) and a second healthy human T cell donor (FIG. 3B); clear histograms denote mock transduction and grey filled histograms denote cells expressing the transduced CAR, with the numbers in the panels indicating the percent of cells that were found to be CAR positive.
Figure 3B:
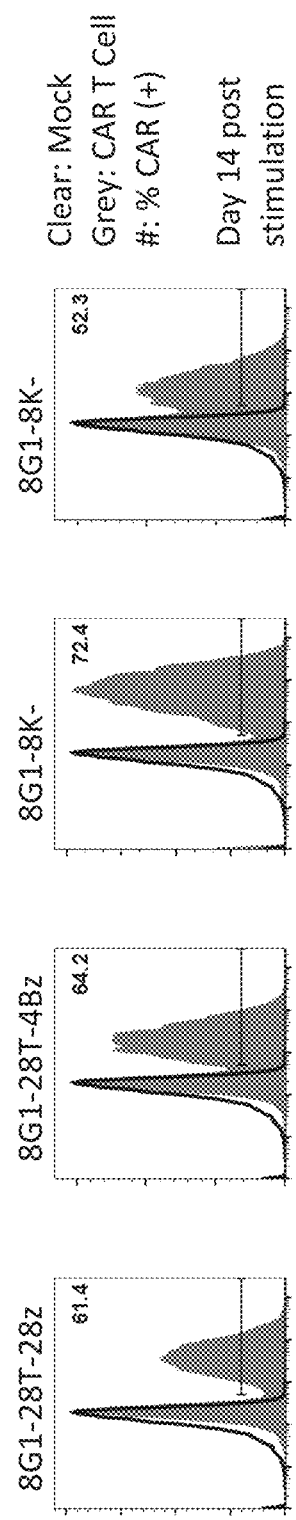

At day 14 post-stimulation, transduced T cells were stained with recombinant CD70-Fc (Sino Biological) in stain buffer (BD Pharmingen) for 30 minutes at 4° C. Cells were then washed and stained with goat anti-human IgG Fc PE (Jackson ImmunoResearch) in stain buffer for 30 minutes at 4° C. Cells were then washed and resuspended in stain buffer with propidium iodide (BD Pharmingen) prior to data acquisition. All experiments were performed in two different donors. CD70 CAR expression was observed for each of the constructs in both Donor 1 (FIG. 3A) and Donor 2 (FIG. 3B) transduced cells.

Figure 4A:
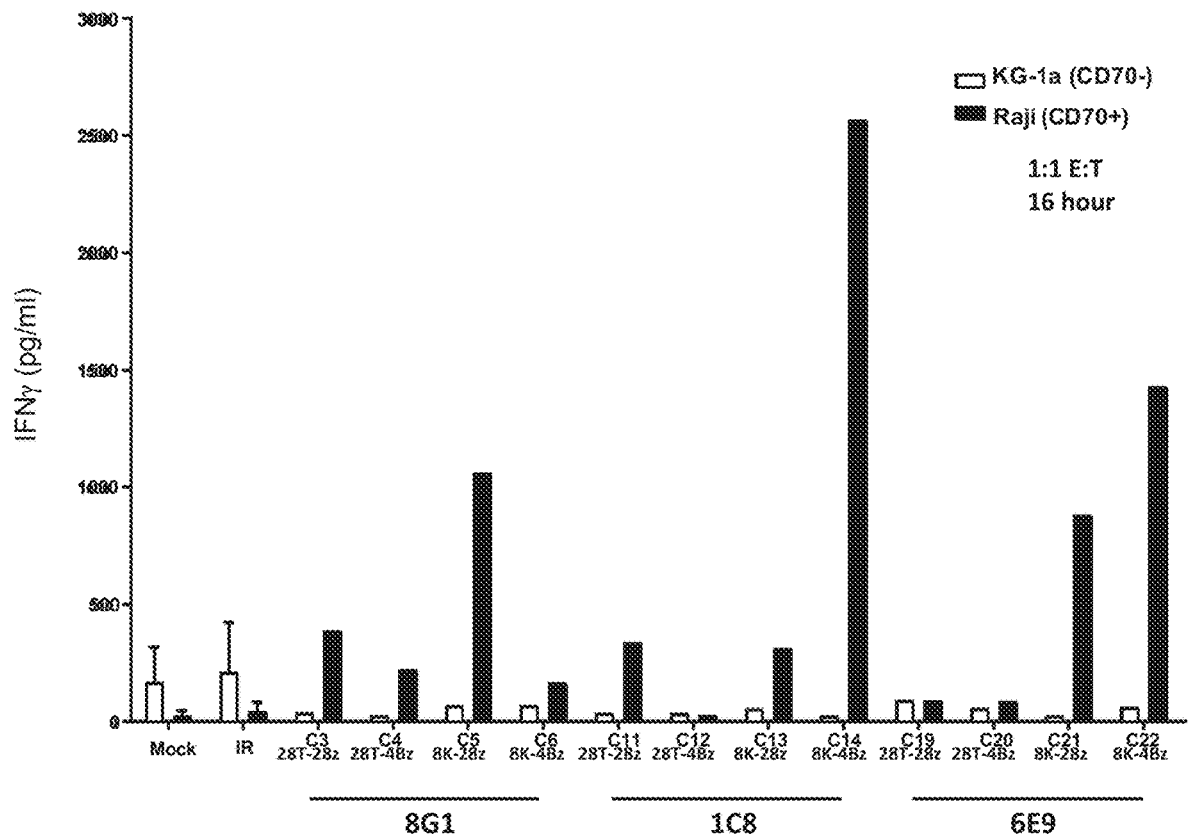
FIGS. 4A-4F are a series of bar graphs depicting IFNγ, TNFα, and IL-2 production by lentivirus transduced T cells from two healthy donors expressing four different CARs (28T-28z, 28T-4Bz, 8K-28z, 8K-4Bz), each comprising a different scFv (8G1, 1C8 and 6E9), following 16 hours of coculturing with KG-1a, Raji or Namalwa target cell lines.
Figure 4B:
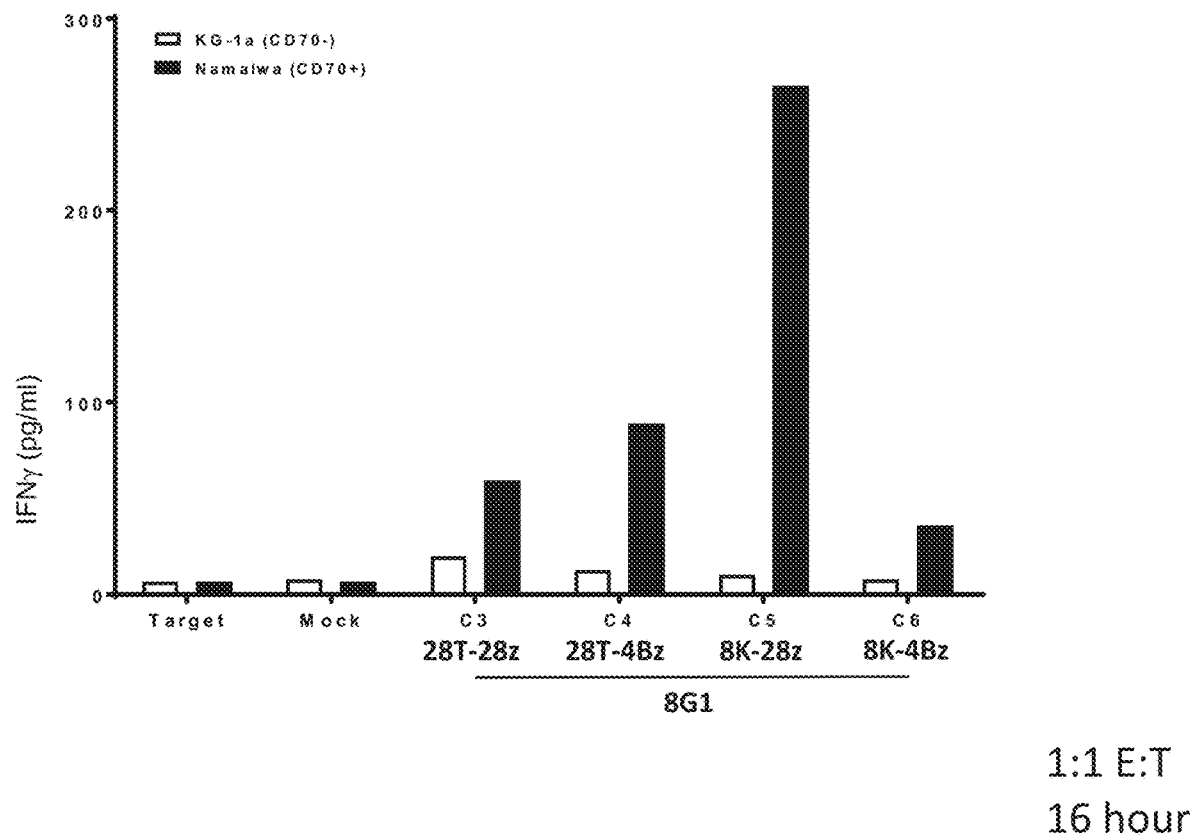
Figure 4C:
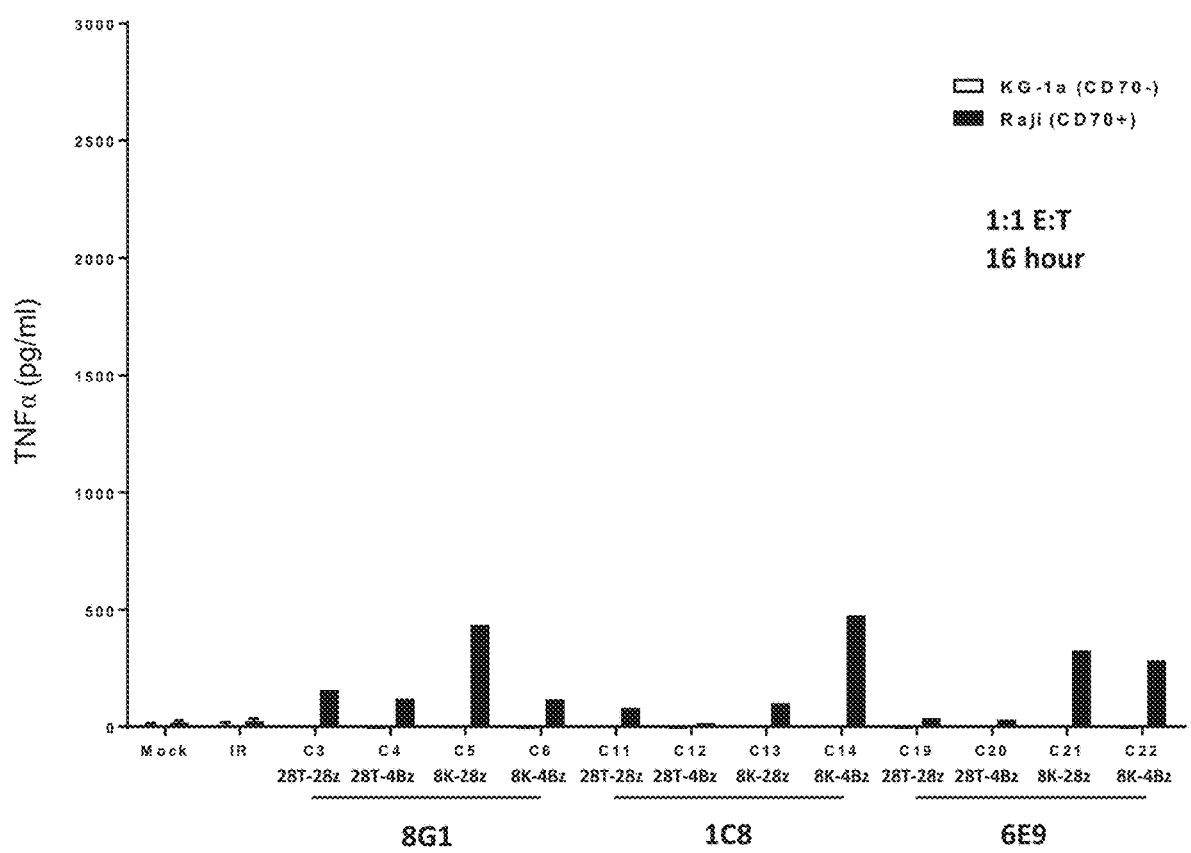
Figure 4D:
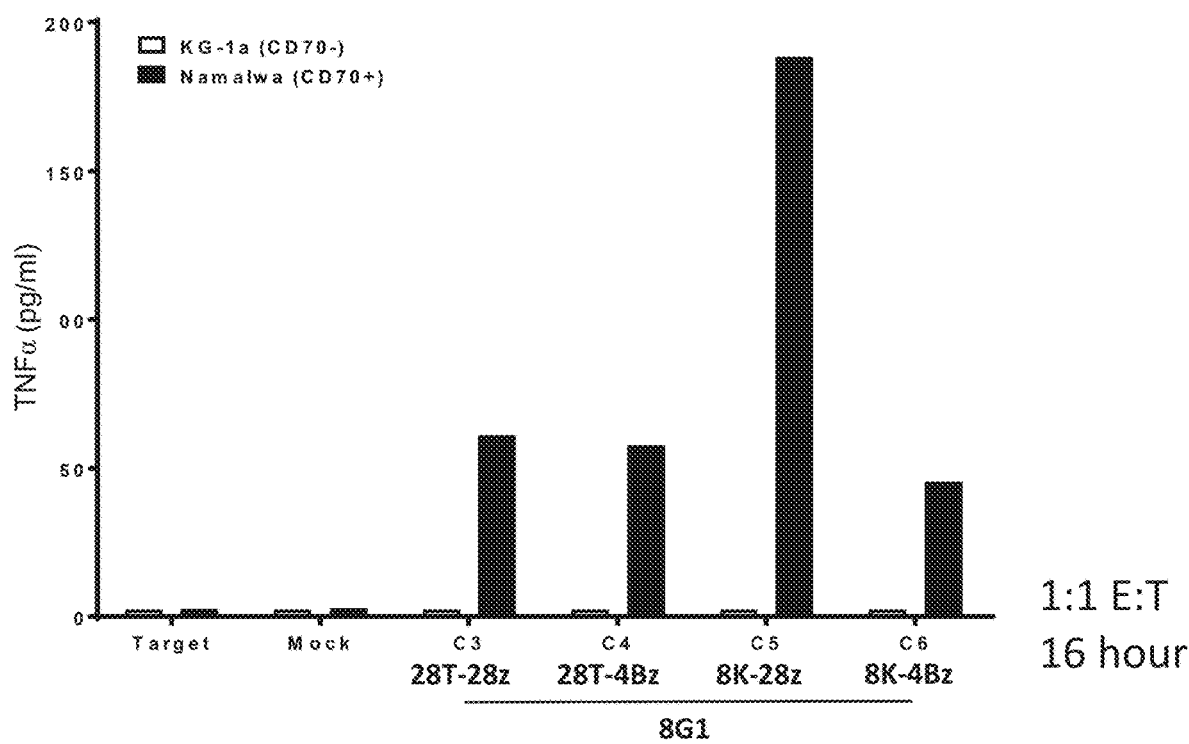
Figure 4E:
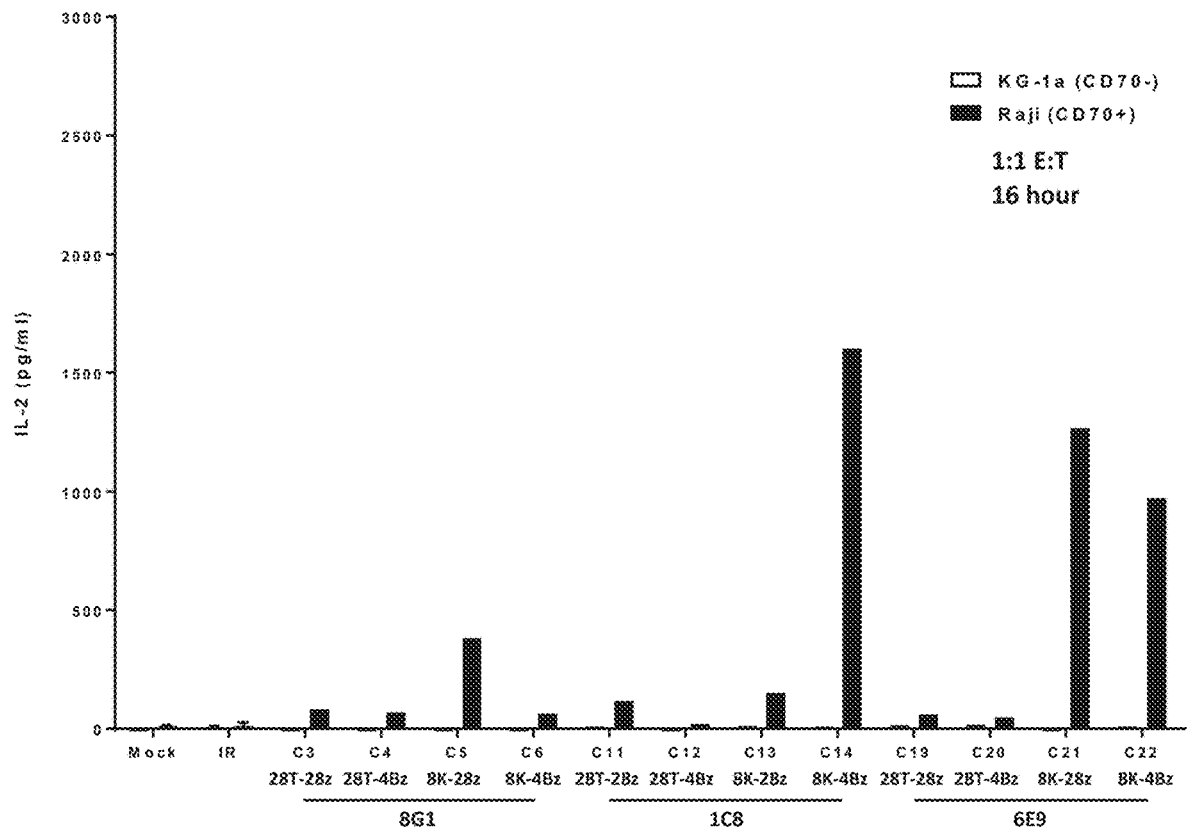
Figure 4F:
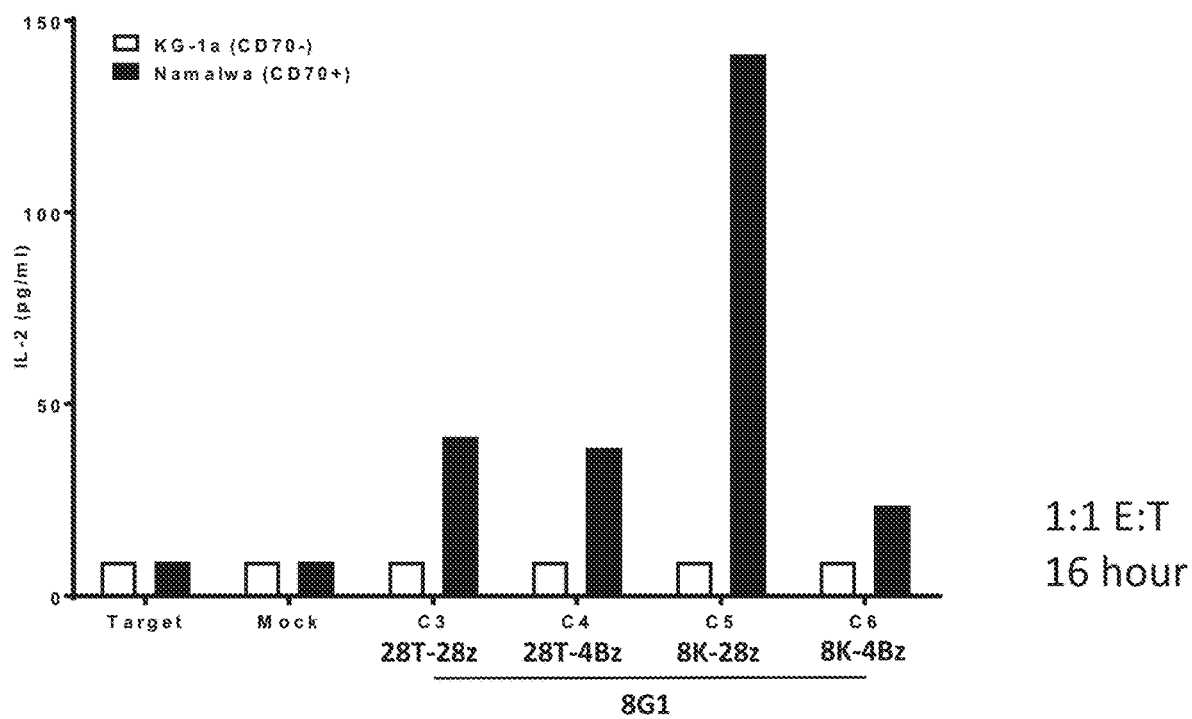

Effector cells, e.g., anti-CD70 CAR T cells, were cultured with target cells at a 1:1 effector cell to target cell (E:T) ratio in R10 media 14 days after T cell stimulation. Cell lines tested included KG-1a, NAMALWA, and Raji. Sixteen hours post-coculture, supernatants were analyzed by Luminex (EMD Millipore), according to the manufacturer's instructions, for production of the cytokines IFNγ (FIGS. 4A-4B), TNFα (FIGS. 4C-4D), and IL-2 (FIGS. 4E-4F). IFNγ (FIGS. 4A-4B), TNFα (FIGS. 4C-4D), and IL-2 (FIGS. 4E-4F) were observed in the supernatant of NAMALWA and Raji target cell cocultures for each anti-CD70 CAR T cell tested in both donors (FIGS. 4A-4F). However, IFNγ (FIGS. 4A-4B), TNFα (FIGS. 4C-4D), and IL-2 (FIGS. 4E-4F) were observed at much lower levels in the supernatant of KG-1a target cell cocultured with various CD70 CAR T cells (FIGS. 4A-4F).

Figure 5B:
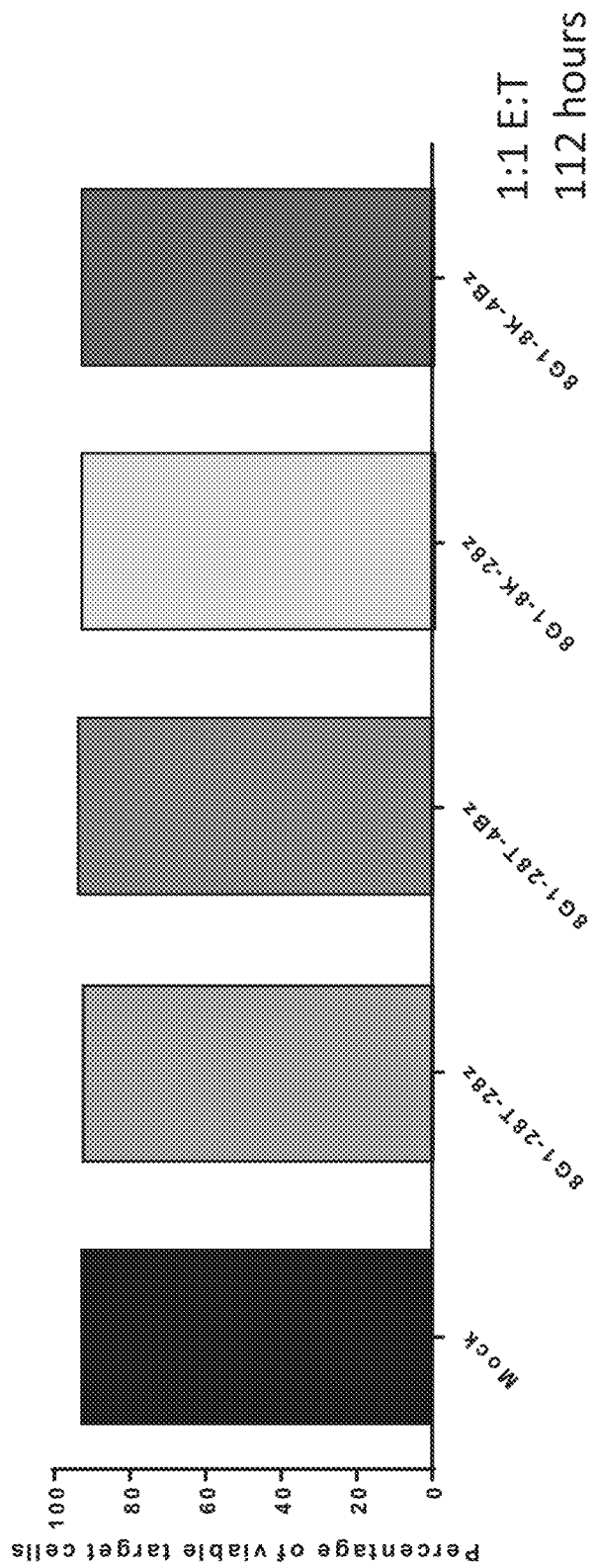
Figure 5D:
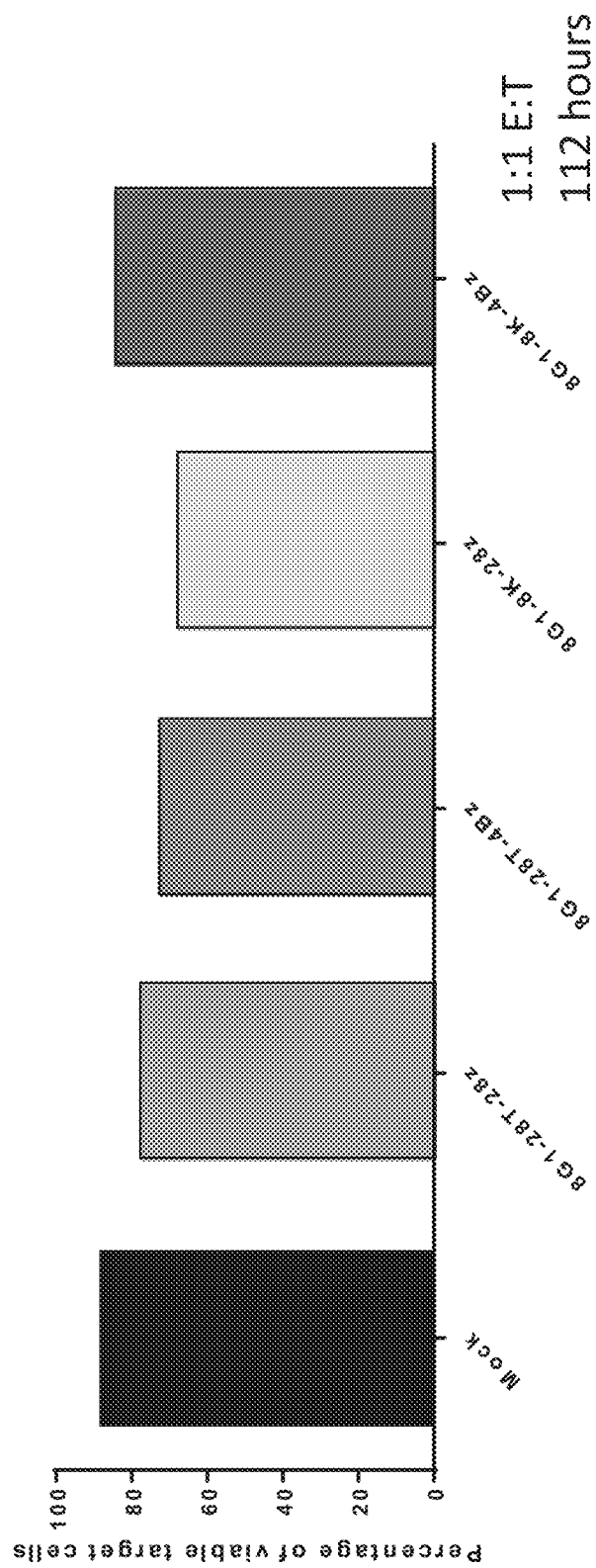

Target cell viability was assessed by flow cytometric analysis of propidium iodide (PI) uptake of CD3 negative cells. The anti-CD70 CAR T cells were cocultured with KG-1a (FIGS. 5A-5B), Raji (FIG. 5C), or NAMALWA (FIG. 5D) target cells for 16 hours, 40 hours, 64 hours, 88 hours, or 112 hours. Little cytolytic activity was observed in the KG-1a cocultures at any time period for the anti-CD70 CAR T cells (FIGS. 5A-5B).

Example 3

Donor CD4+ and CD8+ T cells were thawed and washed twice in OpTmizer media (Life Technologies) supplemented with 1× Penicillin-Streptomycin-L-Glutamine (PSQ) (Gibco). Cells were counted using a Vi-Cell cell analyzer, and cell density was adjusted to $1\times10^6$ cells/mL in OpTmizer media containing 1×PSQ and 300 IU/mL IL-2 (Proleukin®, Prometheus® Therapeutics and Diagnostics). After counting and resuspending T cells in medium, soluble anti-CD28 antibody was added at a final concentration of 1 µg/mL. Cells were then transferred to T25 flasks coated with anti-CD3 antibody (Muromonab-CD3, 50 ng/ml, Miltenyi Biotec) diluted in HBSS to a final concentration of 1.23 µg/mL.

After 24 hours (day 1 post-stimulation), CD70 lentiviral vector comprising a CAR construct (e.g., SEQ ID NOs: 29 and 30) was added to each T cell culture for an MOI of 10. For non-transduced T cells, cells were stimulated and expanded in the presence of 300 IU/mL IL-2 utilizing the same protocol, but without adding viral vector to the cells on day 1. Twenty four hours after transduction, T cells were washed with culture media containing the pre-specified components, counted, and reseeded at $0.5\times10^6$ cells/mL culture medium.

Figure 9:
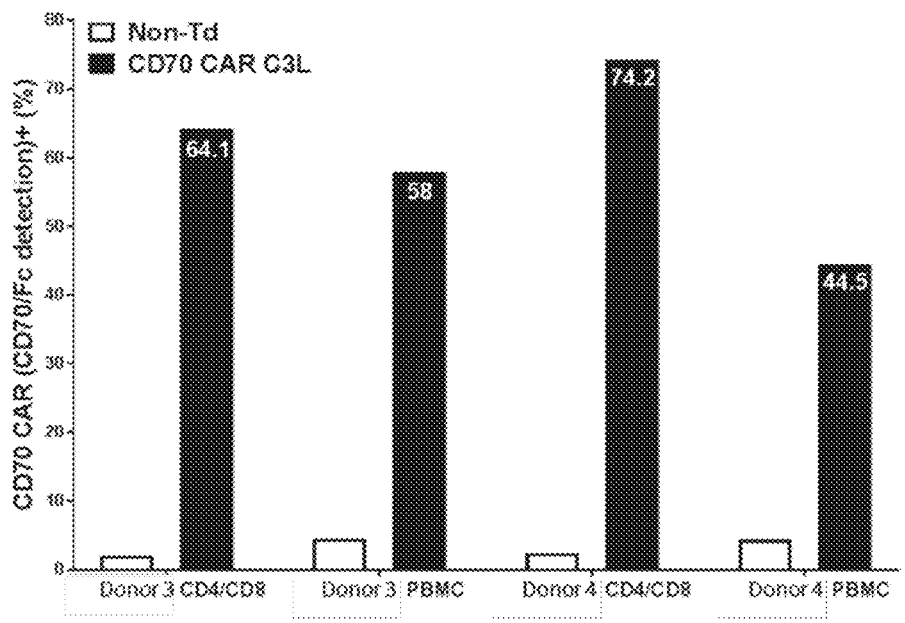
FIG. 9 is bar graph demonstrating expression of CD70 CAR C3L directed against CD70 in lentivirus transduced T cells.
Figure 10A:
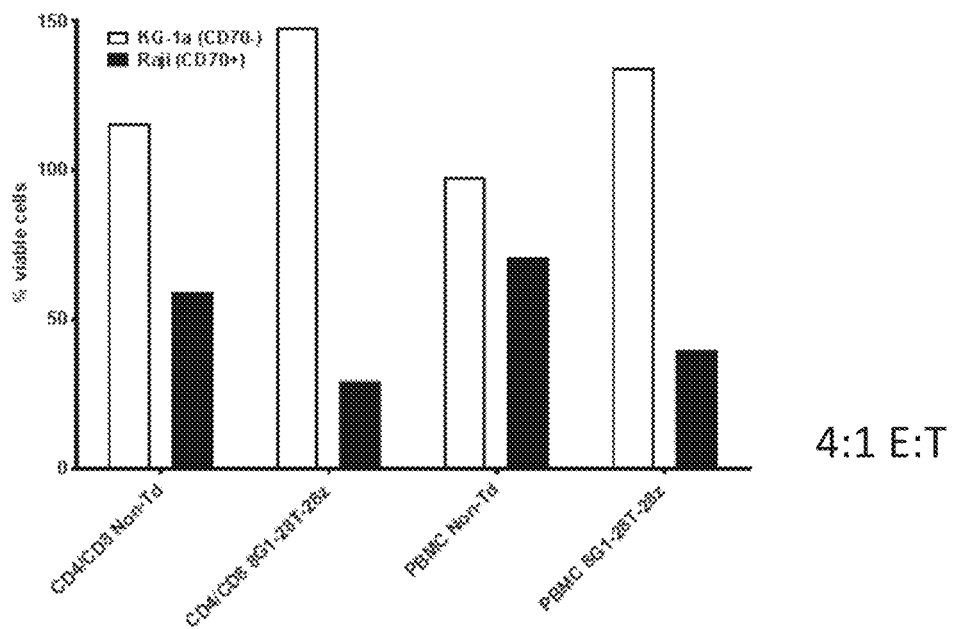
FIGS. 10A-10D shows the cytolytic activity (as a percentage of viable target cells remaining; y-axis) over time of lentivirus transduced T cell obtained from a healthy donor 3 (FIGS. 10A and 10B) or healthy donor 4 (FIGS. 10C and 10D) expressing the indicated CARs cocultured for 112 hours with KG-1a or Raji at an E:T ratio of 4:1 (FIGS. 10A and 10C) or 1:1 (FIGS. 10B and 10D).
Figure 10B:
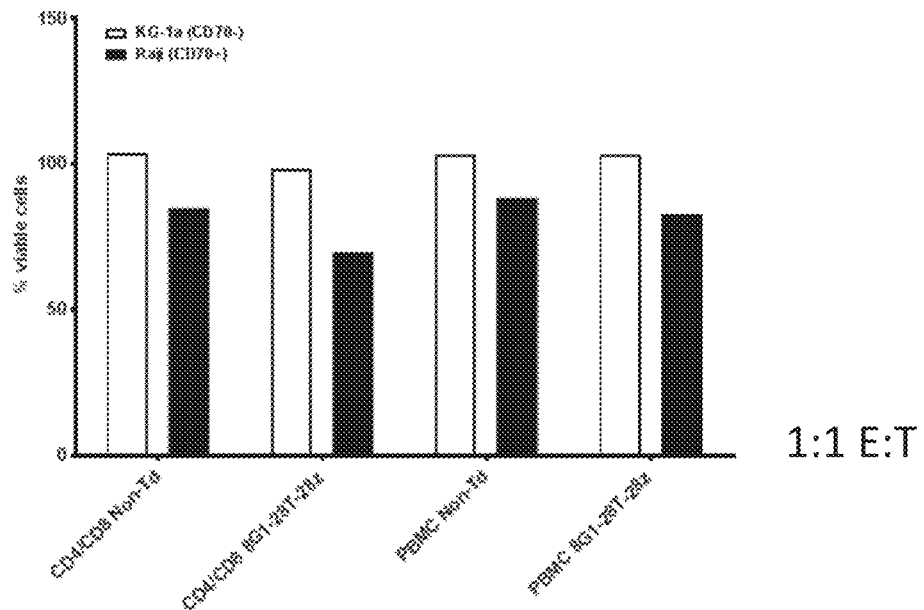
Figure 10C:
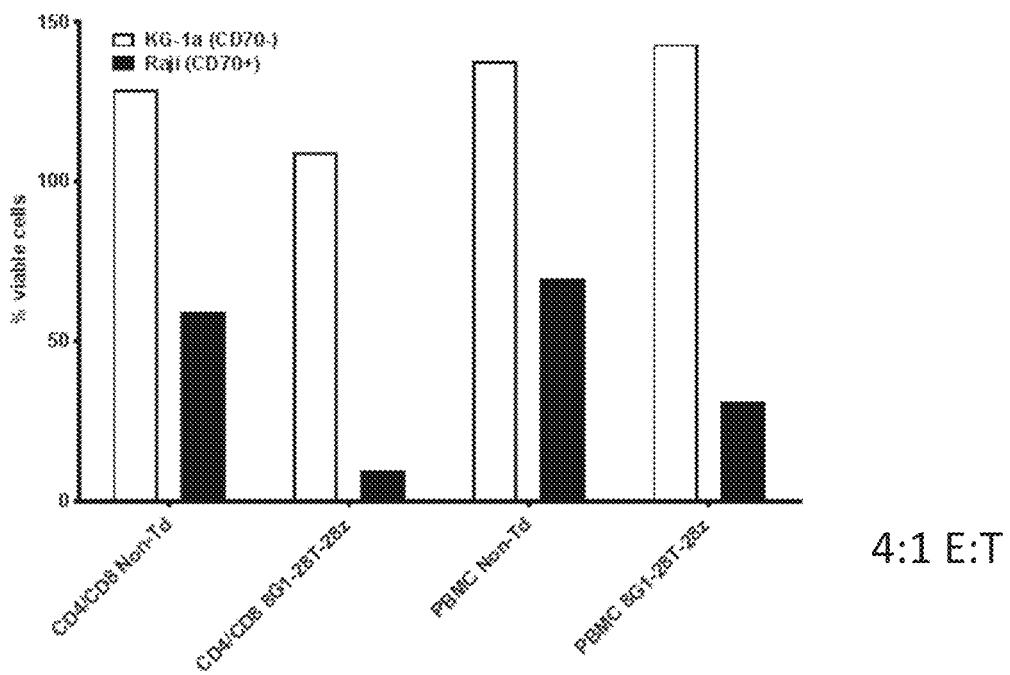
Figure 10D:
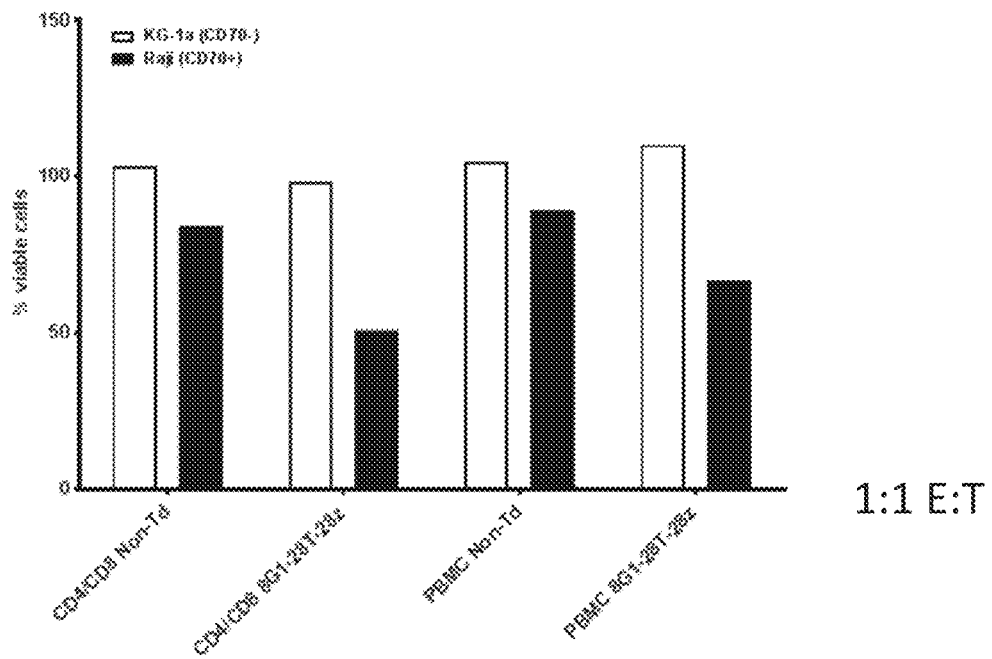
Figure 11A:
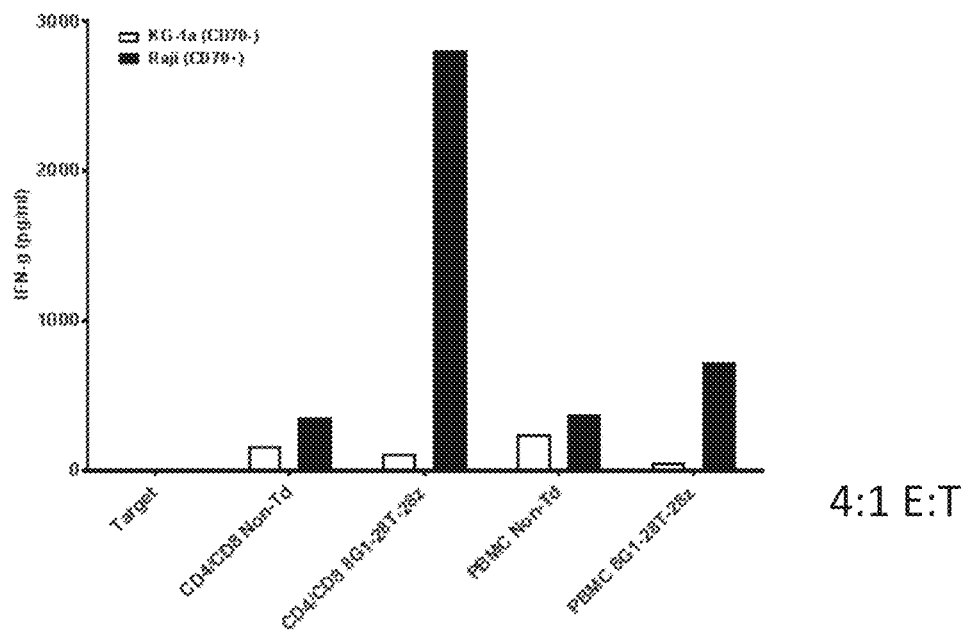
FIGS. 11A-11D are a series of bar graphs depicting IFNγ, production by lentivirus transduced T cells from two healthy donors expressing CD70 CAR C3L (28T-28z, comprising an 8G1 scFv), following 16 hours of coculturing with KG-1a or Raji target cell lines.
Figure 11B:
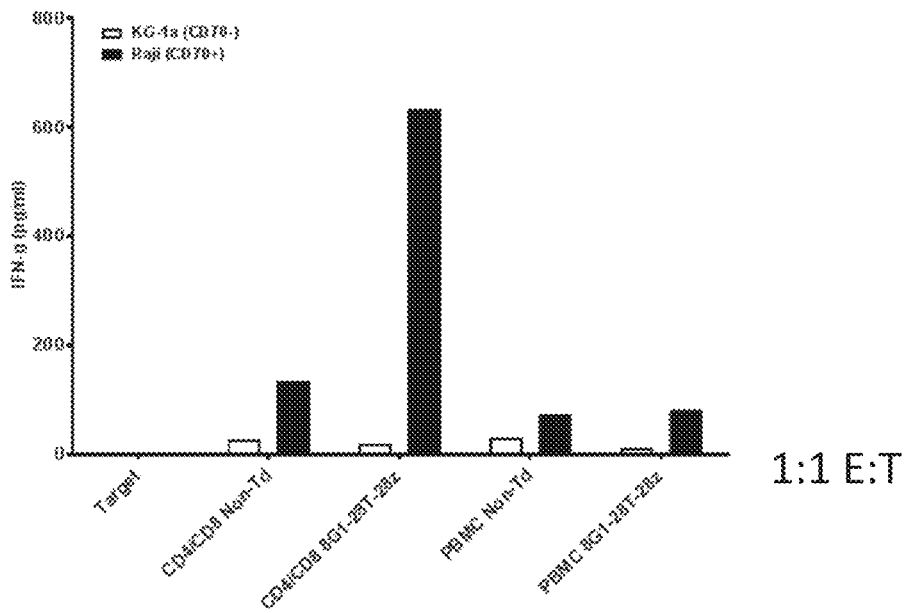
Figure 11C:
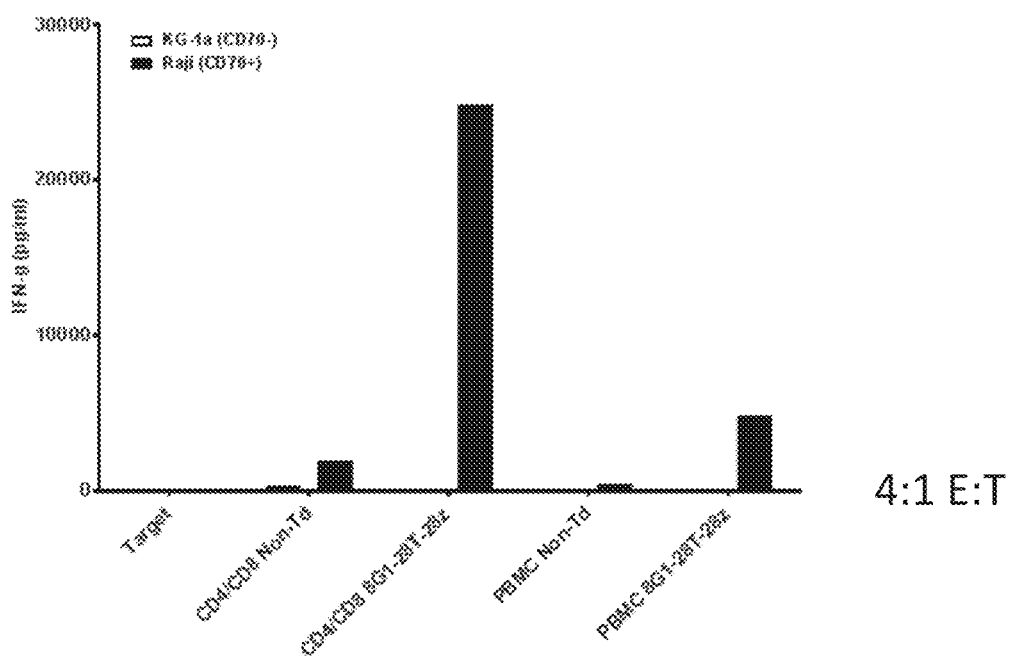
Figure 11D:
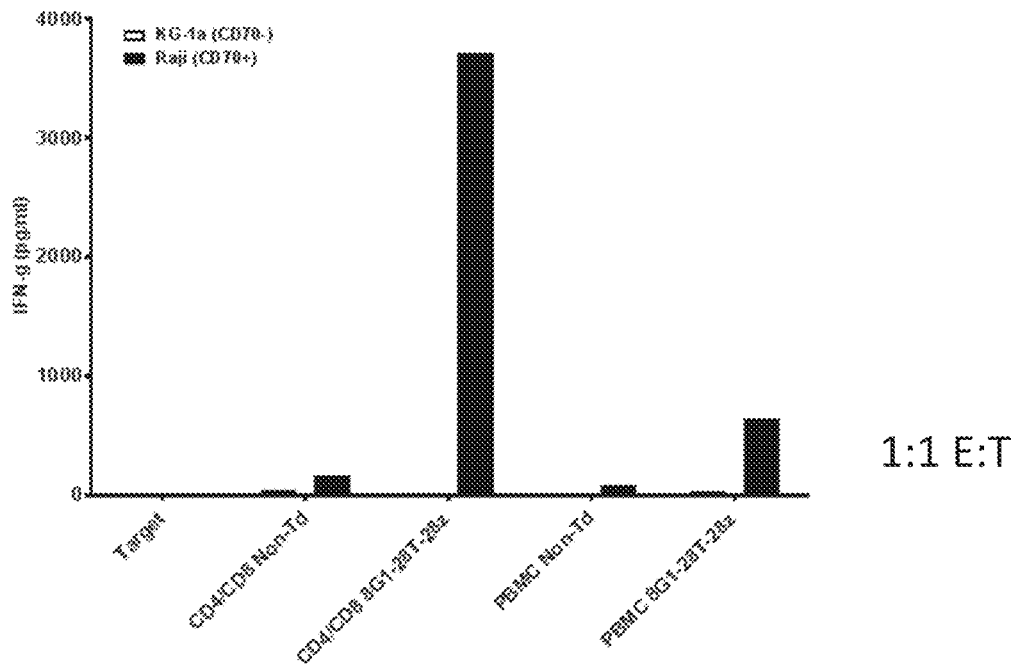
Figure 12A:
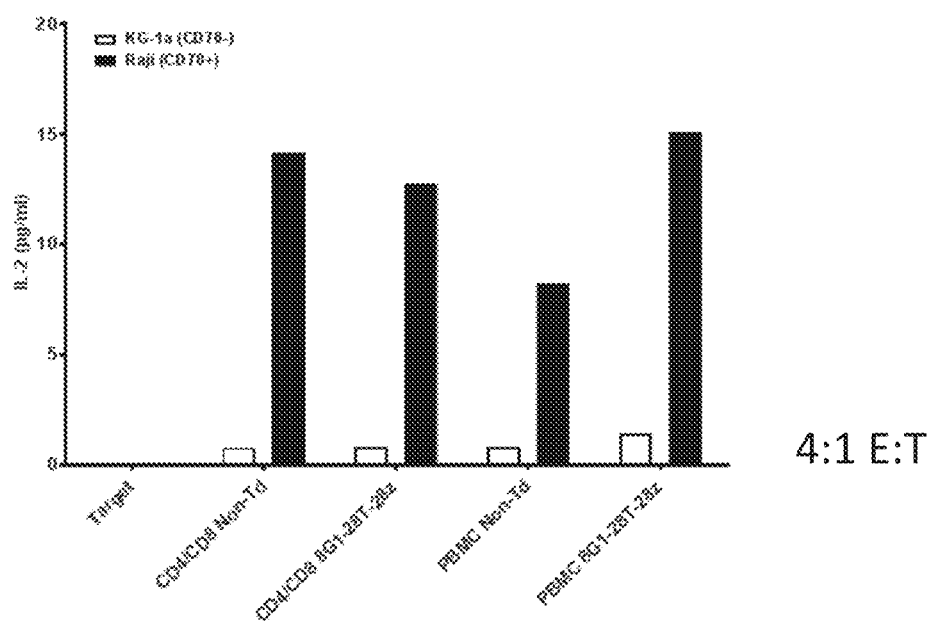
FIGS. 12A-12D are a series of bar graphs depicting IL2, production by lentivirus transduced T cells from two healthy donors expressing a CD70 CAR C3L (28T-28z, comprising an 8G1 scFv) following 16 hours of coculturing with KG-1a or Raji target cell lines.
Figure 12B:
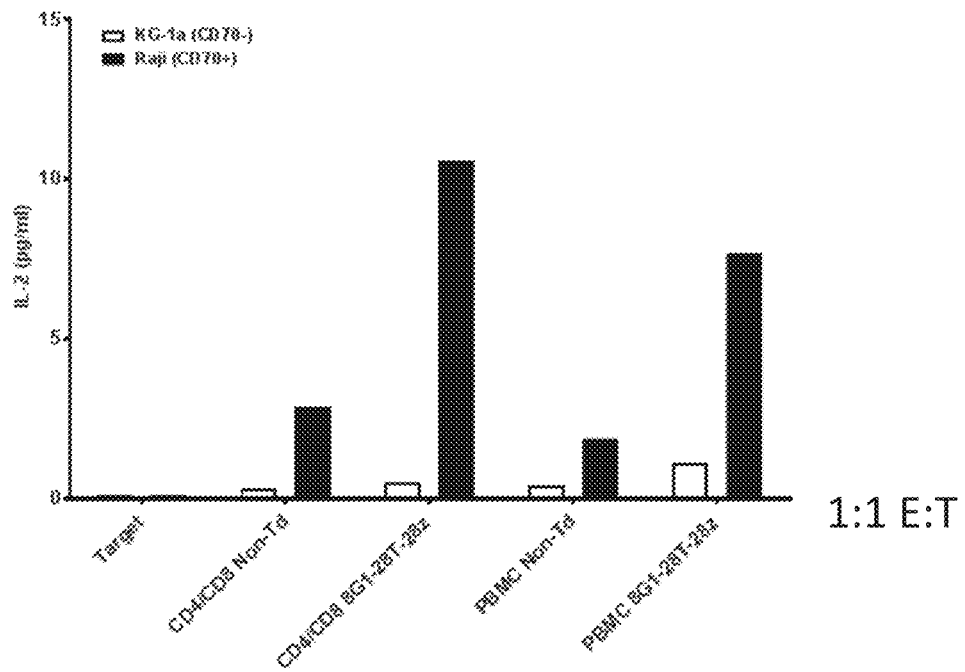
Figure 12C:
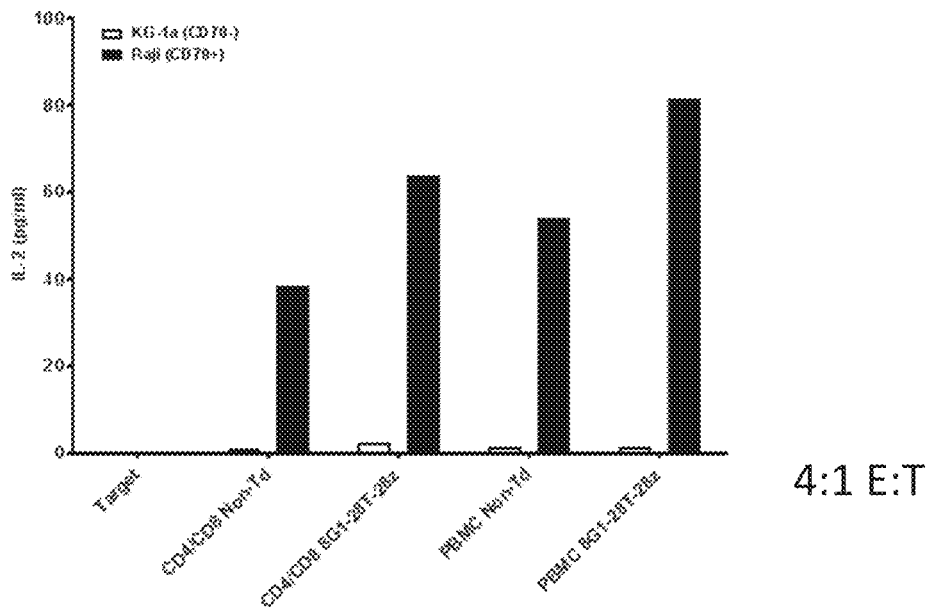
Figure 12D:
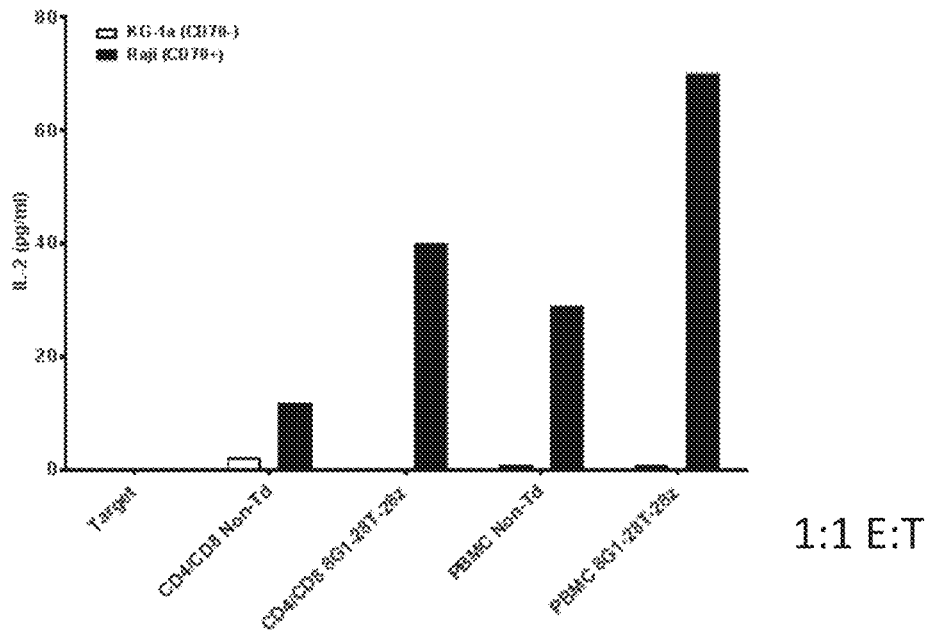
Figure 13A:
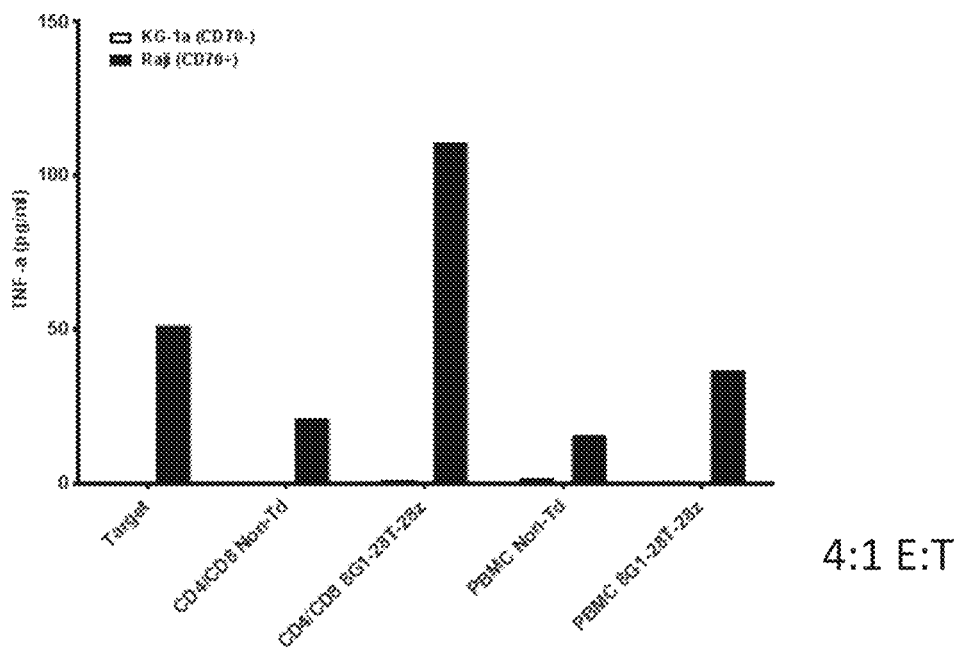
FIGS. 13A-13D are a series of bar graphs depicting TNFα, production by lentivirus transduced T cells from two healthy donors expressing a CD70 CAR C3L (28T-28z, comprising an 8G1 scFv) following 16 hours of coculturing with KG-1a or Raji target cell lines.
Figure 13B:
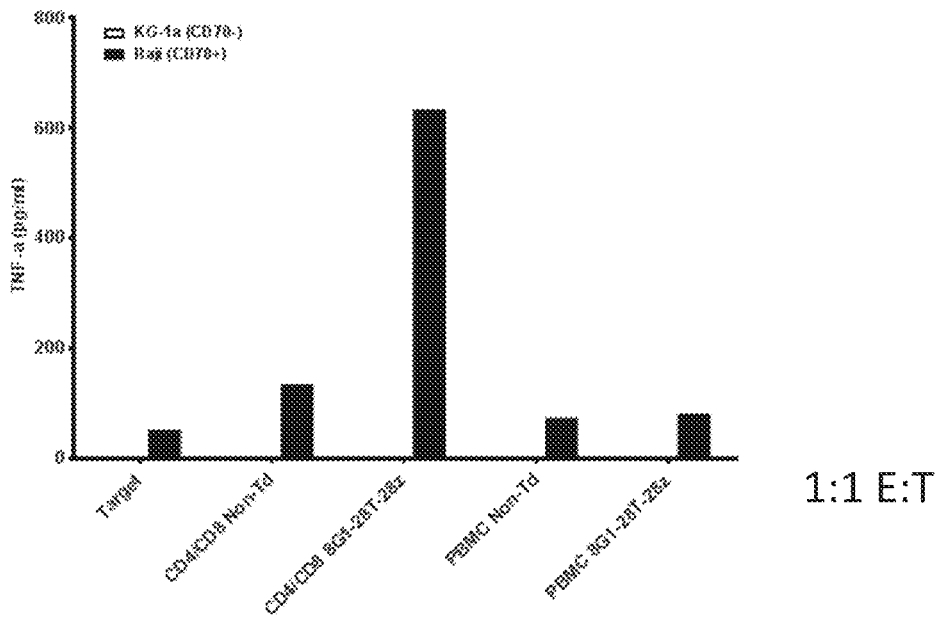
Figure 13C:
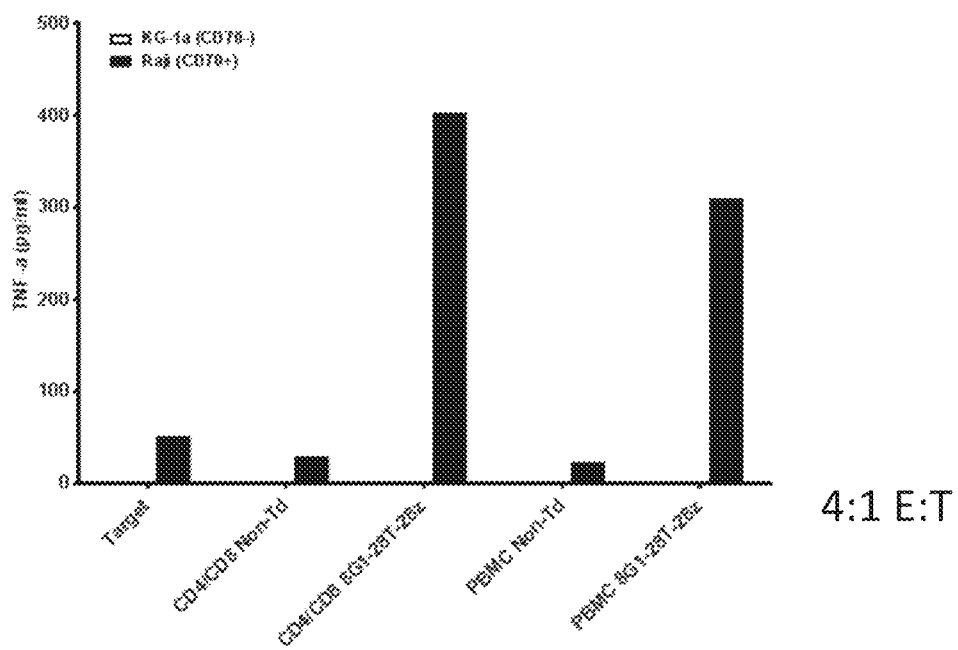
Figure 13D:
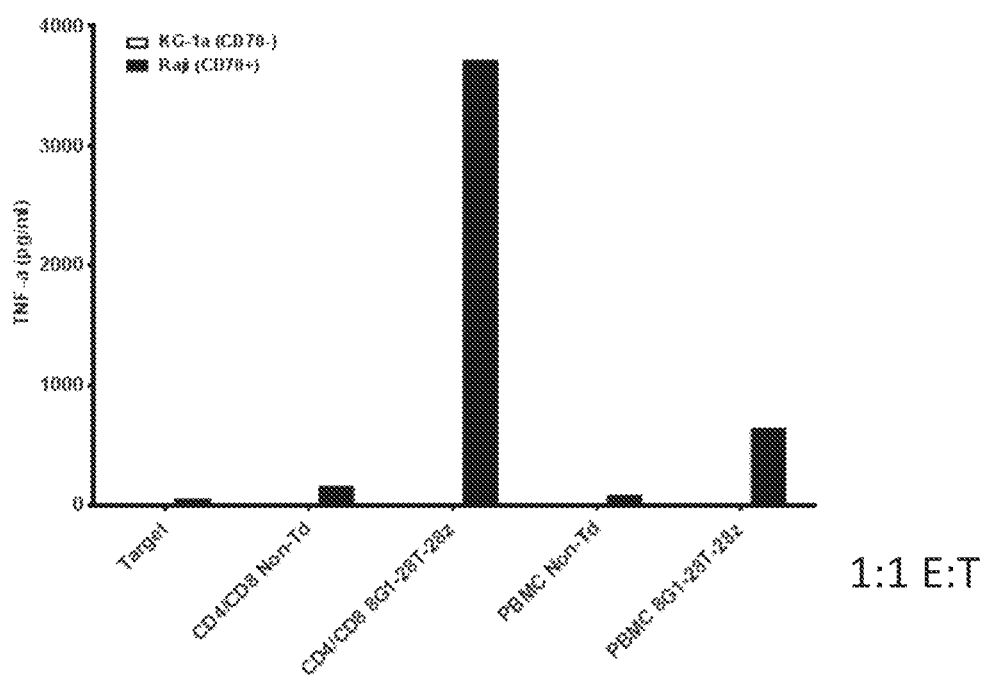

At day 14 post-stimulation, transduced T cells were stained with recombinant CD70-Fc (Sino Biological) in stain buffer (BD Pharmingen) for 30 minutes at 4° C. Cells were then washed and stained with goat anti-human IgG Fc PE (Jackson ImmunoResearch) in stain buffer for 30 minutes at 4° C. Cells were then washed and resuspended in stain buffer with propidium iodide (BD Pharmingen) prior to data acquisition. All experiments were performed in two different donors. CD70 CAR expression was observed for each of the constructs in both Donor 3 and Donor 4 transduced cells (FIG. 9).

Effector cells, e.g., anti-CD70 CAR T cells, were cultured with target cells at a 1:1 or 4:1 effector cell to target cell (E:T) ratio in R10 media 14 days after T cell stimulation. Cell lines tested included KG-1a and Raji. Sixteen hours post-coculture, supernatants were analyzed by Luminex (EMD Millipore), according to the manufacturer's instructions, for production of the cytokines IFNγ (FIGS. 11A-11D), TNFα (FIGS. 13A-13D), and IL-2 (FIGS. 12A-12D). IFNγ (FIGS. 11A-11D), TNFα (FIGS. 13A-13D), and IL-2 (FIGS. 12A-12D) were observed in the supernatant of Raji target cell cocultures for each anti-CD70 CAR T cell tested in both donors (FIGS. 11A-12D, 12A-12D, and 13A-13D).

However, IFNγ (FIGS. 11A-11D), TNFα (FIGS. 13A-13D), and IL-2 (FIGS. 12A-12D) were observed at much lower levels in the supernatant of KG-1a target cell cocultured with various CD70 CAR T cells (FIGS. 11A-12D, 12A-12D, and 13A-13D).

Target cell viability was assessed by flow cytometric analysis of propidium iodide (PI) uptake of CD3 negative cells. The anti-CD70 CAR T cells were cocultured with KG-1a or Raji target cells. Little cytolytic activity was observed in the KG-1a cocultures for the anti-CD70 CAR T cells (FIGS. 10A-10D).

---

What is claimed is:

1. An isolated polynucleotide encoding a chimeric antigen receptor (CAR) or T cell receptor (TCR) comprising an antigen binding molecule that specifically binds to CD70 and a CD8 alpha transmembrane domain, wherein the antigen binding molecule comprises the amino acid sequence of SEQ ID NO: 34.

2. The polynucleotide of claim 1, wherein the antigen binding molecule is single chained.

3. The polynucleotide of claim 1, wherein the antigen binding molecule comprises an scFv.

4. The polynucleotide of claim 1, wherein the antigen binding molecule comprises a variable heavy chain (VH) and a variable light chain (VL), and the VH and VL are joined by a linker.

5. The polynucleotide of claim 4, wherein the VH is located at the N terminus of the linker and the VL is located at the C terminus of the linker.

6. The polynucleotide of claim 4, wherein the VL is located at the N terminus of the linker and the VH is located at the N terminus of the linker.

7. The polynucleotide of claim 4, wherein the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

8. The polynucleotide of claim 4, wherein the linker comprises an amino acid sequence at least 75%, at least 85%, at least 85%, at least 90%, at least 95%, at least 96%, at least 97%, at least 98%, at least 99%, or 100% identical to the amino acid sequence of one of SEQ ID NOs: 80 and 81.

9. The polynucleotide of claim 1, wherein the antigen binding molecule binds to CD70 with a $K_D$ of less than about $1\times10^{-6}$ M, less than about $1\times10^{-7}$ M, less than about $1\times10^{-8}$ M, or less than about $1\times10^{-9}$ M.

10. The polynucleotide of claim 1, wherein the CAR or TCR further comprises a constant region.

11. The polynucleotide of claim 1, wherein the CD8 alpha transmembrane domain comprises an amino acid sequence at least about 80%, at least about 85%, at least about 90%, at least about 95%, at least about 96%, at least about 97%, at least about 98%, at least about 99%, or about 100% identical to SEQ ID NO: 17, 21 or 94.

12. The polynucleotide of claim 1, wherein the CD8 alpha transmembrane domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 16 or 20.

13. The polynucleotide of claim 1, wherein the CAR or TCR further comprises a hinge region between the transmembrane domain and the antigen binding molecule.

14. The polynucleotide of claim 13, wherein the hinge region comprises all or a fragment of IgG1, IgG2, IgG3, IgG4, IgA, IgD, IgE, IgM, CD28, or CD8 alpha.

15. The polynucleotide of claim 14, wherein the hinge region is of CD28T.

16. The polynucleotide of claim 15, wherein the hinge region comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NOs: 15, and 83.

17. The polynucleotide of claim 15, wherein the hinge region is encoded by a nucleotide sequence at least about 80%, at least about 85%, at least about 90%, at least about 95%, at least about 96%, at least about 97%, at least about 98%, at least about 99%, or about 100% identical to a sequence selected from the group consisting of SEQ ID NOs: 14 and 82.

18. The polynucleotide of claim 14, wherein the hinge region is of CD8 alpha.

19. The polynucleotide of claim 18, wherein the hinge region comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 17 and 85.

20. The polynucleotide of claim 18, wherein the hinge region is encoded by a nucleotide sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 16 and 84.

21. The polynucleotide of claim 1, wherein the CAR or TCR further comprises a costimulatory region.

22. The polynucleotide of claim 21, wherein the costimulatory region is a signaling region of CD2, CD3 delta, CD3 epsilon, CD3 gamma, CD4, CD7, CD8a, CD86, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and or fragments or combinations thereof.

23. The polynucleotide of claim 22, wherein the costimulatory region is a CD28 costimulatory region.

24. The polynucleotide of claim 23, wherein the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 23.

25. The polynucleotide of claim 23, wherein the costimulatory region is encoded by a nucleotide sequence at least about 80%, at least about 85%, at least about 90%, at least about 95%, at least about 96%, at least about 97%, at least about 98%, at least about 99%, or about 100% identical to SEQ ID NO: 22.

26. The polynucleotide of claim 22, wherein the costimulatory region is a CD137 (4-1BB) costimulatory region.

27. The polynucleotide of claim 26, wherein the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 25.

28. The polynucleotide of claim 26, wherein the costimulatory region is encoded by a nucleotide sequence at least about 80%, at least about 85%, at least about 90%, at least about 95%, at least about 96%, at least about 97%, at least about 98%, at least about 99%, or about 100% identical to SEQ ID NO: 24.

29. The polynucleotide of claim 1, wherein the CAR or TCR further comprises an activation domain.

30. The polynucleotide of claim 29, wherein the activation domain is a CD3 zeta domain.

31. The polynucleotide of claim 30, wherein the activation domain comprises an amino acid sequence at least about 80%, at least about 85%, at least about 90%, at least about 95%, at least about 96%, at least about 97%, at least about 98%, at least about 99%, or about 100% identical to SEQ ID NO: 27 or 92.

32. The polynucleotide of claim 30, wherein the activation domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 26.

33. The polynucleotide of claim 1, wherein the CAR or TCR further comprises a leader peptide.

34. The polynucleotide of claim 33, wherein the leader peptide comprises an amino acid sequence at least about 80%, at least about 85%, at least about 90%, at least about 95%, at least about 96%, at least about 97%, at least about 98%, at least about 99%, or about 100% identical to SEQ ID NO: 28.

35. The polynucleotide of claim 33, wherein the leader peptide is encoded by a nucleotide sequence at least about 80%, at least about 85%, at least about 90%, at least about 95%, at least about 96%, at least about 97%, at least about 98%, at least about 99%, or about 100% identical to SEQ ID NO: 95.

36. A polynucleotide encoding a CAR or TCR, wherein the polynucleotide comprises the nucleotide sequence of SEQ ID NO: 33.

37. A vector comprising the polynucleotide of claim 1.

38. The vector of claim 37, which is a retroviral vector, a DNA vector, a plasmid, a RNA vector, an adenoviral vector, an adenovirus associated vector, a lentiviral vector, or any combination thereof.

39. A CAR or TCR encoded by the polynucleotide of claim 1.

40. A cell comprising the polynucleotide of claim 1.

41. The cell of claim 40, wherein the cell comprises an immune cell.

42. The cell of claim 41, wherein the cell is a T cell.

43. The cell of claim 42, wherein the T cell is a tumor-infiltrating lymphocyte (TIL), autologous T cell, engineered autologous T cell (eACT), an allogeneic T cell, or any combination thereof.

44. The cell of claim 40, wherein the cell is an in vitro cell.

45. A composition comprising the polynucleotide of claim 1.

46. The composition of claim 45, which is formulated to be delivered to a subject.

47. A method of making a cell expressing a CAR or TCR comprising transducing a cell with the polynucleotide of claim 1 under suitable conditions.

48. The method of claim 47, further comprising isolating the cell.

49. A CAR or TCR, wherein the CAR or TCR comprises SEQ ID NO: 34, wherein the leader sequence of SEQ ID NO: 34 is absent.

50. The CAR or TCR of claim 49, wherein the CAR or TCR comprises the amino acid sequence of SEQ ID NO: 34.

* * * * *

SEQUENCE LISTING

<160> NUMBER OF SEQ ID NOS: 97

<210> SEQ ID NO 1
<211> LENGTH: 193
<212> TYPE: PRT
<213> ORGANISM: Homo sapiens

<400> SEQUENCE: 1

```
Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 2
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: 8G1 VH

<400> SEQUENCE: 2

```
caa gag cag ctg gtt gag tct ggg ggc ggc gtc gtc caa ccc ggc cgg    48
Gln Glu Gln Leu Val Glu Ser Gly Gly Gly Val Val Gln Pro Gly Arg
1               5                   10                  15
```

```
agt ctg agg ttg tcc tgc gct gca agc gga ttt aca ttt tca tct tac      96
Ser Leu Arg Leu Ser Cys Ala Ala Ser Gly Phe Thr Phe Ser Ser Tyr
            20                  25                  30 ggc atg cac tgg gtt agg cag gct cct gga aaa ggg ctg gag tgg gtc     144
Gly Met His Trp Val Arg Gln Ala Pro Gly Lys Gly Leu Glu Trp Val
         35                  40                  45 gcg gtg act tgg tac gac ggc tcc aat aag tat tat ggg gat tcc gtg     192
Ala Val Thr Trp Tyr Asp Gly Ser Asn Lys Tyr Tyr Gly Asp Ser Val
 50                  55                  60 aaa ggt cga ttc aca att agc agg gat aac tcc aaa aac aca ctg tat     240
Lys Gly Arg Phe Thr Ile Ser Arg Asp Asn Ser Lys Asn Thr Leu Tyr
 65                  70                  75                  80 ctc caa atg aac tcc ttg agg gcc gag gac acg gcc gtc tat tat tgt     288
Leu Gln Met Asn Ser Leu Arg Ala Glu Asp Thr Ala Val Tyr Tyr Cys
                 85                  90                  95 gca aga gac ctc ctc cgg ggc gta aag gga tat gct atg gac gtg tgg     336
Ala Arg Asp Leu Leu Arg Gly Val Lys Gly Tyr Ala Met Asp Val Trp
             100                 105                 110 ggt cag ggg acc aca gtt act gtc agt tca                             366
Gly Gln Gly Thr Thr Val Thr Val Ser Ser
         115                 120
```

<210> SEQ ID NO 3
<211> LENGTH: 122
<212> TYPE: PRT
<213> ORGANISM: Homo sapiens

<400> SEQUENCE: 3

```
Gln Glu Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Thr Trp Tyr Asp Gly Ser Asn Lys Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Arg Gly Val Lys Gly Tyr Ala Met Asp Val Trp
             100                 105                 110

Gly Gln Gly Thr Thr Val Thr Val Ser Ser
         115                 120
```

<210> SEQ ID NO 4
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: 8G1 VL

<400> SEQUENCE: 4

```
gaa atc gtt ctc act cag tct ccg ggc aca ctg tcc ctc agc ccc gga      48
Glu Ile Val Leu Thr Gln Ser Pro Gly Thr Leu Ser Leu Ser Pro Gly
1               5                   10                  15 gag cga gcc act ttg agc tgc cgg gcc agc cag tca ctt aga cgc att      96
Glu Arg Ala Thr Leu Ser Cys Arg Ala Ser Gln Ser Leu Arg Arg Ile
            20                  25                  30
```

```
tat ttg gcc tgg tat cag cag aaa cca ggc cag gcg ccc agg ctg ctg      144
Tyr Leu Ala Trp Tyr Gln Gln Lys Pro Gly Gln Ala Pro Arg Leu Leu
         35                  40                  45 ata tac gat gtg ttc gat agg gcc acg ggt atc ccc gat agg ttc tct      192
Ile Tyr Asp Val Phe Asp Arg Ala Thr Gly Ile Pro Asp Arg Phe Ser
 50                  55                  60 ggc ggg ggg tcc ggg act gac ttc acc ctc act ata tca cga ctc gag      240
Gly Gly Gly Ser Gly Thr Asp Phe Thr Leu Thr Ile Ser Arg Leu Glu
 65                  70                  75                  80 ccc gaa gac ttc gca gtt tat tat tgc cag cag tac tcc gac tcc cca      288
Pro Glu Asp Phe Ala Val Tyr Tyr Cys Gln Gln Tyr Ser Asp Ser Pro
                 85                  90                  95 ttc acc ttc ggc cct ggt acc aaa gtg gat att aaa cgg                  327
Phe Thr Phe Gly Pro Gly Thr Lys Val Asp Ile Lys Arg
                100                 105
```

<210> SEQ ID NO 5
<211> LENGTH: 109
<212> TYPE: PRT
<213> ORGANISM: Homo sapiens

<400> SEQUENCE: 5

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Leu Arg Arg Ile
             20                  25                  30

Tyr Leu Ala Trp Tyr Gln Gln Lys Pro Gly Gln Ala Pro Arg Leu Leu
         35                  40                  45

Ile Tyr Asp Val Phe Asp Arg Ala Thr Gly Ile Pro Asp Arg Phe Ser
 50                  55                  60

Gly Gly Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Asp Ser Pro
                 85                  90                  95

Phe Thr Phe Gly Pro Gly Thr Lys Val Asp Ile Lys Arg
                100                 105
```

<210> SEQ ID NO 6
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: 1C8 VH

<400> SEQUENCE: 6

```
cag gtg cag ctc caa gaa tct gga ccg ggt ctc gtc aag cca tca cag       48
Gln Val Gln Leu Gln Glu Ser Gly Pro Gly Leu Val Lys Pro Ser Gln
 1               5                  10                  15 aca ctg tcc ctg acc tgc acc gtc tcc ggc gac tct atc att tca ggc       96
Thr Leu Ser Leu Thr Cys Thr Val Ser Gly Asp Ser Ile Ile Ser Gly
             20                  25                  30 ggc tac tat tgg tcc tgg att aga caa cat ccg gga aag ggt ctt gaa      144
Gly Tyr Tyr Trp Ser Trp Ile Arg Gln His Pro Gly Lys Gly Leu Glu
         35                  40                  45 tgg atc ggc tat att ttc tac agc ggg agt acg gat tac aat cct agt      192
Trp Ile Gly Tyr Ile Phe Tyr Ser Gly Ser Thr Asp Tyr Asn Pro Ser
 50                  55                  60
```

```
ctc aag agc cgc gtt acc att tca gtg gat act tca aaa aac cag ttt    240
Leu Lys Ser Arg Val Thr Ile Ser Val Asp Thr Ser Lys Asn Gln Phe
 65                  70                  75                  80 agc ctg aag ctg tct tct gta aca gct gct gac aca gcc gtg tac tat    288
Ser Leu Lys Leu Ser Ser Val Thr Ala Ala Asp Thr Ala Val Tyr Tyr
                 85                  90                  95 tgc gcc agg agc ggc tac agc tat gcc ctg ttt gac cac tgg ggg caa    336
Cys Ala Arg Ser Gly Tyr Ser Tyr Ala Leu Phe Asp His Trp Gly Gln
            100                 105                 110 ggc act ctt gtg acg gtg tca agt                                    360
Gly Thr Leu Val Thr Val Ser Ser
        115                 120

<210> SEQ ID NO 7
<211> LENGTH: 120
<212> TYPE: PRT
<213> ORGANISM: Homo sapiens

<400> SEQUENCE: 7

Gln Val Gln Leu Gln Glu Ser Gly Pro Gly Leu Val Lys Pro Ser Gln
 1               5                  10                  15

Thr Leu Ser Leu Thr Cys Thr Val Ser Gly Asp Ser Ile Ile Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Phe Tyr Ser Gly Ser Thr Asp Tyr Asn Pro Ser
        50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ser Gly Tyr Ser Tyr Ala Leu Phe Asp His Trp Gly Gln
            100                 105                 110

Gly Thr Leu Val Thr Val Ser Ser
        115                 120

<210> SEQ ID NO 8
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 1C8 VL

<400> SEQUENCE: 8 gac att caa atg acg cag tcc cca agt tct ctg tcc gct agc gtc ggc     48
Asp Ile Gln Met Thr Gln Ser Pro Ser Ser Leu Ser Ala Ser Val Gly
 1               5                  10                  15 gac cga gtg acc atc agc tgc cga gca tcc cag ttt atc ggt aga tat     96
Asp Arg Val Thr Ile Ser Cys Arg Ala Ser Gln Phe Ile Gly Arg Tyr
                20                  25                  30 ttc aat tgg tac cag caa caa ccg ggc aaa gcg ccc aag gtc ctg atc    144
Phe Asn Trp Tyr Gln Gln Gln Pro Gly Lys Ala Pro Lys Val Leu Ile
            35                  40                  45 tac gct gag agc agt ctg caa tcc ggc gta cct agc agg ttc tcc gga    192
Tyr Ala Glu Ser Ser Leu Gln Ser Gly Val Pro Ser Arg Phe Ser Gly
        50                  55                  60 agt ggc agc gga acc gag ttc acc ctg aca att agc tcc ttg cag ccc    240
Ser Gly Ser Gly Thr Glu Phe Thr Leu Thr Ile Ser Ser Leu Gln Pro
 65                  70                  75                  80
```

```
gag gat ttc gct cgc tat tac tgt caa cag agt tat tca acc cct ttt      288
Glu Asp Phe Ala Arg Tyr Tyr Cys Gln Gln Ser Tyr Ser Thr Pro Phe
                85                  90                  95 aca ttc gga cag gga act aaa gtt gaa att aag agg                      324
Thr Phe Gly Gln Gly Thr Lys Val Glu Ile Lys Arg
            100                 105

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
 1               5                  10                  15

Asp Arg Val Thr Ile Ser Cys Arg Ala Ser Gln Phe Ile Gly Arg Tyr
            20                  25                  30

Phe Asn Trp Tyr Gln Gln Pro Gly Lys Ala Pro Lys Val Leu Ile
        35                  40                  45

Tyr Ala Glu Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Arg Tyr Tyr Cys Gln Gln Ser Tyr Ser Thr Pro Phe
                85                  90                  95

Thr Phe Gly Gln Gly Thr Lys Val Glu Ile Lys Arg
            100                 105

<210> SEQ ID NO 10
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: 6E9 VH

<400> SEQUENCE: 10 cag gta cac ctg gtg cag agc ggg gcg gag gtc aag aaa ccg ggc gca       48
Gln Val His Leu Val Gln Ser Gly Ala Glu Val Lys Lys Pro Gly Ala
 1               5                  10                  15 tcc gta cgc gtg agc tgc aag gcc tcc gga tac act ttt act tct tac       96
Ser Val Arg Val Ser Cys Lys Ala Ser Gly Tyr Thr Phe Thr Ser Tyr
            20                  25                  30 tat ctg cat tgg gtc agg cag gca ccg ggt cag gga ctg gag tgg atg      144
Tyr Leu His Trp Val Arg Gln Ala Pro Gly Gln Gly Leu Glu Trp Met
        35                  40                  45 ggc att gtg gac cca agc gga ggg agt acg tca tat gat cag aag ttt      192
Gly Ile Val Asp Pro Ser Gly Gly Ser Thr Ser Tyr Asp Gln Lys Phe
    50                  55                  60 caa ggt agg ttt acc atg aca cgg gac acg tca acg agt acc gtc tac      240
Gln Gly Arg Phe Thr Met Thr Arg Asp Thr Ser Thr Ser Thr Val Tyr
65                  70                  75                  80 atg gag ctc agt agt ctg cgg agc gaa gac acc gca gtc tac tac tgc      288
Met Glu Leu Ser Ser Leu Arg Ser Glu Asp Thr Ala Val Tyr Tyr Cys
                85                  90                  95
```

```
gca cgc gat tat gga gac tat gtc ttt gac tat tgg ggg cag ggg acg    336
Ala Arg Asp Tyr Gly Asp Tyr Val Phe Asp Tyr Trp Gly Gln Gly Thr
            100                 105                 110 ctc gtg acc gtt tca agc                                            354
Leu Val Thr Val Ser Ser
        115

<210> SEQ ID NO 11
<211> LENGTH: 118
<212> TYPE: PRT
<213> ORGANISM: Homo sapiens

<400> SEQUENCE: 11

Gln Val His Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Tyr Leu His Trp Val Arg Gln Ala Pro Gly Gln Gly Leu Glu Trp Met
        35                  40                  45

Gly Ile Val Asp Pro Ser Gly Gly Ser Thr Ser Tyr Asp Gln Lys Phe
    50                  55                  60

Gln Gly Arg Phe Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Asp Tyr Val Phe Asp Tyr Trp Gly Gln Gly Thr
            100                 105                 110

Leu Val Thr Val Ser Ser
        115

<210> SEQ ID NO 12
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: 6E9 VL

<400> SEQUENCE: 12 caa agc gta ctg aca cag ccc ccg agt gca tcc ggg acc ccc ggc caa    48
Gln Ser Val Leu Thr Gln Pro Pro Ser Ala Ser Gly Thr Pro Gly Gln
1               5                   10                  15 agg gtt aca atc agc tgc tct ggc agc tcc agt aac ata ggt acc aac    96
Arg Val Thr Ile Ser Cys Ser Gly Ser Ser Ser Asn Ile Gly Thr Asn
            20                  25                  30 acg gtg aac tgg tac cag cag ttg cct ggc aca gcg cct cag ctg ctc    144
Thr Val Asn Trp Tyr Gln Gln Leu Pro Gly Thr Ala Pro Gln Leu Leu
        35                  40                  45 atc tat atc aac aat cag cgg cca agt ggc gtg ccc gat aga ttc tca    192
Ile Tyr Ile Asn Asn Gln Arg Pro Ser Gly Val Pro Asp Arg Phe Ser
    50                  55                  60 ggc tca aag agc gga acc agc gct agc ttg gca atc agt ggc ctt caa    240
Gly Ser Lys Ser Gly Thr Ser Ala Ser Leu Ala Ile Ser Gly Leu Gln
65                  70                  75                  80 tcc gaa gac gaa gcc gat tac tat tgt gcg acc tgg gac gat agc ctg    288
Ser Glu Asp Glu Ala Asp Tyr Tyr Cys Ala Thr Trp Asp Asp Ser Leu
                85                  90                  95 aac ggc ccc gtc gtg ggc ggc ggg acg aaa ctg aca gtg ttg ggc        333
Asn Gly Pro Val Val Gly Gly Gly Thr Lys Leu Thr Val Leu Gly
            100                 105                 110
```

<210> SEQ ID NO 13
<211> LENGTH: 111
<212> TYPE: PRT
<213> ORGANISM: Homo sapiens

<400> SEQUENCE: 13

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Thr Val Asn Trp Tyr Gln Gln Leu Pro Gly Thr Ala Pro Gln Leu Leu
        35                  40                  45

Ile Tyr Ile Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Pro Val Val Gly Gly Thr Lys Leu Thr Val Leu Gly
            100                 105                 110
```

<210> SEQ ID NO 14
<211> LENGTH: 171
<212> TYPE: DNA
<213> ORGANISM: Homo sapiens
<220> FEATURE:
<221> NAME/KEY: CDS
<222> LOCATION: (1)..(171)
<223> OTHER INFORMATION: CD28T EC/TM

<400> SEQUENCE: 14

```
ctt gat aat gaa aag tca aac gga aca atc att cac gtg aag ggc aag    48
Leu Asp Asn Glu Lys Ser Asn Gly Thr Ile Ile His Val Lys Gly Lys
1               5                   10                  15 cac ctc tgt ccg tca ccc ttg ttc cct ggt cca tcc aag cca ttc tgg    96
His Leu Cys Pro Ser Pro Leu Phe Pro Gly Pro Ser Lys Pro Phe Trp
            20                  25                  30 gtg ttg gtc gta gtg ggt gga gtc ctc gct tgt tac tct ctg ctc gtc   144
Val Leu Val Val Val Gly Gly Val Leu Ala Cys Tyr Ser Leu Leu Val
        35                  40                  45 acc gtg gct ttt ata atc ttc tgg gtt                                171
Thr Val Ala Phe Ile Ile Phe Trp Val
    50                  55
```

<210> SEQ ID NO 15
<211> LENGTH: 57
<212> TYPE: PRT
<213> ORGANISM: Homo sapiens

<400> SEQUENCE: 15

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro Phe Trp
            20                  25                  30

Val Leu Val Val Val Gly Gly Val Leu Ala Cys Tyr Ser Leu Leu Val
        35                  40                  45

Thr Val Ala Phe Ile Ile Phe Trp Val
    50                  55
```

```
<210> SEQ ID NO 16
<211> LENGTH: 249
<212> TYPE: DNA
<213> ORGANISM: Homo sapiens
<220> FEATURE:
<221> NAME/KEY: CDS
<222> LOCATION: (1)..(249)
<223> OTHER INFORMATION: CD8 EC/TM

<400> SEQUENCE: 16 ttc gtg cct gtt ttt ctg ccc gcg aaa ccc aca act acc ccc gcc cct      48
Phe Val Pro Val Phe Leu Pro Ala Lys Pro Thr Thr Thr Pro Ala Pro
1               5                   10                  15 cgg ccc cca act cct gca cca act atc gct tcc caa ccc ctg tct ctg      96
Arg Pro Pro Thr Pro Ala Pro Thr Ile Ala Ser Gln Pro Leu Ser Leu
            20                  25                  30 aga cct gag gca tgc cgc ccc gcg gca ggc ggc gcc gtg cac act aga     144
Arg Pro Glu Ala Cys Arg Pro Ala Ala Gly Gly Ala Val His Thr Arg
        35                  40                  45 ggc ctg gac ttc gcc tgc gat att tat atc tgg gcc ccc ctt gcc ggg     192
Gly Leu Asp Phe Ala Cys Asp Ile Tyr Ile Trp Ala Pro Leu Ala Gly
    50                  55                  60 aca tgc ggg gta ctg ctg ctg tct ctg gtg att acc ctc tac tgc aac     240
Thr Cys Gly Val Leu Leu Leu Ser Leu Val Ile Thr Leu Tyr Cys Asn
65                  70                  75                  80 cac aga aac                                                          249
His Arg Asn <210> SEQ ID NO 17
<211> LENGTH: 83
<212> TYPE: PRT
<213> ORGANISM: Homo sapiens

<400> SEQUENCE: 17

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn

<210> SEQ ID NO 18
<211> LENGTH: 81
<212> TYPE: DNA
<213> ORGANISM: Homo sapiens
<220> FEATURE:
<221> NAME/KEY: CDS
<222> LOCATION: (1)..(81)
<223> OTHER INFORMATION: CD28T TM

<400> SEQUENCE: 18 ttc tgg gtg ttg gtc gta gtg ggt gga gtc ctc gct tgt tac tct ctg      48
Phe Trp Val Leu Val Val Val Gly Gly Val Leu Ala Cys Tyr Ser Leu
1               5                   10                  15 ctc gtc acc gtg gct ttt ata atc ttc tgg gtt                          81
Leu Val Thr Val Ala Phe Ile Ile Phe Trp Val
            20                  25
```

-continued

```
<210> SEQ ID NO 19
<211> LENGTH: 27
<212> TYPE: PRT
<213> ORGANISM: Homo sapiens

<400> SEQUENCE: 19

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 20
<211> LENGTH: 63
<212> TYPE: DNA
<213> ORGANISM: Homo sapiens
<220> FEATURE:
<221> NAME/KEY: CDS
<222> LOCATION: (1)..(63)
<223> OTHER INFORMATION: CD8 TM

<400> SEQUENCE: 20 att tat atc tgg gcc ccc ctt gcc ggg aca tgc ggg gta ctg ctg ctg     48
Ile Tyr Ile Trp Ala Pro Leu Ala Gly Thr Cys Gly Val Leu Leu Leu
1               5                   10                  15 tct ctg gtg att acc                                                 63
Ser Leu Val Ile Thr
            20

<210> SEQ ID NO 21
<211> LENGTH: 21
<212> TYPE: PRT
<213> ORGANISM: Homo sapiens

<400> SEQUENCE: 21

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 22
<211> LENGTH: 123
<212> TYPE: DNA
<213> ORGANISM: Homo sapiens
<220> FEATURE:
<221> NAME/KEY: CDS
<222> LOCATION: (1)..(123)
<223> OTHER INFORMATION: CD28 costim

<400> SEQUENCE: 22 aga tcc aaa aga agc cgc ctg ctc cat agc gat tac atg aat atg act     48
Arg Ser Lys Arg Ser Arg Leu Leu His Ser Asp Tyr Met Asn Met Thr
1               5                   10                  15 cca cgc cgc cct ggc ccc aca agg aaa cac tac cag cct tac gca cca     96
Pro Arg Arg Pro Gly Pro Thr Arg Lys His Tyr Gln Pro Tyr Ala Pro
            20                  25                  30 cct aga gat ttc gct gcc tat cgg agc                                 123
Pro Arg Asp Phe Ala Ala Tyr Arg Ser
            35                  40

<210> SEQ ID NO 23
<211> LENGTH: 41
<212> TYPE: PRT
<213> ORGANISM: Homo sapiens
```

```
<400> SEQUENCE: 23

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 24
<211> LENGTH: 141
<212> TYPE: DNA
<213> ORGANISM: Homo sapiens
<220> FEATURE:
<221> NAME/KEY: CDS
<222> LOCATION: (1)..(141)
<223> OTHER INFORMATION: 4-1BB costim

<400> SEQUENCE: 24 cgc ttt tcc gtc gtt aag cgg ggg aga aaa aag ctg ctg tac att ttc     48
Arg Phe Ser Val Val Lys Arg Gly Arg Lys Lys Leu Leu Tyr Ile Phe
1               5                   10                  15 aaa cag ccg ttt atg agg ccg gtc caa acg act cag gaa gaa gac ggc     96
Lys Gln Pro Phe Met Arg Pro Val Gln Thr Thr Gln Glu Glu Asp Gly
                20                  25                  30 tgc tcc tgc cgc ttt cct gag gag gag gag ggc ggg tgc gaa ctg        141
Cys Ser Cys Arg Phe Pro Glu Glu Glu Glu Gly Gly Cys Glu Leu
            35                  40                  45

<210> SEQ ID NO 25
<211> LENGTH: 47
<212> TYPE: PRT
<213> ORGANISM: Homo sapiens

<400> SEQUENCE: 25

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
                20                  25                  30

Cys Ser Cys Arg Phe Pro Glu Glu Glu Glu Gly Gly Cys Glu Leu
            35                  40                  45

<210> SEQ ID NO 26
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: CD3zeta

<400> SEQUENCE: 26 agg gtg aag ttt tcc aga tct gca gat gca cca gcg tat cag cag ggc     48
Arg Val Lys Phe Ser Arg Ser Ala Asp Ala Pro Ala Tyr Gln Gln Gly
1               5                   10                  15 cag aac caa ctg tat aac gag ctc aac ctg gga cgc agg gaa gag tat     96
Gln Asn Gln Leu Tyr Asn Glu Leu Asn Leu Gly Arg Arg Glu Glu Tyr
                20                  25                  30 gac gtt ttg gac aag cgc aga gga cgg gac cct gag atg ggt ggc aaa    144
Asp Val Leu Asp Lys Arg Arg Gly Arg Asp Pro Glu Met Gly Gly Lys
            35                  40                  45 cca aga cga aaa aac ccc cag gag ggt ctc tat aat gag ctg cag aag    192
Pro Arg Arg Lys Asn Pro Gln Glu Gly Leu Tyr Asn Glu Leu Gln Lys
        50                  55                  60
```

```
gat aag atg gct gaa gcc tat tct gaa ata ggc atg aaa gga gag cgg         240
Asp Lys Met Ala Glu Ala Tyr Ser Glu Ile Gly Met Lys Gly Glu Arg
 65                  70                  75                  80 aga agg gga aaa ggg cac gac ggt ttg tac cag gga ctc agc act gct         288
Arg Arg Gly Lys Gly His Asp Gly Leu Tyr Gln Gly Leu Ser Thr Ala
                 85                  90                  95 acg aag gat act tat gac gct ctc cac atg caa gcc ctg cca cct agg         336
Thr Lys Asp Thr Tyr Asp Ala Leu His Met Gln Ala Leu Pro Pro Arg
            100                 105                 110
```

<210> SEQ ID NO 27
<211> LENGTH: 112
<212> TYPE: PRT
<213> ORGANISM: Homo sapiens

<400> SEQUENCE: 27

```
Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 28
<211> LENGTH: 21
<212> TYPE: PRT
<213> ORGANISM: Homo sapiens

<400> SEQUENCE: 28

```
Met Ala Leu Pro Val Thr Ala Leu Leu Leu Pro Leu Ala Leu Leu Leu
 1               5                  10                  15

His Ala Ala Arg Pro
                20
```

<210> SEQ ID NO 29
<211> LENGTH: 1440
<212> TYPE: DNA
<213> ORGANISM: Homo sapiens
<220> FEATURE:
<221> NAME/KEY: CDS
<222> LOCATION: (1)..(1440)
<223> OTHER INFORMATION: 8G1.1_C28T_28z

<400> SEQUENCE: 29

```
atg gca ctc ccc gta act gct ctg ctg ctg ccg ttg gca ttg ctc ctg          48
Met Ala Leu Pro Val Thr Ala Leu Leu Leu Pro Leu Ala Leu Leu Leu
 1               5                  10                  15 cac gcc gca cgc ccg caa gag cag ctg gtt gag tct ggg ggc ggc gtc          96
His Ala Ala Arg Pro Gln Glu Gln Leu Val Glu Ser Gly Gly Gly Val
                20                  25                  30 gtc caa ccc ggc cgg agt ctg agg ttg tcc tgc gct gca agc gga ttt         144
Val Gln Pro Gly Arg Ser Leu Arg Leu Ser Cys Ala Ala Ser Gly Phe
            35                  40                  45
```

-continued

| | | |
|---|---|---|
| aca ttt tca tct tac ggc atg cac tgg gtt agg cag gct cct gga aaa<br>Thr Phe Ser Ser Tyr Gly Met His Trp Val Arg Gln Ala Pro Gly Lys<br>50            55                60 | 192 | |
| ggg ctg gag tgg gtc gcg gtg act tgg tac gac ggc tcc aat aag tat<br>Gly Leu Glu Trp Val Ala Val Thr Trp Tyr Asp Gly Ser Asn Lys Tyr<br>65            70            75            80 | 240 | |
| tat ggg gat tcc gtg aaa ggt cga ttc aca att agc agg gat aac tcc<br>Tyr Gly Asp Ser Val Lys Gly Arg Phe Thr Ile Ser Arg Asp Asn Ser<br>85            90            95 | 288 | |
| aaa aac aca ctg tat ctc caa atg aac tcc ttg agg gcc gag gac acg<br>Lys Asn Thr Leu Tyr Leu Gln Met Asn Ser Leu Arg Ala Glu Asp Thr<br>100            105            110 | 336 | |
| gcc gtc tat tat tgt gca aga gac ctc ctc cgg ggc gta aag gga tat<br>Ala Val Tyr Tyr Cys Ala Arg Asp Leu Leu Arg Gly Val Lys Gly Tyr<br>115            120            125 | 384 | |
| gct atg gac gtg tgg ggt cag ggg acc aca gtt act gtc agt tca ggt<br>Ala Met Asp Val Trp Gly Gln Gly Thr Thr Val Thr Val Ser Ser Gly<br>130            135            140 | 432 | |
| ggc ggt ggc agt ggc ggc ggg gga agt gga ggc ggg ggc tct gaa atc<br>Gly Gly Gly Ser Gly Gly Gly Gly Ser Gly Gly Gly Gly Ser Glu Ile<br>145            150            155            160 | 480 | |
| gtt ctc act cag tct ccg ggc aca ctg tcc ctc agc ccc gga gag cga<br>Val Leu Thr Gln Ser Pro Gly Thr Leu Ser Leu Ser Pro Gly Glu Arg<br>165            170            175 | 528 | |
| gcc act ttg agc tgc cgg gcc agc cag tca ctt aga cgc att tat ttg<br>Ala Thr Leu Ser Cys Arg Ala Ser Gln Ser Leu Arg Arg Ile Tyr Leu<br>180            185            190 | 576 | |
| gcc tgg tat cag cag aaa cca ggc cag gcg ccc agg ctg ctg ata tac<br>Ala Trp Tyr Gln Gln Lys Pro Gly Gln Ala Pro Arg Leu Leu Ile Tyr<br>195            200            205 | 624 | |
| gat gtg ttc gat agg gcc acg ggt atc ccc gat agg ttc tct ggc ggg<br>Asp Val Phe Asp Arg Ala Thr Gly Ile Pro Asp Arg Phe Ser Gly Gly<br>210            215            220 | 672 | |
| ggg tcc ggg act gac ttc acc ctc act ata tca cga ctc gag ccc gaa<br>Gly Ser Gly Thr Asp Phe Thr Leu Thr Ile Ser Arg Leu Glu Pro Glu<br>225            230            235            240 | 720 | |
| gac ttc gca gtt tat tat tgc cag cag tac tcc gac tcc cca ttc acc<br>Asp Phe Ala Val Tyr Tyr Cys Gln Gln Tyr Ser Asp Ser Pro Phe Thr<br>245            250            255 | 768 | |
| ttc ggc cct ggt acc aaa gtg gat att aaa cgg gcc gct gcc ctt gat<br>Phe Gly Pro Gly Thr Lys Val Asp Ile Lys Arg Ala Ala Ala Leu Asp<br>260            265            270 | 816 | |
| aat gaa aag tca aac gga aca atc att cac gtg aag ggc aag cac ctc<br>Asn Glu Lys Ser Asn Gly Thr Ile Ile His Val Lys Gly Lys His Leu<br>275            280            285 | 864 | |
| tgt ccg tca ccc ttg ttc cct ggt cca tcc aag cca ttc tgg gtg ttg<br>Cys Pro Ser Pro Leu Phe Pro Gly Pro Ser Lys Pro Phe Trp Val Leu<br>290            295            300 | 912 | |
| gtc gta gtg ggt gga gtc ctc gct tgt tac tct ctg ctc gtc acc gtg<br>Val Val Val Gly Gly Val Leu Ala Cys Tyr Ser Leu Leu Val Thr Val<br>305            310            315            320 | 960 | |
| gct ttt ata atc ttc tgg gtt aga tcc aaa aga agc cgc ctg ctc cat<br>Ala Phe Ile Ile Phe Trp Val Arg Ser Lys Arg Ser Arg Leu Leu His<br>325            330            335 | 1008 | |
| agc gat tac atg aat atg act cca cgc cgt cct ggc ccc aca agg aaa<br>Ser Asp Tyr Met Asn Met Thr Pro Arg Arg Pro Gly Pro Thr Arg Lys<br>340            345            350 | 1056 | |
| cac tac cag cct tac gca cca cct aga gat ttc gct gcc tat cgg agc<br>His Tyr Gln Pro Tyr Ala Pro Pro Arg Asp Phe Ala Ala Tyr Arg Ser<br>355            360            365 | 1104 | |

| | | | | | | | | | | | | | | | | |
|---|---|---|---|---|---|---|---|---|---|---|---|---|---|---|---|---|
| agg | gtg | aag | ttt | tcc | aga | tct | gca | gat | gca | cca | gcg | tat | cag | cag | ggc | 1152 |
| Arg | Val | Lys | Phe | Ser | Arg | Ser | Ala | Asp | Ala | Pro | Ala | Tyr | Gln | Gln | Gly | |
| 370 | | | | | 375 | | | | | 380 | | | | | | |

| | | | | | | | | | | | | | | | | |
|---|---|---|---|---|---|---|---|---|---|---|---|---|---|---|---|---|
| cag | aac | caa | ctg | tat | aac | gag | ctc | aac | ctg | gga | cgc | agg | gaa | gag | tat | 1200 |
| Gln | Asn | Gln | Leu | Tyr | Asn | Glu | Leu | Asn | Leu | Gly | Arg | Arg | Glu | Glu | Tyr | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| gac | gtt | ttg | gac | aag | cgc | aga | gga | cgg | gac | cct | gag | atg | ggt | ggc | aaa | 1248 |
| Asp | Val | Leu | Asp | Lys | Arg | Arg | Gly | Arg | Asp | Pro | Glu | Met | Gly | Gly | Lys | |
| | | | | 405 | | | | | 410 | | | | | 415 | | |

| | | | | | | | | | | | | | | | | |
|---|---|---|---|---|---|---|---|---|---|---|---|---|---|---|---|---|
| cca | aga | cga | aaa | aac | ccc | cag | gag | ggt | ctc | tat | aat | gag | ctg | cag | aag | 1296 |
| Pro | Arg | Arg | Lys | Asn | Pro | Gln | Glu | Gly | Leu | Tyr | Asn | Glu | Leu | Gln | Lys | |
| | | | 420 | | | | | 425 | | | | | 430 | | | |

| | | | | | | | | | | | | | | | | |
|---|---|---|---|---|---|---|---|---|---|---|---|---|---|---|---|---|
| gat | aag | atg | gct | gaa | gcc | tat | tct | gaa | ata | ggc | atg | aaa | gga | gag | cgg | 1344 |
| Asp | Lys | Met | Ala | Glu | Ala | Tyr | Ser | Glu | Ile | Gly | Met | Lys | Gly | Glu | Arg | |
| | | 435 | | | | | 440 | | | | | 445 | | | | |

| | | | | | | | | | | | | | | | | |
|---|---|---|---|---|---|---|---|---|---|---|---|---|---|---|---|---|
| aga | agg | gga | aaa | ggg | cac | gac | ggt | ttg | tac | cag | gga | ctc | agc | act | gct | 1392 |
| Arg | Arg | Gly | Lys | Gly | His | Asp | Gly | Leu | Tyr | Gln | Gly | Leu | Ser | Thr | Ala | |
| 450 | | | | | 455 | | | | | 460 | | | | | | |

| | | | | | | | | | | | | | | | | |
|---|---|---|---|---|---|---|---|---|---|---|---|---|---|---|---|---|
| acg | aag | gat | act | tat | gac | gct | ctc | cac | atg | caa | gcc | ctg | cca | cct | agg | 1440 |
| Thr | Lys | Asp | Thr | Tyr | Asp | Ala | Leu | His | Met | Gln | Ala | Leu | Pro | Pro | Arg | |
| 465 | | | | | 470 | | | | | 475 | | | | | 480 | |

```
<210> SEQ ID NO 30
<211> LENGTH: 480
<212> TYPE: PRT
<213> ORGANISM: Homo sapiens

<400> SEQUENCE: 30
```

Met Ala Leu Pro Val Thr Ala Leu Leu Leu Pro Leu Ala Leu Leu Leu
1               5                   10                  15

His Ala Ala Arg Pro Gln Glu Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Thr Trp Tyr Asp Gly Ser Asn Lys Tyr
65                  70                  75                  80

Tyr Gly Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Leu Leu Arg Gly Val Lys Gly Tyr
        115                 120                 125

Ala Met Asp Val Trp Gly Gln Gly Thr Thr Val Thr Val Ser Ser Gly
    130                 135                 140

Gly Gly Gly Ser Gly Gly Gly Ser Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Leu Arg Arg Ile Tyr Leu
            180                 185                 190

Ala Trp Tyr Gln Gln Lys Pro Gly Gln Ala Pro Arg Leu Leu Ile Tyr
        195                 200                 205

Asp Val Phe Asp Arg Ala Thr Gly Ile Pro Asp Arg Phe Ser Gly Gly
    210                 215                 220

```
Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr Ser Asp Ser Pro Phe Thr
            245                 250                 255

Phe Gly Pro Gly Thr Lys Val Asp Ile Lys Arg Ala Ala Ala Leu Asp
        260                 265                 270

Asn Glu Lys Ser Asn Gly Thr Ile Ile His Val Lys Gly Lys His Leu
    275                 280                 285

Cys Pro Ser Pro Leu Phe Pro Gly Pro Ser Lys Pro Phe Trp Val Leu
290                 295                 300

Val Val Val Gly Gly Val Leu Ala Cys Tyr Ser Leu Leu Val Thr Val
305                 310                 315                 320

Ala Phe Ile Ile Phe Trp Val Arg Ser Lys Arg Ser Arg Leu Leu His
            325                 330                 335

Ser Asp Tyr Met Asn Met Thr Pro Arg Arg Pro Gly Pro Thr Arg Lys
        340                 345                 350

His Tyr Gln Pro Tyr Ala Pro Pro Arg Asp Phe Ala Ala Tyr Arg Ser
    355                 360                 365

Arg Val Lys Phe Ser Arg Ser Ala Asp Ala Pro Ala Tyr Gln Gln Gly
370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
            405                 410                 415

Pro Arg Arg Lys Asn Pro Gln Glu Gly Leu Tyr Asn Glu Leu Gln Lys
        420                 425                 430

Asp Lys Met Ala Glu Ala Tyr Ser Glu Ile Gly Met Lys Gly Glu Arg
    435                 440                 445

Arg Arg Gly Lys Gly His Asp Gly Leu Tyr Gln Gly Leu Ser Thr Ala
450                 455                 460

Thr Lys Asp Thr Tyr Asp Ala Leu His Met Gln Ala Leu Pro Pro Arg
465                 470                 475                 480

<210> SEQ ID NO 31
<211> LENGTH: 1458
<212> TYPE: DNA
<213> ORGANISM: Homo sapiens
<220> FEATURE:
<221> NAME/KEY: CDS
<222> LOCATION: (1)..(1458)
<223> OTHER INFORMATION: 8G1.1_C28T_4Bz

<400> SEQUENCE: 31 atg gca ctc ccc gta act gct ctg ctg ctg ccg ttg gca ttg ctc ctg    48
Met Ala Leu Pro Val Thr Ala Leu Leu Leu Pro Leu Ala Leu Leu Leu
1               5                   10                  15 cac gcc gca cgc ccg caa gag cag ctg gtt gag tct ggg ggc gtc        96
His Ala Ala Arg Pro Gln Glu Gln Leu Val Glu Ser Gly Gly Val
            20                  25                  30 gtc caa ccc ggc cgg agt ctg agg ttg tcc tgc gct gca agc gga ttt   144
Val Gln Pro Gly Arg Ser Leu Arg Leu Ser Cys Ala Ala Ser Gly Phe
        35                  40                  45 aca ttt tca tct tac ggc atg cac tgg gtt agg cag gct cct gga aaa   192
Thr Phe Ser Ser Tyr Gly Met His Trp Val Arg Gln Ala Pro Gly Lys
    50                  55                  60 ggg ctg gag tgg gtc gcg gtg act tgg tac gac ggc tcc aat aag tat   240
Gly Leu Glu Trp Val Ala Val Thr Trp Tyr Asp Gly Ser Asn Lys Tyr
65                  70                  75                  80
```

| | | | | | | | | | | | | | | | | |
|---|---|---|---|---|---|---|---|---|---|---|---|---|---|---|---|---|
| tat | ggg | gat | tcc | gtg | aaa | ggt | cga | ttc | aca | att | agc | agg | gat | aac | tcc | 288 |
| Tyr | Gly | Asp | Ser | Val | Lys | Gly | Arg | Phe | Thr | Ile | Ser | Arg | Asp | Asn | Ser | |
| | | | | 85 | | | | 90 | | | | 95 | | | | |
| aaa | aac | aca | ctg | tat | ctc | caa | atg | aac | tcc | ttg | agg | gcc | gag | gac | acg | 336 |
| Lys | Asn | Thr | Leu | Tyr | Leu | Gln | Met | Asn | Ser | Leu | Arg | Ala | Glu | Asp | Thr | |
| | | | 100 | | | | | 105 | | | | | 110 | | | |
| gcc | gtc | tat | tat | tgt | gca | aga | gac | ctc | ctc | cgg | ggc | gta | aag | gga | tat | 384 |
| Ala | Val | Tyr | Tyr | Cys | Ala | Arg | Asp | Leu | Leu | Arg | Gly | Val | Lys | Gly | Tyr | |
| | | 115 | | | | | 120 | | | | | 125 | | | | |
| gct | atg | gac | gtg | tgg | ggt | cag | ggg | acc | aca | gtt | act | gtc | agt | tca | ggt | 432 |
| Ala | Met | Asp | Val | Trp | Gly | Gln | Gly | Thr | Thr | Val | Thr | Val | Ser | Ser | Gly | |
| | 130 | | | | | 135 | | | | | 140 | | | | | |
| ggc | ggt | ggc | agt | ggc | ggt | ggg | gga | agt | gga | ggc | ggg | ggc | tct | gaa | atc | 480 |
| Gly | Gly | Gly | Ser | Gly | Gly | Gly | Gly | Ser | Gly | Gly | Gly | Gly | Ser | Glu | Ile | |
| 145 | | | | | 150 | | | | | 155 | | | | | 160 | |
| gtt | ctc | act | cag | tct | ccg | ggc | aca | ctg | tcc | ctc | agc | ccc | gga | gag | cga | 528 |
| Val | Leu | Thr | Gln | Ser | Pro | Gly | Thr | Leu | Ser | Leu | Ser | Pro | Gly | Glu | Arg | |
| | | | | 165 | | | | | 170 | | | | | 175 | | |
| gcc | act | ttg | agc | tgc | cgg | gcc | agc | cag | tca | ctt | aga | cgc | att | tat | ttg | 576 |
| Ala | Thr | Leu | Ser | Cys | Arg | Ala | Ser | Gln | Ser | Leu | Arg | Arg | Ile | Tyr | Leu | |
| | | | 180 | | | | | 185 | | | | | 190 | | | |
| gcc | tgg | tat | cag | cag | aaa | cca | ggc | cag | gcg | ccc | agg | ctg | ctg | ata | tac | 624 |
| Ala | Trp | Tyr | Gln | Gln | Lys | Pro | Gly | Gln | Ala | Pro | Arg | Leu | Leu | Ile | Tyr | |
| | | 195 | | | | | 200 | | | | | 205 | | | | |
| gat | gtg | ttc | gat | agg | gcc | acg | ggt | atc | ccc | gat | agg | ttc | tct | ggc | ggg | 672 |
| Asp | Val | Phe | Asp | Arg | Ala | Thr | Gly | Ile | Pro | Asp | Arg | Phe | Ser | Gly | Gly | |
| | 210 | | | | | 215 | | | | | 220 | | | | | |
| ggg | tcc | ggg | act | gac | ttc | acc | ctc | act | ata | tca | cga | ctc | gag | ccc | gaa | 720 |
| Gly | Ser | Gly | Thr | Asp | Phe | Thr | Leu | Thr | Ile | Ser | Arg | Leu | Glu | Pro | Glu | |
| 225 | | | | | 230 | | | | | 235 | | | | | 240 | |
| gac | ttc | gca | gtt | tat | tat | tgc | cag | cag | tac | tcc | gac | tcc | cca | ttc | acc | 768 |
| Asp | Phe | Ala | Val | Tyr | Tyr | Cys | Gln | Gln | Tyr | Ser | Asp | Ser | Pro | Phe | Thr | |
| | | | | 245 | | | | | 250 | | | | | 255 | | |
| ttc | ggc | cct | ggt | acc | aaa | gtg | gat | att | aaa | cgg | gcc | gct | gcc | ctt | gat | 816 |
| Phe | Gly | Pro | Gly | Thr | Lys | Val | Asp | Ile | Lys | Arg | Ala | Ala | Ala | Leu | Asp | |
| | | | 260 | | | | | 265 | | | | | 270 | | | |
| aat | gaa | aag | tca | aac | gga | aca | atc | att | cac | gtg | aag | ggc | aag | cac | ctc | 864 |
| Asn | Glu | Lys | Ser | Asn | Gly | Thr | Ile | Ile | His | Val | Lys | Gly | Lys | His | Leu | |
| | | | 275 | | | | | 280 | | | | | 285 | | | |
| tgt | ccg | tca | ccc | ttg | ttc | cct | ggt | cca | tcc | aag | cca | ttc | tgg | gtg | ttg | 912 |
| Cys | Pro | Ser | Pro | Leu | Phe | Pro | Gly | Pro | Ser | Lys | Pro | Phe | Trp | Val | Leu | |
| | 290 | | | | | 295 | | | | | 300 | | | | | |
| gtc | gta | gtg | ggt | gga | gtc | ctc | gct | tgt | tac | tct | ctg | ctc | gtc | acc | gtg | 960 |
| Val | Val | Val | Gly | Gly | Val | Leu | Ala | Cys | Tyr | Ser | Leu | Leu | Val | Thr | Val | |
| 305 | | | | | 310 | | | | | 315 | | | | | 320 | |
| gct | ttt | ata | atc | ttc | tgg | gtt | cgc | ttt | tcc | gtc | gtt | aag | cgg | ggg | aga | 1008 |
| Ala | Phe | Ile | Ile | Phe | Trp | Val | Arg | Phe | Ser | Val | Val | Lys | Arg | Gly | Arg | |
| | | | | 325 | | | | | 330 | | | | | 335 | | |
| aaa | aag | ctg | ctg | tac | att | ttc | aaa | cag | ccg | ttt | atg | agg | ccg | gtc | caa | 1056 |
| Lys | Lys | Leu | Leu | Tyr | Ile | Phe | Lys | Gln | Pro | Phe | Met | Arg | Pro | Val | Gln | |
| | | | 340 | | | | | 345 | | | | | 350 | | | |
| acg | act | cag | gaa | gaa | gac | ggc | tgc | tcc | tgc | cgc | ttt | cct | gag | gag | gag | 1104 |
| Thr | Thr | Gln | Glu | Glu | Asp | Gly | Cys | Ser | Cys | Arg | Phe | Pro | Glu | Glu | Glu | |
| | | 355 | | | | | 360 | | | | | 365 | | | | |
| gag | ggc | ggg | tgc | gaa | ctg | agg | gtg | aag | ttt | tcc | aga | tct | gca | gat | gca | 1152 |
| Glu | Gly | Gly | Cys | Glu | Leu | Arg | Val | Lys | Phe | Ser | Arg | Ser | Ala | Asp | Ala | |
| | 370 | | | | | 375 | | | | | 380 | | | | | |
| cca | gcg | tat | cag | cag | ggc | cag | aac | caa | ctg | tat | aac | gag | ctc | aac | ctg | 1200 |
| Pro | Ala | Tyr | Gln | Gln | Gly | Gln | Asn | Gln | Leu | Tyr | Asn | Glu | Leu | Asn | Leu | |
| 385 | | | | | 390 | | | | | 395 | | | | | 400 | |

```
gga cgc agg gaa gag tat gac gtt ttg gac aag cgc aga gga cgg gac      1248
Gly Arg Arg Glu Glu Tyr Asp Val Leu Asp Lys Arg Arg Gly Arg Asp
            405                 410                 415 cct gag atg ggt ggc aaa cca aga cga aaa aac ccc cag gag ggt ctc      1296
Pro Glu Met Gly Gly Lys Pro Arg Arg Lys Asn Pro Gln Glu Gly Leu
        420                 425                 430 tat aat gag ctg cag aag gat aag atg gct gaa gcc tat tct gaa ata      1344
Tyr Asn Glu Leu Gln Lys Asp Lys Met Ala Glu Ala Tyr Ser Glu Ile
            435                 440                 445 ggc atg aaa gga gag cgg aga agg gga aaa ggg cac gac ggt ttg tac      1392
Gly Met Lys Gly Glu Arg Arg Arg Gly Lys Gly His Asp Gly Leu Tyr
        450                 455                 460 cag gga ctc agc act gct acg aag gat act tat gac gct ctc cac atg      1440
Gln Gly Leu Ser Thr Ala Thr Lys Asp Thr Tyr Asp Ala Leu His Met
465                 470                 475                 480 caa gcc ctg cca cct agg                                              1458
Gln Ala Leu Pro Pro Arg
                485
```

<210> SEQ ID NO 32
<211> LENGTH: 486
<212> TYPE: PRT
<213> ORGANISM: Homo sapiens

<400> SEQUENCE: 32

```
Met Ala Leu Pro Val Thr Ala Leu Leu Leu Pro Leu Ala Leu Leu Leu
1               5                   10                  15

His Ala Ala Arg Pro Gln Glu Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Thr Trp Tyr Asp Gly Ser Asn Lys Tyr
65              70                  75                  80

Tyr Gly Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Leu Leu Arg Gly Val Lys Gly Tyr
        115                 120                 125

Ala Met Asp Val Trp Gly Gln Gly Thr Thr Val Thr Val Ser Ser Gly
    130                 135                 140

Gly Gly Gly Ser Gly Gly Gly Ser Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Leu Arg Arg Ile Tyr Leu
            180                 185                 190

Ala Trp Tyr Gln Gln Lys Pro Gly Gln Ala Pro Arg Leu Leu Ile Tyr
        195                 200                 205

Asp Val Phe Asp Arg Ala Thr Gly Ile Pro Asp Arg Phe Ser Gly Gly
    210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr Ser Asp Ser Pro Phe Thr
                245                 250                 255
```

-continued

```
Phe Gly Pro Gly Thr Lys Val Asp Ile Lys Arg Ala Ala Ala Leu Asp
            260                 265                 270

Asn Glu Lys Ser Asn Gly Thr Ile Ile His Val Lys Gly Lys His Leu
        275                 280                 285

Cys Pro Ser Pro Leu Phe Pro Gly Pro Ser Lys Pro Phe Trp Val Leu
    290                 295                 300

Val Val Val Gly Gly Val Leu Ala Cys Tyr Ser Leu Leu Val Thr Val
305                 310                 315                 320

Ala Phe Ile Ile Phe Trp Val Arg Phe Ser Val Val Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 33
<211> LENGTH: 1518
<212> TYPE: DNA
<213> ORGANISM: Homo sapiens
<220> FEATURE:
<221> NAME/KEY: CDS
<222> LOCATION: (1)..(1518)
<223> OTHER INFORMATION: 8G1.1_C8K_28z

<400> SEQUENCE: 33 atg gca ctc ccc gta act gct ctg ctg ctg ccg ttg gca ttg ctc ctg    48
Met Ala Leu Pro Val Thr Ala Leu Leu Leu Pro Leu Ala Leu Leu Leu
1               5                   10                  15 cac gcc gca cgc ccg caa gag cag ctg gtt gag tct ggg ggc ggc gtc    96
His Ala Ala Arg Pro Gln Glu Gln Leu Val Glu Ser Gly Gly Gly Val
            20                  25                  30 gtc caa ccc ggc cgg agt ctg agg ttg tcc tgc gct gca agc gga ttt   144
Val Gln Pro Gly Arg Ser Leu Arg Leu Ser Cys Ala Ala Ser Gly Phe
        35                  40                  45 aca ttt tca tct tac ggc atg cac tgg gtt agg cag gct cct gga aaa   192
Thr Phe Ser Ser Tyr Gly Met His Trp Val Arg Gln Ala Pro Gly Lys
    50                  55                  60 ggg ctg gag tgg gtc gcg gtg act tgg tac gac ggc tcc aat aag tat   240
Gly Leu Glu Trp Val Ala Val Thr Trp Tyr Asp Gly Ser Asn Lys Tyr
65                  70                  75                  80
```

-continued

| | |
|---|---|
| tat ggg gat tcc gtg aaa ggt cga ttc aca att agc agg gat aac tcc<br>Tyr Gly Asp Ser Val Lys Gly Arg Phe Thr Ile Ser Arg Asp Asn Ser<br>              85                      90                    95 | 288 |
| aaa aac aca ctg tat ctc caa atg aac tcc ttg agg gcc gag gac acg<br>Lys Asn Thr Leu Tyr Leu Gln Met Asn Ser Leu Arg Ala Glu Asp Thr<br>              100                   105                110 | 336 |
| gcc gtc tat tat tgt gca aga gac ctc ctc cgg ggc gta aag gga tat<br>Ala Val Tyr Tyr Cys Ala Arg Asp Leu Leu Arg Gly Val Lys Gly Tyr<br>             115                   120                125 | 384 |
| gct atg gac gtg tgg ggt cag ggg acc aca gtt act gtc agt tca ggt<br>Ala Met Asp Val Trp Gly Gln Gly Thr Thr Val Thr Val Ser Ser Gly<br> 130                  135                   140 | 432 |
| ggc ggt ggc agt ggc ggg gga agt gga ggg ggc tct gaa atc<br>Gly Gly Gly Ser Gly Gly Gly Gly Ser Gly Gly Gly Ser Glu Ile<br>145                 150                  155                  160 | 480 |
| gtt ctc act cag tct ccg ggc aca ctg tcc ctc agc ccc gga gag cga<br>Val Leu Thr Gln Ser Pro Gly Thr Leu Ser Leu Ser Pro Gly Glu Arg<br>              165                   170                175 | 528 |
| gcc act ttg agc tgc cgg gcc agc cag tca ctt aga cgc att tat ttg<br>Ala Thr Leu Ser Cys Arg Ala Ser Gln Ser Leu Arg Arg Ile Tyr Leu<br>         180                   185                   190 | 576 |
| gcc tgg tat cag cag aaa cca ggc cag gcg ccc agg ctg ctg ata tac<br>Ala Trp Tyr Gln Gln Lys Pro Gly Gln Ala Pro Arg Leu Leu Ile Tyr<br>         195                   200                205 | 624 |
| gat gtg ttc gat agg gcc acg ggt atc ccc gat agg ttc tct ggc ggg<br>Asp Val Phe Asp Arg Ala Thr Gly Ile Pro Asp Arg Phe Ser Gly Gly<br> 210                  215                   220 | 672 |
| ggg tcc ggg act gac ttc acc ctc act ata tca cga ctc gag ccc gaa<br>Gly Ser Gly Thr Asp Phe Thr Leu Thr Ile Ser Arg Leu Glu Pro Glu<br>225                 230                  235                  240 | 720 |
| gac ttc gca gtt tat tat tgc cag cag tac tcc gac tcc cca ttc acc<br>Asp Phe Ala Val Tyr Tyr Cys Gln Gln Tyr Ser Asp Ser Pro Phe Thr<br>             245                   250                255 | 768 |
| ttc ggc cct ggt acc aaa gtg gat att aaa cgg gcc gct gcc ttc gtg<br>Phe Gly Pro Gly Thr Lys Val Asp Ile Lys Arg Ala Ala Ala Phe Val<br>         260                   265                270 | 816 |
| cct gtt ttt ctg ccc gcg aaa ccc aca act acc ccc gcc cct cgg ccc<br>Pro Val Phe Leu Pro Ala Lys Pro Thr Thr Thr Pro Ala Pro Arg Pro<br>         275                   280                285 | 864 |
| cca act cct gca cca act atc gct tcc caa ccc ctg tct ctg aga cct<br>Pro Thr Pro Ala Pro Thr Ile Ala Ser Gln Pro Leu Ser Leu Arg Pro<br> 290                  295                   300 | 912 |
| gag gca tgc cgc ccc gcg gca ggc ggc gcc gtg cac act aga ggc ctg<br>Glu Ala Cys Arg Pro Ala Ala Gly Gly Ala Val His Thr Arg Gly Leu<br>305                 310                  315                  320 | 960 |
| gac ttc gcc tgc gat att tat atc tgg gcc ccc ctt gcc ggg aca tgc<br>Asp Phe Ala Cys Asp Ile Tyr Ile Trp Ala Pro Leu Ala Gly Thr Cys<br>             325                   330                335 | 1008 |
| ggg gta ctg ctg ctg tct ctg gtg att acc ctc tac tgc aac cac aga<br>Gly Val Leu Leu Leu Ser Leu Val Ile Thr Leu Tyr Cys Asn His Arg<br>         340                   345                350 | 1056 |
| aac aga tcc aaa aga agc cgc ctg ctc cat agc gat tac atg aat atg<br>Asn Arg Ser Lys Arg Ser Arg Leu Leu His Ser Asp Tyr Met Asn Met<br>         355                   360                365 | 1104 |
| act cca cgc cgc cct ggc ccc aca agg aaa cac tac cag cct tac gca<br>Thr Pro Arg Arg Pro Gly Pro Thr Arg Lys His Tyr Gln Pro Tyr Ala<br> 370                  375                   380 | 1152 |
| cca cct aga gat ttc gct gcc tat cgg agc agg gtg aag ttt tcc aga<br>Pro Pro Arg Asp Phe Ala Ala Tyr Arg Ser Arg Val Lys Phe Ser Arg<br>385                 390                  395                  400 | 1200 |

```
tct gca gat gca cca gcg tat cag cag ggc cag aac caa ctg tat aac    1248
Ser Ala Asp Ala Pro Ala Tyr Gln Gln Gly Gln Asn Gln Leu Tyr Asn
            405                 410                 415 gag ctc aac ctg gga cgc agg gaa gag tat gac gtt ttg gac aag cgc    1296
Glu Leu Asn Leu Gly Arg Arg Glu Glu Tyr Asp Val Leu Asp Lys Arg
            420                 425                 430 aga gga cgg gac cct gag atg ggt ggc aaa cca aga cga aaa aac ccc    1344
Arg Gly Arg Asp Pro Glu Met Gly Gly Lys Pro Arg Arg Lys Asn Pro
            435                 440                 445 cag gag ggt ctc tat aat gag ctg cag aag gat aag atg gct gaa gcc    1392
Gln Glu Gly Leu Tyr Asn Glu Leu Gln Lys Asp Lys Met Ala Glu Ala
        450                 455                 460 tat tct gaa ata ggc atg aaa gga gag cgg aga agg gga aaa ggg cac    1440
Tyr Ser Glu Ile Gly Met Lys Gly Glu Arg Arg Arg Gly Lys Gly His
465                 470                 475                 480 gac ggt ttg tac cag gga ctc agc act gct acg aag gat act tat gac    1488
Asp Gly Leu Tyr Gln Gly Leu Ser Thr Ala Thr Lys Asp Thr Tyr Asp
                485                 490                 495 gct ctc cac atg caa gcc ctg cca cct agg                             1518
Ala Leu His Met Gln Ala Leu Pro Pro Arg
                500                 505

<210> SEQ ID NO 34
<211> LENGTH: 506
<212> TYPE: PRT
<213> ORGANISM: Homo sapiens

<400> SEQUENCE: 34

Met Ala Leu Pro Val Thr Ala Leu Leu Leu Pro Leu Ala Leu Leu Leu
1               5                   10                  15

His Ala Ala Arg Pro Gln Glu Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Thr Trp Tyr Asp Gly Ser Asn Lys Tyr
65                  70                  75                  80

Tyr Gly Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Leu Leu Arg Gly Val Lys Gly Tyr
        115                 120                 125

Ala Met Asp Val Trp Gly Gln Gly Thr Thr Val Thr Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Leu Arg Arg Ile Tyr Leu
            180                 185                 190

Ala Trp Tyr Gln Gln Lys Pro Gly Gln Ala Pro Arg Leu Leu Ile Tyr
        195                 200                 205

Asp Val Phe Asp Arg Ala Thr Gly Ile Pro Asp Arg Phe Ser Gly Gly
    210                 215                 220
```

```
Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr Ser Asp Ser Pro Phe Thr
            245                 250                 255

Phe Gly Pro Gly Thr Lys Val Asp Ile Lys Arg Ala Ala Ala Phe Val
        260                 265                 270

Pro Val Phe Leu Pro Ala Lys Pro Thr Thr Thr Pro Ala Pro Arg Pro
    275                 280                 285

Pro Thr Pro Ala Pro Thr Ile Ala Ser Gln Pro Leu Ser Leu Arg Pro
290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
                500                 505
```

<210> SEQ ID NO 35
<211> LENGTH: 1056
<212> TYPE: DNA
<213> ORGANISM: Homo sapiens
<220> FEATURE:
<221> NAME/KEY: CDS
<222> LOCATION: (1)..(1056)
<223> OTHER INFORMATION: 8G1.1_C8K_4Bz

<400> SEQUENCE: 35

```
gtt ctc act cag tct ccg ggc aca ctg tcc ctc agc ccc gga gag cga      48
Val Leu Thr Gln Ser Pro Gly Thr Leu Ser Leu Ser Pro Gly Glu Arg
1               5                   10                  15 gcc act ttg agc tgc cgg gcc agc cag tca ctt aga cgc att tat ttg      96
Ala Thr Leu Ser Cys Arg Ala Ser Gln Ser Leu Arg Arg Ile Tyr Leu
                20                  25                  30 gcc tgg tat cag cag aaa cca ggc cag gcg ccc agg ctg ctg ata tac    144
Ala Trp Tyr Gln Gln Lys Pro Gly Gln Ala Pro Arg Leu Leu Ile Tyr
            35                  40                  45
```

```
gat gtg ttc gat agg gcc acg ggt atc ccc gat agg ttc tct ggg ggg       192
Asp Val Phe Asp Arg Ala Thr Gly Ile Pro Asp Arg Phe Ser Gly Gly
     50                  55                  60 ggg tcc ggg act gac ttc acc ctc act ata tca cga ctc gag ccc gaa       240
Gly Ser Gly Thr Asp Phe Thr Leu Thr Ile Ser Arg Leu Glu Pro Glu
 65                  70                  75                  80 gac ttc gca gtt tat tat tgc cag cag tac tcc gac tcc cca ttc acc       288
Asp Phe Ala Val Tyr Tyr Cys Gln Gln Tyr Ser Asp Ser Pro Phe Thr
                 85                  90                  95 ttc ggc cct ggt acc aaa gtg gat att aaa cgg gcc gct gcc ttc gtg       336
Phe Gly Pro Gly Thr Lys Val Asp Ile Lys Arg Ala Ala Ala Phe Val
            100                 105                 110 cct gtt ttt ctg ccc gcg aaa ccc aca act acc ccc gcc cct cgg ccc       384
Pro Val Phe Leu Pro Ala Lys Pro Thr Thr Thr Pro Ala Pro Arg Pro
            115                 120                 125 cca act cct gca cca act atc gct tcc caa ccc ctg tct ctg aga cct       432
Pro Thr Pro Ala Pro Thr Ile Ala Ser Gln Pro Leu Ser Leu Arg Pro
    130                 135                 140 gag gca tgc cgc ccc gcg gca ggc ggc gcc gtg cac act aga ggc ctg       480
Glu Ala Cys Arg Pro Ala Ala Gly Gly Ala Val His Thr Arg Gly Leu
145                 150                 155                 160 gac ttc gcc tgc gat att tat atc tgg gcc ccc ctt gcc ggg aca tgc       528
Asp Phe Ala Cys Asp Ile Tyr Ile Trp Ala Pro Leu Ala Gly Thr Cys
                165                 170                 175 ggg gta ctg ctg ctg tct ctg gtg att acc ctc tac tgc aac cac aga       576
Gly Val Leu Leu Leu Ser Leu Val Ile Thr Leu Tyr Cys Asn His Arg
            180                 185                 190 aac cgc ttt tcc gtc gtt aag cgg ggg aga aaa aag ctg ctg tac att       624
Asn Arg Phe Ser Val Val Lys Arg Gly Arg Lys Lys Leu Leu Tyr Ile
            195                 200                 205 ttc aaa cag ccg ttt atg agg ccg gtc caa acg act cag gaa gaa gac       672
Phe Lys Gln Pro Phe Met Arg Pro Val Gln Thr Thr Gln Glu Glu Asp
    210                 215                 220 ggc tgc tcc tgc cgc ttt cct gag gag gag gag ggc ggg tgc gaa ctg       720
Gly Cys Ser Cys Arg Phe Pro Glu Glu Glu Glu Gly Gly Cys Glu Leu
225                 230                 235                 240 agg gtg aag ttt tcc aga tct gca gat gca cca gcg tat cag cag ggc       768
Arg Val Lys Phe Ser Arg Ser Ala Asp Ala Pro Ala Tyr Gln Gln Gly
                245                 250                 255 cag aac caa ctg tat aac gag ctc aac ctg gga cgc agg gaa gag tat       816
Gln Asn Gln Leu Tyr Asn Glu Leu Asn Leu Gly Arg Arg Glu Glu Tyr
            260                 265                 270 gac gtt ttg gac aag cgc aga gga cgg gac cct gag atg ggt ggc aaa       864
Asp Val Leu Asp Lys Arg Arg Gly Arg Asp Pro Glu Met Gly Gly Lys
            275                 280                 285 cca aga cga aaa aac ccc cag gag ggt ctc tat aat gag ctg cag aag       912
Pro Arg Arg Lys Asn Pro Gln Glu Gly Leu Tyr Asn Glu Leu Gln Lys
    290                 295                 300 gat aag atg gct gaa gcc tat tct gaa ata ggc atg aaa gga gag cgg       960
Asp Lys Met Ala Glu Ala Tyr Ser Glu Ile Gly Met Lys Gly Glu Arg
305                 310                 315                 320 aga agg gga aaa ggg cac gac ggt ttg tac cag gga ctc agc act gct      1008
Arg Arg Gly Lys Gly His Asp Gly Leu Tyr Gln Gly Leu Ser Thr Ala
                325                 330                 335 acg aag gat act tat gac gct ctc cac atg caa gcc ctg cca cct agg      1056
Thr Lys Asp Thr Tyr Asp Ala Leu His Met Gln Ala Leu Pro Pro Arg
            340                 345                 350
```

<210> SEQ ID NO 36
<211> LENGTH: 352
<212> TYPE: PRT
<213> ORGANISM: Homo sapiens

<400> SEQUENCE: 36

```
Val Leu Thr Gln Ser Pro Gly Thr Leu Ser Leu Ser Pro Gly Glu Arg
1               5                   10                  15

Ala Thr Leu Ser Cys Arg Ala Ser Gln Ser Leu Arg Arg Ile Tyr Leu
            20                  25                  30

Ala Trp Tyr Gln Gln Lys Pro Gly Gln Ala Pro Arg Leu Leu Ile Tyr
        35                  40                  45

Asp Val Phe Asp Arg Ala Thr Gly Ile Pro Asp Arg Phe Ser Gly Gly
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Ser Asp Ser Pro Phe Thr
                85                  90                  95

Phe Gly Pro Gly Thr Lys Val Asp Ile Lys Arg Ala Ala Phe Val
            100                 105                 110

Pro Val Phe Leu Pro Ala Lys Pro Thr Thr Pro Ala Pro Arg Pro
        115                 120                 125

Pro Thr Pro Ala Pro Thr Ile Ala Ser Gln Pro Leu Ser Leu Arg Pro
    130                 135                 140

Glu Ala Cys Arg Pro Ala Ala Gly Gly Ala Val His Thr Arg Gly Leu
145                 150                 155                 160

Asp Phe Ala Cys Asp Ile Tyr Ile Trp Ala Pro Leu Ala Gly Thr Cys
                165                 170                 175

Gly Val Leu Leu Leu Ser Leu Val Ile Thr Leu Tyr Cys Asn His Arg
            180                 185                 190

Asn Arg Phe Ser Val Val Lys Arg Gly Arg Lys Lys Leu Leu Tyr Ile
        195                 200                 205

Phe Lys Gln Pro Phe Met Arg Pro Val Gln Thr Thr Gln Glu Glu Asp
    210                 215                 220

Gly Cys Ser Cys Arg Phe Pro Glu Glu Glu Glu Gly Gly Cys Glu Leu
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Arg Arg Lys Asn Pro Gln Glu Gly Leu Tyr Asn Glu Leu Gln Lys
    290                 295                 300

Asp Lys Met Ala Glu Ala Tyr Ser Glu Ile Gly Met Lys Gly Glu Arg
305                 310                 315                 320

Arg Arg Gly Lys Gly His Asp Gly Leu Tyr Gln Gly Leu Ser Thr Ala
                325                 330                 335

Thr Lys Asp Thr Tyr Asp Ala Leu His Met Gln Ala Leu Pro Pro Arg
            340                 345                 350
```

<210> SEQ ID NO 37
<211> LENGTH: 1431
<212> TYPE: DNA
<213> ORGANISM: Homo sapiens

```
<220> FEATURE:
<221> NAME/KEY: CDS
<222> LOCATION: (1)..(1431)
<223> OTHER INFORMATION: 1C8.1.001_C28T_28z

<400> SEQUENCE: 37 atg gca ctc ccc gta act gct ctg ctg ctg ccg ttg gca ttg ctc ctg      48
Met Ala Leu Pro Val Thr Ala Leu Leu Leu Pro Leu Ala Leu Leu Leu
1               5                   10                  15 cac gcc gca cgc ccg cag gtg cag ctc caa gaa tct gga ccg ggt ctc      96
His Ala Ala Arg Pro Gln Val Gln Leu Gln Glu Ser Gly Pro Gly Leu
                20                  25                  30 gtc aag cca tca cag aca ctg tcc ctg acc tgc acc gtc tcc ggc gac     144
Val Lys Pro Ser Gln Thr Leu Ser Leu Thr Cys Thr Val Ser Gly Asp
            35                  40                  45 tct atc att tca ggc ggc tac tat tgg tcc tgg att aga caa cat ccg     192
Ser Ile Ile Ser Gly Gly Tyr Tyr Trp Ser Trp Ile Arg Gln His Pro
        50                  55                  60 gga aag ggt ctt gaa tgg atc ggc tat att ttc tac agc ggg agt acg     240
Gly Lys Gly Leu Glu Trp Ile Gly Tyr Ile Phe Tyr Ser Gly Ser Thr
65                  70                  75                  80 gat tac aat cct agt ctc aag agc cgc gtt acc att tca gtg gat act     288
Asp Tyr Asn Pro Ser Leu Lys Ser Arg Val Thr Ile Ser Val Asp Thr
                85                  90                  95 tca aaa aac cag ttt agc ctg aag ctg tct tct gta aca gct gct gac     336
Ser Lys Asn Gln Phe Ser Leu Lys Leu Ser Ser Val Thr Ala Ala Asp
                100                 105                 110 aca gcc gtg tac tat tgc gcc agg agc ggc tac agc tat gcc ctg ttt     384
Thr Ala Val Tyr Tyr Cys Ala Arg Ser Gly Tyr Ser Tyr Ala Leu Phe
            115                 120                 125 gac cac tgg ggg caa ggc act ctt gtg acg gtg tca agt gga ggg gga     432
Asp His Trp Gly Gln Gly Thr Leu Val Thr Val Ser Ser Gly Gly Gly
        130                 135                 140 gga tca ggc ggc ggg gga tcc ggc ggc ggg ggt agt gac att caa atg     480
Gly Ser Gly Gly Gly Gly Ser Gly Gly Gly Gly Ser Asp Ile Gln Met
145                 150                 155                 160 acg cag tcc cca agt tct ctg tcc gct agc gtc ggc gac cga gtg acc     528
Thr Gln Ser Pro Ser Ser Leu Ser Ala Ser Val Gly Asp Arg Val Thr
                165                 170                 175 atc agc tgc cga gca tcc cag ttt atc ggt aga tat ttc aat tgg tac     576
Ile Ser Cys Arg Ala Ser Gln Phe Ile Gly Arg Tyr Phe Asn Trp Tyr
                180                 185                 190 cag caa caa ccg ggc aaa gcg ccc aag gtc ctg atc tac gct gag agc     624
Gln Gln Gln Pro Gly Lys Ala Pro Lys Val Leu Ile Tyr Ala Glu Ser
            195                 200                 205 agt ctg caa tcc ggc gta cct agc agg ttc tcc gga agt ggc agc gga     672
Ser Leu Gln Ser Gly Val Pro Ser Arg Phe Ser Gly Ser Gly Ser Gly
        210                 215                 220 acc gag ttc acc ctg aca att agc tcc ttg cag ccc gag gat ttc gct     720
Thr Glu Phe Thr Leu Thr Ile Ser Ser Leu Gln Pro Glu Asp Phe Ala
225                 230                 235                 240 cgc tat tac tgt caa cag agt tat tca acc cct ttt aca ttc gga cag     768
Arg Tyr Tyr Cys Gln Gln Ser Tyr Ser Thr Pro Phe Thr Phe Gly Gln
                245                 250                 255 gga act aaa gtt gaa att aag agg gcc gct gcc ctt gat aat gaa aag     816
Gly Thr Lys Val Glu Ile Lys Arg Ala Ala Ala Leu Asp Asn Glu Lys
                260                 265                 270 tca aac gga aca atc att cac gtg aag ggc aag cac ctc tgt ccg tca     864
Ser Asn Gly Thr Ile Ile His Val Lys Gly Lys His Leu Cys Pro Ser
            275                 280                 285
```

| | | |
|---|---|---|
| ccc ttg ttc cct ggt cca tcc aag cca ttc tgg gtg ttg gtc gta gtg<br>Pro Leu Phe Pro Gly Pro Ser Lys Pro Phe Trp Val Leu Val Val Val<br>290                             295                    300 | 912 |
| ggt gga gtc ctc gct tgt tac tct ctg ctc gtc acc gtg gct ttt ata<br>Gly Gly Val Leu Ala Cys Tyr Ser Leu Leu Val Thr Val Ala Phe Ile<br>305                         310                      315               320 | 960 |
| atc ttc tgg gtt aga tcc aaa aga agc cgc ctg ctc cat agc gat tac<br>Ile Phe Trp Val Arg Ser Lys Arg Ser Arg Leu Leu His Ser Asp Tyr<br>                  325                      330                   335 | 1008 |
| atg aat atg act cca cgc cgc cct ggc ccc aca agg aaa cac tac cag<br>Met Asn Met Thr Pro Arg Arg Pro Gly Pro Thr Arg Lys His Tyr Gln<br>              340                    345                    350 | 1056 |
| cct tac gca cca cct aga gat ttc gct gcc tat cgg agc agg gtg aag<br>Pro Tyr Ala Pro Pro Arg Asp Phe Ala Ala Tyr Arg Ser Arg Val Lys<br>355                         360                      365 | 1104 |
| ttt tcc aga tct gca gat gca cca gcg tat cag cag ggc cag aac caa<br>Phe Ser Arg Ser Ala Asp Ala Pro Ala Tyr Gln Gln Gly Gln Asn Gln<br>370                       375                    380 | 1152 |
| ctg tat aac gag ctc aac ctg gga cgc agg gaa gag tat gac gtt ttg<br>Leu Tyr Asn Glu Leu Asn Leu Gly Arg Arg Glu Glu Tyr Asp Val Leu<br>385                         390                      395               400 | 1200 |
| gac aag cgc aga gga cgg gac cct gag atg ggt ggc aaa cca aga cga<br>Asp Lys Arg Arg Gly Arg Asp Pro Glu Met Gly Gly Lys Pro Arg Arg<br>                  405                      410                   415 | 1248 |
| aaa aac ccc cag gag ggt ctc tat aat gag ctc cag aag gat aag atg<br>Lys Asn Pro Gln Glu Gly Leu Tyr Asn Glu Leu Gln Lys Asp Lys Met<br>            420                    425                   430 | 1296 |
| gct gaa gcc tat tct gaa ata ggc atg aaa gga gag cgg aga agg gga<br>Ala Glu Ala Tyr Ser Glu Ile Gly Met Lys Gly Glu Arg Arg Arg Gly<br>                 435                      440                   445 | 1344 |
| aaa ggg cac gac ggt ttg tac cag gga ctc agc act gct acg aag gat<br>Lys Gly His Asp Gly Leu Tyr Gln Gly Leu Ser Thr Ala Thr Lys Asp<br>450                         455                    460 | 1392 |
| act tat gac gct ctc cac atg caa gcc ctg cca cct agg<br>Thr Tyr Asp Ala Leu His Met Gln Ala Leu Pro Pro Arg<br>465                         470                      475 | 1431 |

<210> SEQ ID NO 38
<211> LENGTH: 477
<212> TYPE: PRT
<213> ORGANISM: Homo sapiens

<400> SEQUENCE: 38

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Asp
        35                  40                  45

Ser Ile Ile Ser Gly Gly Tyr Tyr Trp Ser Trp Ile Arg Gln His Pro
    50                  55                  60

Gly Lys Gly Leu Glu Trp Ile Gly Tyr Ile Phe Tyr Ser Gly Ser Thr
65                  70                  75                  80

Asp Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Ser Gly Tyr Ser Tyr Ala Leu Phe
        115                 120                 125

Asp His Trp Gly Gln Gly Thr Leu Val Thr Val Ser Gly Gly Gly
130                 135                 140

Gly Ser Gly Gly Gly Ser Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Ser Cys Arg Ala Ser Gln Phe Ile Gly Arg Tyr Phe Asn Trp Tyr
            180                 185                 190

Gln Gln Gln Pro Gly Lys Ala Pro Lys Val Leu Ile Tyr Ala Glu Ser
        195                 200                 205

Ser Leu Gln Ser Gly Val Pro Ser Arg Phe Ser Gly Ser Gly Ser Gly
210                 215                 220

Thr Glu Phe Thr Leu Thr Ile Ser Ser Leu Gln Pro Glu Asp Phe Ala
225                 230                 235                 240

Arg Tyr Tyr Cys Gln Gln Ser Tyr Ser Thr Pro Phe Thr Phe Gly Gln
                245                 250                 255

Gly Thr Lys Val Glu Ile Lys Arg Ala Ala Ala Leu Asp Asn Glu Lys
            260                 265                 270

Ser Asn Gly Thr Ile Ile His Val Lys Gly Lys His Leu Cys Pro Ser
        275                 280                 285

Pro Leu Phe Pro Gly Pro Ser Lys Pro Phe Trp Val Leu Val Val Val
290                 295                 300

Gly Gly Val Leu Ala Cys Tyr Ser Leu Leu Val Thr Val Ala Phe Ile
305                 310                 315                 320

Ile Phe Trp Val Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Arg Val Lys
        355                 360                 365

Phe Ser Arg Ser Ala Asp Ala Pro Ala Tyr Gln Gln Gly Gln Asn Gln
370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
450                 455                 460

Thr Tyr Asp Ala Leu His Met Gln Ala Leu Pro Pro Arg
465                 470                 475

<210> SEQ ID NO 39
<211> LENGTH: 1449
<212> TYPE: DNA
<213> ORGANISM: Homo sapiens
<220> FEATURE:
<221> NAME/KEY: CDS
<222> LOCATION: (1)..(1449)
<223> OTHER INFORMATION: 1C8.1.001_C28T_4Bz

```
<400> SEQUENCE: 39 atg gca ctc ccc gta act gct ctg ctg ctg ccg ttg gca ttg ctc ctg      48
Met Ala Leu Pro Val Thr Ala Leu Leu Leu Pro Leu Ala Leu Leu Leu
1               5                   10                  15 cac gcc gca cgc ccg cag gtg cag ctc caa gaa tct gga ccg ggt ctc      96
His Ala Ala Arg Pro Gln Val Gln Leu Gln Glu Ser Gly Pro Gly Leu
                20                  25                  30 gtc aag cca tca cag aca ctg tcc ctg acc tgc acc gtc tcc ggc gac     144
Val Lys Pro Ser Gln Thr Leu Ser Leu Thr Cys Thr Val Ser Gly Asp
            35                  40                  45 tct atc att tca ggc ggc tac tat tgg tcc tgg att aga caa cat ccg     192
Ser Ile Ile Ser Gly Gly Tyr Tyr Trp Ser Trp Ile Arg Gln His Pro
        50                  55                  60 gga aag ggt ctt gaa tgg atc ggc tat att ttc tac agc ggg agt acg     240
Gly Lys Gly Leu Glu Trp Ile Gly Tyr Ile Phe Tyr Ser Gly Ser Thr
65                  70                  75                  80 gat tac aat cct agt ctc aag agc cgc gtt acc att tca gtg gat act     288
Asp Tyr Asn Pro Ser Leu Lys Ser Arg Val Thr Ile Ser Val Asp Thr
                85                  90                  95 tca aaa aac cag ttt agc ctg aag ctg tct tct gta aca gct gct gac     336
Ser Lys Asn Gln Phe Ser Leu Lys Leu Ser Ser Val Thr Ala Ala Asp
            100                 105                 110 aca gcc gtg tac tat tgc gcc agg agc ggc tac agc tat gcc ctg ttt     384
Thr Ala Val Tyr Tyr Cys Ala Arg Ser Gly Tyr Ser Tyr Ala Leu Phe
        115                 120                 125 gac cac tgg ggg caa ggc act ctt gtg acg gtg tca agt gga ggg gga     432
Asp His Trp Gly Gln Gly Thr Leu Val Thr Val Ser Ser Gly Gly Gly
    130                 135                 140 gga tca ggc ggc ggg gga tcc ggc ggc ggg ggt agt gac att caa atg     480
Gly Ser Gly Gly Gly Gly Ser Gly Gly Gly Gly Ser Asp Ile Gln Met
145                 150                 155                 160 acg cag tcc cca agt tct ctg tcc gct agc gtc ggc gac cga gtg acc     528
Thr Gln Ser Pro Ser Ser Leu Ser Ala Ser Val Gly Asp Arg Val Thr
                165                 170                 175 atc agc tgc cga gca tcc cag ttt atc ggt aga tat ttc aat tgg tac     576
Ile Ser Cys Arg Ala Ser Gln Phe Ile Gly Arg Tyr Phe Asn Trp Tyr
            180                 185                 190 cag caa caa ccg ggc aaa gcg ccc aag gtc ctg atc tac gct gag agc     624
Gln Gln Gln Pro Gly Lys Ala Pro Lys Val Leu Ile Tyr Ala Glu Ser
        195                 200                 205 agt ctg caa tcc ggc gta cct agc agg ttc tcc gga agt ggc agc gga     672
Ser Leu Gln Ser Gly Val Pro Ser Arg Phe Ser Gly Ser Gly Ser Gly
    210                 215                 220 acc gag ttc acc ctg aca att agc tcc ttg cag ccc gag gat ttc gct     720
Thr Glu Phe Thr Leu Thr Ile Ser Ser Leu Gln Pro Glu Asp Phe Ala
225                 230                 235                 240 cgc tat tac tgt caa cag agt tat tca acc cct ttt aca ttc gga cag     768
Arg Tyr Tyr Cys Gln Gln Ser Tyr Ser Thr Pro Phe Thr Phe Gly Gln
                245                 250                 255 gga act aaa gtt gaa att aag agg gcc gct gcc ctt gat aat gaa aag     816
Gly Thr Lys Val Glu Ile Lys Arg Ala Ala Ala Leu Asp Asn Glu Lys
            260                 265                 270 tca aac gga aca atc att cac gtg aag ggc aag cac ctc tgt ccg tca     864
Ser Asn Gly Thr Ile Ile His Val Lys Gly Lys His Leu Cys Pro Ser
        275                 280                 285 ccc ttg ttc cct ggt cca tcc aag cca ttc tgg gtg ttg gtc gta gtg     912
Pro Leu Phe Pro Gly Pro Ser Lys Pro Phe Trp Val Leu Val Val Val
    290                 295                 300
```

-continued

| | | |
|---|---|---|
| ggt gga gtc ctc gct tgt tac tct ctg ctc gtc acc gtg gct ttt ata<br>Gly Gly Val Leu Ala Cys Tyr Ser Leu Leu Val Thr Val Ala Phe Ile<br>305                       310                   315                320 | 960 |
| atc ttc tgg gtt cgc ttt tcc gtc gtt aag cgg ggg aga aaa aag ctg<br>Ile Phe Trp Val Arg Phe Ser Val Val Lys Arg Gly Arg Lys Lys Leu<br>                      325                   330                335 | 1008 |
| ctg tac att ttc aaa cag ccg ttt atg agg ccg gtc caa acg act cag<br>Leu Tyr Ile Phe Lys Gln Pro Phe Met Arg Pro Val Gln Thr Thr Gln<br>                  340                   345               350 | 1056 |
| gaa gaa gac ggc tgc tcc tgc cgc ttt cct gag gag gag gag ggc ggg<br>Glu Glu Asp Gly Cys Ser Cys Arg Phe Pro Glu Glu Glu Glu Gly Gly<br>355                       360                   365 | 1104 |
| tgc gaa ctg agg gtg aag ttt tcc aga tct gca gat gca cca gcg tat<br>Cys Glu Leu Arg Val Lys Phe Ser Arg Ser Ala Asp Ala Pro Ala Tyr<br>    370                   375                  380 | 1152 |
| cag cag ggc cag aac caa ctg tat aac gag ctc aac ctg gga cgc agg<br>Gln Gln Gly Gln Asn Gln Leu Tyr Asn Glu Leu Asn Leu Gly Arg Arg<br>385                       390                   395                400 | 1200 |
| gaa gag tat gac gtt ttg gac aag cgc aga gga cgg gac cct gag atg<br>Glu Glu Tyr Asp Val Leu Asp Lys Arg Arg Gly Arg Asp Pro Glu Met<br>                          405                   410                415 | 1248 |
| ggt ggc aaa cca aga cga aaa aac ccc cag gag ggt ctc tat aat gag<br>Gly Gly Lys Pro Arg Arg Lys Asn Pro Gln Glu Gly Leu Tyr Asn Glu<br>                  420                   425               430 | 1296 |
| ctg cag aag gat aag atg gct gaa gcc tat tct gaa ata ggc atg aaa<br>Leu Gln Lys Asp Lys Met Ala Glu Ala Tyr Ser Glu Ile Gly Met Lys<br>             435                   440                445 | 1344 |
| gga gag cgg aga agg gga aaa ggg cac gac ggt ttg tac cag gga ctc<br>Gly Glu Arg Arg Arg Gly Lys Gly His Asp Gly Leu Tyr Gln Gly Leu<br>450                       455                   460 | 1392 |
| agc act gct acg aag gat act tat gac gct ctc cac atg caa gcc ctg<br>Ser Thr Ala Thr Lys Asp Thr Tyr Asp Ala Leu His Met Gln Ala Leu<br>465                       470                   475                480 | 1440 |
| cca cct agg<br>Pro Pro Arg | 1449 |

<210> SEQ ID NO 40
<211> LENGTH: 483
<212> TYPE: PRT
<213> ORGANISM: Homo sapiens

<400> SEQUENCE: 40

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Asp
        35                  40                  45

Ser Ile Ile Ser Gly Gly Tyr Tyr Trp Ser Trp Ile Arg Gln His Pro
    50                  55                  60

Gly Lys Gly Leu Glu Trp Ile Gly Tyr Ile Phe Tyr Ser Gly Ser Thr
65                  70                  75                  80

Asp Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Ser Gly Tyr Ser Tyr Ala Leu Phe
        115                 120                 125

Asp His Trp Gly Gln Gly Thr Leu Val Thr Val Ser Gly Gly Gly
130                 135                 140

Gly Ser Gly Gly Gly Ser Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Ser Cys Arg Ala Ser Gln Phe Ile Gly Arg Tyr Phe Asn Trp Tyr
            180                 185                 190

Gln Gln Gln Pro Gly Lys Ala Pro Lys Val Leu Ile Tyr Ala Glu Ser
        195                 200                 205

Ser Leu Gln Ser Gly Val Pro Ser Arg Phe Ser Gly Ser Gly Ser Gly
210                 215                 220

Thr Glu Phe Thr Leu Thr Ile Ser Ser Leu Gln Pro Glu Asp Phe Ala
225                 230                 235                 240

Arg Tyr Tyr Cys Gln Gln Ser Tyr Ser Thr Pro Phe Thr Phe Gly Gln
                245                 250                 255

Gly Thr Lys Val Glu Ile Lys Arg Ala Ala Ala Leu Asp Asn Glu Lys
            260                 265                 270

Ser Asn Gly Thr Ile Ile His Val Lys Gly Lys His Leu Cys Pro Ser
        275                 280                 285

Pro Leu Phe Pro Gly Pro Ser Lys Pro Phe Trp Val Leu Val Val Val
290                 295                 300

Gly Gly Val Leu Ala Cys Tyr Ser Leu Leu Val Thr Val Ala Phe Ile
305                 310                 315                 320

Ile Phe Trp Val Arg Phe Ser Val Val Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 41
<211> LENGTH: 1509
<212> TYPE: DNA
<213> ORGANISM: Homo sapiens
<220> FEATURE:
<221> NAME/KEY: CDS
<222> LOCATION: (1)..(1509)
<223> OTHER INFORMATION: 1C8.1.001_C8K_28z

<400> SEQUENCE: 41

```
atg gca ctc ccc gta act gct ctg ctg ctg ccg ttg gca ttg ctc ctg    48
Met Ala Leu Pro Val Thr Ala Leu Leu Leu Pro Leu Ala Leu Leu Leu
 1               5                  10                  15 cac gcc gca cgc ccg cag gtg cag ctc caa gaa tct gga ccg ggt ctc    96
His Ala Ala Arg Pro Gln Val Gln Leu Gln Glu Ser Gly Pro Gly Leu
             20                  25                  30 gtc aag cca tca cag aca ctg tcc ctg acc tgc acc gtc tcc ggc gac   144
Val Lys Pro Ser Gln Thr Leu Ser Leu Thr Cys Thr Val Ser Gly Asp
         35                  40                  45 tct atc att tca ggc ggc tac tat tgg tcc tgg att aga caa cat ccg   192
Ser Ile Ile Ser Gly Gly Tyr Tyr Trp Ser Trp Ile Arg Gln His Pro
     50                  55                  60 gga aag ggt ctt gaa tgg atc ggc tat att ttc tac agc ggg agt acg   240
Gly Lys Gly Leu Glu Trp Ile Gly Tyr Ile Phe Tyr Ser Gly Ser Thr
 65                  70                  75                  80 gat tac aat cct agt ctc aag agc cgc gtt acc att tca gtg gat act   288
Asp Tyr Asn Pro Ser Leu Lys Ser Arg Val Thr Ile Ser Val Asp Thr
                 85                  90                  95 tca aaa aac cag ttt agc ctg aag ctg tct tct gta aca gct gct gac   336
Ser Lys Asn Gln Phe Ser Leu Lys Leu Ser Ser Val Thr Ala Ala Asp
            100                 105                 110 aca gcc gtg tac tat tgc gcc agg agc ggc tac agc tat gcc ctg ttt   384
Thr Ala Val Tyr Tyr Cys Ala Arg Ser Gly Tyr Ser Tyr Ala Leu Phe
        115                 120                 125 gac cac tgg ggg caa ggc act ctt gtg acg gtg tca agt gga ggg gga   432
Asp His Trp Gly Gln Gly Thr Leu Val Thr Val Ser Ser Gly Gly Gly
    130                 135                 140 gga tca ggc ggc ggg gga tcc ggc ggc ggg ggt agt gac att caa atg   480
Gly Ser Gly Gly Gly Gly Ser Gly Gly Gly Gly Ser Asp Ile Gln Met
145                 150                 155                 160 acg cag tcc cca agt tct ctg tcc gct agc gtc ggc gac cga gtg acc   528
Thr Gln Ser Pro Ser Ser Leu Ser Ala Ser Val Gly Asp Arg Val Thr
                165                 170                 175 atc agc tgc cga gca tcc cag ttt atc ggt aga tat ttc aat tgg tac   576
Ile Ser Cys Arg Ala Ser Gln Phe Ile Gly Arg Tyr Phe Asn Trp Tyr
            180                 185                 190 cag caa caa ccg ggc aaa gcg ccc aag gtc ctg atc tac gct gag agc   624
Gln Gln Gln Pro Gly Lys Ala Pro Lys Val Leu Ile Tyr Ala Glu Ser
        195                 200                 205 agt ctg caa tcc ggc gta cct agc agg ttc tcc gga agt ggc agc gga   672
Ser Leu Gln Ser Gly Val Pro Ser Arg Phe Ser Gly Ser Gly Ser Gly
    210                 215                 220 acc gag ttc acc ctg aca att agc tcc ttg cag ccc gag gat ttc gct   720
Thr Glu Phe Thr Leu Thr Ile Ser Ser Leu Gln Pro Glu Asp Phe Ala
225                 230                 235                 240 cgc tat tac tgt caa cag agt tat tca acc cct ttt aca ttc gga cag   768
Arg Tyr Tyr Cys Gln Gln Ser Tyr Ser Thr Pro Phe Thr Phe Gly Gln
                245                 250                 255 gga act aaa gtt gaa att aag agg gcc gct gcc ttc gtg cct gtt ttt   816
Gly Thr Lys Val Glu Ile Lys Arg Ala Ala Ala Phe Val Pro Val Phe
            260                 265                 270 ctg ccc gcg aaa ccc aca act acc ccc gcc cct cgg ccc cca act cct   864
Leu Pro Ala Lys Pro Thr Thr Thr Pro Ala Pro Arg Pro Pro Thr Pro
        275                 280                 285 gca cca act atc gct tcc caa ccc ctg tct ctg aga cct gag gca tgc   912
Ala Pro Thr Ile Ala Ser Gln Pro Leu Ser Leu Arg Pro Glu Ala Cys
    290                 295                 300
```

```
cgc ccc gcg gca ggc ggc gcc gtg cac act aga ggc ctg gac ttc gcc       960
Arg Pro Ala Ala Gly Gly Ala Val His Thr Arg Gly Leu Asp Phe Ala
305                 310                 315                 320 tgc gat att tat atc tgg gcc ccc ctt gcc ggg aca tgc ggg gta ctg      1008
Cys Asp Ile Tyr Ile Trp Ala Pro Leu Ala Gly Thr Cys Gly Val Leu
                325                 330                 335 ctg ctg tct ctg gtg att acc ctc tac tgc aac cac aga aac aga tcc      1056
Leu Leu Ser Leu Val Ile Thr Leu Tyr Cys Asn His Arg Asn Arg Ser
            340                 345                 350 aaa aga agc cgc ctg ctc cat agc gat tac atg aat atg act cca cgc      1104
Lys Arg Ser Arg Leu Leu His Ser Asp Tyr Met Asn Met Thr Pro Arg
        355                 360                 365 cgc cct ggc ccc aca agg aaa cac tac cag cct tac gca cca cct aga      1152
Arg Pro Gly Pro Thr Arg Lys His Tyr Gln Pro Tyr Ala Pro Pro Arg
    370                 375                 380 gat ttc gct gcc tat cgg agc agg gtg aag ttt tcc aga tct gca gat      1200
Asp Phe Ala Ala Tyr Arg Ser Arg Val Lys Phe Ser Arg Ser Ala Asp
385                 390                 395                 400 gca cca gcg tat cag cag ggc cag aac caa ctg tat aac gag ctc aac      1248
Ala Pro Ala Tyr Gln Gln Gly Gln Asn Gln Leu Tyr Asn Glu Leu Asn
                405                 410                 415 ctg gga cgc agg gaa gag tat gac gtt ttg gac aag cgc aga gga cgg      1296
Leu Gly Arg Arg Glu Glu Tyr Asp Val Leu Asp Lys Arg Arg Gly Arg
            420                 425                 430 gac cct gag atg ggt ggc aaa cca aga cga aaa aac ccc cag gag ggt      1344
Asp Pro Glu Met Gly Gly Lys Pro Arg Arg Lys Asn Pro Gln Glu Gly
        435                 440                 445 ctc tat aat gag ctg cag aag gat aag atg gct gaa gcc tat tct gaa      1392
Leu Tyr Asn Glu Leu Gln Lys Asp Lys Met Ala Glu Ala Tyr Ser Glu
    450                 455                 460 ata ggc atg aaa gga gag cgg aga agg gga aaa ggg cac gac ggt ttg      1440
Ile Gly Met Lys Gly Glu Arg Arg Arg Gly Lys Gly His Asp Gly Leu
465                 470                 475                 480 tac cag gga ctc agc act gct acg aag gat act tat gac gct ctc cac      1488
Tyr Gln Gly Leu Ser Thr Ala Thr Lys Asp Thr Tyr Asp Ala Leu His
                485                 490                 495 atg caa gcc ctg cca cct agg                                          1509
Met Gln Ala Leu Pro Pro Arg
            500
```

<210> SEQ ID NO 42
<211> LENGTH: 503
<212> TYPE: PRT
<213> ORGANISM: Homo sapiens

<400> SEQUENCE: 42

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Gln Thr Leu Ser Leu Thr Cys Thr Val Ser Gly Asp
            35                  40                  45

Ser Ile Ile Ser Gly Gly Tyr Tyr Trp Ser Trp Ile Arg Gln His Pro
        50                  55                  60

Gly Lys Gly Leu Glu Trp Ile Gly Tyr Ile Phe Tyr Ser Gly Ser Thr
65                  70                  75                  80

Asp Tyr Asn Pro Ser Leu Lys Ser Arg Val Thr Ile Ser Val Asp Thr
                85                  90                  95
```

-continued

Ser Lys Asn Gln Phe Ser Leu Lys Leu Ser Ser Val Thr Ala Ala Asp
            100                 105                 110

Thr Ala Val Tyr Tyr Cys Ala Arg Ser Gly Tyr Ser Tyr Ala Leu Phe
        115                 120                 125

Asp His Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Ser Cys Arg Ala Ser Gln Phe Ile Gly Arg Tyr Phe Asn Trp Tyr
            180                 185                 190

Gln Gln Gln Pro Gly Lys Ala Pro Lys Val Leu Ile Tyr Ala Glu Ser
        195                 200                 205

Ser Leu Gln Ser Gly Val Pro Ser Arg Phe Ser Gly Ser Gly Ser Gly
    210                 215                 220

Thr Glu Phe Thr Leu Thr Ile Ser Ser Leu Gln Pro Glu Asp Phe Ala
225                 230                 235                 240

Arg Tyr Tyr Cys Gln Gln Ser Tyr Ser Thr Pro Phe Thr Phe Gly Gln
                245                 250                 255

Gly Thr Lys Val Glu Ile Lys Arg Ala Ala Ala Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Ser
            340                 345                 350

Lys Arg Ser Arg Leu Leu His Ser Asp Tyr Met Asn Met Thr Pro Arg
        355                 360                 365

Arg Pro Gly Pro Thr Arg Lys His Tyr Gln Pro Tyr Ala Pro Pro Arg
    370                 375                 380

Asp Phe Ala Ala Tyr Arg Ser Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500

-continued

```
<210> SEQ ID NO 43
<211> LENGTH: 1527
<212> TYPE: DNA
<213> ORGANISM: Homo sapiens
<220> FEATURE:
<221> NAME/KEY: CDS
<222> LOCATION: (1)..(1527)
<223> OTHER INFORMATION: 1C8.1.001_C8K_4Bz

<400> SEQUENCE: 43 atg gca ctc ccc gta act gct ctg ctg ctg ccg ttg gca ttg ctc ctg      48
Met Ala Leu Pro Val Thr Ala Leu Leu Leu Pro Leu Ala Leu Leu Leu
1               5                   10                  15 cac gcc gca cgc ccg cag gtg cag ctc caa gaa tct gga ccg ggt ctc      96
His Ala Ala Arg Pro Gln Val Gln Leu Gln Glu Ser Gly Pro Gly Leu
                20                  25                  30 gtc aag cca tca cag aca ctg tcc ctg acc tgc acc gtc tcc ggc gac     144
Val Lys Pro Ser Gln Thr Leu Ser Leu Thr Cys Thr Val Ser Gly Asp
            35                  40                  45 tct atc att tca ggc ggc tac tat tgg tcc tgg att aga caa cat ccg     192
Ser Ile Ile Ser Gly Gly Tyr Tyr Trp Ser Trp Ile Arg Gln His Pro
        50                  55                  60 gga aag ggt ctt gaa tgg atc ggc tat att ttc tac agc ggg agt acg     240
Gly Lys Gly Leu Glu Trp Ile Gly Tyr Ile Phe Tyr Ser Gly Ser Thr
65                  70                  75                  80 gat tac aat cct agt ctc aag agc cgc gtt acc att tca gtg gat act     288
Asp Tyr Asn Pro Ser Leu Lys Ser Arg Val Thr Ile Ser Val Asp Thr
                85                  90                  95 tca aaa aac cag ttt agc ctg aag ctg tct tct gta aca gct gct gac     336
Ser Lys Asn Gln Phe Ser Leu Lys Leu Ser Ser Val Thr Ala Ala Asp
                100                 105                 110 aca gcc gtg tac tat tgc gcc agg agc ggc tac agc tat gcc ctg ttt     384
Thr Ala Val Tyr Tyr Cys Ala Arg Ser Gly Tyr Ser Tyr Ala Leu Phe
            115                 120                 125 gac cac tgg ggg caa ggc act ctt gtg acg gtg tca agt gga ggg gga     432
Asp His Trp Gly Gln Gly Thr Leu Val Thr Val Ser Ser Gly Gly Gly
        130                 135                 140 gga tca ggc ggc ggg gga tcc ggc ggc ggg ggt agt gac att caa atg     480
Gly Ser Gly Gly Gly Gly Ser Gly Gly Gly Gly Ser Asp Ile Gln Met
145                 150                 155                 160 acg cag tcc cca agt tct ctg tcc gct agc gtc ggc gac cga gtg acc     528
Thr Gln Ser Pro Ser Ser Leu Ser Ala Ser Val Gly Asp Arg Val Thr
                165                 170                 175 atc agc tgc cga gca tcc cag ttt atc ggt aga tat ttc aat tgg tac     576
Ile Ser Cys Arg Ala Ser Gln Phe Ile Gly Arg Tyr Phe Asn Trp Tyr
                180                 185                 190 cag caa caa ccg ggc aaa gcg ccc aag gtc ctg atc tac gct gag agc     624
Gln Gln Gln Pro Gly Lys Ala Pro Lys Val Leu Ile Tyr Ala Glu Ser
            195                 200                 205 agt ctg caa tcc ggc gta cct agc agg ttc tcc gga agt ggc agc gga     672
Ser Leu Gln Ser Gly Val Pro Ser Arg Phe Ser Gly Ser Gly Ser Gly
        210                 215                 220 acc gag ttc acc ctg aca att agc tcc ttg cag ccc gag gat ttc gct     720
Thr Glu Phe Thr Leu Thr Ile Ser Ser Leu Gln Pro Glu Asp Phe Ala
225                 230                 235                 240 cgc tat tac tgt caa cag agt tat tca acc cct ttt aca ttc gga cag     768
Arg Tyr Tyr Cys Gln Gln Ser Tyr Ser Thr Pro Phe Thr Phe Gly Gln
                245                 250                 255 gga act aaa gtt gaa att aag agg gcc gct gcc ttc gtg cct gtt ttt     816
Gly Thr Lys Val Glu Ile Lys Arg Ala Ala Ala Phe Val Pro Val Phe
                260                 265                 270
```

```
ctg ccc gcg aaa ccc aca act acc ccc gcc cct cgg ccc cca act cct      864
Leu Pro Ala Lys Pro Thr Thr Thr Pro Ala Pro Arg Pro Pro Thr Pro
        275                 280                 285 gca cca act atc gct tcc caa ccc ctg tct ctg aga cct gag gca tgc      912
Ala Pro Thr Ile Ala Ser Gln Pro Leu Ser Leu Arg Pro Glu Ala Cys
290                 295                 300 cgc ccc gcg gca ggc ggc gcc gtg cac act aga ggc ctg gac ttc gcc      960
Arg Pro Ala Ala Gly Gly Ala Val His Thr Arg Gly Leu Asp Phe Ala
305                 310                 315                 320 tgc gat att tat atc tgg gcc ccc ctt gcc ggg aca tgc ggg gta ctg     1008
Cys Asp Ile Tyr Ile Trp Ala Pro Leu Ala Gly Thr Cys Gly Val Leu
            325                 330                 335 ctg ctg tct ctg gtg att acc ctc tac tgc aac cac aga aac cgc ttt     1056
Leu Leu Ser Leu Val Ile Thr Leu Tyr Cys Asn His Arg Asn Arg Phe
        340                 345                 350 tcc gtc gtt aag cgg ggg aga aaa aag ctg ctg tac att ttc aaa cag     1104
Ser Val Val Lys Arg Gly Arg Lys Lys Leu Leu Tyr Ile Phe Lys Gln
    355                 360                 365 ccg ttt atg agg ccg gtc caa acg act cag gaa gaa gac ggc tgc tcc     1152
Pro Phe Met Arg Pro Val Gln Thr Thr Gln Glu Glu Asp Gly Cys Ser
370                 375                 380 tgc cgc ttt cct gag gag gag gag ggg ggg tgc gaa ctg agg gtg aag     1200
Cys Arg Phe Pro Glu Glu Glu Glu Gly Gly Cys Glu Leu Arg Val Lys
385                 390                 395                 400 ttt tcc aga tct gca gat gca cca gcg tat cag cag ggc cag aac caa     1248
Phe Ser Arg Ser Ala Asp Ala Pro Ala Tyr Gln Gln Gly Gln Asn Gln
            405                 410                 415 ctg tat aac gag ctc aac ctg gga cgc agg gaa gag tat gac gtt ttg     1296
Leu Tyr Asn Glu Leu Asn Leu Gly Arg Arg Glu Glu Tyr Asp Val Leu
        420                 425                 430 gac aag cgc aga gga cgg gac cct gag atg ggt ggc aaa cca aga cga     1344
Asp Lys Arg Arg Gly Arg Asp Pro Glu Met Gly Gly Lys Pro Arg Arg
    435                 440                 445 aaa aac ccc cag gag ggt ctc tat aat gag ctg cag aag gat aag atg     1392
Lys Asn Pro Gln Glu Gly Leu Tyr Asn Glu Leu Gln Lys Asp Lys Met
450                 455                 460 gct gaa gcc tat tct gaa ata ggc atg aaa gga gag cgg aga agg gga     1440
Ala Glu Ala Tyr Ser Glu Ile Gly Met Lys Gly Glu Arg Arg Arg Gly
465                 470                 475                 480 aaa ggg cac gac ggt ttg tac cag gga ctc agc act gct acg aag gat     1488
Lys Gly His Asp Gly Leu Tyr Gln Gly Leu Ser Thr Ala Thr Lys Asp
            485                 490                 495 act tat gac gct ctc cac atg caa gcc ctg cca cct agg                 1527
Thr Tyr Asp Ala Leu His Met Gln Ala Leu Pro Pro Arg
        500                 505

<210> SEQ ID NO 44
<211> LENGTH: 509
<212> TYPE: PRT
<213> ORGANISM: Homo sapiens

<400> SEQUENCE: 44

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Asp
        35                  40                  45

Ser Ile Ile Ser Gly Gly Tyr Tyr Trp Ser Trp Ile Arg Gln His Pro
    50                  55                  60
```

```
Gly Lys Gly Leu Glu Trp Ile Gly Tyr Ile Phe Tyr Ser Gly Ser Thr
 65                  70                  75                  80

Asp Tyr Asn Pro Ser Leu Lys Ser Arg Val Thr Ile Ser Val Asp Thr
                 85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Ser Gly Tyr Ser Tyr Ala Leu Phe
        115                 120                 125

Asp His Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Ser Cys Arg Ala Ser Gln Phe Ile Gly Arg Tyr Phe Asn Trp Tyr
            180                 185                 190

Gln Gln Gln Pro Gly Lys Ala Pro Lys Val Leu Ile Tyr Ala Glu Ser
        195                 200                 205

Ser Leu Gln Ser Gly Val Pro Ser Arg Phe Ser Gly Ser Gly Ser Gly
    210                 215                 220

Thr Glu Phe Thr Leu Thr Ile Ser Ser Leu Gln Pro Glu Asp Phe Ala
225                 230                 235                 240

Arg Tyr Tyr Cys Gln Gln Ser Tyr Ser Thr Pro Phe Thr Phe Gly Gln
                245                 250                 255

Gly Thr Lys Val Glu Ile Lys Arg Ala Ala Ala Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Phe
        340                 345                 350

Ser Val Val Lys Arg Gly Arg Lys Lys Leu Leu Tyr Ile Phe Lys Gln
    355                 360                 365

Pro Phe Met Arg Pro Val Gln Thr Thr Gln Glu Glu Asp Gly Cys Ser
370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
        420                 425                 430

Asp Lys Arg Arg Gly Arg Asp Pro Glu Met Gly Gly Lys Pro Arg Arg
    435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480
```

```
Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
        500                 505
```

<210> SEQ ID NO 45
<211> LENGTH: 1434
<212> TYPE: DNA
<213> ORGANISM: Homo sapiens
<220> FEATURE:
<221> NAME/KEY: CDS
<222> LOCATION: (1)..(1434)
<223> OTHER INFORMATION: 6E9.1_C28T_28z

<400> SEQUENCE: 45

```
atg gca ctc ccc gta act gct ctg ctg ctg ccg ttg gca ttg ctc ctg      48
Met Ala Leu Pro Val Thr Ala Leu Leu Leu Pro Leu Ala Leu Leu Leu
1               5                   10                  15 cac gcc gca cgc ccg cag gta cac ctg gtg cag agc ggg gcg gag gtc      96
His Ala Ala Arg Pro Gln Val His Leu Val Gln Ser Gly Ala Glu Val
            20                  25                  30 aag aaa ccg ggc gca tcc gta cgc gtg agc tgc aag gcc tcc gga tac     144
Lys Lys Pro Gly Ala Ser Val Arg Val Ser Cys Lys Ala Ser Gly Tyr
        35                  40                  45 act ttt act tct tac tat ctg cat tgg gtc agg cag gca ccg ggt cag     192
Thr Phe Thr Ser Tyr Tyr Leu His Trp Val Arg Gln Ala Pro Gly Gln
    50                  55                  60 gga ctg gag tgg atg ggc att gtg gac cca agc gga ggg agt acg tca     240
Gly Leu Glu Trp Met Gly Ile Val Asp Pro Ser Gly Gly Ser Thr Ser
65                  70                  75                  80 tat gat cag aag ttt caa ggt agg ttt acc atg aca cgg gac acg tca     288
Tyr Asp Gln Lys Phe Gln Gly Arg Phe Thr Met Thr Arg Asp Thr Ser
                85                  90                  95 acg agt acc gtc tac atg gag ctc agt agt ctg cgg agc gaa gac acc     336
Thr Ser Thr Val Tyr Met Glu Leu Ser Ser Leu Arg Ser Glu Asp Thr
            100                 105                 110 gca gtc tac tac tgc gca cgc gat tat gga gac tat gtc ttt gac tat     384
Ala Val Tyr Tyr Cys Ala Arg Asp Tyr Gly Asp Tyr Val Phe Asp Tyr
        115                 120                 125 tgg ggg cag ggg acg ctc gtg acc gtt tca agc ggg ggg ggc gga tcc     432
Trp Gly Gln Gly Thr Leu Val Thr Val Ser Ser Gly Gly Gly Gly Ser
    130                 135                 140 ggt ggg gga ggt tcc ggc ggt ggg ggt tca caa agc gta ctg aca cag     480
Gly Gly Gly Gly Ser Gly Gly Gly Gly Ser Gln Ser Val Leu Thr Gln
145                 150                 155                 160 ccc ccg agt gca tcc ggg acc ccc ggc caa agg gtt aca atc agc tgc     528
Pro Pro Ser Ala Ser Gly Thr Pro Gly Gln Arg Val Thr Ile Ser Cys
                165                 170                 175 tct ggc agc tcc agt aac ata ggt acc aac acg gtg aac tgg tac cag     576
Ser Gly Ser Ser Ser Asn Ile Gly Thr Asn Thr Val Asn Trp Tyr Gln
            180                 185                 190 cag ttg cct ggc aca gcg cct cag ctg ctc atc tat atc aac aat cag     624
Gln Leu Pro Gly Thr Ala Pro Gln Leu Leu Ile Tyr Ile Asn Asn Gln
        195                 200                 205 cgg cca agt ggc gtg ccc gat aga ttc tca ggc tca aag agc gga acc     672
Arg Pro Ser Gly Val Pro Asp Arg Phe Ser Gly Ser Lys Ser Gly Thr
    210                 215                 220 agc gct agc ttg gca atc agt ggc ctt caa tcc gaa gac gaa gcc gat     720
Ser Ala Ser Leu Ala Ile Ser Gly Leu Gln Ser Glu Asp Glu Ala Asp
225                 230                 235                 240
```

```
tac tat tgt gcg acc tgg gac gat agc ctg aac ggc ccc gtc gtg ggc        768
Tyr Tyr Cys Ala Thr Trp Asp Asp Ser Leu Asn Gly Pro Val Val Gly
                245                 250                 255 ggc ggg acg aaa ctg aca gtg ttg ggc gcc gct gcc ctt gat aat gaa        816
Gly Gly Thr Lys Leu Thr Val Leu Gly Ala Ala Ala Leu Asp Asn Glu
            260                 265                 270 aag tca aac gga aca atc att cac gtg aag ggc aag cac ctc tgt ccg        864
Lys Ser Asn Gly Thr Ile Ile His Val Lys Gly Lys His Leu Cys Pro
        275                 280                 285 tca ccc ttg ttc cct ggt cca tcc aag cca ttc tgg gtg ttg gtc gta        912
Ser Pro Leu Phe Pro Gly Pro Ser Lys Pro Phe Trp Val Leu Val Val
    290                 295                 300 gtg ggt gga gtc ctc gct tgt tac tct ctc gtc acc gtg gct ttt            960
Val Gly Gly Val Leu Ala Cys Tyr Ser Leu Leu Val Thr Val Ala Phe
305                 310                 315                 320 ata atc ttc tgg gtt aga tcc aaa aga agc cgc ctg ctc cat agc gat       1008
Ile Ile Phe Trp Val Arg Ser Lys Arg Ser Arg Leu Leu His Ser Asp
                325                 330                 335 tac atg aat atg act cca cgc cgc cct ggc ccc aca agg aaa cac tac       1056
Tyr Met Asn Met Thr Pro Arg Arg Pro Gly Pro Thr Arg Lys His Tyr
            340                 345                 350 cag cct tac gca cca cct aga gat ttc gct gcc tat cgg agc agg gtg       1104
Gln Pro Tyr Ala Pro Pro Arg Asp Phe Ala Ala Tyr Arg Ser Arg Val
        355                 360                 365 aag ttt tcc aga tct gca gat gca cca gcg tat cag cag ggc cag aac       1152
Lys Phe Ser Arg Ser Ala Asp Ala Pro Ala Tyr Gln Gln Gly Gln Asn
    370                 375                 380 caa ctg tat aac gag ctc aac ctg gga cgc agg gaa gag tat gac gtt       1200
Gln Leu Tyr Asn Glu Leu Asn Leu Gly Arg Arg Glu Glu Tyr Asp Val
385                 390                 395                 400 ttg gac aag cgc aga gga cgg gac cct gag atg ggt ggc aaa cca aga       1248
Leu Asp Lys Arg Arg Gly Arg Asp Pro Glu Met Gly Gly Lys Pro Arg
                405                 410                 415 cga aaa aac ccc cag gag ggt ctc tat aat gag ctg cag aag gat aag       1296
Arg Lys Asn Pro Gln Glu Gly Leu Tyr Asn Glu Leu Gln Lys Asp Lys
            420                 425                 430 atg gct gaa gcc tat tct gaa ata ggc atg aaa gga gag cgg aga agg       1344
Met Ala Glu Ala Tyr Ser Glu Ile Gly Met Lys Gly Glu Arg Arg Arg
        435                 440                 445 gga aaa ggg cac gac ggt ttg tac cag gga ctc agc act gct acg aag       1392
Gly Lys Gly His Asp Gly Leu Tyr Gln Gly Leu Ser Thr Ala Thr Lys
    450                 455                 460 gat act tat gac gct ctc cac atg caa gcc ctg cca cct agg               1434
Asp Thr Tyr Asp Ala Leu His Met Gln Ala Leu Pro Pro Arg
465                 470                 475

<210> SEQ ID NO 46
<211> LENGTH: 478
<212> TYPE: PRT
<213> ORGANISM: Homo sapiens

<400> SEQUENCE: 46

Met Ala Leu Pro Val Thr Ala Leu Leu Leu Pro Leu Ala Leu Leu Leu
1               5                   10                  15

His Ala Ala Arg Pro Gln Val His Leu Val Gln Ser Gly Ala Glu Val
            20                  25                  30

Lys Lys Pro Gly Ala Ser Val Arg Val Ser Cys Lys Ala Ser Gly Tyr
        35                  40                  45

Thr Phe Thr Ser Tyr Tyr Leu His Trp Val Arg Gln Ala Pro Gly Gln
    50                  55                  60
```

```
Gly Leu Glu Trp Met Gly Ile Val Asp Pro Ser Gly Gly Ser Thr Ser
 65                  70                  75                  80

Tyr Asp Gln Lys Phe Gln Gly Arg Phe Thr Met Thr Arg Asp Thr Ser
                 85                  90                  95

Thr Ser Thr Val Tyr Met Glu Leu Ser Ser Leu Arg Ser Glu Asp Thr
            100                 105                 110

Ala Val Tyr Tyr Cys Ala Arg Asp Tyr Gly Asp Tyr Val Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gln Ser Val Leu Thr Gln
145                 150                 155                 160

Pro Pro Ser Ala Ser Gly Thr Pro Gly Gln Arg Val Thr Ile Ser Cys
                165                 170                 175

Ser Gly Ser Ser Ser Asn Ile Gly Thr Asn Thr Val Asn Trp Tyr Gln
            180                 185                 190

Gln Leu Pro Gly Thr Ala Pro Gln Leu Leu Ile Tyr Ile Asn Asn Gln
        195                 200                 205

Arg Pro Ser Gly Val Pro Asp Arg Phe Ser Gly Ser Lys Ser Gly Thr
    210                 215                 220

Ser Ala Ser Leu Ala Ile Ser Gly Leu Gln Ser Glu Asp Glu Ala Asp
225                 230                 235                 240

Tyr Tyr Cys Ala Thr Trp Asp Ser Leu Asn Gly Pro Val Val Gly
                245                 250                 255

Gly Gly Thr Lys Leu Thr Val Leu Gly Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475
```

```
<210> SEQ ID NO 47
<211> LENGTH: 1452
<212> TYPE: DNA
<213> ORGANISM: Homo sapiens
<220> FEATURE:
<221> NAME/KEY: CDS
<222> LOCATION: (1)..(1452)
<223> OTHER INFORMATION: 6E9.1_C28T_4Bz

<400> SEQUENCE: 47
```

| | | | | | | | | | | | | | | | | |
|---|---|---|---|---|---|---|---|---|---|---|---|---|---|---|---|---|
| atg | gca | ctc | ccc | gta | act | gct | ctg | ctg | ctg | ccg | ttg | gca | ttg | ctc | ctg | 48 |
| Met | Ala | Leu | Pro | Val | Thr | Ala | Leu | Leu | Leu | Pro | Leu | Ala | Leu | Leu | Leu | |
| 1 | | | | 5 | | | | | 10 | | | | | 15 | | |
| cac | gcc | gca | cgc | ccg | cag | gta | cac | ctg | gtg | cag | agc | ggg | gcg | gag | gtc | 96 |
| His | Ala | Ala | Arg | Pro | Gln | Val | His | Leu | Val | Gln | Ser | Gly | Ala | Glu | Val | |
| | | | 20 | | | | | 25 | | | | | 30 | | | |
| aag | aaa | ccg | ggc | gca | tcc | gta | cgc | gtg | agc | tgc | aag | gcc | tcc | gga | tac | 144 |
| Lys | Lys | Pro | Gly | Ala | Ser | Val | Arg | Val | Ser | Cys | Lys | Ala | Ser | Gly | Tyr | |
| | | | | 35 | | | | | 40 | | | | | 45 | | |
| act | ttt | act | tct | tac | tat | ctg | cat | tgg | gtc | agg | cag | gca | ccg | ggt | cag | 192 |
| Thr | Phe | Thr | Ser | Tyr | Tyr | Leu | His | Trp | Val | Arg | Gln | Ala | Pro | Gly | Gln | |
| | | 50 | | | | | 55 | | | | | 60 | | | | |
| gga | ctg | gag | tgg | atg | ggc | att | gtg | gac | cca | agc | gga | ggg | agt | acg | tca | 240 |
| Gly | Leu | Glu | Trp | Met | Gly | Ile | Val | Asp | Pro | Ser | Gly | Gly | Ser | Thr | Ser | |
| 65 | | | | | 70 | | | | | 75 | | | | | 80 | |
| tat | gat | cag | aag | ttt | caa | ggt | agg | ttt | acc | atg | aca | cgg | gac | acg | tca | 288 |
| Tyr | Asp | Gln | Lys | Phe | Gln | Gly | Arg | Phe | Thr | Met | Thr | Arg | Asp | Thr | Ser | |
| | | | | 85 | | | | | 90 | | | | | 95 | | |
| acg | agt | acc | gtc | tac | atg | gag | ctc | agt | agt | ctg | cgg | agc | gaa | gac | acc | 336 |
| Thr | Ser | Thr | Val | Tyr | Met | Glu | Leu | Ser | Ser | Leu | Arg | Ser | Glu | Asp | Thr | |
| | | | 100 | | | | | 105 | | | | | 110 | | | |
| gca | gtc | tac | tac | tgc | gca | cgc | gat | tat | gga | gac | tat | gtc | ttt | gac | tat | 384 |
| Ala | Val | Tyr | Tyr | Cys | Ala | Arg | Asp | Tyr | Gly | Asp | Tyr | Val | Phe | Asp | Tyr | |
| | | | | 115 | | | | | 120 | | | | | 125 | | |
| tgg | ggg | cag | ggg | acg | ctc | gtg | acc | gtt | tca | agc | ggg | ggg | ggc | gga | tcc | 432 |
| Trp | Gly | Gln | Gly | Thr | Leu | Val | Thr | Val | Ser | Ser | Gly | Gly | Gly | Gly | Ser | |
| | | 130 | | | | | 135 | | | | | 140 | | | | |
| ggt | ggg | gga | ggt | tcc | ggc | ggt | ggg | ggt | tca | caa | agc | gta | ctg | aca | cag | 480 |
| Gly | Gly | Gly | Gly | Ser | Gly | Gly | Gly | Gly | Ser | Gln | Ser | Val | Leu | Thr | Gln | |
| 145 | | | | | 150 | | | | | 155 | | | | | 160 | |
| ccc | ccg | agt | gca | tcc | ggg | acc | ccc | ggc | caa | agg | gtt | aca | atc | agc | tgc | 528 |
| Pro | Pro | Ser | Ala | Ser | Gly | Thr | Pro | Gly | Gln | Arg | Val | Thr | Ile | Ser | Cys | |
| | | | | 165 | | | | | 170 | | | | | 175 | | |
| tct | ggc | agc | tcc | agt | aac | ata | ggt | acc | aac | acg | gtg | aac | tgg | tac | cag | 576 |
| Ser | Gly | Ser | Ser | Ser | Asn | Ile | Gly | Thr | Asn | Thr | Val | Asn | Trp | Tyr | Gln | |
| | | | 180 | | | | | 185 | | | | | 190 | | | |
| cag | ttg | cct | ggc | aca | gcg | cct | cag | ctg | ctc | atc | tat | atc | aac | aat | cag | 624 |
| Gln | Leu | Pro | Gly | Thr | Ala | Pro | Gln | Leu | Leu | Ile | Tyr | Ile | Asn | Asn | Gln | |
| | | 195 | | | | | 200 | | | | | 205 | | | | |
| cgg | cca | agt | ggc | gtg | ccc | gat | aga | ttc | tca | ggc | tca | aag | agc | gga | acc | 672 |
| Arg | Pro | Ser | Gly | Val | Pro | Asp | Arg | Phe | Ser | Gly | Ser | Lys | Ser | Gly | Thr | |
| | 210 | | | | | 215 | | | | | 220 | | | | | |
| agc | gct | agc | ttg | gca | atc | agt | ggc | ctt | caa | tcc | gaa | gac | gaa | gcc | gat | 720 |
| Ser | Ala | Ser | Leu | Ala | Ile | Ser | Gly | Leu | Gln | Ser | Glu | Asp | Glu | Ala | Asp | |
| 225 | | | | | 230 | | | | | 235 | | | | | 240 | |
| tac | tat | tgt | gcg | acc | tgg | gac | gat | agc | ctg | aac | ggc | ccc | gtc | gtg | ggc | 768 |
| Tyr | Tyr | Cys | Ala | Thr | Trp | Asp | Asp | Ser | Leu | Asn | Gly | Pro | Val | Val | Gly | |
| | | | | 245 | | | | | 250 | | | | | 255 | | |
| ggc | ggg | acg | aaa | ctg | aca | gtg | ttg | ggc | gcc | gct | gcc | ctt | gat | aat | gaa | 816 |
| Gly | Gly | Thr | Lys | Leu | Thr | Val | Leu | Gly | Ala | Ala | Ala | Leu | Asp | Asn | Glu | |
| | | | 260 | | | | | 265 | | | | | 270 | | | |

-continued

| | |
|---|---|
| aag tca aac gga aca atc att cac gtg aag ggc aag cac ctc tgt ccg<br>Lys Ser Asn Gly Thr Ile Ile His Val Lys Gly Lys His Leu Cys Pro<br>275                                280                              285 | 864 |
| tca ccc ttg ttc cct ggt cca tcc aag cca ttc tgg gtg ttg gtc gta<br>Ser Pro Leu Phe Pro Gly Pro Ser Lys Pro Phe Trp Val Leu Val Val<br>290                                295                              300 | 912 |
| gtg ggt gga gtc ctc gct tgt tac tct ctg ctc gtc acc gtg gct ttt<br>Val Gly Gly Val Leu Ala Cys Tyr Ser Leu Leu Val Thr Val Ala Phe<br>305                                310                          315                    320 | 960 |
| ata atc ttc tgg gtt cgc ttt tcc gtc gtt aag cgg ggg aga aaa aag<br>Ile Ile Phe Trp Val Arg Phe Ser Val Val Lys Arg Gly Arg Lys Lys<br>                         325                            330                          335 | 1008 |
| ctg ctg tac att ttc aaa cag ccg ttt atg agg ccg gtc caa acg act<br>Leu Leu Tyr Ile Phe Lys Gln Pro Phe Met Arg Pro Val Gln Thr Thr<br>340                                345                          350 | 1056 |
| cag gaa gaa gac ggc tgc tcc tgc cgc ttt cct gag gag gag gag ggc<br>Gln Glu Glu Asp Gly Cys Ser Cys Arg Phe Pro Glu Glu Glu Glu Gly<br>                         355                            360                          365 | 1104 |
| ggg tgc gaa ctg agg gtg aag ttt tcc aga tct gca gat gca cca gcg<br>Gly Cys Glu Leu Arg Val Lys Phe Ser Arg Ser Ala Asp Ala Pro Ala<br>370                                375                          380 | 1152 |
| tat cag cag ggc cag aac caa ctg tat aac gag ctc aac ctg gga cgc<br>Tyr Gln Gln Gly Gln Asn Gln Leu Tyr Asn Glu Leu Asn Leu Gly Arg<br>385                                390                          395                    400 | 1200 |
| agg gaa gag tat gac gtt ttg gac aag cgc aga gga cgg gac cct gag<br>Arg Glu Glu Tyr Asp Val Leu Asp Lys Arg Arg Gly Arg Asp Pro Glu<br>                         405                            410                          415 | 1248 |
| atg ggt ggc aaa cca aga cga aaa aac ccc cag gag ggt ctc tat aat<br>Met Gly Gly Lys Pro Arg Arg Lys Asn Pro Gln Glu Gly Leu Tyr Asn<br>                    420                            425                          430 | 1296 |
| gag ctg cag aag gat aag atg gct gaa gcc tat tct gaa ata ggc atg<br>Glu Leu Gln Lys Asp Lys Met Ala Glu Ala Tyr Ser Glu Ile Gly Met<br>                         435                            440                          445 | 1344 |
| aaa gga gag cgg aga agg gga aaa ggg cac gac ggt ttg tac cag gga<br>Lys Gly Glu Arg Arg Arg Gly Lys Gly His Asp Gly Leu Tyr Gln Gly<br>                    450                            455                          460 | 1392 |
| ctc agc act gct acg aag gat act tat gac gct ctc cac atg caa gcc<br>Leu Ser Thr Ala Thr Lys Asp Thr Tyr Asp Ala Leu His Met Gln Ala<br>465                                470                          475                    480 | 1440 |
| ctg cca cct agg<br>Leu Pro Pro Arg | 1452 |

<210> SEQ ID NO 48
<211> LENGTH: 484
<212> TYPE: PRT
<213> ORGANISM: Homo sapiens

<400> SEQUENCE: 48

Met Ala Leu Pro Val Thr Ala Leu Leu Leu Pro Leu Ala Leu Leu Leu
1                 5                    10                   15

His Ala Ala Arg Pro Gln Val His Leu Val Gln Ser Gly Ala Glu Val
                 20                    25                    30

Lys Lys Pro Gly Ala Ser Val Arg Val Ser Cys Lys Ala Ser Gly Tyr
        35                    40                    45

Thr Phe Thr Ser Tyr Tyr Leu His Trp Val Arg Gln Ala Pro Gly Gln
    50                    55                    60

Gly Leu Glu Trp Met Gly Ile Val Asp Pro Ser Gly Gly Ser Thr Ser
65                 70                    75                    80

```
Tyr Asp Gln Lys Phe Gln Gly Arg Phe Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Asp Tyr Gly Asp Tyr Val Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gln Ser Val Leu Thr Gln
145                 150                 155                 160

Pro Pro Ser Ala Ser Gly Thr Pro Gly Gln Arg Val Thr Ile Ser Cys
                165                 170                 175

Ser Gly Ser Ser Ser Asn Ile Gly Thr Asn Thr Val Asn Trp Tyr Gln
            180                 185                 190

Gln Leu Pro Gly Thr Ala Pro Gln Leu Leu Ile Tyr Ile Asn Asn Gln
        195                 200                 205

Arg Pro Ser Gly Val Pro Asp Arg Phe Ser Gly Ser Lys Ser Gly Thr
    210                 215                 220

Ser Ala Ser Leu Ala Ile Ser Gly Leu Gln Ser Glu Asp Glu Ala Asp
225                 230                 235                 240

Tyr Tyr Cys Ala Thr Trp Asp Ser Leu Asn Gly Pro Val Val Gly
                245                 250                 255

Gly Gly Thr Lys Leu Thr Val Leu Gly Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Phe Ser Val Val Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg
```

```
<210> SEQ ID NO 49
<211> LENGTH: 1452
<212> TYPE: DNA
<213> ORGANISM: Homo sapiens
<220> FEATURE:
<221> NAME/KEY: CDS
<222> LOCATION: (1)..(1452)
<223> OTHER INFORMATION: 6E9.1_C8K_28z

<400> SEQUENCE: 49 atg gca ctc ccc gta act gct ctg ctg ctg ccg ttg gca ttg ctc ctg      48
Met Ala Leu Pro Val Thr Ala Leu Leu Leu Pro Leu Ala Leu Leu Leu
1               5                   10                  15 cac gcc gca cgc ccg cag gta cac ctg gtg cag agc ggg gcg gag gtc      96
His Ala Ala Arg Pro Gln Val His Leu Val Gln Ser Gly Ala Glu Val
                20                  25                  30 aag aaa ccg ggc gca tcc gta cgc gtg agc tgc aag gcc tcc gga tac     144
Lys Lys Pro Gly Ala Ser Val Arg Val Ser Cys Lys Ala Ser Gly Tyr
            35                  40                  45 act ttt act tct tac tat ctg cat tgg gtc agg cag gca ccg ggt cag     192
Thr Phe Thr Ser Tyr Tyr Leu His Trp Val Arg Gln Ala Pro Gly Gln
        50                  55                  60 gga ctg gag tgg atg ggc att gtg gac cca agc gga ggg agt acg tca     240
Gly Leu Glu Trp Met Gly Ile Val Asp Pro Ser Gly Gly Ser Thr Ser
65                  70                  75                  80 tat gat cag aag ttt caa ggt agg ttt acc atg aca cgg gac acg tca     288
Tyr Asp Gln Lys Phe Gln Gly Arg Phe Thr Met Thr Arg Asp Thr Ser
                85                  90                  95 acg agt acc gtc tac atg gag ctc agt agt ctg cgg agc gaa gac acc     336
Thr Ser Thr Val Tyr Met Glu Leu Ser Ser Leu Arg Ser Glu Asp Thr
            100                 105                 110 gca gtc tac tac tgc gca cgc gat tat gga gac tat gtc ttt gac tat     384
Ala Val Tyr Tyr Cys Ala Arg Asp Tyr Gly Asp Tyr Val Phe Asp Tyr
        115                 120                 125 tgg ggg cag ggg acg ctc gtg acc gtt tca agc ggg ggg ggc gga tcc     432
Trp Gly Gln Gly Thr Leu Val Thr Val Ser Ser Gly Gly Gly Gly Ser
130                 135                 140 ggt ggg gga ggt tcc ggc ggt ggg ggt tca caa agc gta ctg aca cag     480
Gly Gly Gly Gly Ser Gly Gly Gly Gly Ser Gln Ser Val Leu Thr Gln
145                 150                 155                 160 ccc ccg agt gca tcc ggg acc ccc ggc caa agg gtt aca atc agc tgc     528
Pro Pro Ser Ala Ser Gly Thr Pro Gly Gln Arg Val Thr Ile Ser Cys
                165                 170                 175 tct ggc agc tcc agt aac ata ggt acc aac acg gtg aac tgg tac cag     576
Ser Gly Ser Ser Ser Asn Ile Gly Thr Asn Thr Val Asn Trp Tyr Gln
            180                 185                 190 cag ttg cct ggc aca gcg cct cag ctg ctc atc tat atc aac aat cag     624
Gln Leu Pro Gly Thr Ala Pro Gln Leu Leu Ile Tyr Ile Asn Asn Gln
        195                 200                 205 cgg cca agt ggc gtg ccc gat aga ttc tca ggc tca aag agc gga acc     672
Arg Pro Ser Gly Val Pro Asp Arg Phe Ser Gly Ser Lys Ser Gly Thr
    210                 215                 220 agc gct agc ttg gca atc agt ggc ctt caa tcc gaa gac gaa gcc gat     720
Ser Ala Ser Leu Ala Ile Ser Gly Leu Gln Ser Glu Asp Glu Ala Asp
225                 230                 235                 240 tac tat tgt gcg acc tgg gac gat agc ctg aac ggc ccc gtc gtg ggc     768
Tyr Tyr Cys Ala Thr Trp Asp Asp Ser Leu Asn Gly Pro Val Val Gly
                245                 250                 255 ggc ggg acg aaa ctg aca gtg ttg ggc gcc gct gcc ctt gat aat gaa     816
Gly Gly Thr Lys Leu Thr Val Leu Gly Ala Ala Ala Leu Asp Asn Glu
            260                 265                 270
```

|  |  |
|---|---|
| aag tca aac gga aca atc att cac gtg aag ggc aag cac ctc tgt ccg<br>Lys Ser Asn Gly Thr Ile Ile His Val Lys Gly Lys His Leu Cys Pro<br>275                                280                             285 | 864 |
| tca ccc ttg ttc cct ggt cca tcc aag cca ttc tgg gtg ttg gtc gta<br>Ser Pro Leu Phe Pro Gly Pro Ser Lys Pro Phe Trp Val Leu Val Val<br>290                             295                            300 | 912 |
| gtg ggt gga gtc ctc gct tgt tac tct ctg ctc gtc acc gtg gct ttt<br>Val Gly Gly Val Leu Ala Cys Tyr Ser Leu Leu Val Thr Val Ala Phe<br>305                             310                           315                  320 | 960 |
| ata atc ttc tgg gtt cgc ttt tcc gtc gtt aag cgg ggg aga aaa aag<br>Ile Ile Phe Trp Val Arg Phe Ser Val Val Lys Arg Gly Arg Lys Lys<br>                     325                            330                           335 | 1008 |
| ctg ctg tac att ttc aaa cag ccg ttt atg agg ccg gtc caa acg act<br>Leu Leu Tyr Ile Phe Lys Gln Pro Phe Met Arg Pro Val Gln Thr Thr<br>                 340                           345                           350 | 1056 |
| cag gaa gaa gac ggc tgc tcc tgc cgc ttt cct gag gag gag gag ggc<br>Gln Glu Glu Asp Gly Cys Ser Cys Arg Phe Pro Glu Glu Glu Glu Gly<br>                     355                            360                           365 | 1104 |
| ggg tgc gaa ctg agg gtg aag ttt tcc aga tct gca gat gca cca gcg<br>Gly Cys Glu Leu Arg Val Lys Phe Ser Arg Ser Ala Asp Ala Pro Ala<br>370                             375                             380 | 1152 |
| tat cag cag ggc cag aac caa ctg tat aac gag ctc aac ctg gga cgc<br>Tyr Gln Gln Gly Gln Asn Gln Leu Tyr Asn Glu Leu Asn Leu Gly Arg<br>385                             390                           395                  400 | 1200 |
| agg gaa gag tat gac gtt ttg gac aag cgc aga gga cgg gac cct gag<br>Arg Glu Glu Tyr Asp Val Leu Asp Lys Arg Arg Gly Arg Asp Pro Glu<br>                                405                           410                           415 | 1248 |
| atg ggt ggc aaa cca aga cga aaa aac ccc cag gag ggt ctc tat aat<br>Met Gly Gly Lys Pro Arg Arg Lys Asn Pro Gln Glu Gly Leu Tyr Asn<br>                 420                           425                           430 | 1296 |
| gag ctg cag aag gat aag atg gct gaa gcc tat tct gaa ata ggc atg<br>Glu Leu Gln Lys Asp Lys Met Ala Glu Ala Tyr Ser Glu Ile Gly Met<br>                     435                            440                           445 | 1344 |
| aaa gga gag cgg aga agg gga aaa ggg cac gac ggt ttg tac cag gga<br>Lys Gly Glu Arg Arg Arg Gly Lys Gly His Asp Gly Leu Tyr Gln Gly<br>450                             455                             460 | 1392 |
| ctc agc act gct acg aag gat act tat gac gct ctc cac atg caa gcc<br>Leu Ser Thr Ala Thr Lys Asp Thr Tyr Asp Ala Leu His Met Gln Ala<br>465                             470                           475                  480 | 1440 |
| ctg cca cct agg<br>Leu Pro Pro Arg | 1452 |

<210> SEQ ID NO 50
<211> LENGTH: 484
<212> TYPE: PRT
<213> ORGANISM: Homo sapiens

<400> SEQUENCE: 50

Met Ala Leu Pro Val Thr Ala Leu Leu Leu Pro Leu Ala Leu Leu Leu
1               5                    10                       15

His Ala Ala Arg Pro Gln Val His Leu Val Gln Ser Gly Ala Glu Val
               20                      25                        30

Lys Lys Pro Gly Ala Ser Val Arg Val Ser Cys Lys Ala Ser Gly Tyr
            35                     40                      45

Thr Phe Thr Ser Tyr Tyr Leu His Trp Val Arg Gln Ala Pro Gly Gln
    50                      55                      60

Gly Leu Glu Trp Met Gly Ile Val Asp Pro Ser Gly Gly Ser Thr Ser
65                   70                    75                    80

```
Tyr Asp Gln Lys Phe Gln Gly Arg Phe Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Asp Tyr Gly Asp Tyr Val Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gln Ser Val Leu Thr Gln
145                 150                 155                 160

Pro Pro Ser Ala Ser Gly Thr Pro Gly Gln Arg Val Thr Ile Ser Cys
                165                 170                 175

Ser Gly Ser Ser Ser Asn Ile Gly Thr Asn Thr Val Asn Trp Tyr Gln
            180                 185                 190

Gln Leu Pro Gly Thr Ala Pro Gln Leu Leu Ile Tyr Ile Asn Asn Gln
        195                 200                 205

Arg Pro Ser Gly Val Pro Asp Arg Phe Ser Gly Ser Lys Ser Gly Thr
    210                 215                 220

Ser Ala Ser Leu Ala Ile Ser Gly Leu Gln Ser Glu Asp Glu Ala Asp
225                 230                 235                 240

Tyr Tyr Cys Ala Thr Trp Asp Ser Leu Asn Gly Pro Val Val Gly
                245                 250                 255

Gly Gly Thr Lys Leu Thr Val Leu Gly Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Phe Ser Val Val Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg
```

<210> SEQ ID NO 51
<211> LENGTH: 1530
<212> TYPE: DNA
<213> ORGANISM: Homo sapiens
<220> FEATURE:
<221> NAME/KEY: CDS
<222> LOCATION: (1)..(1530)
<223> OTHER INFORMATION: 6E9.1_C8K_4Bz

<400> SEQUENCE: 51

| | | | | | | | | | | | | | | | | |
|---|---|---|---|---|---|---|---|---|---|---|---|---|---|---|---|---|
| atg | gca | ctc | ccc | gta | act | gct | ctg | ctg | ctg | ccg | ttg | gca | ttg | ctc | ctg | 48 |
| Met | Ala | Leu | Pro | Val | Thr | Ala | Leu | Leu | Leu | Pro | Leu | Ala | Leu | Leu | Leu | |
| 1 | | | | 5 | | | | | 10 | | | | | 15 | | |
| cac | gcc | gca | cgc | ccg | cag | gta | cac | ctg | gtg | cag | agc | ggg | gcg | gag | gtc | 96 |
| His | Ala | Ala | Arg | Pro | Gln | Val | His | Leu | Val | Gln | Ser | Gly | Ala | Glu | Val | |
| | | | 20 | | | | | 25 | | | | | 30 | | | |
| aag | aaa | ccg | ggc | gca | tcc | gta | cgc | gtg | agc | tgc | aag | gcc | tcc | gga | tac | 144 |
| Lys | Lys | Pro | Gly | Ala | Ser | Val | Arg | Val | Ser | Cys | Lys | Ala | Ser | Gly | Tyr | |
| | | 35 | | | | | 40 | | | | | 45 | | | | |
| act | ttt | act | tct | tac | tat | ctg | cat | tgg | gtc | agg | cag | gca | ccg | ggt | cag | 192 |
| Thr | Phe | Thr | Ser | Tyr | Tyr | Leu | His | Trp | Val | Arg | Gln | Ala | Pro | Gly | Gln | |
| | 50 | | | | | 55 | | | | | 60 | | | | | |
| gga | ctg | gag | tgg | atg | ggc | att | gtg | gac | cca | agc | gga | ggg | agt | acg | tca | 240 |
| Gly | Leu | Glu | Trp | Met | Gly | Ile | Val | Asp | Pro | Ser | Gly | Gly | Ser | Thr | Ser | |
| 65 | | | | | 70 | | | | | 75 | | | | | 80 | |
| tat | gat | cag | aag | ttt | caa | ggt | agg | ttt | acc | atg | aca | cgg | gac | acg | tca | 288 |
| Tyr | Asp | Gln | Lys | Phe | Gln | Gly | Arg | Phe | Thr | Met | Thr | Arg | Asp | Thr | Ser | |
| | | | | 85 | | | | | 90 | | | | | 95 | | |
| acg | agt | acc | gtc | tac | atg | gag | ctc | agt | agt | ctg | cgg | agc | gaa | gac | acc | 336 |
| Thr | Ser | Thr | Val | Tyr | Met | Glu | Leu | Ser | Ser | Leu | Arg | Ser | Glu | Asp | Thr | |
| | | | 100 | | | | | 105 | | | | | 110 | | | |
| gca | gtc | tac | tac | tgc | gca | cgc | gat | tat | gga | gac | tat | gtc | ttt | gac | tat | 384 |
| Ala | Val | Tyr | Tyr | Cys | Ala | Arg | Asp | Tyr | Gly | Asp | Tyr | Val | Phe | Asp | Tyr | |
| | | 115 | | | | | 120 | | | | | 125 | | | | |
| tgg | ggg | cag | ggg | acg | ctc | gtg | acc | gtt | tca | agc | ggg | ggg | ggc | gga | tcc | 432 |
| Trp | Gly | Gln | Gly | Thr | Leu | Val | Thr | Val | Ser | Ser | Gly | Gly | Gly | Gly | Ser | |
| | 130 | | | | | 135 | | | | | 140 | | | | | |
| ggt | ggg | gga | ggt | tcc | ggc | ggt | ggg | ggt | tca | caa | agc | gta | ctg | aca | cag | 480 |
| Gly | Gly | Gly | Gly | Ser | Gly | Gly | Gly | Gly | Ser | Gln | Ser | Val | Leu | Thr | Gln | |
| 145 | | | | | 150 | | | | | 155 | | | | | 160 | |
| ccc | ccg | agt | gca | tcc | ggg | acc | ccc | ggc | caa | agg | gtt | aca | atc | agc | tgc | 528 |
| Pro | Pro | Ser | Ala | Ser | Gly | Thr | Pro | Gly | Gln | Arg | Val | Thr | Ile | Ser | Cys | |
| | | | | 165 | | | | | 170 | | | | | 175 | | |
| tct | ggc | agc | tcc | agt | aac | ata | ggt | acc | aac | acg | gtg | aac | tgg | tac | cag | 576 |
| Ser | Gly | Ser | Ser | Ser | Asn | Ile | Gly | Thr | Asn | Thr | Val | Asn | Trp | Tyr | Gln | |
| | | | 180 | | | | | 185 | | | | | 190 | | | |
| cag | ttg | cct | ggc | aca | gcg | cct | cag | ctg | ctc | atc | tat | atc | aac | aat | cag | 624 |
| Gln | Leu | Pro | Gly | Thr | Ala | Pro | Gln | Leu | Leu | Ile | Tyr | Ile | Asn | Asn | Gln | |
| | | 195 | | | | | 200 | | | | | 205 | | | | |
| cgg | cca | agt | ggc | gtg | ccc | gat | aga | ttc | tca | ggc | tca | aag | agc | gga | acc | 672 |
| Arg | Pro | Ser | Gly | Val | Pro | Asp | Arg | Phe | Ser | Gly | Ser | Lys | Ser | Gly | Thr | |
| | 210 | | | | | 215 | | | | | 220 | | | | | |
| agc | gct | agc | ttg | gca | atc | agt | ggc | ctt | caa | tcc | gaa | gac | gaa | gcc | gat | 720 |
| Ser | Ala | Ser | Leu | Ala | Ile | Ser | Gly | Leu | Gln | Ser | Glu | Asp | Glu | Ala | Asp | |
| 225 | | | | | 230 | | | | | 235 | | | | | 240 | |
| tac | tat | tgt | gcg | acc | tgg | gac | gat | agc | ctg | aac | ggc | ccc | gtc | gtg | ggc | 768 |
| Tyr | Tyr | Cys | Ala | Thr | Trp | Asp | Asp | Ser | Leu | Asn | Gly | Pro | Val | Val | Gly | |
| | | | | 245 | | | | | 250 | | | | | 255 | | |
| ggc | ggg | acg | aaa | ctg | aca | gtg | ttg | ggc | gcc | gct | gcc | ttc | gtg | cct | gtt | 816 |
| Gly | Gly | Thr | Lys | Leu | Thr | Val | Leu | Gly | Ala | Ala | Ala | Phe | Val | Pro | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| ttt | ctg | ccc | gcg | aaa | ccc | aca | act | acc | ccc | gcc | cct | cgg | ccc | cca | act | 864 |
| Phe | Leu | Pro | Ala | Lys | Pro | Thr | Thr | Thr | Pro | Ala | Pro | Arg | Pro | Pro | Thr | |
| | | 275 | | | | | 280 | | | | | 285 | | | | |
| cct | gca | cca | act | atc | gct | tcc | caa | ccc | ctg | tct | ctg | aga | cct | gag | gca | 912 |
| Pro | Ala | Pro | Thr | Ile | Ala | Ser | Gln | Pro | Leu | Ser | Leu | Arg | Pro | Glu | Ala | |
| | 290 | | | | | 295 | | | | | 300 | | | | | |
| tgc | cgc | ccc | gcg | gca | ggc | ggc | gcc | gtg | cac | act | aga | ggc | ctg | gac | ttc | 960 |
| Cys | Arg | Pro | Ala | Ala | Gly | Gly | Ala | Val | His | Thr | Arg | Gly | Leu | Asp | Phe | |
| 305 | | | | | 310 | | | | | 315 | | | | | 320 | |
| gcc | tgc | gat | att | tat | atc | tgg | gcc | ccc | ctt | gcc | ggg | aca | tgc | ggg | gta | 1008 |
| Ala | Cys | Asp | Ile | Tyr | Ile | Trp | Ala | Pro | Leu | Ala | Gly | Thr | Cys | Gly | Val | |
| | | | | 325 | | | | | 330 | | | | | 335 | | |
| ctg | ctg | ctg | tct | ctg | gtg | att | acc | ctc | tac | tgc | aac | cac | aga | aac | cgc | 1056 |
| Leu | Leu | Leu | Ser | Leu | Val | Ile | Thr | Leu | Tyr | Cys | Asn | His | Arg | Asn | Arg | |
| | | | 340 | | | | | 345 | | | | | 350 | | | |
| ttt | tcc | gtc | gtt | aag | cgg | ggg | aga | aaa | aag | ctg | ctg | tac | att | ttc | aaa | 1104 |
| Phe | Ser | Val | Val | Lys | Arg | Gly | Arg | Lys | Lys | Leu | Leu | Tyr | Ile | Phe | Lys | |
| | | 355 | | | | | 360 | | | | | 365 | | | | |
| cag | ccg | ttt | atg | agg | ccg | gtc | caa | acg | act | cag | gaa | gaa | gac | ggc | tgc | 1152 |
| Gln | Pro | Phe | Met | Arg | Pro | Val | Gln | Thr | Thr | Gln | Glu | Glu | Asp | Gly | Cys | |
| | 370 | | | | | 375 | | | | | 380 | | | | | |
| tcc | tgc | cgc | ttt | cct | gag | gag | gag | gag | ggc | ggg | tgc | gaa | ctg | agg | gtg | 1200 |
| Ser | Cys | Arg | Phe | Pro | Glu | Glu | Glu | Glu | Gly | Gly | Cys | Glu | Leu | Arg | Val | |
| 385 | | | | | 390 | | | | | 395 | | | | | 400 | |
| aag | ttt | tcc | aga | tct | gca | gat | gca | cca | gcg | tat | cag | cag | ggc | cag | aac | 1248 |
| Lys | Phe | Ser | Arg | Ser | Ala | Asp | Ala | Pro | Ala | Tyr | Gln | Gln | Gly | Gln | Asn | |
| | | | | 405 | | | | | 410 | | | | | 415 | | |
| caa | ctg | tat | aac | gag | ctc | aac | ctg | gga | cgc | agg | gaa | gag | tat | gac | gtt | 1296 |
| Gln | Leu | Tyr | Asn | Glu | Leu | Asn | Leu | Gly | Arg | Arg | Glu | Glu | Tyr | Asp | Val | |
| | | | 420 | | | | | 425 | | | | | 430 | | | |
| ttg | gac | aag | cgc | aga | gga | cgg | gac | cct | gag | atg | ggt | ggc | aaa | cca | aga | 1344 |
| Leu | Asp | Lys | Arg | Arg | Gly | Arg | Asp | Pro | Glu | Met | Gly | Gly | Lys | Pro | Arg | |
| | | 435 | | | | | 440 | | | | | 445 | | | | |
| cga | aaa | aac | ccc | cag | gag | ggt | ctc | tat | aat | gag | ctg | cag | aag | gat | aag | 1392 |
| Arg | Lys | Asn | Pro | Gln | Glu | Gly | Leu | Tyr | Asn | Glu | Leu | Gln | Lys | Asp | Lys | |
| | 450 | | | | | 455 | | | | | 460 | | | | | |
| atg | gct | gaa | gcc | tat | tct | gaa | ata | ggc | atg | aaa | gga | gag | cgg | aga | agg | 1440 |
| Met | Ala | Glu | Ala | Tyr | Ser | Glu | Ile | Gly | Met | Lys | Gly | Glu | Arg | Arg | Arg | |
| 465 | | | | | 470 | | | | | 475 | | | | | 480 | |
| gga | aaa | ggg | cac | gac | ggt | ttg | tac | cag | gga | ctc | agc | act | gct | acg | aag | 1488 |
| Gly | Lys | Gly | His | Asp | Gly | Leu | Tyr | Gln | Gly | Leu | Ser | Thr | Ala | Thr | Lys | |
| | | | | 485 | | | | | 490 | | | | | 495 | | |
| gat | act | tat | gac | gct | ctc | cac | atg | caa | gcc | ctg | cca | cct | agg | | | 1530 |
| Asp | Thr | Tyr | Asp | Ala | Leu | His | Met | Gln | Ala | Leu | Pro | Pro | Arg | | | |
| | | | 500 | | | | | 505 | | | | | 510 | | | |

```
<210> SEQ ID NO 52
<211> LENGTH: 510
<212> TYPE: PRT
<213> ORGANISM: Homo sapiens

<400> SEQUENCE: 52
```

Met Ala Leu Pro Val Thr Ala Leu Leu Leu Pro Leu Ala Leu Leu Leu
1               5                   10                  15

His Ala Ala Arg Pro Gln Val His Leu Val Gln Ser Gly Ala Glu Val
                20                  25                  30

Lys Lys Pro Gly Ala Ser Val Arg Val Ser Cys Lys Ala Ser Gly Tyr
            35                  40                  45

Thr Phe Thr Ser Tyr Tyr Leu His Trp Val Arg Gln Ala Pro Gly Gln
        50                  55                  60

```
Gly Leu Glu Trp Met Gly Ile Val Asp Pro Ser Gly Ser Thr Ser
 65                  70                  75                  80

Tyr Asp Gln Lys Phe Gln Gly Arg Phe Thr Met Thr Arg Asp Thr Ser
                 85                  90                  95

Thr Ser Thr Val Tyr Met Glu Leu Ser Ser Leu Arg Ser Glu Asp Thr
            100                 105                 110

Ala Val Tyr Tyr Cys Ala Arg Asp Tyr Gly Asp Tyr Val Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gln Ser Val Leu Thr Gln
145                 150                 155                 160

Pro Pro Ser Ala Ser Gly Thr Pro Gly Gln Arg Val Thr Ile Ser Cys
                165                 170                 175

Ser Gly Ser Ser Ser Asn Ile Gly Thr Asn Thr Val Asn Trp Tyr Gln
            180                 185                 190

Gln Leu Pro Gly Thr Ala Pro Gln Leu Leu Ile Tyr Ile Asn Asn Gln
        195                 200                 205

Arg Pro Ser Gly Val Pro Asp Arg Phe Ser Gly Ser Lys Ser Gly Thr
210                 215                 220

Ser Ala Ser Leu Ala Ile Ser Gly Leu Gln Ser Glu Asp Glu Ala Asp
225                 230                 235                 240

Tyr Tyr Cys Ala Thr Trp Asp Ser Leu Asn Gly Pro Val Val Gly
                245                 250                 255

Gly Gly Thr Lys Leu Thr Val Leu Gly Ala Ala Ala Phe Val Pro Val
            260                 265                 270

Phe Leu Pro Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Asn His Arg Asn Arg
            340                 345                 350

Phe Ser Val Val Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480
```

-continued

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 53
<211> LENGTH: 12
<212> TYPE: PRT
<213> ORGANISM: Homo sapiens

<400> SEQUENCE: 53

Arg Ala Ser Gln Ser Leu Arg Arg Ile Tyr Leu Ala
1               5                   10

<210> SEQ ID NO 54
<211> LENGTH: 7
<212> TYPE: PRT
<213> ORGANISM: Homo sapiens

<400> SEQUENCE: 54

Asp Val Phe Asp Arg Ala Thr
1               5

<210> SEQ ID NO 55
<211> LENGTH: 9
<212> TYPE: PRT
<213> ORGANISM: Homo sapiens

<400> SEQUENCE: 55

Gln Gln Tyr Ser Asp Ser Pro Phe Thr
1               5

<210> SEQ ID NO 56
<211> LENGTH: 11
<212> TYPE: PRT
<213> ORGANISM: Homo sapiens

<400> SEQUENCE: 56

Arg Ala Ser Gln Phe Ile Gly Arg Tyr Phe Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Glu Ser Ser Leu Gln Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln Ser Tyr Ser Thr Pro Phe Thr
1               5

```
<210> SEQ ID NO 59
<211> LENGTH: 13
<212> TYPE: PRT
<213> ORGANISM: Homo sapiens

<400> SEQUENCE: 59

Ser Gly Ser Ser Ser Asn Ile Gly Thr Asn Thr Val Asn
1               5                   10

<210> SEQ ID NO 60
<211> LENGTH: 7
<212> TYPE: PRT
<213> ORGANISM: Homo sapiens

<400> SEQUENCE: 60

Ile Asn Asn Gln Arg Pro Ser
1               5

<210> SEQ ID NO 61
<211> LENGTH: 12
<212> TYPE: PRT
<213> ORGANISM: Homo sapiens

<400> SEQUENCE: 61

Ala Thr Trp Asp Asp Ser Leu Asn Gly Pro Val Val
1               5                   10

<210> SEQ ID NO 62
<211> LENGTH: 5
<212> TYPE: PRT
<213> ORGANISM: Homo sapiens

<400> SEQUENCE: 62

Ser Tyr Gly Met His
1               5

<210> SEQ ID NO 63
<211> LENGTH: 17
<212> TYPE: PRT
<213> ORGANISM: Homo sapiens

<400> SEQUENCE: 63

Val Thr Trp Tyr Asp Gly Ser Asn Lys Tyr Tyr Gly Asp Ser Val Lys
1               5                   10                  15

Gly

<210> SEQ ID NO 64
<211> LENGTH: 13
<212> TYPE: PRT
<213> ORGANISM: Homo sapiens

<400> SEQUENCE: 64

Asp Leu Leu Arg Gly Val Lys Gly Tyr Ala Met Asp Val
1               5                   10

<210> SEQ ID NO 65
<211> LENGTH: 7
<212> TYPE: PRT
<213> ORGANISM: Homo sapiens

<400> SEQUENCE: 65

Ser Gly Gly Tyr Tyr Trp Ser
1               5
```

```
<210> SEQ ID NO 66
<211> LENGTH: 16
<212> TYPE: PRT
<213> ORGANISM: Homo sapiens

<400> SEQUENCE: 66

Tyr Ile Phe Tyr Ser Gly Ser Thr Asp Tyr Asn Pro Ser Leu Lys Ser
1               5                   10                  15

<210> SEQ ID NO 67
<211> LENGTH: 10
<212> TYPE: PRT
<213> ORGANISM: Homo sapiens

<400> SEQUENCE: 67

Ser Gly Tyr Ser Tyr Ala Leu Phe Asp His
1               5                   10

<210> SEQ ID NO 68
<211> LENGTH: 5
<212> TYPE: PRT
<213> ORGANISM: Homo sapiens

<400> SEQUENCE: 68

Ser Tyr Tyr Leu His
1               5

<210> SEQ ID NO 69
<211> LENGTH: 17
<212> TYPE: PRT
<213> ORGANISM: Homo sapiens

<400> SEQUENCE: 69

Ile Val Asp Pro Ser Gly Gly Ser Thr Ser Tyr Asp Gln Lys Phe Gln
1               5                   10                  15

Gly

<210> SEQ ID NO 70
<211> LENGTH: 9
<212> TYPE: PRT
<213> ORGANISM: Homo sapiens

<400> SEQUENCE: 70

Asp Tyr Gly Asp Tyr Val Phe Asp Tyr
1               5

<210> SEQ ID NO 71
<211> LENGTH: 7
<212> TYPE: PRT
<213> ORGANISM: Homo sapiens

<400> SEQUENCE: 71

Gly Phe Thr Phe Ser Ser Tyr
1               5

<210> SEQ ID NO 72
<211> LENGTH: 6
<212> TYPE: PRT
<213> ORGANISM: Homo sapiens

<400> SEQUENCE: 72

Trp Tyr Asp Gly Ser Asn
1               5
```

```
<210> SEQ ID NO 73
<211> LENGTH: 9
<212> TYPE: PRT
<213> ORGANISM: Homo sapiens

<400> SEQUENCE: 73

Gly Asp Ser Ile Ile Ser Gly Gly Tyr
1               5

<210> SEQ ID NO 74
<211> LENGTH: 5
<212> TYPE: PRT
<213> ORGANISM: Homo sapiens

<400> SEQUENCE: 74

Phe Tyr Ser Gly Ser
1               5

<210> SEQ ID NO 75
<211> LENGTH: 7
<212> TYPE: PRT
<213> ORGANISM: Homo sapiens

<400> SEQUENCE: 75

Gly Tyr Thr Phe Thr Ser Tyr
1               5

<210> SEQ ID NO 76
<211> LENGTH: 6
<212> TYPE: PRT
<213> ORGANISM: Homo sapiens

<400> SEQUENCE: 76

Asp Pro Ser Gly Gly Ser
1               5

<210> SEQ ID NO 77
<211> LENGTH: 10
<212> TYPE: PRT
<213> ORGANISM: Homo sapiens

<400> SEQUENCE: 77

Gly Phe Thr Phe Ser Ser Tyr Gly Met His
1               5                   10

<210> SEQ ID NO 78
<211> LENGTH: 12
<212> TYPE: PRT
<213> ORGANISM: Homo sapiens

<400> SEQUENCE: 78

Gly Asp Ser Ile Ile Ser Gly Gly Tyr Tyr Trp Ser
1               5                   10

<210> SEQ ID NO 79
<211> LENGTH: 10
<212> TYPE: PRT
<213> ORGANISM: Homo sapiens

<400> SEQUENCE: 79

Gly Tyr Thr Phe Thr Ser Tyr Tyr Leu His
1               5                   10
```

```
<210> SEQ ID NO 80
<211> LENGTH: 15
<212> TYPE: PRT
<213> ORGANISM: Homo sapiens

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 18
<212> TYPE: PRT
<213> ORGANISM: Homo sapiens

<400> SEQUENCE: 81

Gly Ser Thr Ser Gly Ser Gly Lys Pro Gly Ser Gly Glu Gly Ser Thr
1               5                   10                  15

Lys Gly

<210> SEQ ID NO 82
<211> LENGTH: 90
<212> TYPE: DNA
<213> ORGANISM: Homo sapiens
<220> FEATURE:
<221> NAME/KEY: CDS
<222> LOCATION: (1)..(90)
<223> OTHER INFORMATION: CD28T EC/spacer

<400> SEQUENCE: 82 ctt gat aat gaa aag tca aac gga aca atc att cac gtg aag ggc aag      48
Leu Asp Asn Glu Lys Ser Asn Gly Thr Ile Ile His Val Lys Gly Lys
1               5                   10                  15 cac ctc tgt ccg tca ccc ttg ttc cct ggt cca tcc aag cca              90
His Leu Cys Pro Ser Pro Leu Phe Pro Gly Pro Ser Lys Pro
            20                  25                  30

<210> SEQ ID NO 83
<211> LENGTH: 30
<212> TYPE: PRT
<213> ORGANISM: Homo sapiens

<400> SEQUENCE: 83

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 84
<211> LENGTH: 165
<212> TYPE: DNA
<213> ORGANISM: Homo sapiens
<220> FEATURE:
<221> NAME/KEY: CDS
<222> LOCATION: (1)..(165)
<223> OTHER INFORMATION: CD8 EC/spacer

<400> SEQUENCE: 84 ttc gtg cct gtt ttt ctg ccc gcg aaa ccc aca act acc ccc gcc cct      48
Phe Val Pro Val Phe Leu Pro Ala Lys Pro Thr Thr Thr Pro Ala Pro
1               5                   10                  15 cgg ccc cca act cct gca cca act atc gct tcc caa ccc ctg tct ctg      96
Arg Pro Pro Thr Pro Ala Pro Thr Ile Ala Ser Gln Pro Leu Ser Leu
            20                  25                  30
```

-continued

```
aga cct gag gca tgc cgc ccc gcg gca ggc ggc gcc gtg cac act aga        144
Arg Pro Glu Ala Cys Arg Pro Ala Ala Gly Gly Ala Val His Thr Arg
         35                  40                  45 ggc ctg gac ttc gcc tgc gat                                            165
Gly Leu Asp Phe Ala Cys Asp
 50                  55
```

<210> SEQ ID NO 85
<211> LENGTH: 55
<212> TYPE: PRT
<213> ORGANISM: Homo sapiens

<400> SEQUENCE: 85

```
Phe Val Pro Val Phe Leu Pro Ala Lys Pro Thr Thr Thr Pro Ala Pro
 1               5                   10                  15

Arg Pro Pro Thr Pro Ala Pro Thr Ile Ala Ser Gln Pro Leu Ser Leu
             20                  25                  30

Arg Pro Glu Ala Cys Arg Pro Ala Ala Gly Gly Ala Val His Thr Arg
         35                  40                  45

Gly Leu Asp Phe Ala Cys Asp
 50                  55
```

<210> SEQ ID NO 86
<211> LENGTH: 21
<212> TYPE: DNA
<213> ORGANISM: Homo sapiens
<220> FEATURE:
<221> NAME/KEY: CDS
<222> LOCATION: (1)..(21)
<223> OTHER INFORMATION: CD8 Intracellular bit

<400> SEQUENCE: 86

```
ctc tac tgc aac cac aga aac                                            21
Leu Tyr Cys Asn His Arg Asn
 1               5
```

<210> SEQ ID NO 87
<211> LENGTH: 7
<212> TYPE: PRT
<213> ORGANISM: Homo sapiens

<400> SEQUENCE: 87

```
Leu Tyr Cys Asn His Arg Asn
 1               5
```

<210> SEQ ID NO 88
<211> LENGTH: 12
<212> TYPE: DNA
<213> ORGANISM: Homo sapiens
<220> FEATURE:
<221> NAME/KEY: CDS
<222> LOCATION: (1)..(12)
<223> OTHER INFORMATION: Furin cleavage site

<400> SEQUENCE: 88

```
gcc aag aga agt                                                        12
Ala Lys Arg Ser
 1
```

<210> SEQ ID NO 89
<211> LENGTH: 4
<212> TYPE: PRT
<213> ORGANISM: Homo sapiens

<400> SEQUENCE: 89

Ala Lys Arg Ser
1

<210> SEQ ID NO 90
<211> LENGTH: 54
<212> TYPE: DNA
<213> ORGANISM: Homo sapiens
<220> FEATURE:
<221> NAME/KEY: CDS
<222> LOCATION: (1)..(54)
<223> OTHER INFORMATION: T2A peptide

<400> SEQUENCE: 90 gag ggc cgg gga tct ctc ctt aca tgt ggg gac gtg gaa gaa aat ccg     48
Glu Gly Arg Gly Ser Leu Leu Thr Cys Gly Asp Val Glu Glu Asn Pro
1               5                   10                  15 ggg cct                                                              54
Gly Pro

<210> SEQ ID NO 91
<211> LENGTH: 18
<212> TYPE: PRT
<213> ORGANISM: Homo sapiens

<400> SEQUENCE: 91

Glu Gly Arg Gly Ser Leu Leu Thr Cys Gly Asp Val Glu Glu Asn Pro
1               5                   10                  15

Gly Pro

<210> SEQ ID NO 92
<211> LENGTH: 112
<212> TYPE: PRT
<213> ORGANISM: Homo sapiens

<400> SEQUENCE: 92

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 93
<211> LENGTH: 47
<212> TYPE: PRT
<213> ORGANISM: Homo sapiens

```
<400> SEQUENCE: 93

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
            35                  40                  45

<210> SEQ ID NO 94
<211> LENGTH: 22
<212> TYPE: PRT
<213> ORGANISM: Homo sapiens

<400> SEQUENCE: 94

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 95
<211> LENGTH: 60
<212> TYPE: DNA
<213> ORGANISM: Homo sapiens

<400> SEQUENCE: 95
atggcactcc ccgtaactgc tctgctgctg ccgttggcat tgctcctgca cgccgcacgc    60

<210> SEQ ID NO 96
<211> LENGTH: 822
<212> TYPE: DNA
<213> ORGANISM: Homo sapiens
<220> FEATURE:
<221> NAME/KEY: CDS
<222> LOCATION: (1)..(822)
<223> OTHER INFORMATION: tLNGFR

<400> SEQUENCE: 96 atg ggt gcc ggc gcc acg gga agg gct atg gat ggc ccg cga ctg ctt    48
Met Gly Ala Gly Ala Thr Gly Arg Ala Met Asp Gly Pro Arg Leu Leu
1               5                   10                  15 ctc ctg ctg ttg ttg ggc gtg tct ctc gga ggc gct aag gag gcc tgt    96
Leu Leu Leu Leu Leu Gly Val Ser Leu Gly Gly Ala Lys Glu Ala Cys
            20                  25                  30 cca acg ggc ctc tac act cac tcc ggt gaa tgt tgc aaa gcc tgt aac   144
Pro Thr Gly Leu Tyr Thr His Ser Gly Glu Cys Cys Lys Ala Cys Asn
            35                  40                  45 ctt ggc gag ggc gtc gca caa cct tgt ggt gct aac cag aca gtc tgt   192
Leu Gly Glu Gly Val Ala Gln Pro Cys Gly Ala Asn Gln Thr Val Cys
    50                  55                  60 gaa cca tgc ctg gat tca gtg aca ttc agc gat gtt gtc tca gcc acc   240
Glu Pro Cys Leu Asp Ser Val Thr Phe Ser Asp Val Val Ser Ala Thr
65                  70                  75                  80 gag cct tgc aag cct tgt acc gaa tgt gtg ggc ctt cag tcc atg tcc   288
Glu Pro Cys Lys Pro Cys Thr Glu Cys Val Gly Leu Gln Ser Met Ser
                85                  90                  95 gcc ccc tgt gtc gaa gcc gat gat gca gtg tgc aga tgt gcc tat gga   336
Ala Pro Cys Val Glu Ala Asp Asp Ala Val Cys Arg Cys Ala Tyr Gly
            100                 105                 110 tat tac cag gac gaa act acc ggg cgg tgt gag gcc tgc cgg gtg tgt   384
Tyr Tyr Gln Asp Glu Thr Thr Gly Arg Cys Glu Ala Cys Arg Val Cys
            115                 120                 125
```

| | | |
|---|---|---|
| gaa gcc ggc tct ggc ctc gtg ttc agt tgc cag gat aag caa aac aca<br>Glu Ala Gly Ser Gly Leu Val Phe Ser Cys Gln Asp Lys Gln Asn Thr<br>130                         135                         140 | | 432 |
| gta tgt gag gag tgt cca gac gga acc tac agc gac gag gcg aac cac<br>Val Cys Glu Glu Cys Pro Asp Gly Thr Tyr Ser Asp Glu Ala Asn His<br>145                         150                       155                       160 | | 480 |
| gtc gac cct tgc ttg ccg tgc acc gtc tgc gag gat acc gaa cgc cag<br>Val Asp Pro Cys Leu Pro Cys Thr Val Cys Glu Asp Thr Glu Arg Gln<br>                         165                       170                       175 | | 528 |
| ctg aga gag tgt acg cgc tgg gca gac gct gag tgc gag gag atc cct<br>Leu Arg Glu Cys Thr Arg Trp Ala Asp Ala Glu Cys Glu Glu Ile Pro<br>                 180                       185                       190 | | 576 |
| ggg aga tgg atc acc cgg agc aca cct cct gag gga tca gac agt aca<br>Gly Arg Trp Ile Thr Arg Ser Thr Pro Pro Glu Gly Ser Asp Ser Thr<br>             195                       200                       205 | | 624 |
| gcc ccg agt acc caa gaa ccg gag gcc cct cca gag cag gac ctg atc<br>Ala Pro Ser Thr Gln Glu Pro Glu Ala Pro Pro Glu Gln Asp Leu Ile<br>210                         215                       220 | | 672 |
| gct tct aca gtt gct ggc gtg gtg acg aca gtc atg gga tcc tca caa<br>Ala Ser Thr Val Ala Gly Val Val Thr Thr Val Met Gly Ser Ser Gln<br>225                         230                       235                       240 | | 720 |
| cca gtc gtg acg cgg ggc aca acc gac aat ctg att cct gtc tac tgt<br>Pro Val Val Thr Arg Gly Thr Thr Asp Asn Leu Ile Pro Val Tyr Cys<br>                 245                       250                       255 | | 768 |
| agc atc ttg gca gcc gtg gtc gtg ggc ctg gta gcc tac atc gcc ttt<br>Ser Ile Leu Ala Ala Val Val Val Gly Leu Val Ala Tyr Ile Ala Phe<br>             260                       265                       270 | | 816 |
| aag aga<br>Lys Arg | | 822 |

<210> SEQ ID NO 97
<211> LENGTH: 274
<212> TYPE: PRT
<213> ORGANISM: Homo sapiens

<400> SEQUENCE: 97

Met Gly Ala Gly Ala Thr Gly Arg Ala Met Asp Gly Pro Arg Leu Leu
1                 5                    10                  15

Leu Leu Leu Leu Leu Gly Val Ser Leu Gly Gly Ala Lys Glu Ala Cys
                 20                       25                       30

Pro Thr Gly Leu Tyr Thr His Ser Gly Glu Cys Cys Lys Ala Cys Asn
               35                       40                       45

Leu Gly Glu Gly Val Ala Gln Pro Cys Gly Ala Asn Gln Thr Val Cys
    50                    55                    60

Glu Pro Cys Leu Asp Ser Val Thr Phe Ser Asp Val Val Ser Ala Thr
65                  70                    75                    80

Glu Pro Cys Lys Pro Cys Thr Glu Cys Val Gly Leu Gln Ser Met Ser
                 85                       90                       95

Ala Pro Cys Val Glu Ala Asp Asp Ala Val Cys Arg Cys Ala Tyr Gly
             100                       105                     110

Tyr Tyr Gln Asp Glu Thr Thr Gly Arg Cys Glu Ala Cys Arg Val Cys
        115                     120                     125

Glu Ala Gly Ser Gly Leu Val Phe Ser Cys Gln Asp Lys Gln Asn Thr
130                         135                         140

Val Cys Glu Glu Cys Pro Asp Gly Thr Tyr Ser Asp Glu Ala Asn His
145                         150                       155                       160

Val Asp Pro Cys Leu Pro Cys Thr Val Cys Glu Asp Thr Glu Arg Gln
                 165                       170                       175

```
Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg
```

UNITED STATES PATENT AND TRADEMARK OFFICE
CERTIFICATE OF CORRECTION

PATENT NO. : 11,046,775 B2
APPLICATION NO. : 15/896619
DATED : June 29, 2021
INVENTOR(S) : Alvarez Rodriguez et al.

Page 1 of 1

It is certified that error appears in the above-identified patent and that said Letters Patent is hereby corrected as shown below:

In the Claims

Claim 22, Column 203, Line 3, delete "CD8a, CD86" and insert in place thereof --CD8α, CD8β--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*